United States Patent
Ji

(10) Patent No.: US 11,530,186 B2
(45) Date of Patent: Dec. 20, 2022

(54) INHIBITORS FOR THE β-CATENIN / T-CELL FACTOR PROTEIN-PROTEIN INTERACTION

(71) Applicant: H. LEE MOFFITT CANCER CENTER AND RESEARCH INSTITUTE, INC., Tampa, FL (US)

(72) Inventor: Haitao Ji, Tampa, FL (US)

(73) Assignee: H. Lee Moffitt Cancer Center and Research Center Institute, Inc., Tampa, FL (US)

( * ) Notice: Subject to any disclaimer, the term of this patent is extended or adjusted under 35 U.S.C. 154(b) by 0 days.

(21) Appl. No.: 17/042,588

(22) PCT Filed: Mar. 28, 2019

(86) PCT No.: PCT/US2019/024556
§ 371 (c)(1),
(2) Date: Sep. 28, 2020

(87) PCT Pub. No.: WO2019/191410
PCT Pub. Date: Oct. 3, 2019

(65) Prior Publication Data
US 2021/0017139 A1   Jan. 21, 2021

Related U.S. Application Data

(60) Provisional application No. 62/649,782, filed on Mar. 29, 2018.

(51) Int. Cl.
| | | |
|---|---|---|
| C07D 257/04 | (2006.01) |
| C07D 209/42 | (2006.01) |
| C07D 401/14 | (2006.01) |
| C07D 403/06 | (2006.01) |
| C07D 403/14 | (2006.01) |
| C07D 405/14 | (2006.01) |
| C07D 409/14 | (2006.01) |
| C07D 417/06 | (2006.01) |
| C07D 417/14 | (2006.01) |
| A61P 35/00 | (2006.01) |

(52) U.S. Cl.
CPC ............ *C07D 257/04* (2013.01); *A61P 35/00* (2018.01); *C07D 209/42* (2013.01); *C07D 401/14* (2013.01); *C07D 403/06* (2013.01); *C07D 403/14* (2013.01); *C07D 405/14* (2013.01); *C07D 409/14* (2013.01); *C07D 417/06* (2013.01); *C07D 417/14* (2013.01)

(58) Field of Classification Search
CPC .. C07D 257/04; C07D 209/42; C07D 401/14; C07D 403/06; C07D 403/14; C07D 405/14; C07D 409/14; C07D 417/06; C07D 417/14
See application file for complete search history.

(56) References Cited

U.S. PATENT DOCUMENTS

| | | | | |
|---|---|---|---|---|
| 4,273,782 A | * | 6/1981 | Cross | C07D 231/12 548/254 |
| 2012/0270912 A1 | | 10/2012 | Jones et al. | |
| 2013/0225592 A1 | | 8/2013 | Wasmuth et al. | |

OTHER PUBLICATIONS

International Search Report and Written Opinion in PCT/US2019/024556, dated Jul. 25, 2019. 12 pages.

* cited by examiner

*Primary Examiner* — Rebecca L Anderson
(74) *Attorney, Agent, or Firm* — Meunier Carlin & Curfman LLC

(57) ABSTRACT

Disclosed are inhibitors for the β-catenin/T-cell factor interaction. The inhibitors are selective for β-catenin/T-cell factor over β-catenin/cadherin and β-catenin/APC interactions. Methods of using the disclosed compounds to treat cancer are also disclosed.

27 Claims, 10 Drawing Sheets

Specification includes a Sequence Listing.

SEQUENCE LISTING

```
<160> NUMBER OF SEQ ID NOS: 3

<210> SEQ ID NO 1
<211> LENGTH: 53
<212> TYPE: PRT
<213> ORGANISM: Artificial Sequence
<220> FEATURE:
<223> OTHER INFORMATION: Synthetic construct

<400> SEQUENCE: 1

His Gly Gly Gly Asp Asp Leu Gly Ala Asn Asp Glu Leu Ile Ser Phe
1               5                   10                  15

Lys Asp Glu Gly Glu Gln Glu Glu Lys Ser Ser Glu Asn Ser Ser Ala
            20                  25                  30

Glu Arg Asp Leu Ala Asp Val Lys Ser Ser Leu Val Asn Glu Lys Phe
        35                  40                  45

Ile Thr Cys Asn His
    50
```

```
<210> SEQ ID NO 2
<211> LENGTH: 63
<212> TYPE: PRT
<213> ORGANISM: Artificial Sequence
<220> FEATURE:
<223> OTHER INFORMATION: Synthetic construct

<400> SEQUENCE: 2

His Asp Thr Asp Pro Thr Ala Pro Pro Tyr Asp Ser Leu Leu Val Phe
1               5                   10                  15

Asp Tyr Glu Gly Ser Gly Ser Glu Ala Ala Ser Leu Ser Ser Leu Asn
            20                  25                  30

Ser Ser Glu Ser Asp Lys Asp Gln Asp Tyr Asp Tyr Leu Asn Glu Trp
        35                  40                  45

Gly Asn Arg Phe Lys Lys Leu Ala Lys Phe Ile Thr Cys Asn His
    50                  55                  60

<210> SEQ ID NO 3
<211> LENGTH: 51
<212> TYPE: PRT
<213> ORGANISM: Artificial Sequence
<220> FEATURE:
<223> OTHER INFORMATION: Synthetic construct

<400> SEQUENCE: 3

His Gln Arg Val Gln Val Leu Pro Asp Ala Asp Thr Leu Leu His Phe
1               5                   10                  15

Ala Thr Glu Ser Thr Pro Asp Gly Phe Ser Cys Ser Ser Ser Leu Ser
            20                  25                  30

Ala Leu Ser Leu Asp Glu Pro Phe Ile Gln Lys Asp Lys Phe Ile Thr
        35                  40                  45

Cys Asn His
    50
```

INHIBITORS FOR THE β-CATENIN / T-CELL FACTOR PROTEIN-PROTEIN INTERACTION

CROSS REFERENCE TO RELATED APPLICATIONS

This application is a United States National Phase Patent Application of International Patent Application Number PCT/US2019/024556, filed on Mar. 28, 2019, which claims the benefit of priority to U.S. Provisional Application No. 62/649,782, filed Mar. 29, 2018, which is incorporated by reference herein in its entirety.

BACKGROUND

The Wnt/β-catenin signaling pathway plays a critical role in regulation of cell proliferation, differentiation, and survival (Clevers H (2012) Wnt/beta-catenin signaling and disease. Cell 149(6):1192-1205; Nusse R (2017) Wnt/beta-Catenin Signaling, Disease, and Emerging Therapeutic Modalities. Cell 169(6):985-999; Akhmetshina A, et al. (2012) Activation of canonical Wnt signalling is required for TGF-beta-mediated fibrosis. Nature communications 3:735). The aberrant activation of Wnt/β-catenin signaling has been implicated in initiation and progression of many cancers (van de Wetering M, et al. (2002) The beta-catenin/TCF-4 complex imposes a crypt progenitor phenotype on colorectal cancer cells. Cell 111(2):241-250; Dow L E, et al. (2015) Apc Restoration Promotes Cellular Differentiation and Reestablishes Crypt Homeostasis in Colorectal Cancer. Cell 161(7):1539-1552; Lu D, et al. (2004) Activation of the Wnt signaling pathway in chronic lymphocytic leukemia. Proc Nat Acad Sci USA 101(9):3118-3123; Sukhdeo K, et al. (2007) Targeting the beta-catenin/TCF transcriptional complex in the treatment of multiple myeloma. Proc Nat Acad Sci USA 104(18):7516-7521; Bafico A, et al., (2004) An autocrine mechanism for constitutive Wnt pathway activation in human cancer cells. Cancer Cell 6(5):497-506; Scheel C, et al. (2011) Paracrine and autocrine signals induce and maintain mesenchymal and stem cell states in the breast. Cell 145(6):926-940) and fibroses (Brack A S, et al. (2007) Increased Wnt signaling during aging alters muscle stem cell fate and increases fibrosis. Science (New York, N.Y.) 317(5839):807-810; Lancaster M A, et al. (2009) Impaired Wnt-beta-catenin signaling disrupts adult renal homeostasis and leads to cystic kidney ciliopathy. Nature Med 15(9):1046-1054). For instance, loss of adenomatous polyposis coli (APC) function can lead to the inappropriate stabilization of β-catenin and promote the formation of the constitutive complex between β-catenin and the T-cell factor (Tcf)/lymphoid enhancer-binding factor (Lef) family of transcriptional factors, which transcribes specific Wnt target genes that produce crypt progenitor-like cells in the surface intestinal epithelium, eventually causing sporadic colorectal cancer (van de Wetering M, et al. (2012) supra; Dow L E, et al. (2015) supra). The autocrine activation of Wnt ligands can stabilize β-catenin into the dephosphorylated state and result in an increased level of nuclear β-catenin to interact with Tcf/Lef to induce overexpression of Wnt target genes and cause initiation and progression of triple negative breast cancers (TNBCs) (Bafico A, et al. (2004) supra; Scheel C, et al. (2011) supra). Hyperactivation of β-catenin signaling was detected in cancer stem cells, which control tumor growth, seed metastases, and result in cancer recurrence after remission (Malanchi I, et al. (2008) Cutaneous cancer stem cell maintenance is dependent on beta-catenin signaling. Nature 452(7187):650-653; Barker N, et al. (2009) Crypt stem cells as the cells-of-origin of intestinal cancer. Nature 457(7229):608-611; Yeung J, et al. (2010) beta-Catenin mediates the establishment and drug resistance of MLL leukemic stem cells. Cancer Cell 18(6):606-618). In addition, activation of β-catenin signaling was demonstrated to exclude CD8$^+$ T cells from the tumor microenvironment and promote intratumoral regulator T cell (Treg) survival and infiltration, thus impairing antitumor immunity (Spranger S, et al. (2015) Melanoma-intrinsic beta-catenin signalling prevents anti-tumour immunity. Nature 523 (7559):231-235; Spranger S, et al. (2017) Tumor-Residing Batf3 Dendritic Cells Are Required for Effector T Cell Trafficking and Adoptive T Cell Therapy. Cancer Cell 31(5):711-723.e714; Ding Y, et al. (2008) Beta-catenin stabilization extends regulatory T cell survival and induces anergy in nonregulatory T cells. Nature Med 14(2):162-169; Keerthivasan S, et al. (2014) beta-Catenin promotes colitis and colon cancer through imprinting of proinflammatory properties in T cells. Science Trans Med 6(225):225ra228). Therefore, the suppression of this signaling pathway holds great promise for designing new targeted cancer therapy. Further biological studies indicated that the formation of β-catenin/Tcf complex in the cell nucleus is the penultimate step of the Wnt/β-catenin signaling pathway and the activation of Wnt/β-catenin target genes is dependent on the formation of this complex (Kim J S, et al. (2002) Proof-of-principle: oncogenic beta-catenin is a valid molecular target for the development of pharmacological inhibitors. Mol Cancer Ther 1(14):1355-1359; Ashihara E, et al. (2009) beta-catenin small interfering RNA successfully suppressed progression of multiple myeloma in a mouse model. Clinical Cancer Res 15(8):2731-2738; Scholer-Dahirel A, et al. (2011) Maintenance of adenomatous polyposis coli (APC)-mutant colorectal cancer is dependent on Wnt/beta-catenin signaling. Proc Nat Acad Sci USA 108(41):17135-17140). Therefore, the β-catenin/Tcf PPI has emerged as an appealing therapeutic target to suppress hyperactive β-catenin signaling.

In previous studies, small-molecule inhibitors for the β-catenin/Tcf PPI using different strategies were reported (Yu B, et al. (2013) Rational design of small-molecule inhibitors for beta-catenin/T-cell factor protein-protein interactions by bioisostere replacement. ACS Chemical Bio 8(3): 524-529; Huang Z, et al. (2014) Targeting the Tcf4 G13ANDE17 binding site to selectively disrupt beta-catenin/T-cell factor protein-protein interactions. ACS Chem Bio 9(1):193-201; Catrow J L, et al. (2015) Discovery of Selective Small-Molecule Inhibitors for the beta-Catenin/T-Cell Factor Protein-Protein Interaction through the Optimization of the Acyl Hydrazone Moiety. J Med Chem 58(11): 4678-4692). But what are still needed are new, potent and selective inhibitors for the β-catenin/T-cell factor interaction and methods for their use. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors for the β-catenin/T-cell factor interaction. Further, the subject matter disclosed herein relates to inhibitors that are selective for β-catenin/ T-cell factor interactions over β-catenin/phosphocadherin, and β-catenin/phosphoAPC interactions. Also disclosed are methods of inhibiting the β-catenin/T-cell factor interaction, as well as methods of treating certain cancers.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
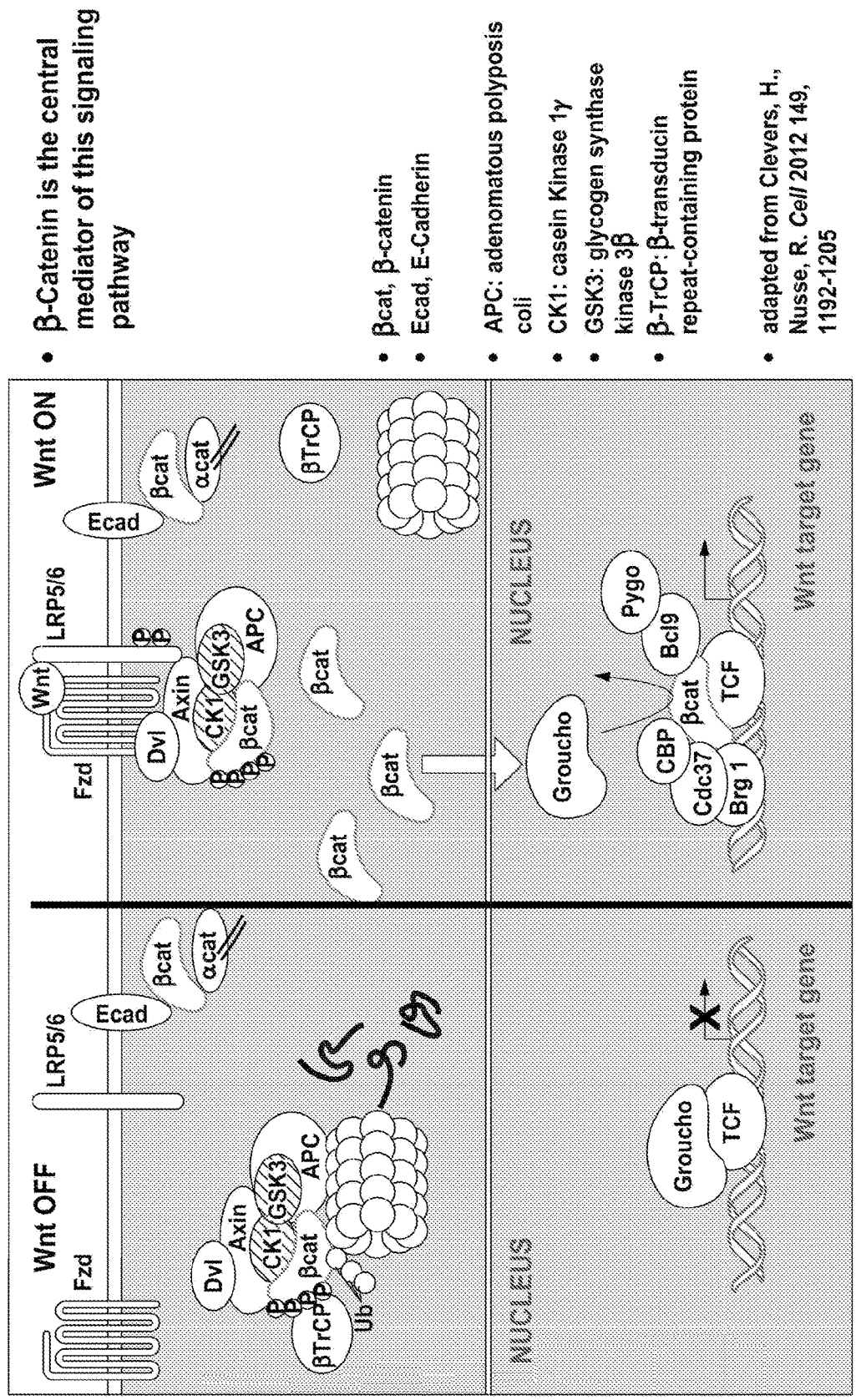
FIG. 1 is a schematic showing the Wnt/β-catenin signaling pathway.
Figure 2:
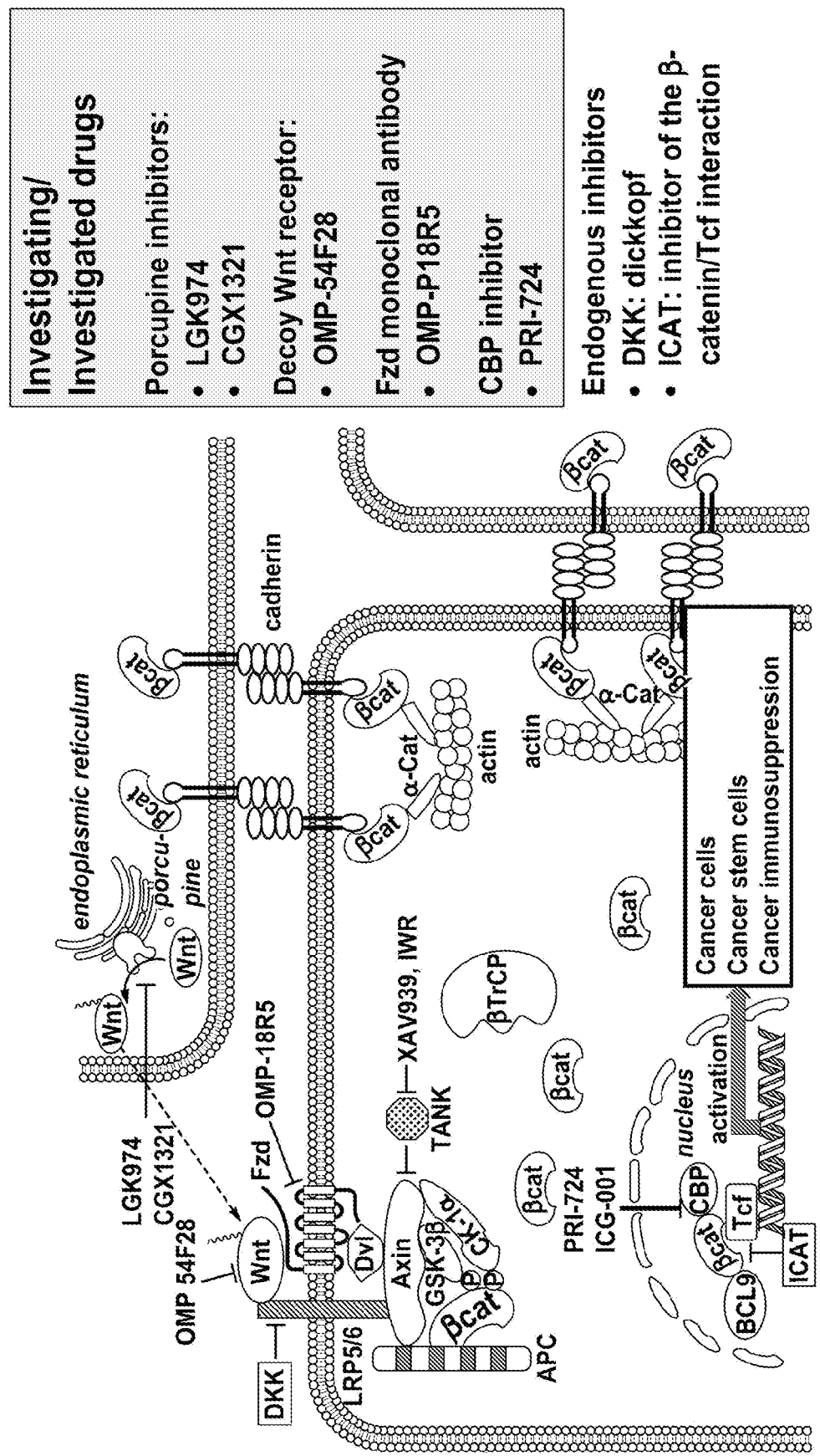
FIG. 2 is a schematic showing some investigational drugs targeting the Wnt/β-catenin pathway.
Figure 3:
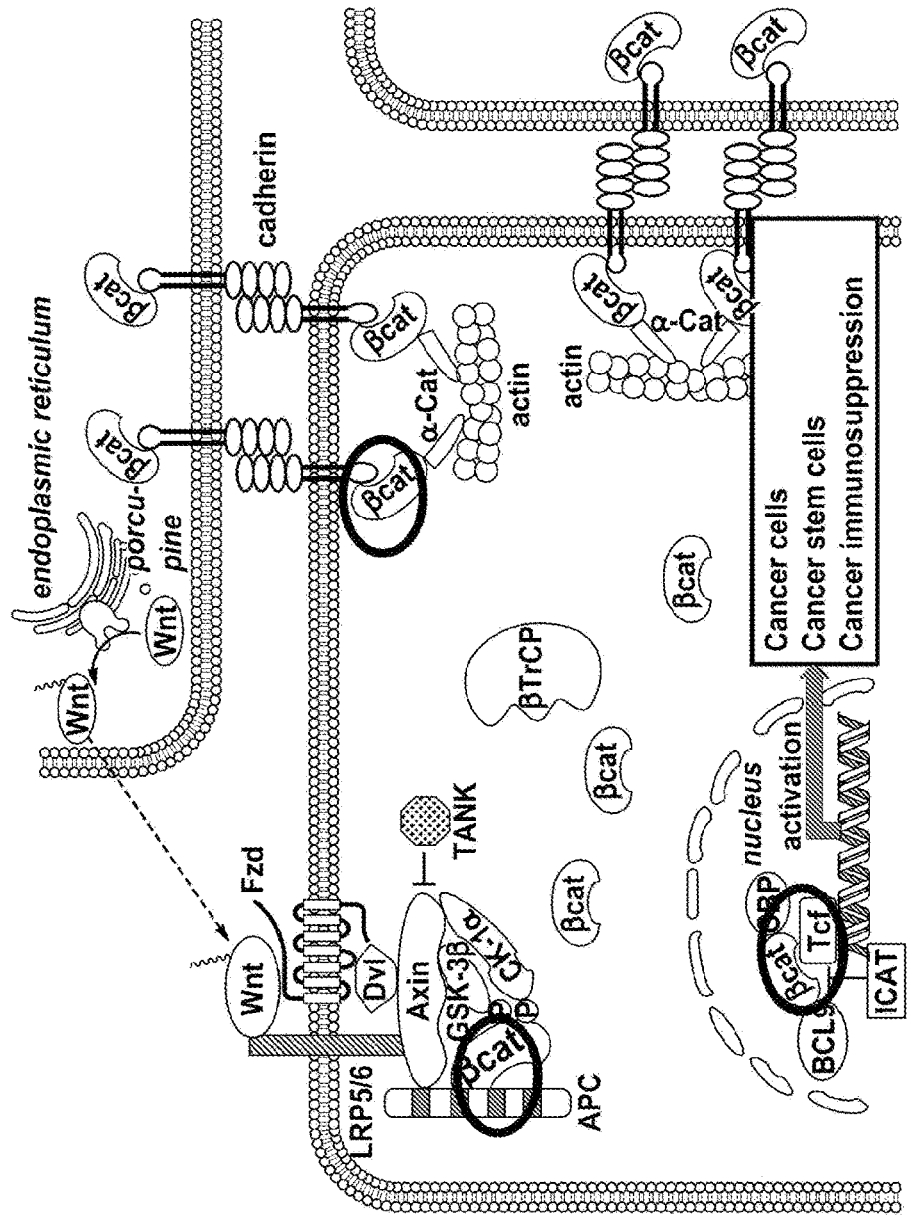
FIG. 3 is a schematic showing selective inhibition of the β-catenin/Tcf interaction.
Figure 4:
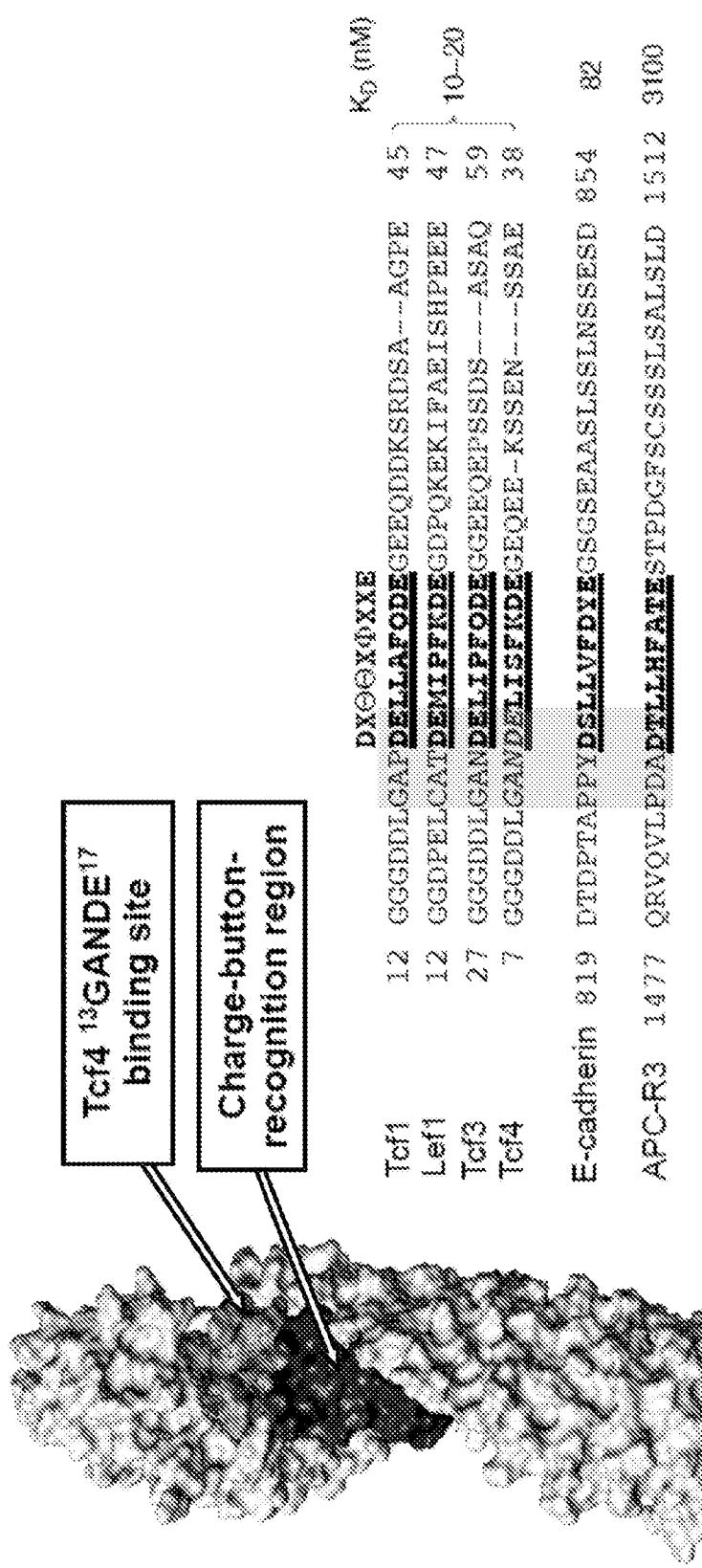
FIG. 4 is a schematic showing the selective binding site of Tcf4.
Figure 5:
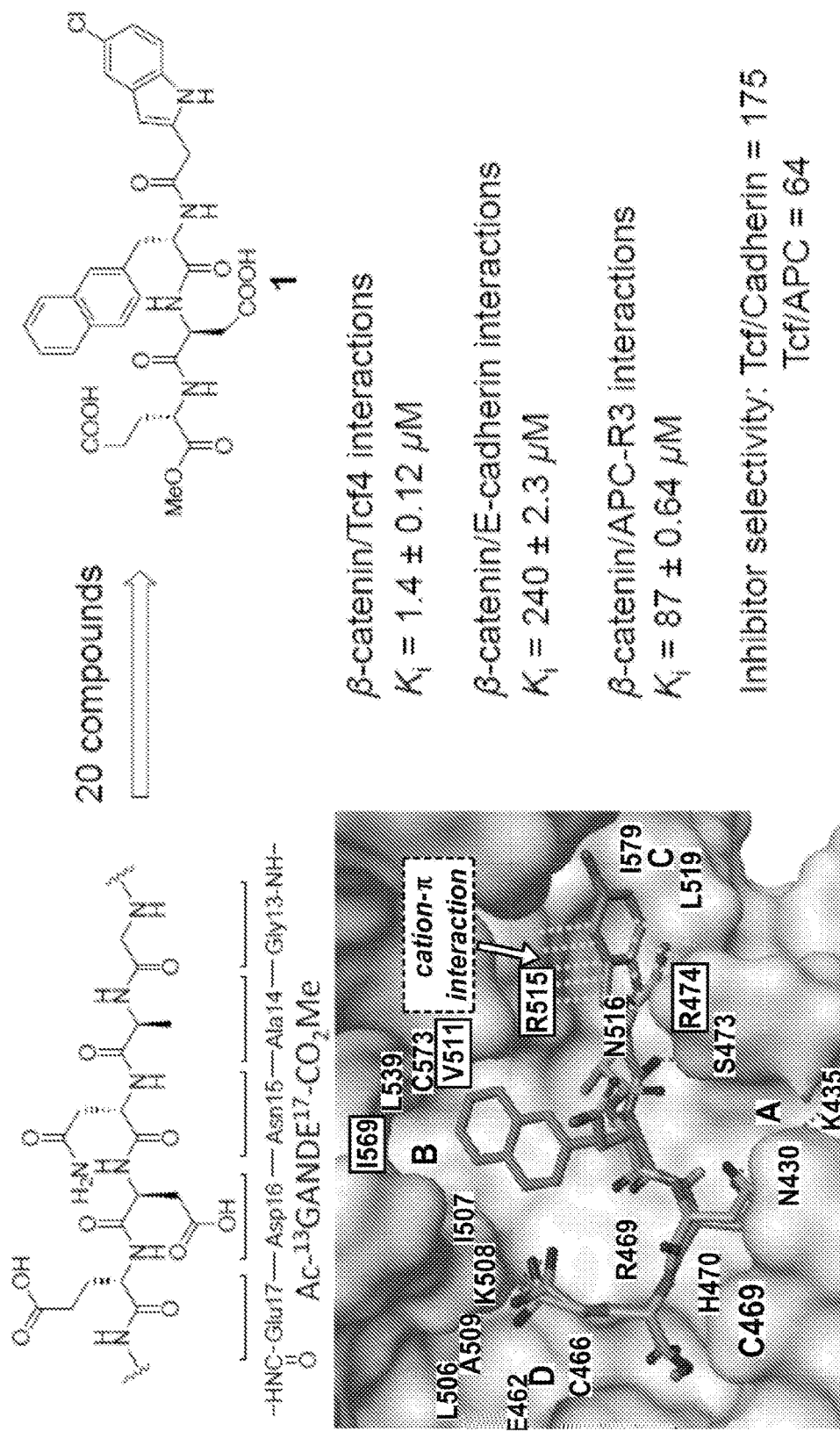
FIG. 5 is a schematic showing the design of the prototypic inhibitor.
Figure 6:
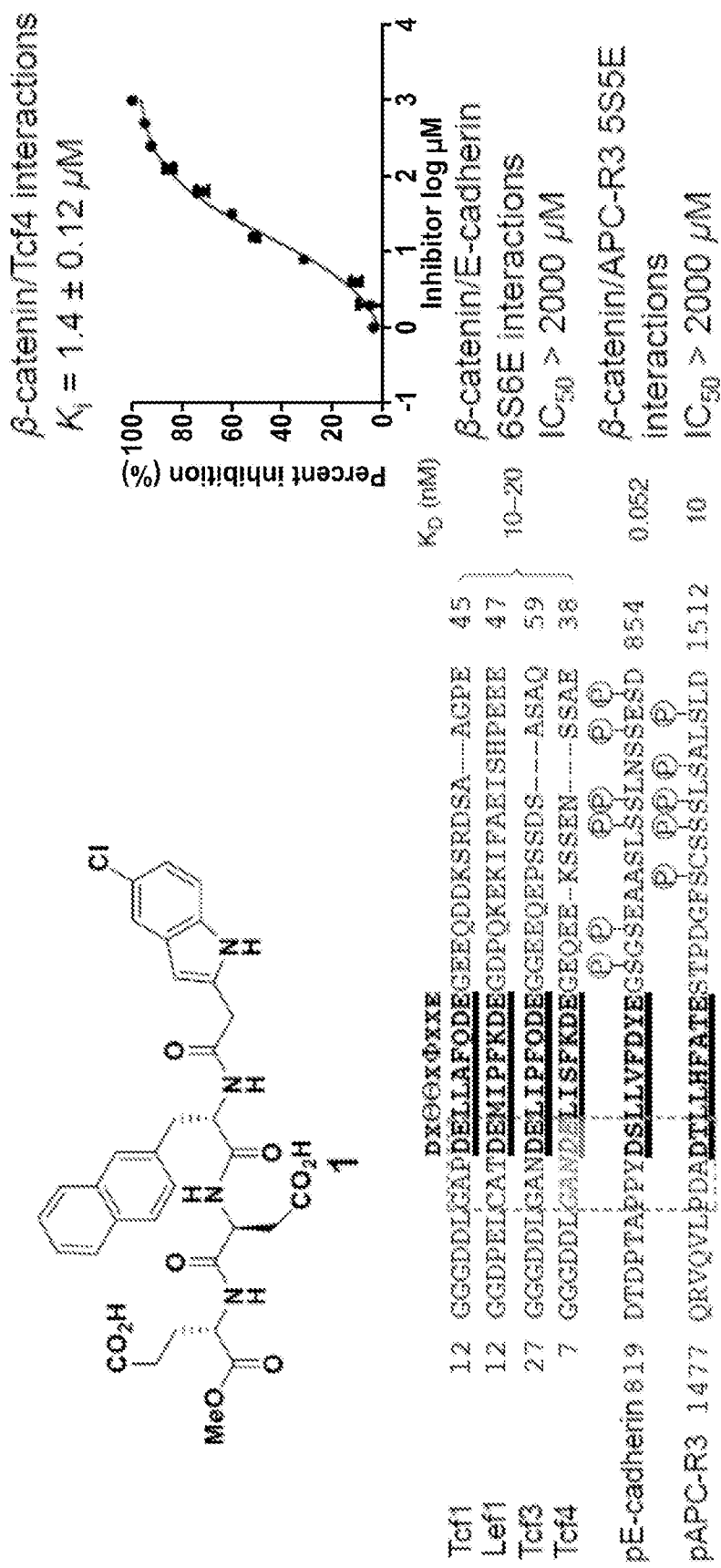
FIG. 6 is a schematic showing the inhibitor selectivity for β-catenin/Tcf, β-catenin/phosphocadherin, and β-catenin/ phosphoAPC interactions.
Figure 7:
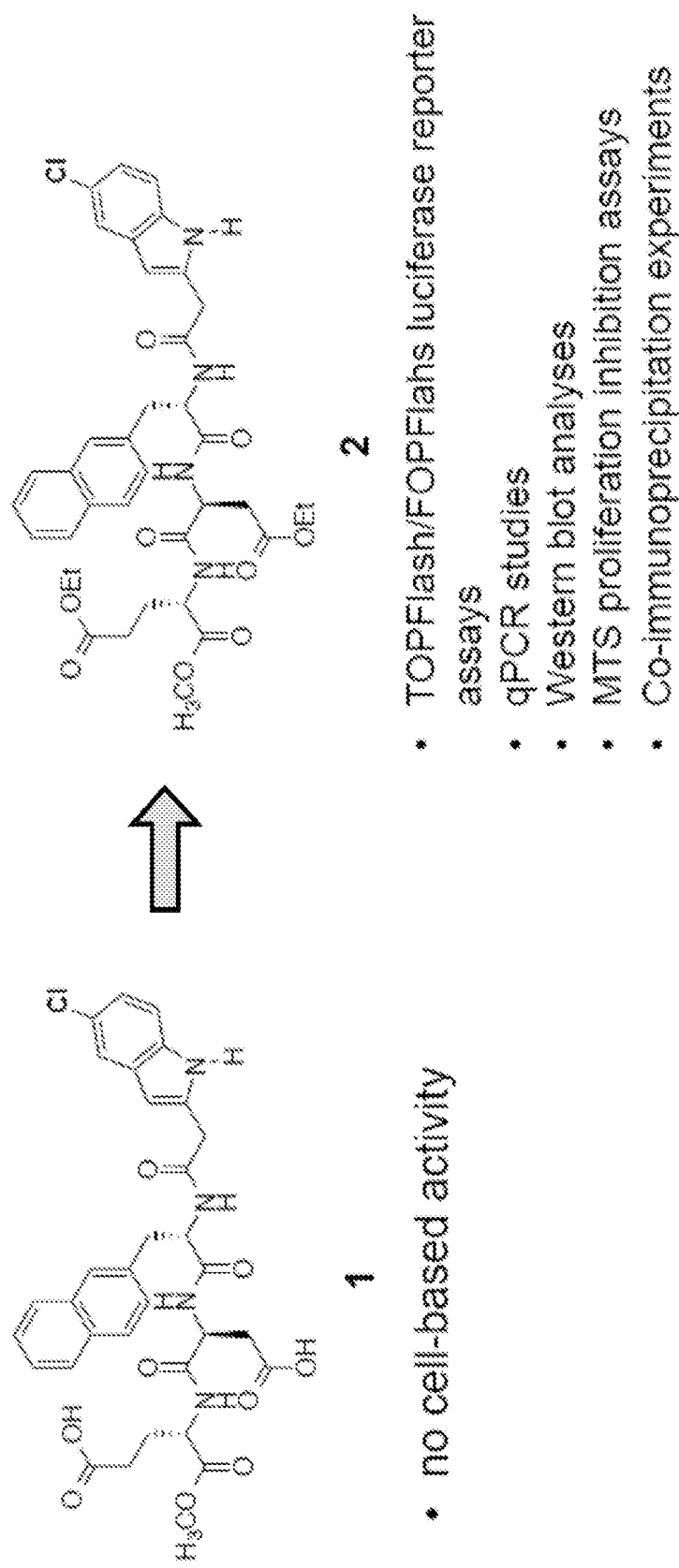
FIG. 7 is a schematic of cell-based studies.
Figure 8:
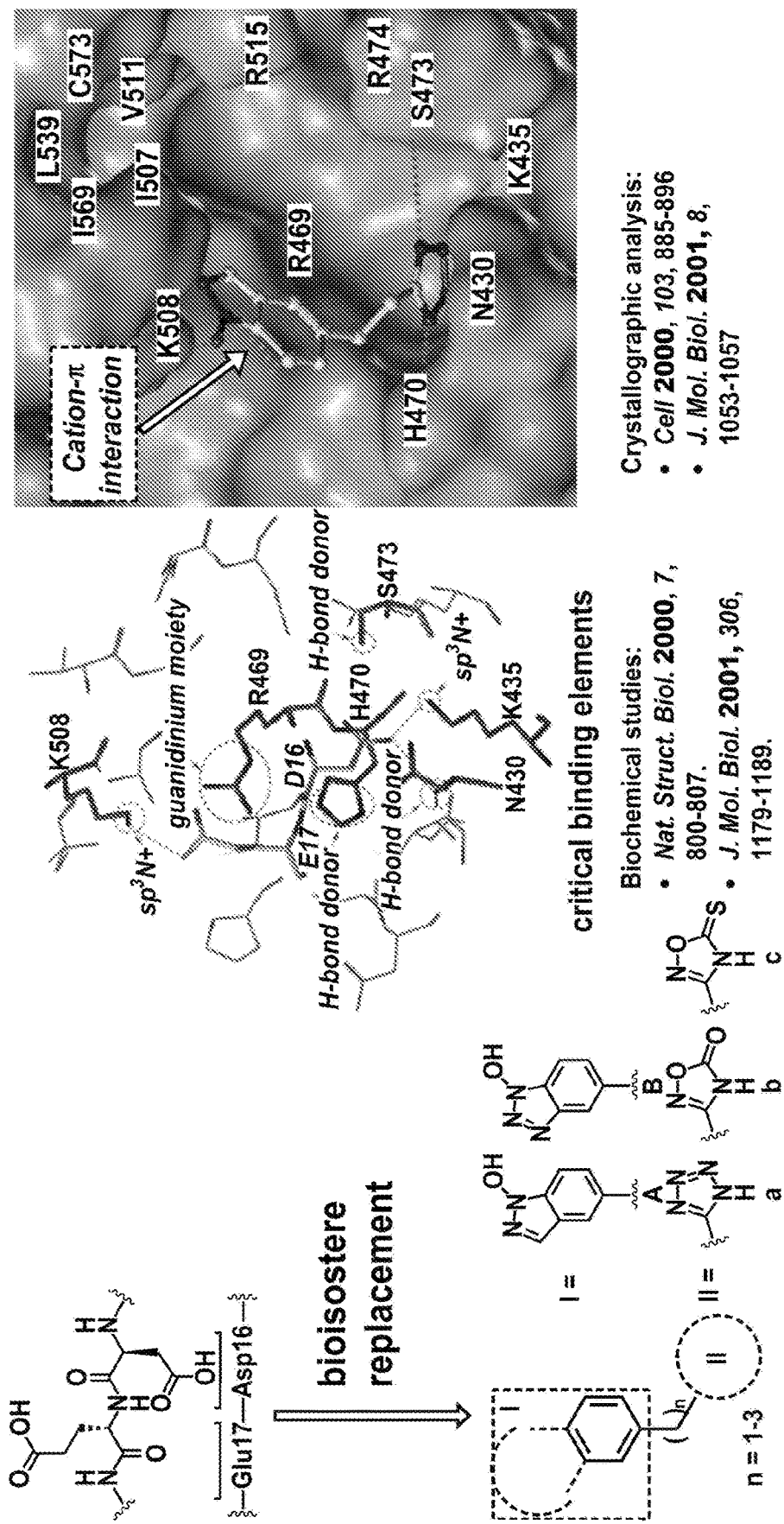
FIGS. 8 and 9 are schematics showing design of small molecule β-catenin/Tcf protein-protein interactions.
Figure 9:
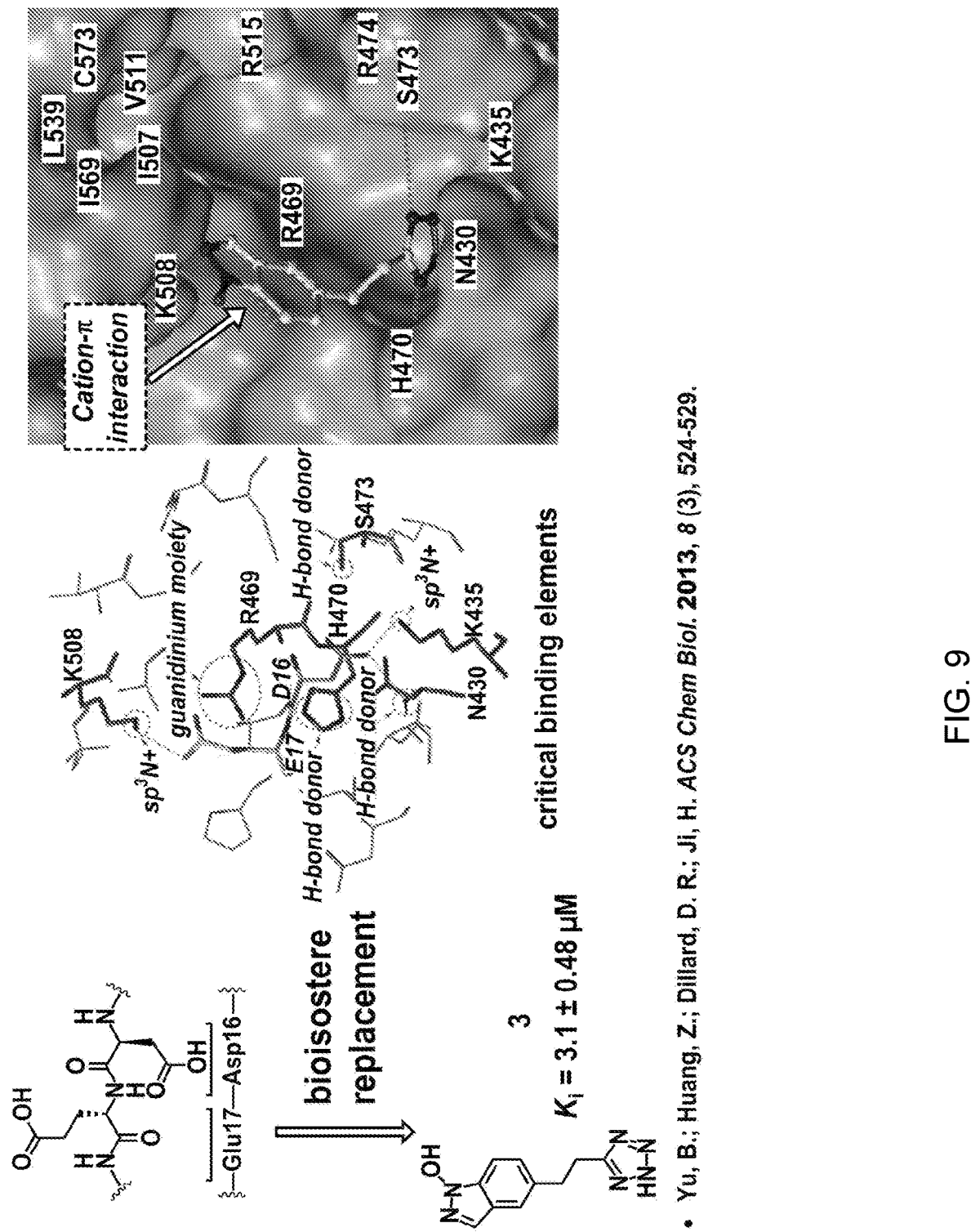
Figure 10:
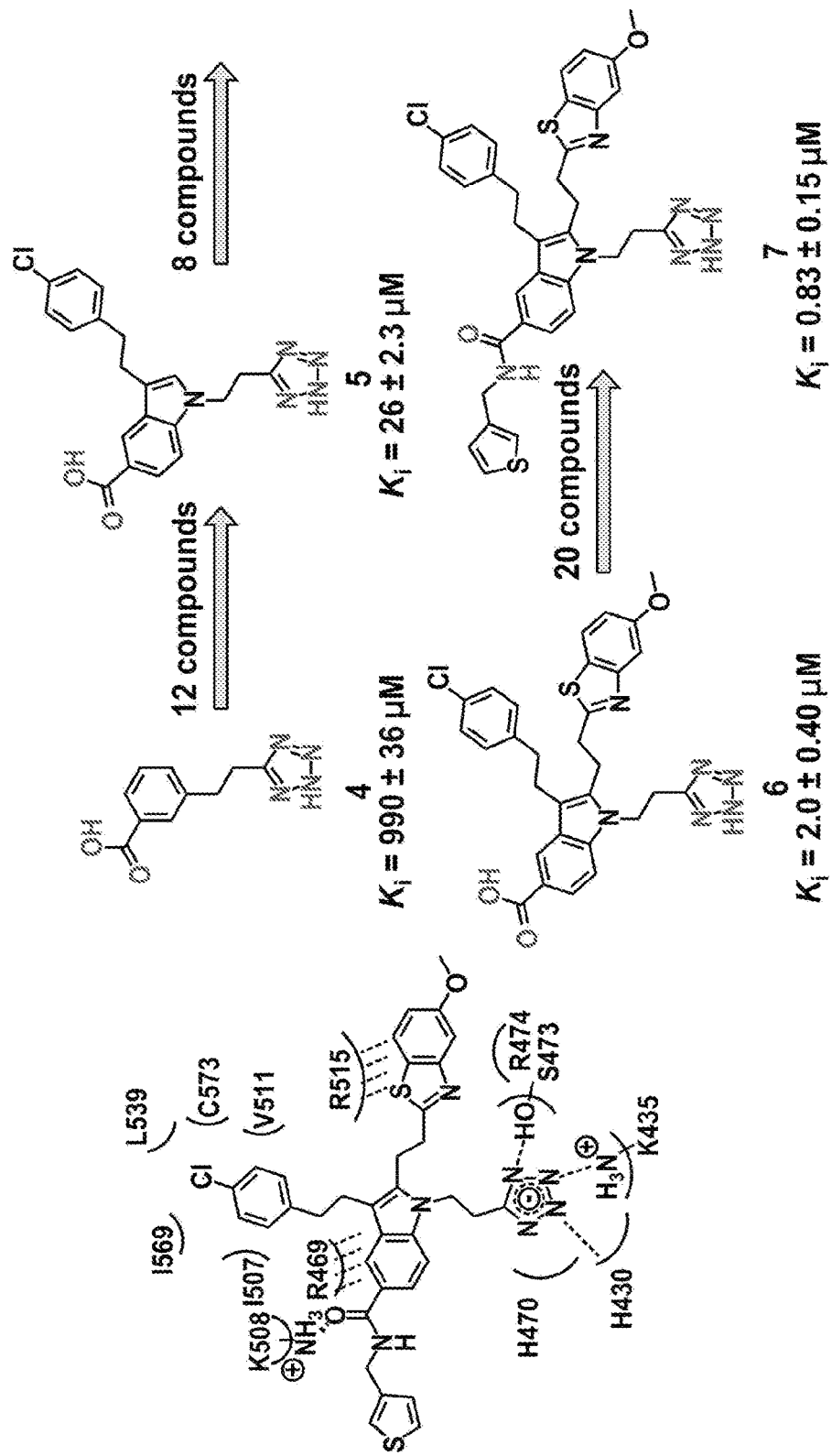
FIG. 10 is a schematic showing fragment evolution to design β-catenin/Tcf inhibitors.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substituent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $AC(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO₂.

The term "cyano" as used herein is represented by the formula —CN.

The term "azido" as used herein is represented by the formula —N₃.

The term "sulfonyl" is used herein to refer to the sulfo-oxo group represented by the formula —S(O)₂$A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)₂NH₂.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt;

similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

In certain aspects, disclosed herein are compounds having Formula I.

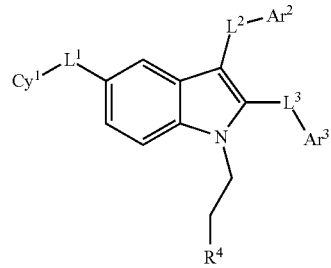

wherein
$Cy^1$ is H or substituted or unsubstituted, mono or bicyclic aryl, heteroaryl, cycloalkyl, or cycloheteroalkyl;
$L^1$ is $(CH_2)_{1-4}$, $CH_2NHC(O)$, $C(O)NHCH_2$, $NHC(O)CH_2$, $CH_2C(O)NH$, $NHC(O)$, $C(O)NH$, $CH_2C(O)NH$, $NHC(O)CH_2$, $C(O)NHCH_2$, $CH_2NHC(O)$, $C(O)NHO$, $ONHC(O)$, $C(O)NHOCH_2$, $CH_2ONHC(O)$, $C(O)NHCH_2CH_2O$, $OCH_2CH_2NHC(O)$, $C(O)NHCH_2CH(OH)CH(OH)$, $CH_2C(O)O$, $OC(O)CH_2$, $C(O)OCH_2$, $CH_2OC(O)$, $C(O)O$, $OC(O)$, $CH_2C(O)$, $C(O)CH_2$, $CH_2CH_2C(O)$, $C(O)CH_2CH_2$, $NH_2$, or $O$;
$Ar^2$ is substituted or unsubstituted, mono or bicyclic aryl, heteroaryl, or cycloheteroalkyl;
$L^2$ is $(CH_2)_{1-4}$;
$Ar^3$ is null, or substituted or unsubstituted, mono or bicyclic heteroaryl;
$L^3$ is H, a bond, C≡C, or $(CH_2)_{1-4}$; and
$R^4$ is $CO_2H$, $C(O)OC_{1-6}$ alkyl, tetrazole, or CN;
Wherein, when substituted, the substituent is one or more of halo, $C_{1-6}$ alkyl, $C_{1-6}$ haloalky, $C_{1-6}$ alkoxyl, $C_{1-6}$ haloalkoxyl, or amino,
or a pharmaceutically acceptable salt thereof.
In specific examples, $L^1$ is $CH_2NHC(O)$.
In specific examples, $Cy^1$ is

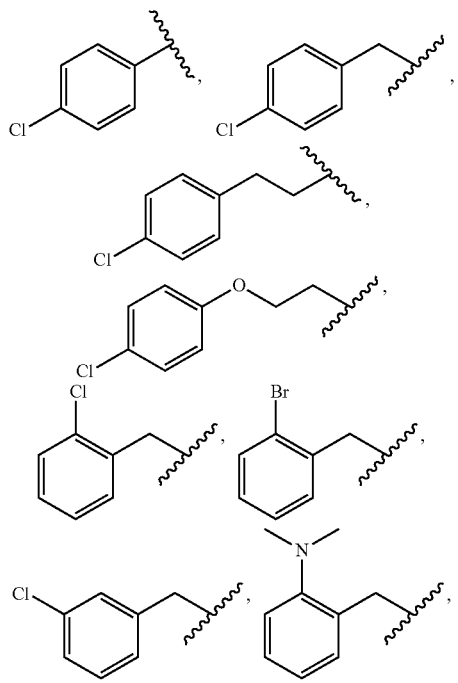

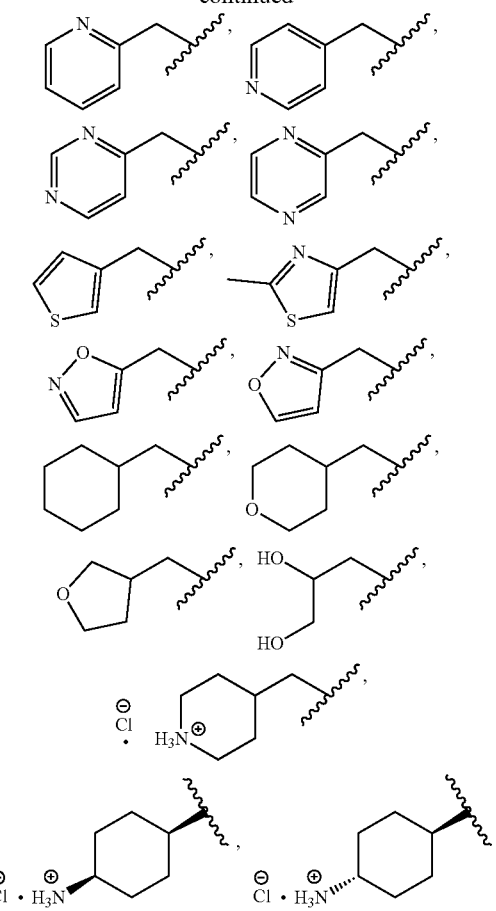

In specific examples, $Cy^1$ is H and $L^1$ is OC(O), which together is HOC(O). Exemplary compounds have Formula II

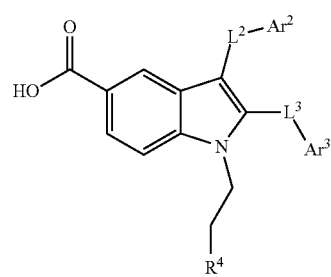

wherein $Ar^2$, $L^2$, $Ar^3$, $L^3$, and $R^4$ are as defined herein.

In other examples of Formula I or II, $L^2$ and $L^3$ are $(CH_2)_{1-4}$, e.g., $CH_2CH_2$. In other examples $L^2$ is $(CH_2)_{1-4}$ and $L^3$ is a bond.

In further examples, $Ar^2$ is aryl substituted with one or more of halogen, amino, $C_{1-6}$ alkyl, $C_{1-6}$ alkoxyl, $C_{1-6}$ haloalkyl, or $C_{1-6}$ haloalkoxyl. In other examples, $Ar^2$ is napthyl. In further examples $Ar^2$ is biphenyl, pyranyl, or thiazolinyl. In specific examples, $Ar^2$ is chosen from

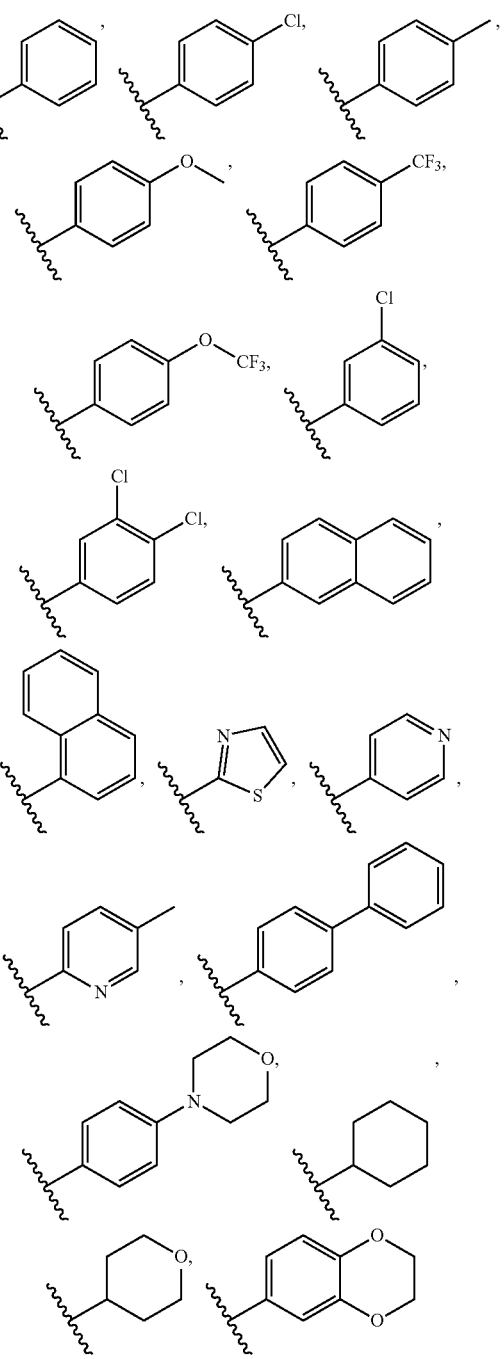

In further examples, $Ar^3$ is a phenyl, or heterocyclic, such as thiophenyl, pyrollyl, pyridinyl, pyrazolyl, benzothiophenyl, 2-oxo-1,2-dihydropyridin, benzothiazolyl, and benzoimidazolyl. In specific examples, $Ar^3$ is a substituted benzothiazole or benzoxazole. In further examples, $Ar^3$ has the following formula

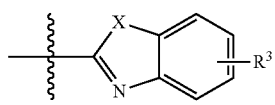

wherein X is O, S, NH, or $CH_2$; and $R^3$ is H, halogen, amino, $C_{1-6}$ alkyl, $C_{1-6}$ alkoxyl, $C_{1-6}$ haloalkyl, or $C_{1-6}$ haloalkoxyl.

In specific examples $R^4$ is tetrazole. In other examples, $R^4$ is $CO_2H$.

Further exemplary compounds have Formula III

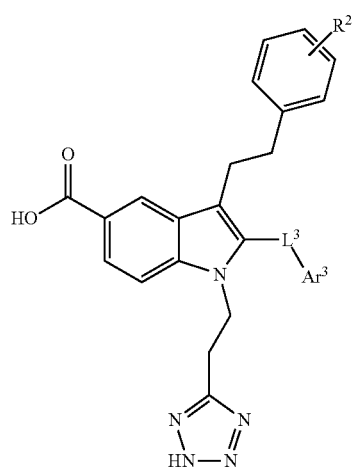

wherein $Ar^3$, $L^3$, are as defined herein, and $R^2$ is H, halogen, amino, $C_{1-6}$ alkyl, $C_{1-6}$ alkoxyl, $C_{1-6}$ haloalkyl, or $C_{1-6}$ haloalkoxyl.

Exemplary compounds have Formula IV

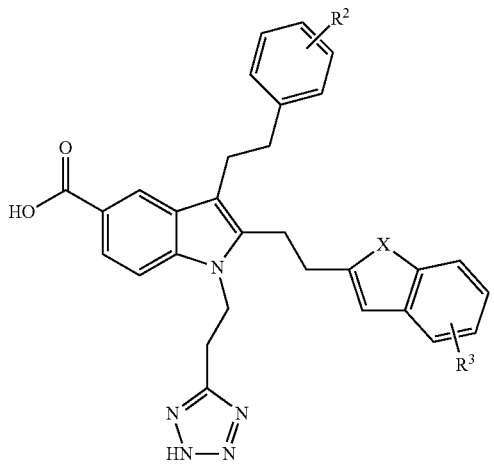

wherein X is O, S, NH, or $CH_2$, $R^2$ is as defined herein, and $R^3$ is H, halogen, amino, $C_{1-6}$ alkyl, $C_{1-6}$ alkoxyl, $C_{1-6}$ haloalkyl, or $C_{1-6}$ haloalkoxyl.

Further exemplary compounds have Formula V

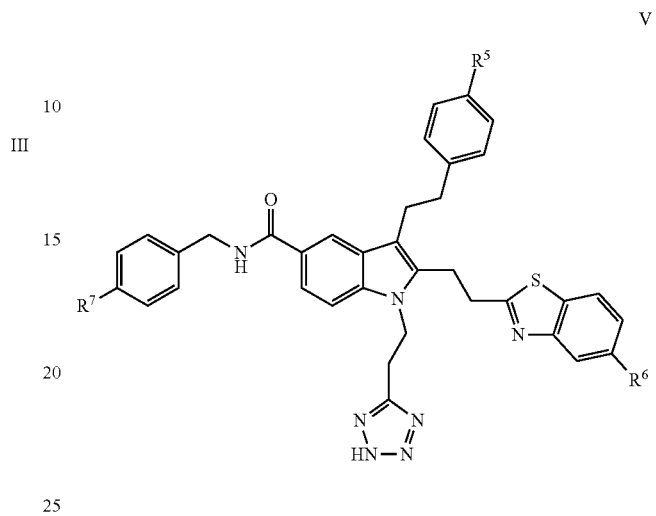

wherein $R^5$, $R^6$, and $R^7$ are independently selected from H, halo, amino, $C_{1-6}$ alkyl, $C_{1-6}$ alkoxyl, $C_{1-6}$ haloalkyl, $C_{1-6}$ haloalkoxyl, and $C_{1-6}$ heteroalkyl. In specific examples, $R^5$ and $R^7$ can independently be fluoro or chloro. In further examples, $R^6$ can be H or $C_{1-6}$ heteroalkyl. In specific examples, compounds of Formula V can be

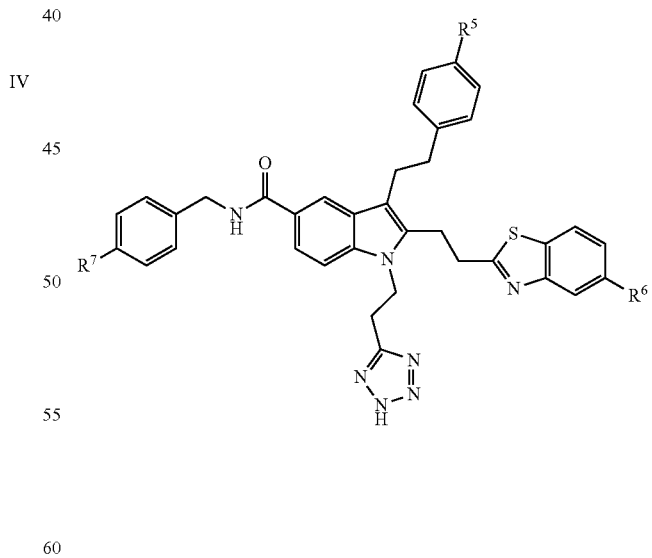

44. $R^5$ = F, $R^6$ = H, $R^7$ = F
45. $R^5$ = F, $R^6$ = H, $R^7$ = Cl
46. $R^5$ = Cl, $R^6$ = , $R^7$ = Cl Further exemplary compounds have Formula VI

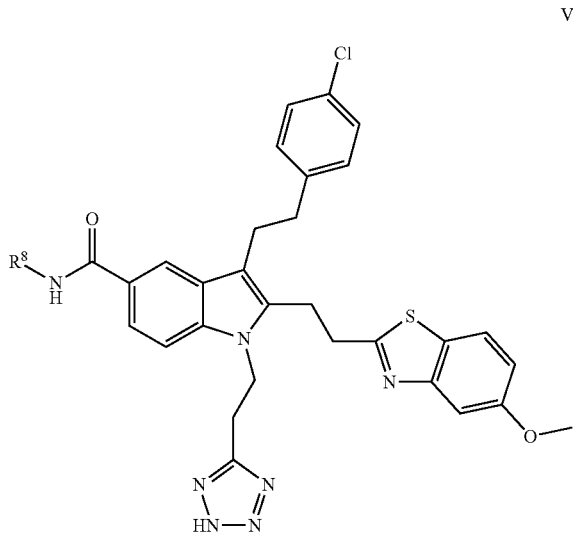

VI wherein R⁸ is substituted or unsubstituted, mono or bicyclic aryl, heteroaryl, cycloalkyl, cycloheteroalkyl, or dihydroxy-substituted alkyl. In specific examples R⁸ is phenyl substituted with one or more (e.g., 1, 2, or 3) halo, $C_{1-6}$ alkyl, $C_{1-6}$ haloalky, $C_{1-6}$ alkoxyl, or amino. In other examples, R⁸ is pyridinyl, pyrimidinyl, pyrazinyl, pyrrolyl, isoxazolyl, isothiazolyl, oxazolyl, thiazolyl, pyranyl, or furanyl, any of which is optionally substituted with one or more halo, $C_{1-6}$ alkyl, $C_{1-6}$ haloalky, $C_{1-6}$ alkoxyl, or amino. In other examples, R is cyclopenyl, cyclohexyl, tetrahydropyranyl, or tetrahydrofuranyl, any of which is optionally substituted with one or more halo, $C_{1-6}$ alkyl, $C_{1-6}$ haloalky, $C_{1-6}$ alkoxyl, or amino. In specific examples, compounds of Formula VI can be

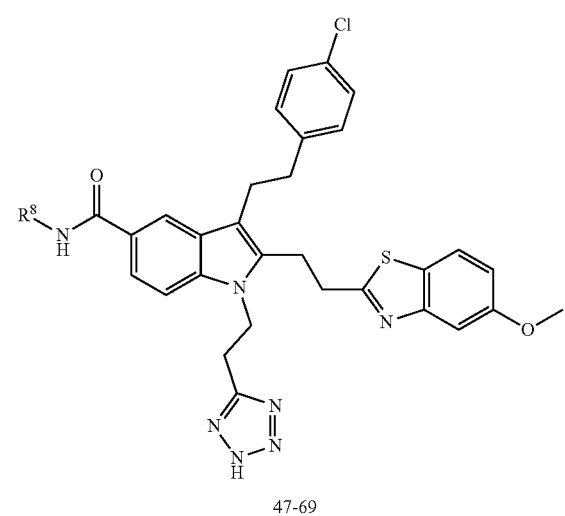

47-69

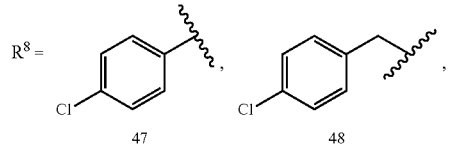

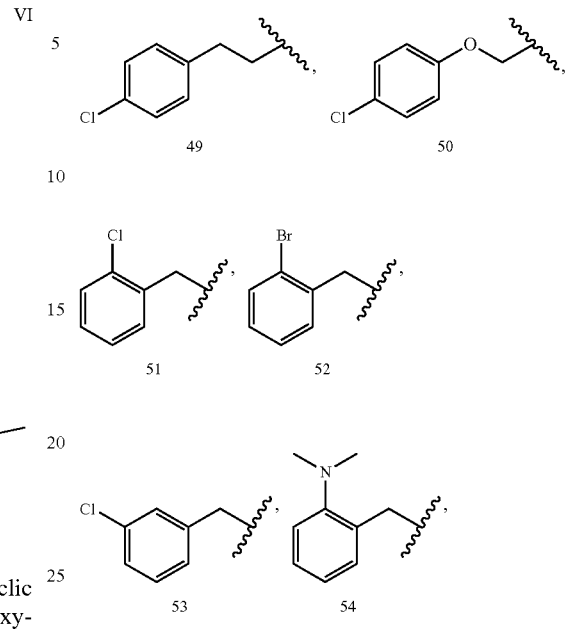

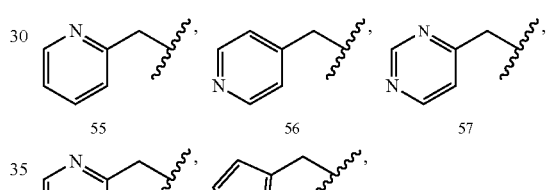

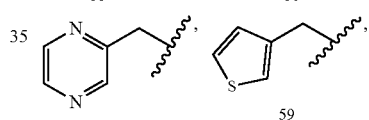

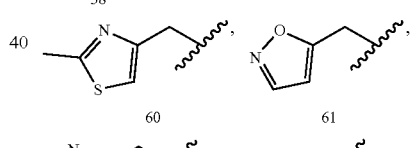

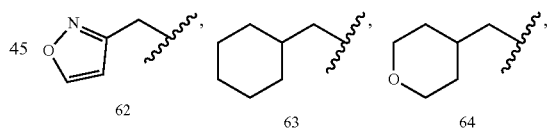

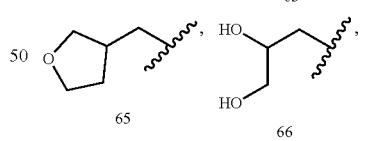

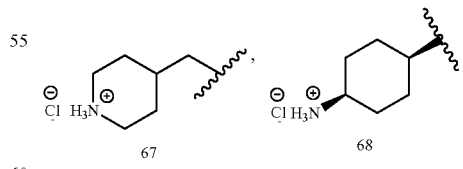

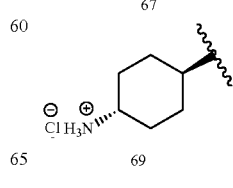

Still further examples are compounds having Formula VII-A or VII-B

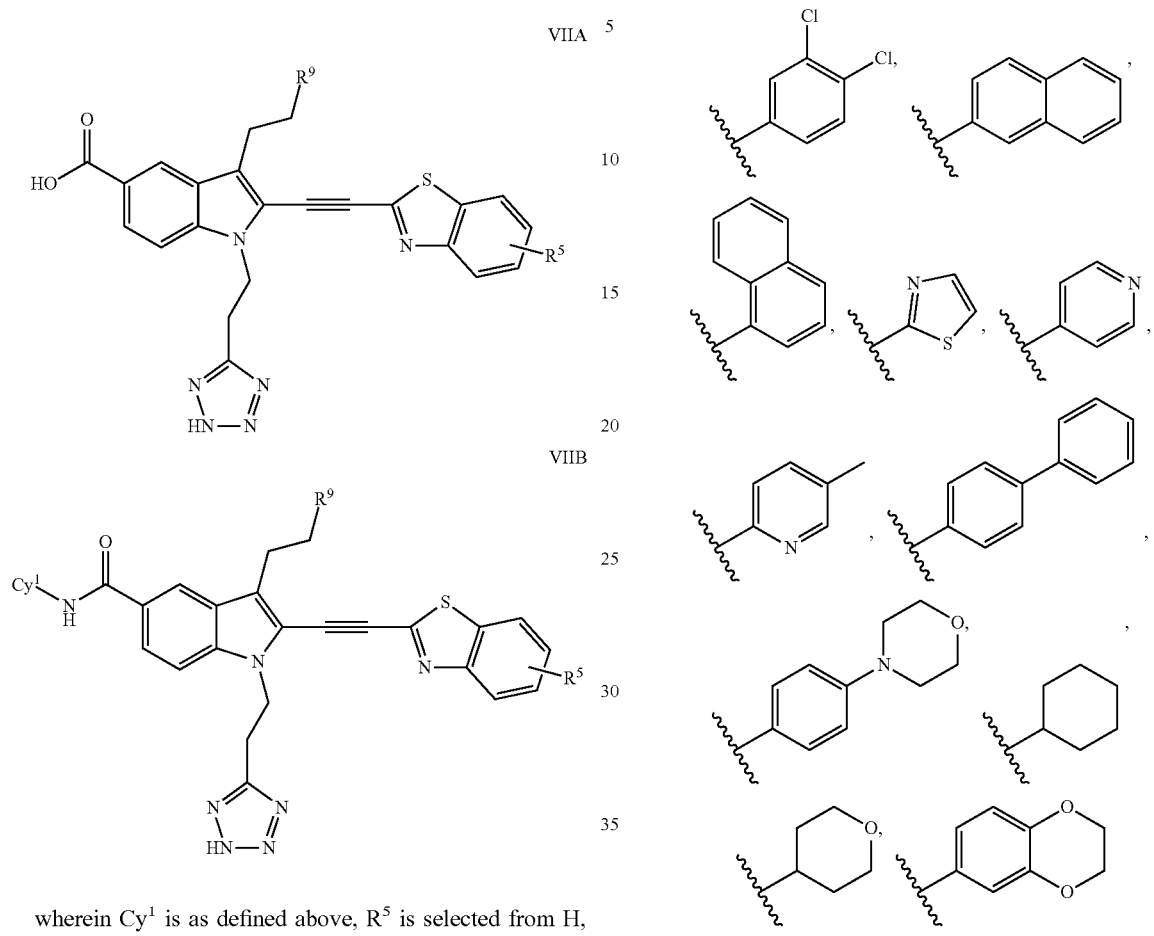

wherein Cy¹ is as defined above, R⁵ is selected from H, halo, amino, $C_{1-6}$ alkyl, $C_{1-6}$ alkoxyl, $C_{1-6}$ haloalkyl, $C_{1-6}$ haloalkoxyl, or $C_{1-6}$ heteroalkyl, and R⁹ is substituted or unsubstituted, mono or bicyclic aryl, heteroaryl, or cycloheteroalkyl. In specific examples, R⁵ is OMe. In other examples, R⁹ is aryl substituted with one or more of halogen, amino, $C_{1-6}$ alkyl, $C_{1-6}$ alkoxyl, $C_{1-6}$ haloalkyl, or $C_{1-6}$ haloalkoxyl. In further examples R⁹ is chosen from In specific examples, compounds of Formula VII-A can be

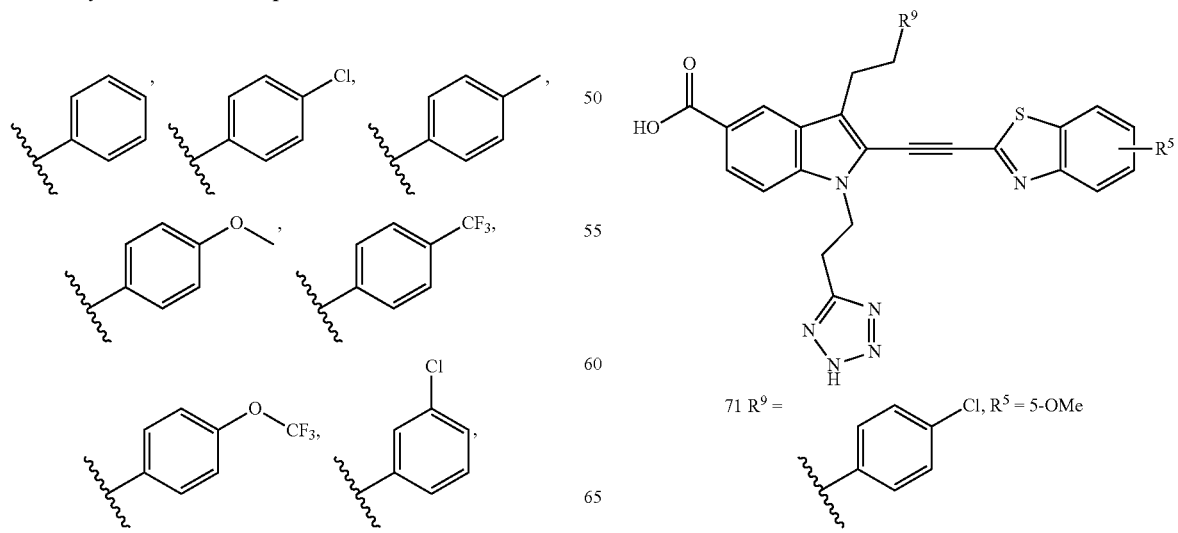

72 R⁹ = 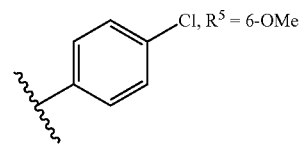, R⁵ = 6-OMe

73 R⁹ = 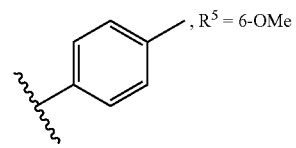, R⁵ = 6-OMe

74 R⁹ = 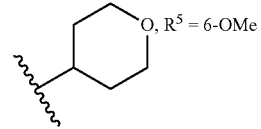, R⁵ = 6-OMe

75 R⁹ = 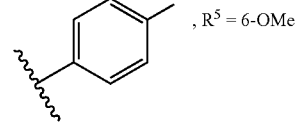, R⁵ = 6-OMe

Further exemplary compounds have Formula VIII

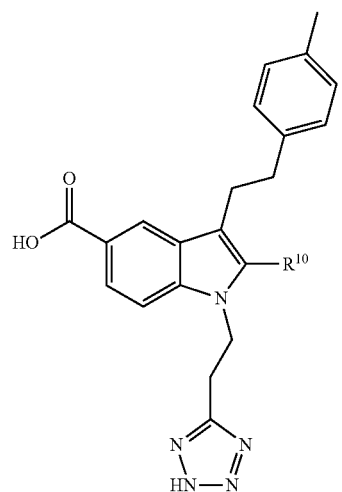

VIII wherein R¹⁰ is substituted or unsubstituted, mono or bicyclic heteroaryl. In specific examples, R¹⁰ can be pyridinyl, pyrimidinyl, pyrazinyl, pyrrolyl, isoxazolyl, isothiazolyl, oxazolyl, thiazolyl, pyranyl, pyrazolyl, furanyl, thiophenyl, benzothiophenyl, benzothiozolyl, any of which is optionally substituted with one or more halo, $C_{1-6}$ alkyl, $C_{1-6}$ haloalky, $C_{1-6}$ alkoxyl, $C_{1-6}$ haloalkoxyl, or amino. In specific examples, compounds of Formula VIII can be 77-84

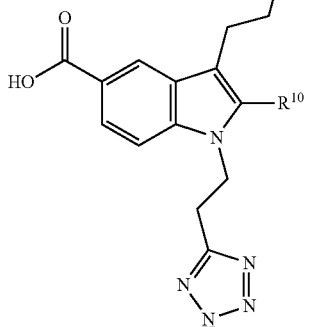

R¹⁰ = 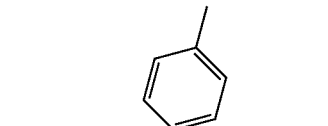

77, 78, 79

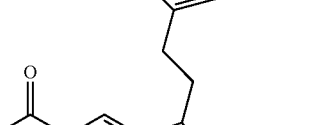

80, 81, 82

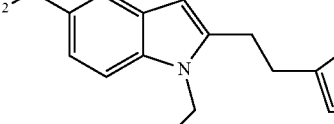

83, 84

Further exemplary compounds can have Formula IX

IX

wherein R¹² is NH₂, NHC₁₋₆ alkyl, NHOH, NHOC₁₋₆ alkyl, NHO-cycloalkyl, or NHO-cycloheteroalkyl. In specific examples, compounds of Formula IX can be

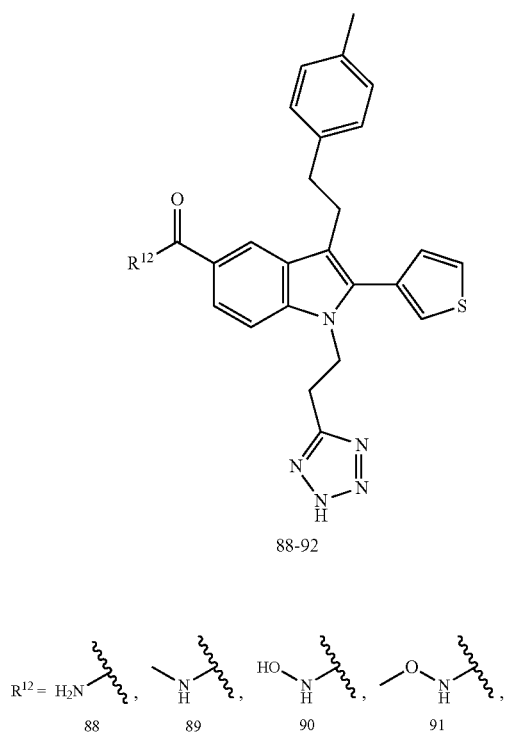

88-92

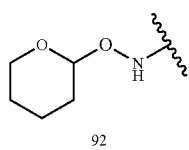

Further exemplary compounds can have Formula X

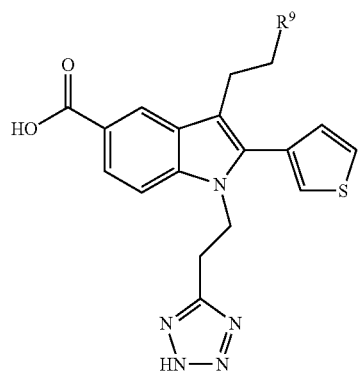

X wherein $R^9$ can be substituted or unsubstituted, mono or bicyclic aryl, heteroaryl, or cycloheteroalkyl. Specific examples of compounds of Formula X can be

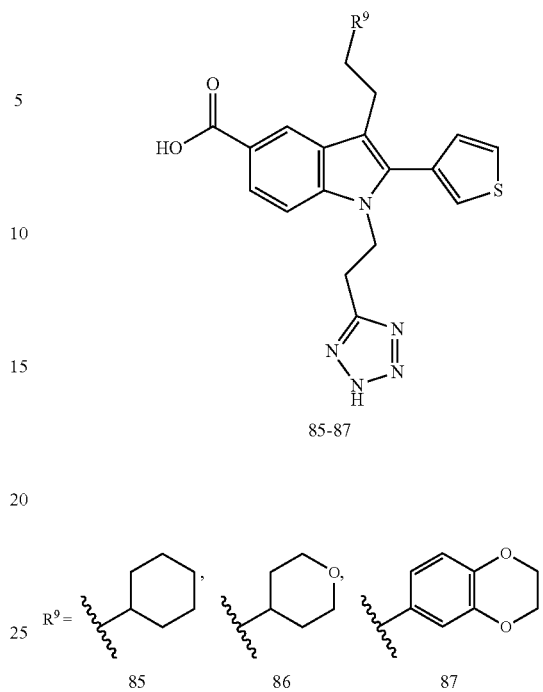

85-87

Further examples of compounds can have Formula XI

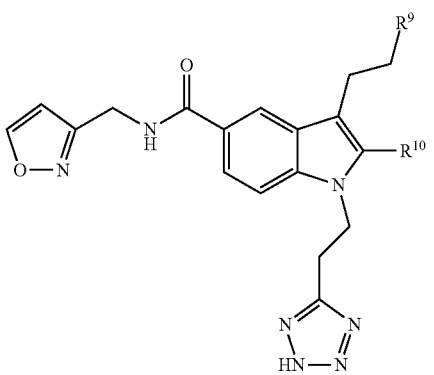

XI wherein $R^9$ can be substituted or unsubstituted, mono or bicyclic aryl, heteroaryl, or cycloheteroalkyl and $R^{10}$ can be substituted or unsubstituted, mono or bicyclic heteroaryl. In specific examples, $R^9$ is aryl substituted with one or more of halogen, amino, $C_{1-6}$ alkyl, $C_{1-6}$ alkoxyl, $C_{1-6}$ haloalkyl, or $C_{1-6}$ haloalkoxyl. In specific examples, $R^{10}$ can be pyridinyl, pyrimidinyl, pyrazinyl, pyrrolyl, isoxazolyl, isothiazolyl, oxazolyl, thiazolyl, pyranyl, pyrazolyl, furanyl, thiophenyl, benzothiophenyl, benzothiozolyl, any of which is optionally substituted with one or more halo, $C_{1-6}$ alkyl, $C_{1-6}$ haloalky, $C_{1-6}$ alkoxyl, $C_{1-6}$ haloalkoxyl, or amino. Specific examples of compounds of Formula XI are

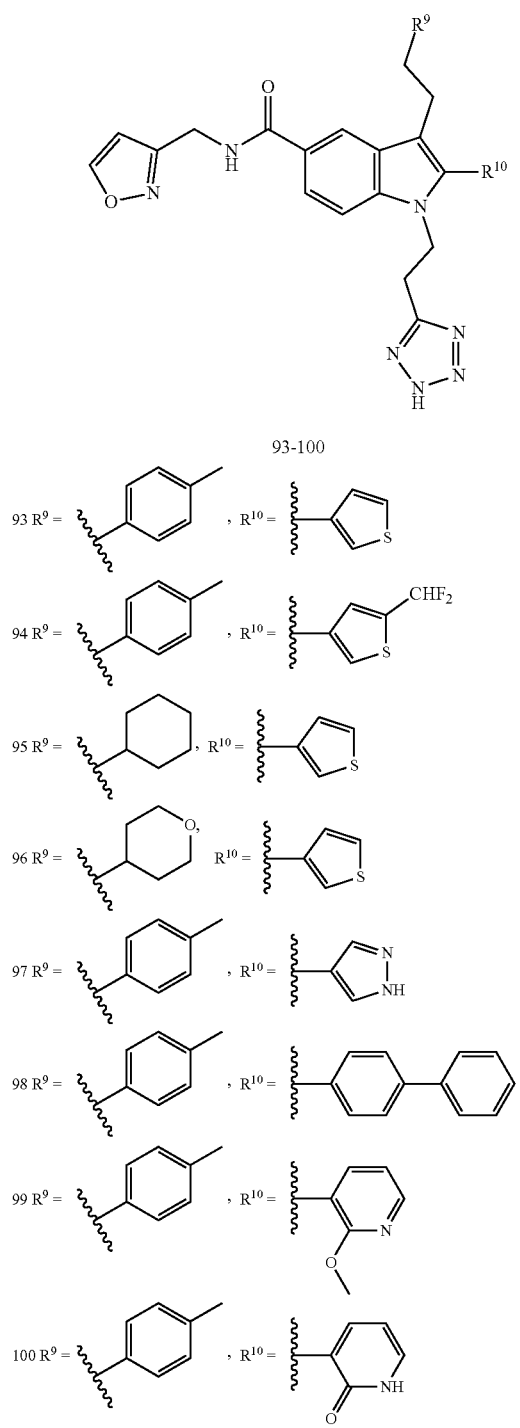

93-100

Also disclosed are pharmaceutical compositions comprising a therapeutically effective amount of a disclosed compound, or a pharmaceutically acceptable salt thereof, and a pharmaceutically acceptable carrier.

In some specific examples of the compounds disclosed herein $L^1$ is $C(O)OCH_2$ or $C(O)O$ and $Cy^1$ is H. In other specific examples, $L^1$ is $CH_2CH_2C(O)$. In other examples, $L^1$ is $CH_2NHC(O)$. In still other examples, $L^1$ is $NHC(O)$, $C(O)NH$, $C(O)NHCH_2$, $CH_2NHC(O)$, $C(O)NHO$, $ONHC(O)$, $C(O)NHOCH_2$, or $CH_2ONHC(O)$.

In some examples, $Cy^1$ is phenyl substituted with one or more (e.g., 1, 2, or 3) halo, $C_{1-6}$ alkyl, $C_{1-6}$ haloalky, $C_{1-6}$ alkoxyl, or amino. In other examples, $Cy^1$ is pyridinyl, pyrimidinyl, pyrazinyl, pyrrolyl, isoxazolyl, isothiazolyl, oxazolyl, thiazolyl, pyranyl, or furanyl, any of which is optionally substituted with one or more halo, $C_{1-6}$ alkyl, $C_{1-6}$ haloalky, $C_{1-6}$ alkoxyl, or amino. In other examples, $Cy^1$ is cyclopenyl, cyclohexyl, tetrahydropyranyl, or tetrahydrofuranyl, any of which is optionally substituted with one or more halo, $C_{1-6}$ alkyl, $C_{1-6}$ haloalky, $C_{1-6}$ alkoxyl, or amino.

In some examples, $L^2$ is $C_2H_4$.

In some examples, $Ar^2$ is phenyl substituted with one or more (e.g., 1, 2, or 3) halo, $C_{1-6}$ alkyl, $C_{1-6}$ haloalky, $C_{1-6}$ alkoxyl, $C_{1-6}$ haloalkoxyl, amino, phenyl, or morpholino. In some examples, $Ar^2$ is phenyl substituted with chloro, fluoro, or methyl. In some examples, $Ar^2$ is pyridinyl, pyrimidinyl, pyrazinyl, pyrrolyl, isoxazolyl, isothiazolyl, oxazolyl, thiazolyl, pyranyl, or furanyl, any of which is optionally substituted with one or more halo, $C_{1-6}$ alkyl, $C_{1-6}$ haloalky, $C_{1-6}$ alkoxyl, $C_{1-6}$ haloalkoxyl, or amino. In some examples, $Ar^2$ is naphthyl.

In some examples, $L^3$ is $C_2H_4$ or $C\equiv C$.

In some examples, $Ar^3$ is pyridinyl, pyrimidinyl, pyrazinyl, pyrrolyl, isoxazolyl, isothiazolyl, oxazolyl, thiazolyl, pyranyl, pyrazolyl, furanyl, thiophenyl, benzothiophenyl, benzothiozolyl, any of which is optionally substituted with one or more halo, $C_{1-6}$ alkyl, $C_{1-6}$ haloalky, $C_{1-6}$ alkoxyl, $C_{1-6}$ haloalkoxyl, or amino. In some examples, $Ar^3$ is naphthyl.

In some examples, $Ar^4$ is a tetrazole, $C(O)OH$, or $C(O)OMe$.

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is breast cancer, e.g., TNBC.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly [bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$ etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

The structure of compounds 1-100 are shown below.

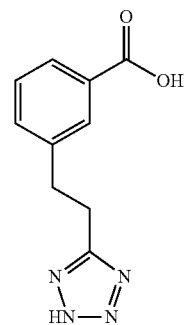

1

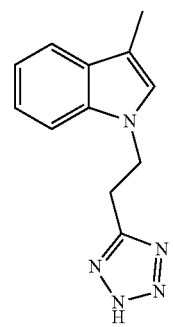

2

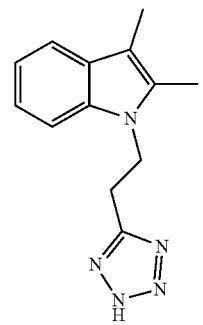

3

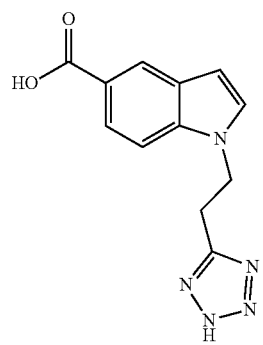

4

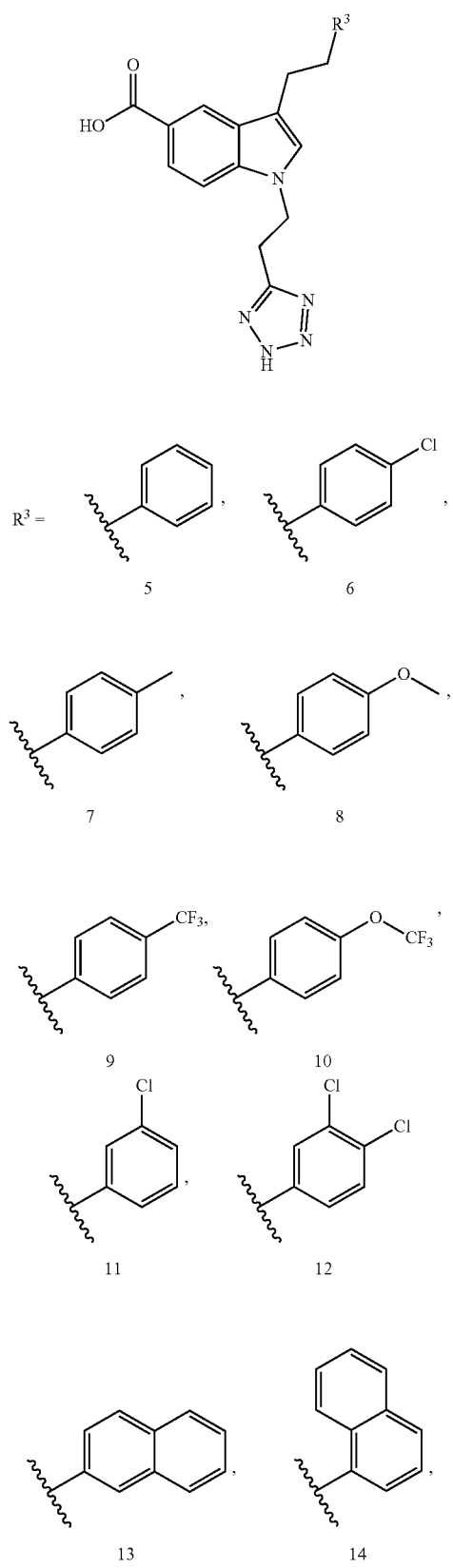
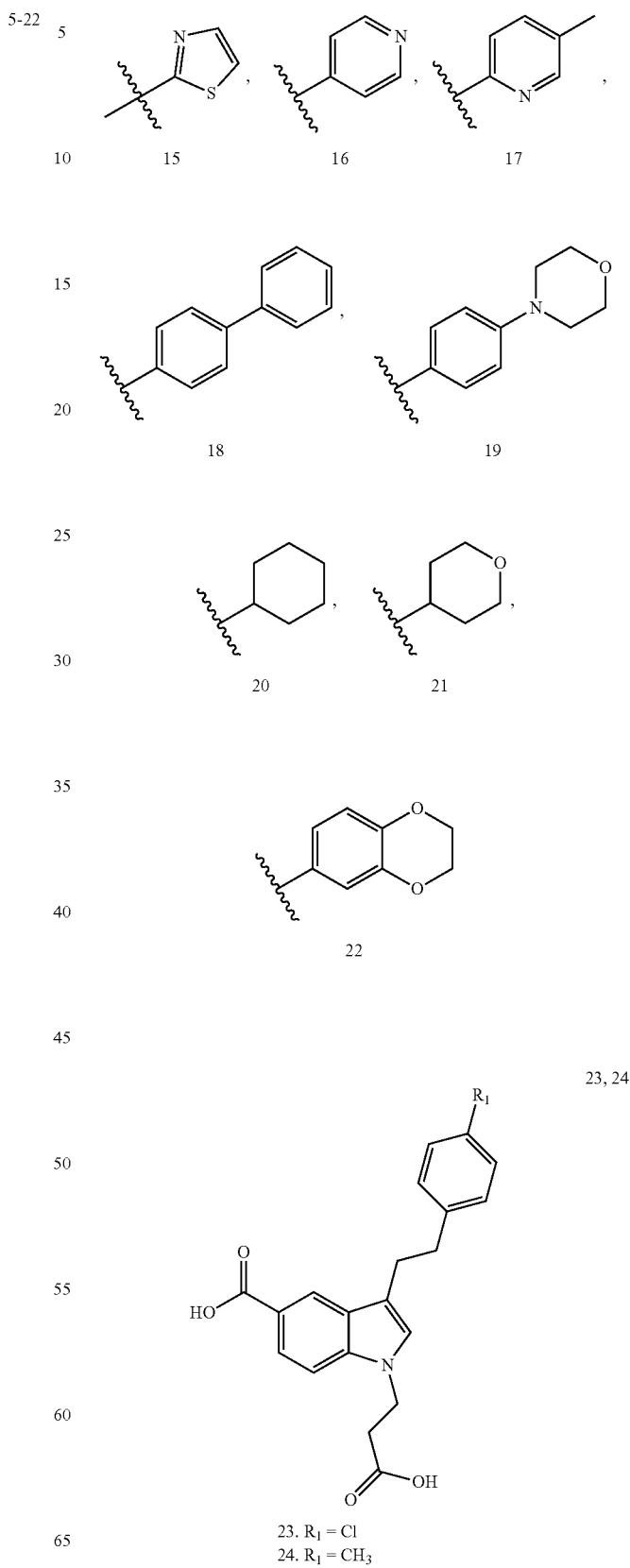

35
-continued
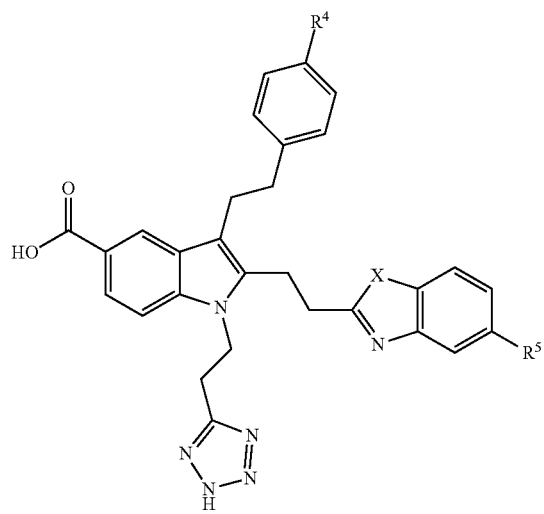
25-32
25. $R^4$ = H, $R^5$ = H, X = S
26. $R^4$ = F, $R^5$ = H, X = S
27. $R^4$ = Cl, $R^5$ = H, X = S
28. $R^4$ = CH$_3$, $R^5$ = H, X = S
29. $R^4$ = Cl, $R^5$ = H, X = NH
30. $R^4$ = Cl, $R^5$ = Cl, X = S
31. $R^4$ = Cl, $R^5$ = ⟅O—OMe⟆ , X = S
32. $R^4$ = Cl, $R^5$ = ⟅O—O—OMe⟆ , X = S
33. $R^5$ = Cl, $R^4$ = 6-OMe, X = S
34, 35
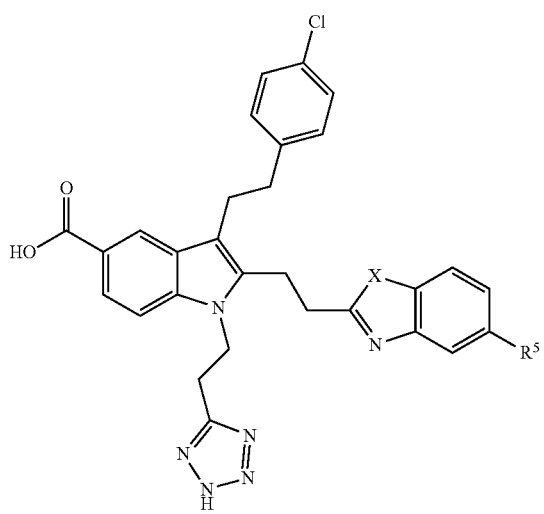
34. $R^5$ = H, X = NH
35. $R^5$ = OCH$_3$, X = S
36
-continued
36
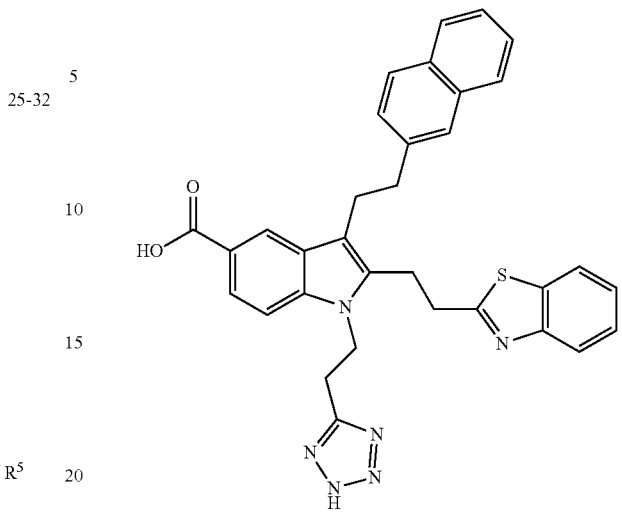
37-42
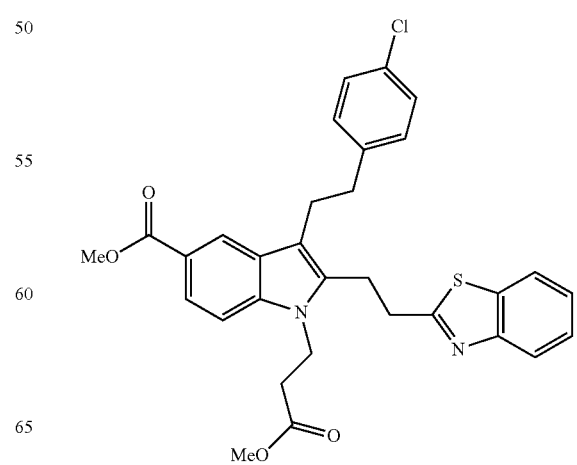
37. $R_6$ = H, X = S
38. $R_6$ = F, X = S
39. $R_6$ = Cl, X = S
40. $R_6$ = CH$_3$, X = S
41. $R_6$ = Cl, X = NH
42. $R_6$ = CH$_3$, X = NH
43

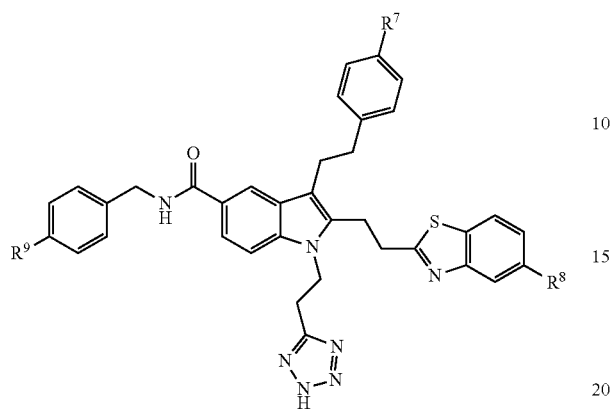
44. R⁷ = F, R⁸ = H, R⁹ = F
45. R⁷ = F, R⁸ = H, R⁹ = Cl
46. R⁷ = Cl, R⁸ = *~O~OMe, R⁹ = Cl
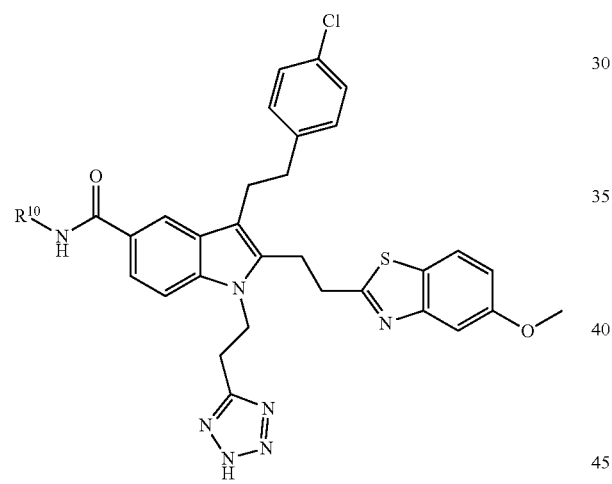
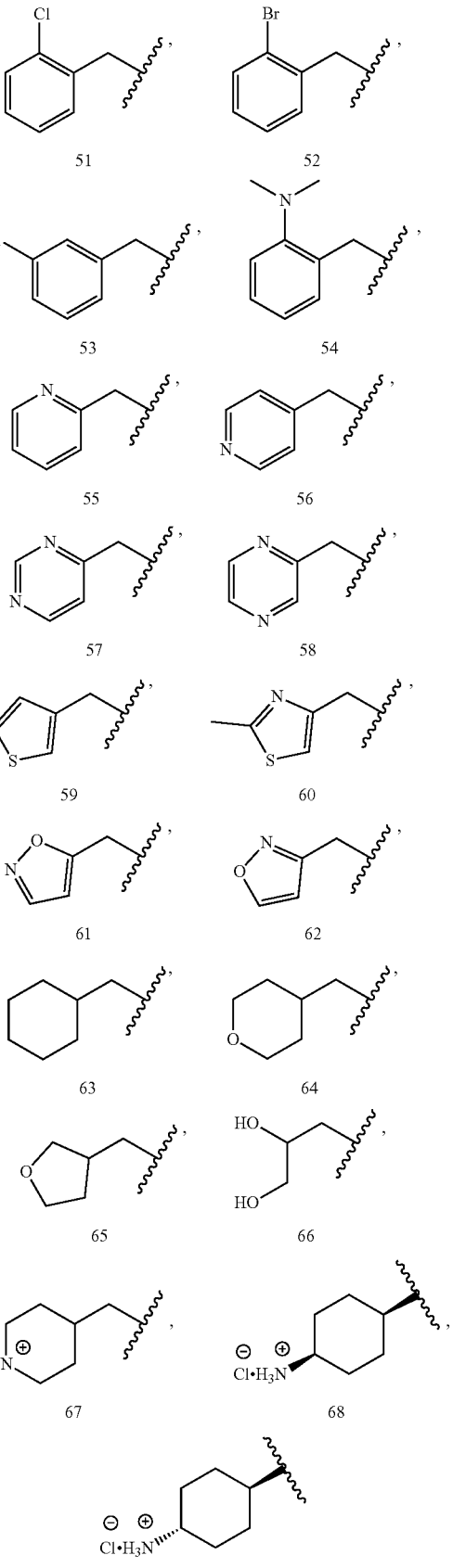

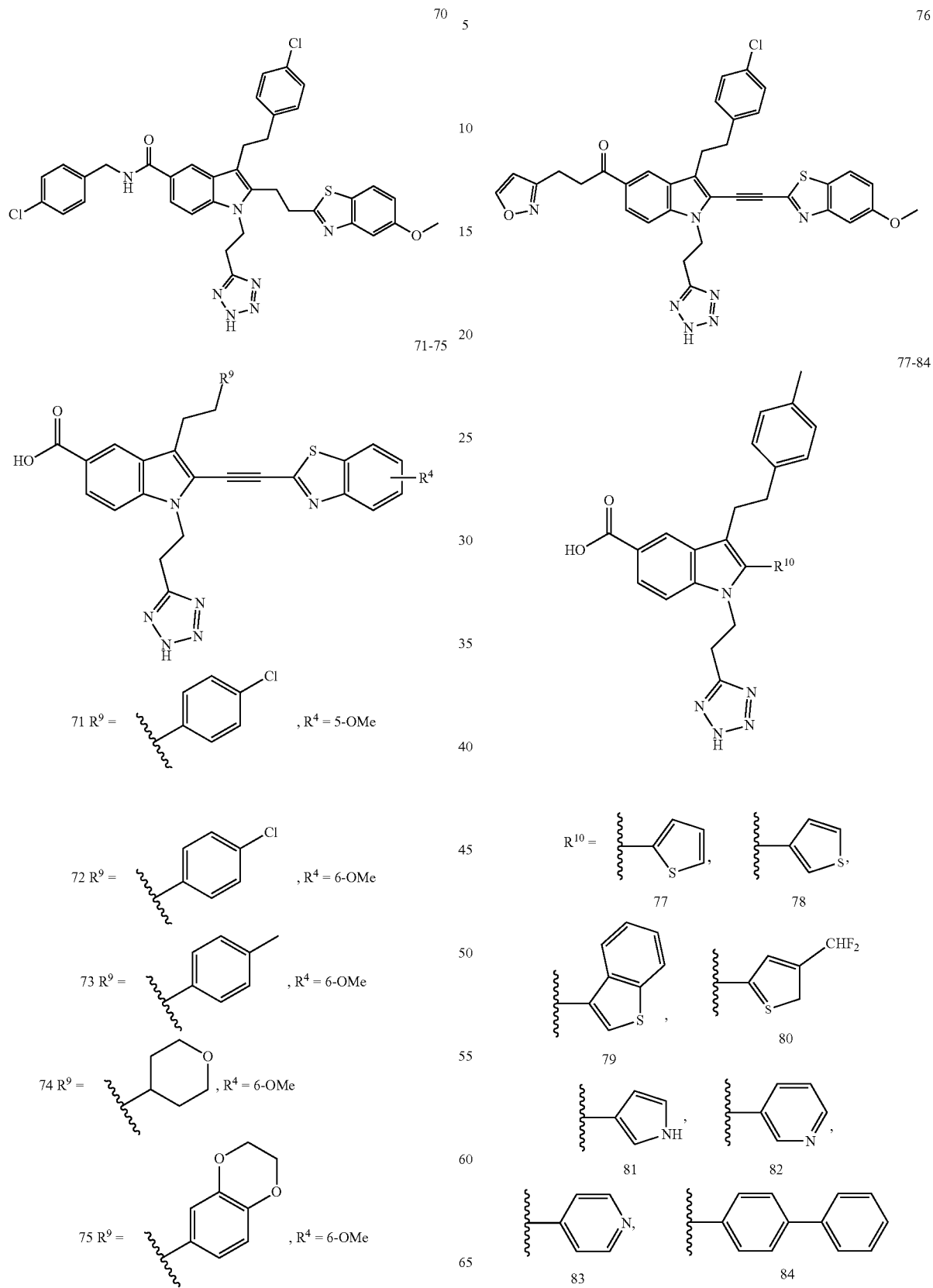

-continued
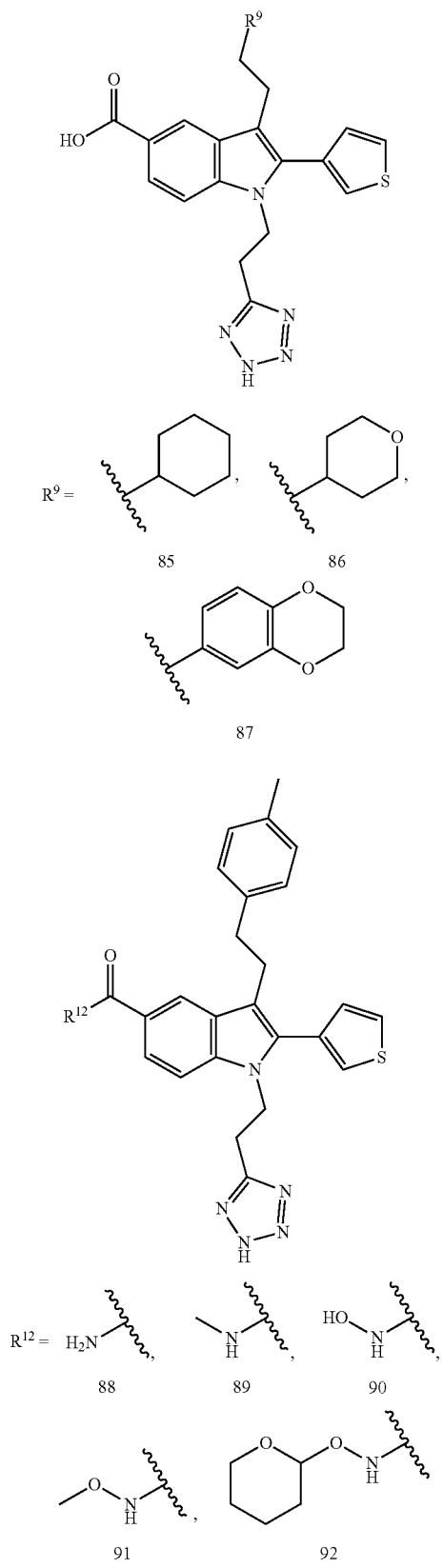
85-87
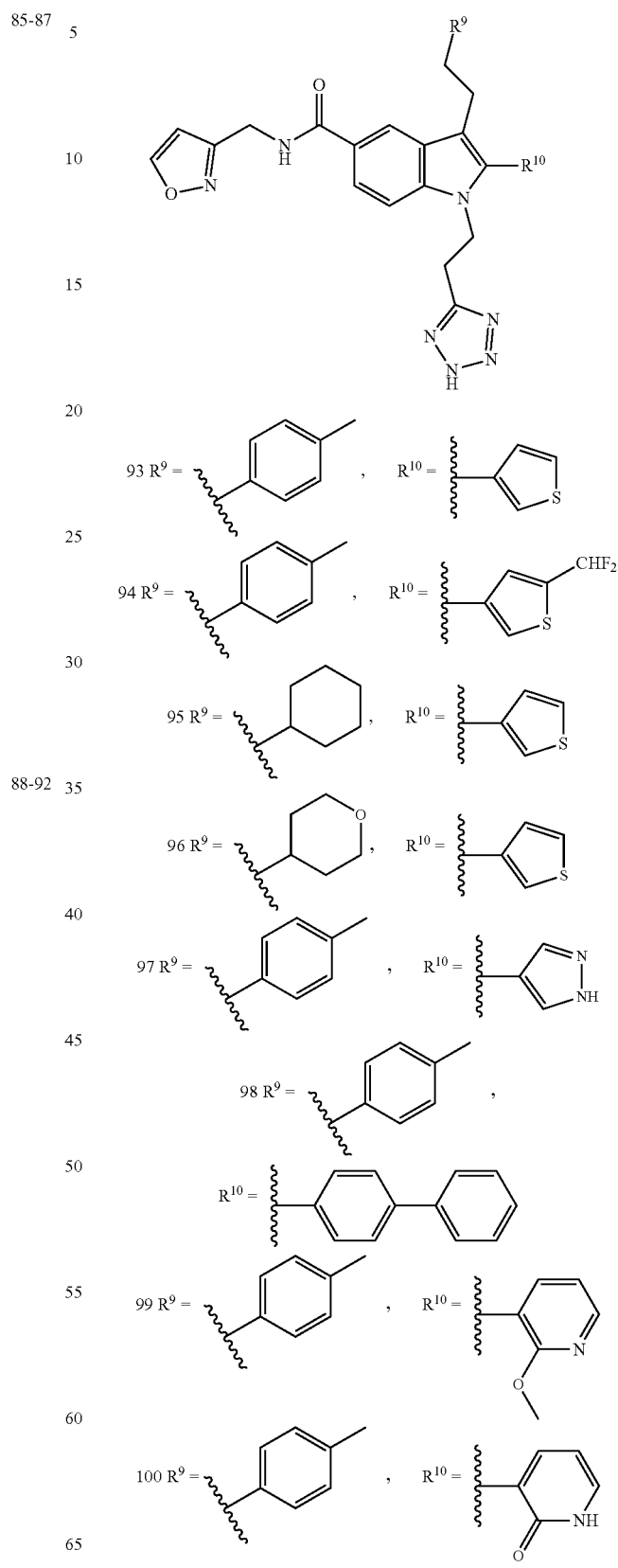
93-100

General Procedure A: Alkylation of 1H-Indole.

In a 50 mL oven-dried round bottom flask, 1H-indoles (1.71 mmol) was dissolved in 20 mL anhydrous DMF and cooled down to 0° C. NaH (0.10 g, 2.57 mmol) was added portionwise. The resulting heterogeneous mixture was stirred at 0° C. for 45 min 3-Bromopropanenitrile (0.21 mL, 2.57 mmol) was then added dropwise via syringe and the reaction mixture was allowed to warm up to room temperature. After 6 h, the reaction was quenched with 1M HCl, extracted two times with ethyl acetate and concentrated under vacuum. The crude product was purified via flash column chromatography to offer the desired product.

General Procedure B: The Wittig Reaction with Indole-3-Aldehydes.

To a solution of substituted bromides or iodides (6.0 mmol) in anhydrous tetrahydrofuran (30 mL) was added triphenylphosphine (1.73 g, 6.6 mmol) under argon. The resulting solution was heated to reflux for 12 h. The reaction was filtered, and the cake was washed with anhydrous tetrahydrofuran. The resultant product (1.2 eq) was suspended in anhydrous tetrahydrofuran (5 mL/g) at 40° C. Then, n-BuLi (1.6 M THF solution, 1.2 eq) was added to the above solution dropwise. The resulting solution was allowed to warm to room temperature naturally. A solution of substituted indole-3-aldehydes (1.0 eq) in anhydrous tetrahydrofuran (20 mL/g) was added dropwise to the above solution. Then, the reaction mixture was stirred for additional 3 h. The reaction was quenched with $NH_4Cl$ aqueous solution and extracted with EtOAc. The organic layer was washed with water and brine, dried with $Na_2SO_4$, and concentrated under vacuum. The crude product was purified via flash chromatography.

General Procedure C: The Sonogashira Reaction with Substituted Iodoindoles.

To a solution of halo indoles (1.0 eq) in $DMF/Et_3N$ (1:1, 15 mL/mmol) was added $Pd(PPh_3)_4$ (0.1 eq) and CuI (0.15 eq). The flask was evacuated and flushed three times with argon. The resulting mixture was heated to 60° C. for 0.5 h. A solution of the corresponding alkynes (1.5 eq) in DMF was added dropwise to the above mixture. The resultant mixture was stirred at 60° C. for 1 h. Upon cooling to room temperature, the volatile was removed under vacuum. The crude product was purified with column chromatography.

General Procedure D: Hydrogenation of Alkenes/Alkynes to Alkanes.

To a solution of alkenes or alkyne in MeOH/THF (1:1, 50 mL/g) was added 10% Pd/C (10% mass equivalent) under Ar. After evacuating and flushing the flask with hydrogen gas three times, the reaction mixture was stirred under hydrogen atmosphere for 12 h. After the starting material was consumed, Pd/C was removed via filtration. The filtrate was concentrated under vacuum. The desired product was isolated via flash chromatography.

General Procedure E: 2-Iodionation of Indoles.

In a 25 mL round bottom flask, substituted indoles (0.43 mmol) and AgOTf (133.5 mg, 0.52 mmol) were dissolved in 10 mL $CH_2Cl_2$. A solution of 12 (106.5 mg, 0.42 mmol) in 5 mL THF was added dropwise through the additional funnel. The reaction was finished within 30 min and quenched with 10% aqueous $Na_2S_2O_3$ solution. The crude product was extracted 2 times with ethyl acetate, concentrated under vacuum and purified via flash column chromatography.

General Procedure F: The 1,3-Dipolar Reaction to Synthesize Tetrazoles.

To a solution of organic cyanides (0.6 mmol) in toluene (21 mL) was added $SnN_3(n-Bu)_3$ (0.85 mL, 3.0 mmol). The mixture was heated to reflux for 48 h. Upon completion, the reaction was cooled down to room temperature and acetic acid (3.0 mL) was added. The resulting mixture was allowed to stir for another 12 h at room temperature. Then, the mixture was evaporated to dryness. The desired product was purified via flash chromatography.

General Procedure G: Hydrolysis of Substituted 1H-Indole-5-Carboxylic Acid Methyl Esters Using NaOH.

To a solution of substituted 1H-indole-5-carboxylic acid methyl esters (0.23 mmol) in i-PrOH (15 mL) was added NaOH (3 mL, 3 M aqueous solution). The resulting mixture was refluxed for 12 h. Upon completion, the reaction was cooled down to room temperature and evaporated to dryness. The residue was dissolved in water and extracted with EtOAc (3 times). Then, the aqueous layer was acidified with 3 M HCl until pH<4 and stirred for additional 3 h. A white precipitate appeared and was filtered, and the filter cake was wash with water and dried with lyophilization.

General Procedure H: Amidation of Substituted 1H-Indole-5-Carboxylic Acids.

To a solution of substituted 1H-indole-5-carboxylic acids (1.0 eq), substituted amines (2.0 eq), EDCI (2.0 eq), HOAt (2.0 eq) in anhydrous DMF (18.0 mL/mmol) was added trimethylamine (0.11 mL, 0.4 mmol) under Ar. The resulting mixture was stirred at 70° C. for 12 h. Upon completion, the mixture was partitioned between EtOAc and water. The organic layer was evaporated to dryness. The desired product was purified via flash chromatography.

General Procedure I: The Suzuki Reaction with Substituted 2-Iodoindoles Using $Pd(Dppf)_2Cl_2$ as the Catalyst.

To a solution of substituted 2-iodo-indoles (1.0 eq), boronic acid (0.77 g, 1.5 eq) and CsF (1.82 g, 3.0 eq) in 1,4-dioxane/water (33 mL, v/v=10/1) was added Pd(dppf)$_2Cl_2$ (0.29 g, 0.1 eq). The mixture was evacuated and flashed three times with argon, and then heated at 86° C. overnight. After cooling, the solvent was evaporated under reduced pressure. The residue was dissolved in $CH_2Cl_2$ and filtered. The filtrate was concentrated. Purification by column chromatography through silica gel afforded the product.

General Procedure J: hydrolysis of substituted 1H-indole-5-carboxylic acid methyl esters using LiOH.

To a solution of substituted 1H-indole-5-carboxylic acid methyl esters (0.82 g) in 30 mL THF/MeOH (v/v=2/1) was added aqueous LiOH (1.0 M, 17 mL). The mixture was stirred for 3 h at 70° C. Upon completion, the reaction was evaporated to dryness under vacuum, and the residue was dissolved in water. The aqueous layer was washed with EtOAc for 5 times. To the aqueous layer was added dropwise 1.0 M HCl until pH<4. Then, the mixture was filtered, and the filter cake was washed with water for several times and dried by lyophilization to provide the desirable product.

General Procedure K: The Suzuki Reaction with Substituted 2-Iodoindoles Using Pd(PPh3)4 as the Catalyst.

To a solution of substituted 2-iodo-indoles (1.0 eq), corresponding boronic acid or boronic acid pinacol ester (1.2 eq) and $K_3PO_4$ (2.0 eq) in 1,4-dioxane/water (33 mL/mmol, v/v=10/1) was added $Pd(PPh_3)_4$ (0.1 eq). The mixture was evacuated and flashed three times with argon, then heated at 89° C. overnight. After cooling, the solvent was evaporated under reduced pressure. The residue was dissolved in $CH_2Cl_2$ and filtered. The filtrate was concentrated. Purification by column chromatography through silica gel afforded the desired product.

Scheme 1.

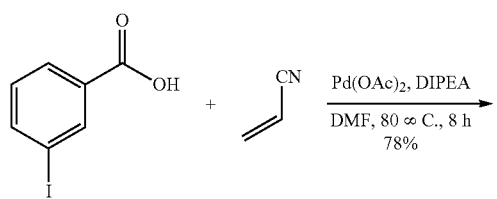
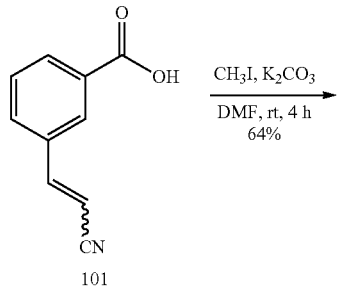
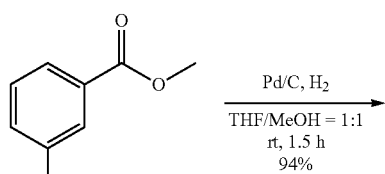
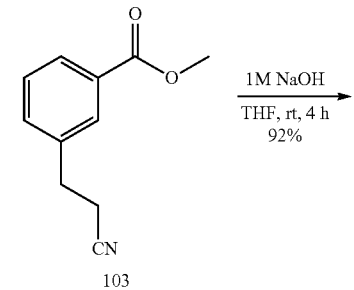
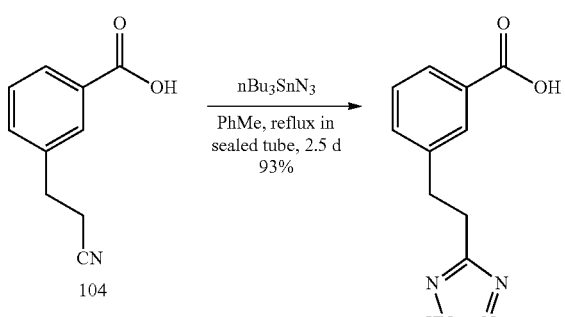

(E/Z) 3-(2-cyanovinyl)benzoic acid (101). To a round-bottom flask were added 4-iodobenzoic acid (2.0 g, 8.06 mmol), Pd(OAc)$_2$ (90 mg, 0.403 mmol) and DMF (40 mL). The mixture was stirred at room temperature and flushed with argon and evacuated 3 times. DIPEA (1.92 mL) and acrylonitrile (1.33 mL, 20.16 mmol) were then added. The reaction mixture was heated up to 80° C. for at least 12 h. Upon completion, the reaction mixture was cooled down and acidified. EtOAc was then added. The organic layer was washed with water and brine. The organic layer was concentrated under vacuum. The residue was purified by flash column chromatography to offer to offer the E/Z alkene as yellow solid (hexanes:ethyl acetate=1:1, 1.09 g, 78% yield).

(E/Z) methyl 3-(2-cyanovinyl)benzoate (102). (E/Z)-4-(2-cyanovinyl)benzoic acid (0.9 g, 5.2 mmol) and K$_2$CO$_3$ (1.8 g, 12.9 mmol) were added to acetone (25 mL) at 0° C. Methyl iodide (0.97 mL, 15.6 mmol) was then added, and the reaction mixture was stirred for 2 h at room temperature. Upon completion, the solvent was removed, and the residue was partitioned between EtOAc and water. The organic layers were collected and concentrated under vacuum. The residue was purified by flash column chromatography to offer the desired product as yellow oil (hexanes:ethyl acetate=4:1, 0.555 g, 64% yield). $^1$H NMR (300 MHz, Chloroform-d) δ 8.27 (d, J=1.9 Hz, 1H), 8.14-8.02 (m, 9H), 7.65-7.57 (m, 4H), 7.56-7.35 (m, 9H), 5.96 (dd, J=16.7, 0.7 Hz, 4H), 5.56-5.46 (m, 1H), 3.91 (t, J=0.6 Hz, 15H). $^{13}$C NMR (75 MHz, Chloroform-d) δ 166.01, 149.30, 147.55, 133.70, 132.14, 131.81, 131.62, 131.42, 131.04, 130.63, 129.22, 129.09, 128.18, 117.68, 97.74, 96.52, 52.38.

methyl 3-(2-cyanoethyl)benzoate (103). The synthesis of 103 followed general procedure D to obtain the desired product as colorless oil (hexanes:ethyl acetate=4:1, 94% yield). $^1$H NMR (CDCl$_3$, 500 MHz): δ 7.99-7.83 (m, 1H), 7.44-7.31 (m, 2H), 3.87 (s, 1H), 2.96 (t, J=7.2 Hz, 2H), 2.62 (t, J=7.2 Hz, 2H). $^{13}$C NMR (CDCl$_3$, 75 MHz): δ 167.0, 138.6, 133.2, 130.9, 129.6, 129.2, 128.7, 119.1, 52.5, 31.5, 19.4. LRMS (ESI) [M+H]$^+$ m/z=190.1.

3-(2-cyanoethyl)benzoic acid (104). Methyl 4-(2-cyanoethyl)benzoate (1.164 g, 6.155 mmol) was dissolved in a solution of 50 mL THF and 1.0 M NaOH aqueous solution (v/v=1/1). The starting material was consumed within 4 h. The reaction mixture was then acidified in ice bath to pH=2, and extracted 2 times with EtOAc. White solid was obtained after the removal of organic solvent in vacuo (0.992 g, 92% yield). $^1$H NMR (300 MHz, Methanol-d$_4$) δ 7.99-7.90 (m, 2H), 7.58-7.52 (m, 1H), 7.45 (dd, J=8.6, 6.6 Hz, 1H), 3.02 (t, J=7.2 Hz, 2H), 2.78 (td, J=7.2, 0.7 Hz, 2H).

3-(2-(2H-tetrazol-5-yl)ethyl)benzoic acid (1). The synthesis of 103 followed general procedure F to obtain the desired product as white solid (93% yield). R$_f$=0.2 (CH$_2$Cl$_2$:MeOH=20:1). $^1$H NMR (DMSO-d$_6$, 300 MHz): δ 7.75-7.72 (m, 2H), 7.43 (d, J=6.9 Hz, 1H), 7.36 (t, J=6.9 Hz, 1H), 3.23 (t, J=7.8 Hz, 2H), 3.08 (t, J=7.2 Hz, 2H). $^{13}$C NMR (DMSO-d$_6$, 75 MHz): δ 168.0, 155.9, 141.1, 133.6, 131.6, 129.8, 129.3, 128.0, 33.1, 25.1. LRMS (ESI) [M+H]$^+$ m/z=219.1.

Scheme 2.

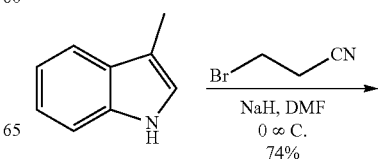

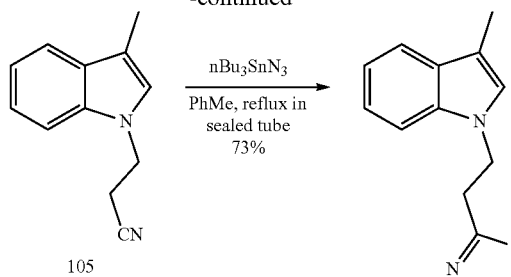

3-(3-methyl-1H-indol-1-yl)propanenitrile (105). The synthesis of 105 followed general procedure A to obtain the desired product as white solid (74% yield). (hexanes:ethyl acetate=4:1, 74% yield). $^1$H NMR (300 MHz, Chloroform-d) δ 7.72 (dp, J=7.7, 1.2 Hz, 1H), 7.41-7.25 (m, 3H), 6.95 (d, J=1.2 Hz, 1H), 4.31 (t, J=6.7 Hz, 2H), 2.70 (t, J=6.7 Hz, 2H), 2.45 (q, J=1.1 Hz, 3H). $^{13}$C NMR (75 MHz, Chloroform-d) δ 135.50, 129.05, 124.83, 121.89, 119.28, 119.22, 117.47, 111.60, 108.44, 41.46, 18.81, 9.43.

1-(2-(2H-tetrazol-5-yl)ethyl)-3-methyl-1H-indole (2). The synthesis of 2 followed general procedure F to obtain the desired product as yellow solid (73% yield). $^1$H NMR (300 MHz, DMSO-d$_6$) δ 7.46 (dt, J=7.8, 1.0 Hz, 1H), 7.38 (d, J=8.1 Hz, 1H), 7.11 (ddd, J=8.2, 7.0, 1.3 Hz, 1H), 7.04 (d, J=1.3 Hz, 1H), 7.03-6.97 (m, 1H), 4.54 (t, J=7.0 Hz, 2H), 3.35 (t, J=7.0 Hz, 2H). $^{13}$C NMR (75 MHz, DMSO-d$_6$) δ 153.93, 135.76, 128.33, 125.82, 121.22, 118.64, 118.47, 109.32, 43.17, 24.50, 9.45.

Scheme 3.

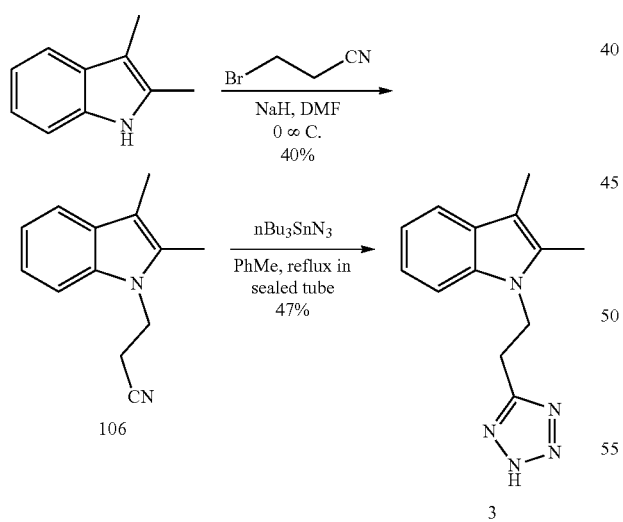

3-(2,3-dimethyl-1H-indol-1-yl)propanenitrile (106). The synthesis of 106 followed general procedure A to obtain the desired product as red solid (hexanes:ethyl acetate=4:1, 40% yield). $^1$H NMR (300 MHz, Chloroform-d) δ 7.64-7.51 (m, 1H), 7.35-7.13 (m, 3H), 4.31 (t, J=6.9 Hz, 2H), 2.65 (t, J=6.9 Hz, 2H), 2.43 (s, 3H), 2.33 (s, 3H). $^{13}$C NMR (75 MHz, Chloroform-d) δ 135.05, 131.43, 128.98, 121.06, 119.36, 118.31, 117.41, 107.89, 107.78, 38.60, 18.26, 9.89, 8.72.

1-(2-(2H-tetrazol-5-yl)ethyl)-2,3-dimethyl-1H-indole (3). The synthesis of 3 followed general procedure F to obtain the desired product as white solid (47% yield). $^1$H NMR (300 MHz, DMSO-d$_6$) δ 7.42-7.36 (m, 1H), 7.29 (d, J=7.9 Hz, 1H), 7.10-6.92 (m, 2H), 4.49 (t, J=7.2 Hz, 2H), 3.26 (t, J=7.2 Hz, 2H), 2.23 (s, 3H), 2.16 (s, 3H). $^{13}$C NMR (75 MHz, DMSO-d$_6$) δ 153.78, 135.32, 132.19, 128.30, 120.43, 118.58, 117.69, 108.69, 105.83, 40.80, 24.10, 9.57, 8.72.

Scheme 4.

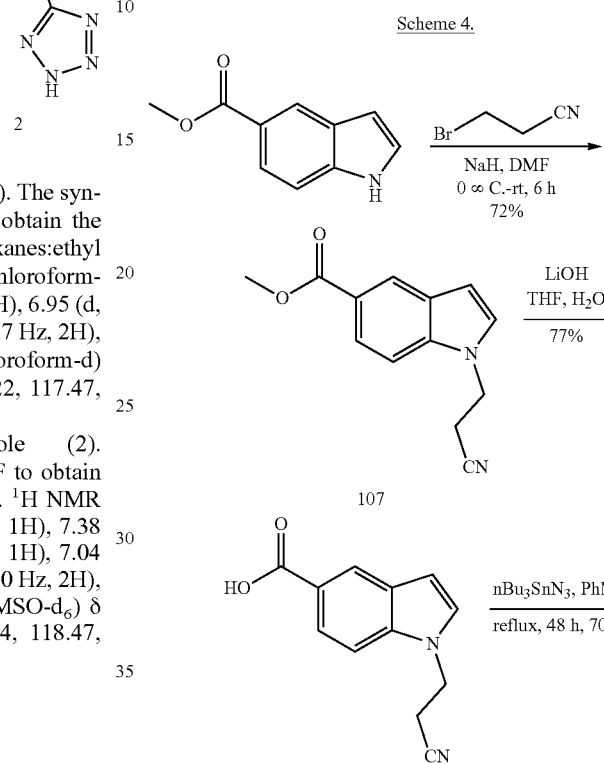

Methyl 1-(2-cyanoethyl)-1H-indole-5-carboxylate (107). The synthesis of 106 followed general procedure A to obtain the desired product as pale yellow solid (hexanes:ethyl acetate=3:1 to 2:1, 72% yield). $^1$H-NMR (CDCl$_3$, 300 MHz) δ 8.39 (s, 1H), 7.93 (dd, J=1.5, 8.7 Hz, 1H), 7.30 (d, J=8.7 Hz, 1H), 7.20 (d, J=3.3 Hz, 1H), 6.63 (d, J=3.3 Hz, 1H), 4.42 (t, J=6.6 Hz, 2H), 3.92 (s, 3H), 2.80 (t, J=6.6 Hz, 2H). $^{13}$C-NMR (CDCl$_3$, 75 MHz) δ 168.15, 138.07, 129.08, 128.66, 124.53, 123.78, 122.48, 117.33, 108.62, 104.55, 52.19, 42.41, 19.43. MS (ESI) m/z=229.2 [M+H]$^+$.

1-(2-cyanoethyl)-1H-indole-5-carboxylic acid (108). Compound 107 (1.405 g, 6.155 mmol) was dissolved in a solution of 50 mL THF and 1.0 M NaOH aqueous solution (v/v=1/1). The starting material will be consumed within 4 h. The mixture will be acidified in ice bath to pH=2, and extracted 2 times with EtOAc. After the organic solvent was removed, the desired product (DCM:MeOH=15:1, 77% yield) was obtained as white solid.

1-(2-(2H-tetrazol-5-yl)ethyl)-1H-indole-5-carboxylic acid (4). The synthesis of 4 followed general procedure F to obtain the desired product as pale yellow solid (DCM:MeOH=15:1, 70% yield). $^1$H NMR (300 MHz, Methanol-$d_4$) δ 8.29 (d, J=1.7 Hz, 1H), 7.84 (dd, J=8.7, 1.7 Hz, 1H), 7.41 (dd, J=8.7, 0.8 Hz, 1H), 7.17 (d, J=3.3 Hz, 1H), 6.54 (d, J=3.2 Hz, 1H), 4.69 (t, J=6.8 Hz, 2H), 3.46 (t, J=6.8 Hz, 2H). $^{13}$C NMR (75 MHz, DMSO-$d_6$) δ 168.30, 153.84, 137.86, 130.15, 127.70, 123.19, 122.43, 121.78, 109.45, 102.64, 43.67, 24.47.

Scheme 5.

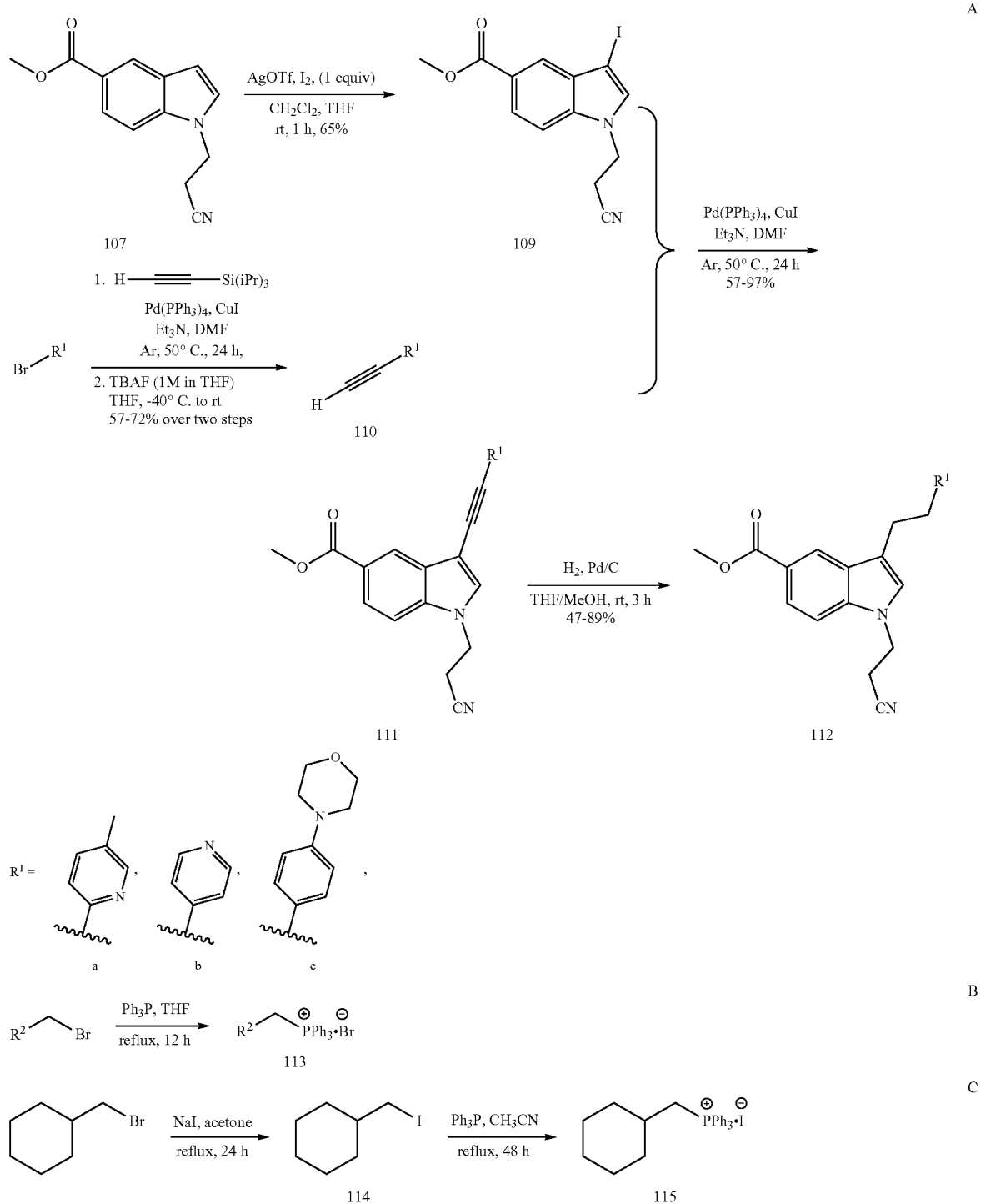

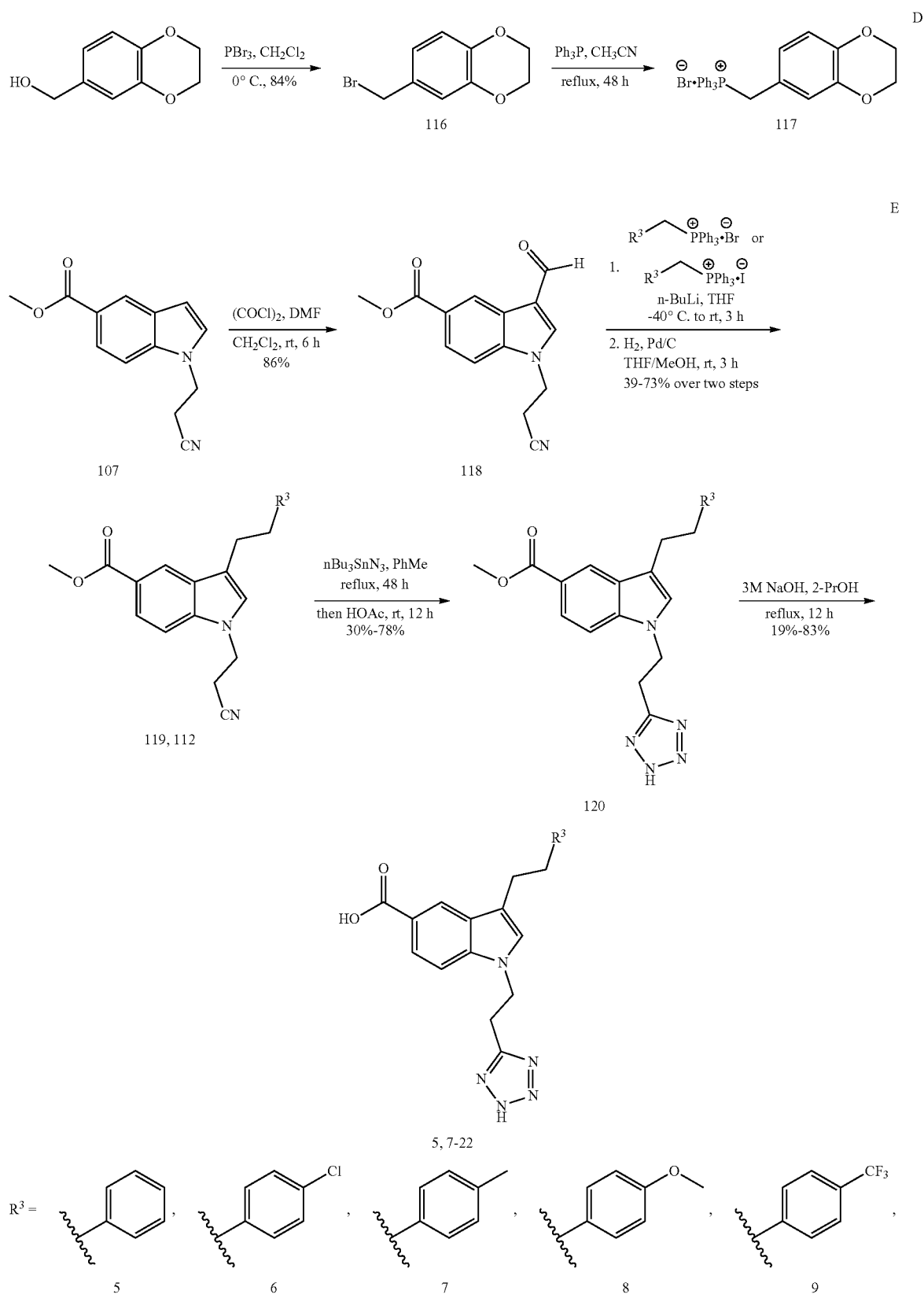

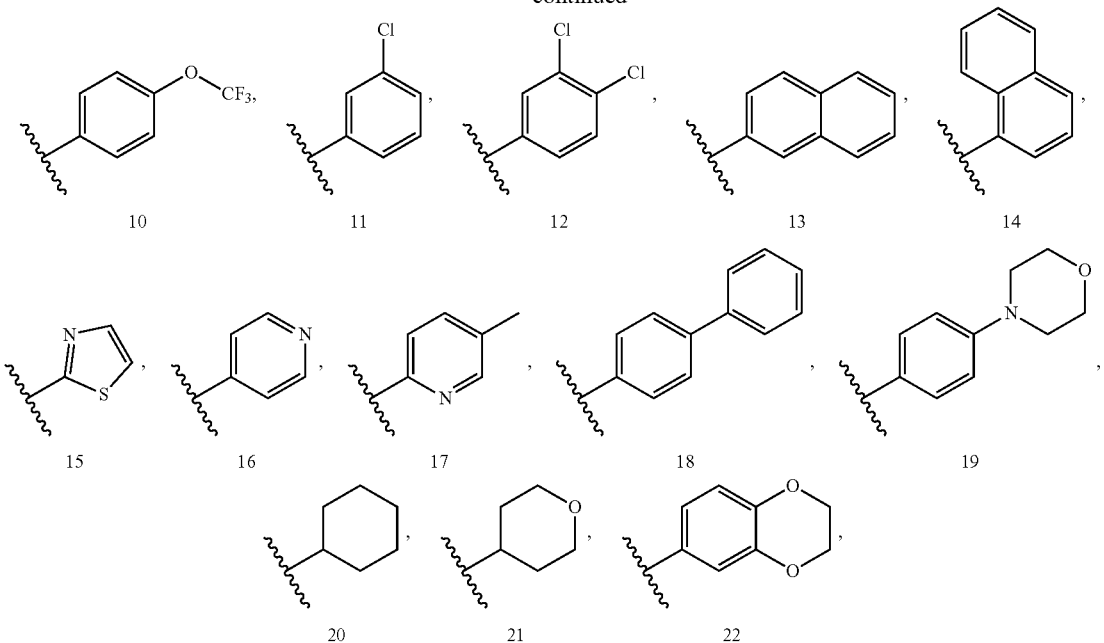

methyl 1-(2-cyanoethyl)-3-iodo-1H-indole-5-carboxylate (109). To a solution of methyl 1-(2-cyanoethyl)-1H-indole-5-carboxylate (2.0 g, 8.7 mmol) and AgOTf (2.5 g, 9.6 mmol) in dry $CH_2Cl_2$ (40 mL) at 0° C. was added dropwise a solution of 12 (2.21 g, 8.7 mmol) in dry THF. The reaction was allowed to warm to room temperature and stirred for additional 1 h. The reaction was quenched with saturated $Na_2S_2O_3$ aqueous solution, filtered through a Celite plug, and extracted with $CH_2Cl_2$. The organic layer was concentrated under reduced pressure. The desired product (white solid, 2.0 g, 65% yield) was recrystallization in EtOAc.

Substituted alkynes (110). To a solution of substituted aryl bromines (20 mmol), $Pd(PPh_3)_4$ (2.31 g, 2 mmol) and CuI (0.76 g, 4.0 mmol) in trimethylamine (50 mL) under Ar was added ethynyltriisopropylsilane (8.95 mL, 40 mmol). The resulting solution was stirred at 65° C. for 24 h. The mixture was evaporated to dryness, and the residue was dissolved in $CH_2Cl_2$ and filtered through a Celite plug. The filtrate was concentrated under vacuum. The desired product was purified via flash column chromatography.

To a solution of substituted 2-((triisopropylsilyl)ethynyl) arenes (18.0 mmol) in dry THF at −40° C. was added TBAF (27 mL, 1 M THF solution). The resulting mixture was allowed to warm to room temperature and stirred for additional 1 h. The mixture was partitioned between water and EtOAc. The organic layer was concentrated under vacuum. The desired product was purified via flash chromatography.

2-ethynyl-5-methylpyridine (110a). Light yellow solid (hexanes:ethyl acetate=20:1, 1.52 g, 65% yield over two steps) was obtained from the above procedure. $^1$H NMR (500 MHz, Chloroform-d) δ 8.41 (dt, J=2.4, 0.8 Hz, 1H), 7.48-7.41 (m, 1H), 7.36 (dd, J=7.9, 0.8 Hz, 1H), 3.09 (s, 1H), 2.33 (d, J=0.9 Hz, 3H). $^{13}$C NMR (126 MHz, Chloroform-d) δ 150.61, 139.51, 136.62, 133.43, 126.93, 82.86, 76.42, 18.52.

4-(4-ethynylphenyl)morpholine (110b). White solid (hexanes:ethyl acetate=3:1, 1.19 g, 72% yield) was synthesized following the above general procedure. Low resolution mass spectrometry [M]$^+$: 188.2. $^1$H NMR (500 MHz, Chloroform-d) δ 7.43-7.36 (m, 2H), 6.85-6.79 (m, 2H), 3.90-3.80 (m, 4H), 3.22-3.16 (m, 4H), 2.99 (s, 1H). $^{13}$C NMR (126 MHz, Chloroform-d) δ 151.24, 133.27, 114.75, 112.56, 84.11, 75.62, 66.76, 48.46.

4-ethynylpyridine (110c). White solid (hexanes:ethyl acetate=20:1, 0.56 g, 57% yield). $^1$H NMR (500 MHz, Chloroform-d) δ 8.63-8.56 (m, 2H), 7.38-7.31 (m, 2H), 3.29 (s, 1H). $^{13}$C NMR (126 MHz, Chloroform-d) δ 149.87, 130.35, 126.12, 81.89, 80.99. Low resolution mass spectrometry [M]$^+$: 104.2.

methyl 1-(2-cyanoethyl)-3-((5-methylpyridin-2-yl)ethynyl)-1H-indole-5-carboxylate (111a). The synthesis of 11a followed general procedure C to obtain the desired product as brown solid (hexanes:ethyl acetate=1:1, 1.45 g, 94% yield). $^1$H NMR (500 MHz, Chloroform-d) δ 8.61-8.53 (m, 1H), 8.45 (dd, J=2.1, 1.0 Hz, 1H), 8.00 (dd, J=8.7, 1.7 Hz, 1H), 7.52 (s, 1H), 7.50 (ddd, J=8.0, 2.2, 0.7 Hz, 1H), 7.47 (dd, J=8.0, 1.0 Hz, 1H), 7.34 (dd, J=8.7, 0.6 Hz, 1H), 4.47 (t, J=6.8 Hz, 2H), 3.95 (s, 3H), 2.86 (t, J=6.7 Hz, 2H), 2.36 (s, 3H). $^{13}$C NMR (126 MHz, Chloroform-d) δ 167.55, 150.54, 140.91, 137.37, 136.72, 132.79, 132.43, 128.86, 126.51, 124.89, 123.56, 123.54, 116.60, 108.92, 100.04, 91.90, 81.01, 52.06, 42.52, 19.22, 18.54.

methyl 1-(2-cyanoethyl)-3-(pyridin-4-ylethynyl)-1H-indole-5-carboxylate (111b). The synthesis of 111b followed general procedure C to obtain the desired product as yellow solid (hexanes:ethyl acetate=1:1, 0.319 g, 97% yield). $^1$H NMR (500 MHz, Chloroform-d) δ 8.62-8.57 (m, 2H), 8.52 (d, J=1.8 Hz, 1H), 8.02 (dd, J=8.6, 1.9 Hz, 1H), 7.55 (d, J=1.3 Hz, 1H), 7.42-7.38 (m, 2H), 7.36 (d, J=8.6 Hz, 1H), 4.47 (t, J=6.6 Hz, 2H), 3.96 (d, J=1.4 Hz, 3H), 2.87 (t, J=6.6 Hz, 2H). $^{13}$C NMR (126 MHz, Chloroform-d) δ 167.44, 149.75, 137.37, 132.87, 131.77, 128.77, 125.27, 125.01, 123.73, 123.30, 116.59, 109.02, 99.68, 90.05, 86.58, 52.16, 42.54, 19.24. Low resolution mass spectrometry [M]$^+$: 330.2.

methyl 1-(2-cyanoethyl)-3-((4-morpholinophenyl)ethynyl)-1H-indole-5-carboxylate (111c). The synthesis of 111c followed general procedure C to obtain the desired product as white solid (hexanes:ethyl acetate=1:1, 0.704 g, 57% yield). $^1$H NMR (500 MHz, Chloroform-d) δ 8.50 (d, J=1.5 Hz, 1H), 7.94 (dd, J=8.7, 1.7 Hz, 1H), 7.45 (d, J=8.8 Hz, 2H), 7.41 (s, 1H), 7.29 (d, J=8.6 Hz, 1H), 6.83 (d, J=8.9 Hz, 2H), 4.36 (t, J=6.7 Hz, 2H), 3.93 (s, 3H), 3.85-3.80 (m, 4H), 3.17 (dd, J=5.8, 4.0 Hz, 4H), 2.79 (t, J=6.7 Hz, 2H). $^{13}$C NMR (126 MHz, Chloroform-d) δ 162.31, 150.52, 137.21, 132.32, 131.30, 128.70, 124.33, 123.07, 122.82, 116.81, 114.69, 113.73, 108.81, 100.69, 92.41, 79.60, 66.51, 51.86, 42.10, 36.26, 31.19, 18.91. Low resolution mass spectrometry [M]$^+$: 414.3.

methyl 1-(2-cyanoethyl)-3-(2-(5-methylpyridin-2-yl)ethyl)-1H-indole-5-carboxylate (112a). The synthesis of 112a followed general procedure D to obtain the desired product as yellow solid (hexanes:ethyl acetate=1:1, 1.24 g, 89% yield). Low resolution mass spectrometry [M+H]$^+$: 348.2. $^1$H NMR (500 MHz, Chloroform-d) δ 8.42-8.36 (m, 1H), 8.33 (d, J=1.4 Hz, 1H), 7.93 (dt, J=8.6, 1.6 Hz, 1H), 7.36 (dd, J=7.9, 2.2 Hz, 1H), 7.28-7.23 (m, 1H), 6.99 (d, J=7.8 Hz, 1H), 6.92 (s, 1H), 4.41-4.34 (m, 2H), 3.93 (d, J=1.0 Hz, 3H), 3.23-3.17 (m, 2H), 3.17-3.11 (m, 2H), 2.77 (td, J=6.8, 1.4 Hz, 2H), 2.29 (s, 3H). $^{13}$C NMR (126 MHz, Chloroform-d) δ 167.95, 158.26, 149.67, 138.24, 136.91, 130.46, 128.14, 125.89, 123.66, 122.52, 122.44, 121.69, 118.11, 116.98, 108.25, 51.90, 42.05, 38.22, 25.05, 19.17, 18.08.

methyl 1-(2-cyanoethyl)-3-(2-(pyridin-4-yl)ethyl)-1H-indole-5-carboxylate (112b). The synthesis of 112b followed general procedure D to obtain the desired product as white solid (hexanes: ethyl acetate=1:1, 0.15 g, 47% yield). $^1$H NMR (500 MHz, Chloroform-d) δ 8.48 (s, 2H), 8.35 (d, J=1.5 Hz, 1H), 7.95 (dd, J=8.7, 1.6 Hz, 1H), 7.29 (d, J=8.6 Hz, 1H), 7.09 (d, J=5.1 Hz, 2H), 6.90 (s, 1H), 4.36 (t, J=6.6 Hz, 2H), 3.93 (s, 3H), 3.14-3.03 (m, 2H), 3.00 (dd, J=8.4, 6.1 Hz, 2H), 2.77 (t, J=6.6 Hz, 2H). $^{13}$C NMR (126 MHz, Chloroform-d) δ 167.71, 150.41, 149.47, 138.15, 127.62, 125.98, 123.83, 123.53, 122.00, 121.60, 117.00, 116.71, 108.40, 51.79, 41.82, 35.34, 25.44, 19.02. Low resolution mass spectrometry [M]$^+$: 334.2.

methyl 1-(2-cyanoethyl)-3-(4-morpholinophenethyl)-1H-indole-5-carboxylate (112c). The synthesis of 112c followed general procedure D to obtain the desired product as yellow solid (hexanes:ethyl acetate=1:1, 0.508 g, 71% yield). $^1$H NMR (500 MHz, Chloroform-d) δ 8.36 (dd, J=1.6, 0.7 Hz, 1H), 7.95 (dd, J=8.7, 1.6 Hz, 1H), 7.27 (dd, J=8.7, 0.7 Hz, 1H), 7.12 (d, J=8.6 Hz, 2H), 6.89 (d, J=0.9 Hz, 1H), 6.88-6.82 (m, 2H), 4.40 (t, J=6.8 Hz, 2H), 3.94 (s, 3H), 3.88-3.85 (m, 4H), 3.16-3.11 (m, 4H), 3.08-3.03 (m, 2H), 2.94 (dd, J=9.2, 6.4 Hz, 2H), 2.79 (t, J=6.8 Hz, 2H). $^{13}$C NMR (126 MHz, Chloroform-d) δ 168.00, 149.64, 138.26, 133.50, 129.20, 128.16, 125.84, 123.68, 122.54, 121.72, 118.30, 117.03, 115.91, 108.26, 67.02, 51.97, 49.75, 42.08, 35.44, 26.98, 19.24. Low resolution mass spectrometry [M]$^+$: 418.3.

6-(bromomethyl)-2,3-dihydrobenzo[b][1,4]dioxine (116). To a solution of (2,3-dihydrobenzo[b][1,4]dioxin-6-yl)methanol (2.77 g, 16.66 mmol) in CH$_2$Cl$_2$ was added PBr$_3$ (0.63 mL, 6.66 mmol) dropwise at 0° C. The mixture was stirred at 0° C. for 0.5 h. Upon completion, the mixture was diluted with CH$_2$Cl$_2$ and washed with saturated NaHCO$_3$. The organic layer was concentrated under vacuum. Colorless oil (hexanes:ethyl acetate=20:1, 3.22 g, 84% yield) was isolated with column chromatography. H NMR (500 MHz, Chloroform-d) δ 6.92 (d, J=3.1 Hz, 1H), 6.88 (dd, J=8.4, 2.5 Hz, 1H), 6.82 (dt, J=8.4, 2.4 Hz, 1H), 4.44 (t, J=2.0 Hz, 2H), 4.28-4.21 (m, 4H). $^{13}$C NMR (126 MHz, Chloroform-d) δ 143.82, 143.46, 130.93, 122.28, 118.02, 117.55, 64.39, 64.27, 33.82.

methyl 1-(2-cyanoethyl)-3-formyl-1H-indole-5-carboxylate (Vilsmeier-Haack reaction) (118). To a solution of oxalyl chloride (0.10 mL, 1.19 mmol) in 5 mL anhydrous CH$_2$Cl$_2$ at 0° C. was added dropwise 0.09 mL anhydrous DMF in 5 mL DCM. The heterogeneous mixture was stirred in an ice bath for 45 min. Compound 107 (0.26 g, 1.14 mmol) was added slowly while allowing the reaction mixture to warm up to room temperature. It was stirred for 6 h and monitored via TLC. Upon completion, the solvent was removed. The crude product was treated with a 20% aqueous NH$_4$OAc solution (10 mL) and THF (15 mL). The solution was refluxed for 30 min. Upon cooling down, the product was extracted two times with ethyl acetate and concentrated under vacuum. The pale yellow solid was isolated (0.28 g, 86% yield) as the desired product, which was used without further purification. $^1$H-NMR (CDCl$_3$, 300 MHz) δ 10.05 (s, 1H), 9.01 (s, 1H), 8.07 (dd, J=1.5, 8.7 Hz, 1H), 7.89 (s, 1H), 7.38 (d, J=8.7 Hz, 1H), 4.55 (t, J=6.6 Hz, 2H), 3.95 (s, 3H), 2.95 (t, J=6.6 Hz, 2H). $^{13}$C-NMR (CDCl$_3$, 75 MHz) δ 184.69, 167.49, 138.97, 126.30, 125.83, 125.32, 125.27, 120.09, 116.58, 109.26, 98.81, 52.41, 43.21, 19.40. MS (ESI) m/z=257.2 [M+H]$^+$.

methyl 1-(2-cyanoethyl)-3-phenethyl-1H-indole-5-carboxylate (119a). The synthesis of 119a followed general procedures B and D to obtain the desired product as white solid (hexanes:ethyl acetate=3:1, 72% yield over two steps). Low resolution mass spectrometry [M+Na]$^+$: 355.2. $^1$H NMR (500 MHz, Chloroform-d) δ 8.38 (s, 1H), 7.97 (d, J=8.6 Hz, 1H), 7.32-7.27 (m, 3H), 7.21 (d, J=7.3 Hz, 3H), 6.89 (s, 1H), 4.38 (t, J=6.8 Hz, 2H), 3.96 (s, 3H), 3.13-3.07 (m, 2H), 3.03 (t, J=7.7 Hz, 2H), 2.77 (t, J=6.8 Hz, 2H). $^{13}$C NMR (126 MHz, Chloroform-d) δ 167.95, 141.78, 138.25, 128.47, 128.33, 128.05, 125.98, 125.85, 123.64, 122.42, 121.70, 118.04, 117.02, 108.30, 51.91, 42.00, 36.31, 26.80, 19.15.

methyl 3-(4-chlorophenethyl)-1-(2-cyanoethyl)-1H-indole-5-carboxylate (119b). The synthesis of 119b followed general procedures B and D to obtain the desired product as white solid (hexanes:ethyl acetate=5:1, 66% yield). $^1$H-NMR (CDCl$_3$, 300 MHz) δ 8.31 (d, J=0.9 Hz, 1H), 7.95 (dd, J=1.3, 8.4 Hz, 1H), 7.27 (d, J=9.0 Hz, 1H), 7.25 (d, J=8.4 Hz, 2H), 7.09 (d, J=8.4 Hz, 2H), 6.87 (s, 1H), 4.37 (t, J=6.6 Hz, 2H), 3.94 (s, 3H), 3.09-3.05 (m, 2H), 2.99-2.94 (m, 2H), 2.77 (t, J=6.6 Hz, 2H). $^{13}$C-NMR (CDCl$_3$, 75 MHz) δ 168.19, 140.43, 138.46, 131.90, 130.12, 128.72, 128.63, 128.58, 128.17, 126.23, 123.91, 122.59, 121.94, 117.75, 117.32, 108.61, 52.23, 42.23, 35.92, 26.98, 19.44. MS (ESI) m/z=367.2 [M+H]$^+$.

methyl 1-(2-cyanoethyl)-3-(4-methylphenethyl)-1H-indole-5-carboxylate (119c). The synthesis of 119c followed procedures B and D to obtain the desired product as white solid (hexanes:ethyl acetate=5:1, 79% yield). Low resolution mass spectrometry [M+Na]$^+$: 369.2. $^1$H NMR (500 MHz, DMSO-d$_6$) δ 8.20 (t, J=1.3 Hz, 1H), 7.81-7.74 (m, 1H), 7.64 (d, J=8.7 Hz, 1H), 7.34 (s, 1H), 7.14 (d, J=7.9 Hz, 2H), 7.07 (d, J=7.8 Hz, 2H), 4.48 (t, J=6.6 Hz, 2H), 3.85 (s, 3H), 3.04-2.97 (m, 4H), 2.93-2.88 (m, 2H), 2.26 (s, 3H). $^{13}$C NMR (126 MHz, DMSO-d$_6$) δ 167.14, 138.59, 138.38, 134.66, 128.78, 128.19, 127.23, 127.22, 122.23, 121.19, 120.34, 118.71, 116.26, 109.85, 51.67, 41.19, 35.39, 26.48, 20.61, 18.56.

methyl 1-(2-cyanoethyl)-3-(4-methoxyphenethyl)-1H-indole-5-carboxylate (119d). The synthesis of 119d followed procedures B and D to obtain the desired product as white solid (hexanes:ethyl acetate=3:1, 87% yield) $^1$H NMR (500 MHz, Chloroform-d) δ 8.34 (d, J=1.6 Hz, 1H), 7.95 (dd, J=8.7, 1.6 Hz, 1H), 7.28 (d, J=8.7 Hz, 1H), 7.11 (d, J=8.6 Hz, 2H), 6.88 (s, 1H), 6.83 (d, J=8.5 Hz, 2H), 4.39 (t, J=6.7 Hz, 2H), 3.95 (s, 3H), 3.79 (s, 3H), 3.05 (dd, J=9.0, 6.3 Hz, 2H), 2.95 (dd, J=8.8, 6.1 Hz, 2H), 2.78 (t, J=6.7 Hz, 2H). $^{13}$C NMR (126 MHz, Chloroform-d) δ 167.99, 157.92, 138.25, 133.92, 129.40, 128.10, 125.87, 123.65, 122.50, 121.69, 118.15, 117.03, 113.76, 108.28, 55.29, 51.94, 42.04, 35.46, 27.10, 19.20.

methyl 1-(2-cyanoethyl)-3-(4-(trifluoromethyl)phenethyl)-1H-indole-5-carboxylate (119e). The synthesis of 119e followed procedures B and D to obtain the desired product as white solid (hexanes:ethyl acetate=3:1, 70% yield) Low resolution mass spectrometry [M+Na]$^+$: 423.2. $^1$H NMR (500 MHz, Chloroform-d) δ 8.33 (d, J=1.6 Hz, 1H), 7.97 (dd, J=8.7, 1.7 Hz, 1H), 7.54 (d, J=7.9 Hz, 2H), 7.34-7.26 (m, 3H), 6.91 (s, 1H), 4.39 (t, J=6.6 Hz, 2H), 3.96 (s, 3H), 3.14-3.04 (m, 4H), 2.78 (t, J=6.6 Hz, 2H). $^{13}$C NMR (126 MHz, Chloroform-d) δ 167.86, 145.82, 138.25, 128.81, 127.89, 126.00, 125.20, 125.17, 123.68, 122.24, 121.77, 117.28, 117.02, 108.40, 51.89, 41.97, 36.16, 26.50, 19.14.

methyl 1-(2-cyanoethyl)-3-(4-(trifluoromethoxy)phenethyl)-1H-indole-5-carboxylate (119f). The synthesis of 119f followed procedures B and D to obtain the desired product as white solid (hexanes:ethyl acetate=3:1, 78% yield) $^1$H NMR (500 MHz, Chloroform-d) δ 8.25 (d, J=1.6 Hz, 1H), 7.88 (dd, J=8.7, 1.6 Hz, 1H), 7.21 (d, J=8.7 Hz, 1H), 7.11 (d, J=8.6 Hz, 2H), 7.06-7.02 (m, 2H), 6.80 (s, 1H), 4.32 (t, J=6.7 Hz, 2H), 3.87 (s, 3H), 3.03-2.98 (m, 2H), 2.94 (ddd, J=8.6, 6.4, 1.7 Hz, 2H), 2.71 (t, J=6.7 Hz, 2H). $^{13}$C NMR (126 MHz, Chloroform-d) δ 167.94, 140.50, 138.28, 129.78, 128.00, 125.95, 123.79, 122.39, 121.85, 120.92, 117.59, 116.98, 108.36, 51.99, 42.08, 35.71, 26.81, 19.24.

methyl 3-(3-chlorophenethyl)-1-(2-cyanoethyl)-1H-indole-5-carboxylate (119g). The synthesis of 119g followed procedures B and D to obtain the desired product as white solid (hexanes:ethyl acetate=3:1, 67% yield). Low resolution mass spectrometry [M+Na]$^+$: 389.1. $^1$H NMR (500 MHz, Chloroform-d) δ 8.33 (dd, J=1.6, 0.7 Hz, 1H), 7.96 (dd, J=8.6, 1.6 Hz, 1H), 7.29 (dd, J=8.7, 0.7 Hz, 1H), 7.22-7.15 (m, 3H), 7.05 (dt, J=7.0, 1.7 Hz, 1H), 6.87 (d, J=1.0 Hz, 1H), 4.39 (t, J=6.8 Hz, 2H), 3.95 (s, 3H), 3.10-3.05 (m, 2H), 3.01-2.96 (m, 2H), 2.78 (t, J=6.8 Hz, 2H). $^{13}$C NMR (126 MHz, Chloroform-d) δ 167.93, 143.79, 138.28, 134.04, 129.62, 128.66, 127.97, 126.78, 126.22, 125.96, 123.80, 122.38, 121.86, 117.55, 116.99, 108.37, 51.97, 42.08, 36.07, 26.63, 19.22.

methyl 1-(2-cyanoethyl)-3-(3,4-dichlorophenethyl)-1H-indole-5-carboxylate (119h). The synthesis of 119h followed procedures B and D to obtain the desired product as white solid (hexanes:ethyl acetate=3:1, 47% yield over two steps). $^1$H NMR (500 MHz, Chloroform-d) δ 8.28 (d, J=1.5 Hz, 1H), 7.96 (dd, J=8.7, 1.6 Hz, 1H), 7.31 (d, J=8.2 Hz, 1H), 7.28 (d, J=8.6 Hz, 1H), 7.24 (d, J=2.1 Hz, 1H), 6.98 (dd, J=8.2, 2.1 Hz, 1H), 6.88 (s, 1H), 4.40 (t, J=6.7 Hz, 2H), 3.95 (s, 3H), 3.10-3.02 (m, 2H), 2.96 (dd, J=8.5, 6.6 Hz, 2H), 2.79 (t, J=6.7 Hz, 2H). $^{13}$C NMR (126 MHz, Chloroform-d) δ 167.88, 141.95, 138.27, 132.13, 130.47, 130.24, 129.96, 128.08, 127.89, 126.06, 123.82, 122.32, 121.89, 117.16, 116.98, 108.41, 52.01, 42.08, 35.57, 26.56, 19.24. Low resolution mass spectrometry [M+H]$^+$: 401.1.

methyl 1-(2-cyanoethyl)-3-(2-(naphthalen-2-yl)ethyl)-1H-indole-5-carboxylate (119i). The synthesis of 119i followed procedures B and D to obtain the desired product as white solid (hexanes:ethyl acetate=3:1, 75% yield over two steps) $^1$H NMR (500 MHz, Chloroform-d) δ 8.39 (dd, J=1.6, 0.6 Hz, 1H), 7.96 (dd, J=8.6, 1.6 Hz, 1H), 7.83-7.80 (m, 1H), 7.80-7.74 (m, 2H), 7.63-7.61 (m, 1H), 7.44 (dtd, J=7.9, 6.8, 5.3 Hz, 2H), 7.35 (dd, J=8.3, 1.8 Hz, 1H), 7.28 (dd, J=8.7, 0.7 Hz, 1H), 6.85 (s, 1H), 4.36 (t, J=6.8 Hz, 2H), 3.94 (s, 3H), 3.18 (s, 4H), 2.72 (t, J=6.8 Hz, 2H). $^{13}$C NMR (126 MHz, Chloroform-d) δ 167.99, 139.32, 138.29, 133.60, 132.10, 128.08, 127.90, 127.65, 127.48, 127.36, 126.60, 125.95, 125.93, 125.25, 123.73, 122.50, 121.77, 118.00, 117.01, 108.33, 51.98, 42.03, 36.52, 26.74, 19.18.

methyl 1-(2-cyanoethyl)-3-(2-(naphthalen-1-yl)ethyl)-1H-indole-5-carboxylate (119j). The synthesis of 119j followed procedures B and D to obtain the desired product as white solid (hexanes:ethyl acetate=3:1, 66% yield over two steps). $^1$H NMR (500 MHz, Chloroform-d) δ 8.40-8.36 (m, 1H), 8.09-8.04 (m, 1H), 7.98 (dd, J=8.6, 1.6 Hz, 1H), 7.92-7.86 (m, 1H), 7.74 (d, J=8.2 Hz, 1H), 7.50 (dq, J=5.4, 3.1, 1.7 Hz, 2H), 7.39 (t, J=7.6 Hz, 1H), 7.32-7.25 (m, 2H), 6.84 (s, 1H), 4.33 (t, J=6.8 Hz, 2H), 3.96 (s, 3H), 3.47 (dd, J=9.0, 6.6 Hz, 2H), 3.23 (dd, J=9.0, 6.6 Hz, 2H), 2.69 (t, J=6.7 Hz, 2H). $^{13}$C NMR (126 MHz, Chloroform-d) δ 167.93, 138.26, 137.79, 133.85, 131.85, 128.81, 128.03, 126.78, 126.15, 125.84, 125.83, 125.52, 125.45, 123.67, 122.37, 121.73, 118.12, 117.03, 108.35, 51.90, 41.94, 33.37, 26.08, 19.09. Low resolution mass spectrometry [M+Na]$^+$: 405.2.

methyl 1-(2-cyanoethyl)-3-(2-(thiazol-2-yl)ethyl)-1H-indole-5-carboxylate (119k). The synthesis of 119k followed general procedures B and D to obtain the desired product as white solid (hexanes:ethyl acetate=1:1, 69% yield over two steps). $^1$H NMR (500 MHz, Chloroform-d) δ 8.36 (dd, J=1.6, 0.6 Hz, 1H), 7.96 (dd, J=8.6, 1.6 Hz, 1H), 7.72 (d, J=3.3 Hz, 1H), 7.28 (dd, J=8.7, 0.7 Hz, 1H), 7.20 (d, J=3.3 Hz, 1H), 7.00 (d, J=1.0 Hz, 1H), 4.41 (t, J=6.8 Hz, 2H), 3.94 (s, 3H), 3.46 (dd, J=8.5, 6.7 Hz, 2H), 3.33-3.28 (m, 2H), 2.80 (t, J=6.7 Hz, 2H). $^{13}$C NMR (126 MHz, Chloroform-d) δ 170.46, 167.89, 141.73, 138.30, 127.91, 126.31, 123.92, 122.32, 122.02, 118.53, 116.94, 116.66, 108.43, 51.99, 42.15, 33.56, 25.25, 19.25. Low resolution mass spectrometry [M]$^+$: 340.2.

methyl 3-(2-([1,1'-biphenyl]-4-yl)ethyl)-1-(2-cyanoethyl)-1H-indole-5-carboxylate (119l). The synthesis of 119l followed procedures B and D to obtain the desired product as white solid (hexanes:ethyl acetate=3:1, 63% yield over two steps). $^1$H NMR (500 MHz, DMSO-d$_6$) δ 8.23 (d, J=1.6 Hz, 1H), 7.80 (dd, J=8.6, 1.6 Hz, 1H), 7.65 (d, J=8.7 Hz, 1H), 7.64-7.60 (m, 2H), 7.57-7.54 (m, 2H), 7.44 (dd, J=8.4, 7.0 Hz, 2H), 7.38 (s, 1H), 7.36-7.31 (m, 3H), 4.49 (t, J=6.5 Hz, 2H), 3.83 (s, 3H), 3.09-2.98 (m, 6H). $^{13}$C NMR (126 MHz, DMSO-d$_6$) δ 167.13, 140.98, 140.13, 138.39, 137.77, 128.95, 128.83, 127.29, 127.24, 127.10, 126.51, 126.45, 122.27, 121.25, 120.38, 118.71, 116.18, 109.85, 51.64, 41.21, 35.42, 26.30, 18.58. Low resolution mass spectrometry [M+Na]$^+$: 431.3.

methyl 1-(2-cyanoethyl)-3-(2-cyclohexylethyl)-1H-indole-5-carboxylate (119m). The synthesis of 119e followed procedures B and D to obtain the desired product as white solid (hexanes:ethyl acetate=3:1, 39% yield over two steps). Low resolution mass spectrometry [M+H]$^+$: 339.3. $^1$H NMR (500 MHz, Chloroform-d) δ 8.36 (dd, J=1.6, 0.6 Hz, 1H), 7.94 (dd, J=8.7, 1.6 Hz, 1H), 7.27 (d, J=0.6 Hz, 1H), 6.97 (d, J=1.0 Hz, 1H), 4.42 (t, J=6.8 Hz, 2H), 3.94 (s, 3H), 2.81 (t, J=6.8 Hz, 2H), 2.79-2.73 (m, 2H), 1.85-1.77 (m, 2H), 1.72 (dt, J=12.3, 3.3 Hz, 2H), 1.66 (dtd, J=10.6, 3.1, 1.6 Hz, 1H), 1.63-1.57 (m, 2H), 1.40-1.30 (m, 1H), 1.29-1.15 (m, 3H), 1.02-0.91 (m, 2H). $^{13}$C NMR (126 MHz, Chloroform-d) δ

168.07, 138.33, 128.34, 125.38, 123.64, 122.64, 121.60, 119.56, 117.08, 108.18, 51.95, 42.12, 37.71, 37.57, 33.36, 26.76, 26.41, 22.19, 19.26.

methyl 1-(2-cyanoethyl)-3-(2-(tetrahydro-2H-pyran-4-yl)ethyl)-1H-indole-5-carboxylate (119n). The synthesis of 119n followed procedures B and D to obtain the desired product as white solid (hexanes:ethyl acetate=2:1, 60% yield over two steps). $^1$H NMR (500 MHz, Chloroform-d) δ 8.37 (dd, J=1.7, 0.7 Hz, 1H), 7.95 (dd, J=8.6, 1.6 Hz, 1H), 7.29 (dd, J=8.6, 0.7 Hz, 1H), 7.01 (d, J=1.1 Hz, 1H), 4.40 (t, J=6.6 Hz, 2H), 4.04-3.93 (m, 5H), 3.40 (td, J=11.8, 2.1 Hz, 2H), 2.86-2.74 (m, 4H), 1.75-1.65 (m, 4H), 1.65-1.55 (m, 1H), 1.43-1.30 (m, 2H). $^{13}$C NMR (126 MHz, Chloroform-d) δ 167.86, 138.22, 128.02, 125.50, 123.45, 122.27, 121.44, 118.53, 117.10, 108.25, 67.94, 51.81, 41.90, 36.95, 34.59, 32.96, 21.54, 19.08. Low resolution mass spectrometry [M+Na]$^+$: 363.2.

methyl 1-(2-cyanoethyl)-3-(2-(2,3-dihydrobenzo[b][1,4]dioxin-6-yl)ethyl)-1H-indole-5-carboxylate (119o). The synthesis of 119o followed procedures B and D to obtain the desired product as white solid (hexanes: ethyl acetate=1:1, 39% yield over two steps). Low resolution mass spectrometry [M+H]$^+$: 391.2. $^1$H NMR (500 MHz, Chloroform-d) δ 8.32 (dd, J=1.6, 0.7 Hz, 1H), 7.95 (dd, J=8.7, 1.6 Hz, 1H), 7.27 (dd, J=8.6, 0.6 Hz, 1H), 6.90 (d, J=1.0 Hz, 1H), 6.78 (d, J=8.2 Hz, 1H), 6.70 (d, J=2.0 Hz, 1H), 6.67 (dd, J=8.2, 2.1 Hz, 1H), 4.40 (t, J=6.8 Hz, 2H), 4.24 (s, 4H), 3.94 (s, 3H), 3.08-2.99 (m, 2H), 2.90 (dd, J=9.1, 6.6 Hz, 2H), 2.79 (t, J=6.8 Hz, 2H). $^{13}$C NMR (126 MHz, Chloroform-d) δ 168.00, 143.30, 141.83, 138.26, 135.18, 128.13, 125.85, 123.72, 122.52, 121.75, 121.43, 118.18, 117.11, 117.05, 117.02, 108.28, 64.46, 64.38, 51.95, 42.10, 35.66, 26.96, 19.21.

methyl 1-(2-(2H-tetrazol-5-yl)ethyl)-3-phenethyl-1H-indole-5-carboxylate (120a). The synthesis of 120a followed general procedure F to obtain the desired product as yellow solid (CH$_2$Cl$_2$:MeOH=15:1, 69% yield). Low resolution mass spectrometry [M+Na]$^+$: 398.2. $^1$H NMR (500 MHz, DMSO-d$_6$) δ 8.17 (dd, J=1.7, 0.6 Hz, 1H), 7.73 (dd, J=8.7, 1.7 Hz, 1H), 7.50 (dd, J=8.7, 0.6 Hz, 1H), 7.28-7.25 (m, 2H), 7.24 (dd, J=8.3, 1.6 Hz, 3H), 4.59 (t, J=7.1 Hz, 2H), 3.84 (s, 3H), 3.37 (t, J=7.1 Hz, 2H), 2.98 (ddd, J=8.1, 6.6, 3.9 Hz, 2H), 2.94-2.88 (m, 2H). $^{13}$C NMR (126 MHz, DMSO-d$_6$) δ 167.14, 141.71, 138.25, 128.30, 128.27, 128.20, 127.34, 127.10, 125.80, 122.13, 121.17, 120.08, 115.87, 109.52, 51.66, 43.39, 35.83, 26.32, 24.43.

methyl 1-(2-(2H-tetrazol-5-yl)ethyl)-3-(4-methylphenethyl)-1H-indole-5-carboxylate (120c). The synthesis of 120c followed general procedure F to obtain the desired product as yellow solid (CH$_2$Cl$_2$:MeOH=15:1, 68% yield). Low resolution mass spectrometry [M+Na]$^+$: 412.2. $^1$H NMR (500 MHz, Chloroform-d) δ 8.20 (d, J=1.7 Hz, 1H), 7.72 (dd, J=8.6, 1.6 Hz, 1H), 7.17 (d, J=8.7 Hz, 1H), 7.06 (dd, J=12.0, 3.9 Hz, 4H), 6.77 (s, 1H), 4.53 (t, J=7.0 Hz, 2H), 3.87 (s, 3H), 3.46 (t, J=7.0 Hz, 2H), 2.93 (ddd, J=10.2, 6.5, 2.1 Hz, 2H), 2.86 (ddd, J=8.8, 6.8, 1.9 Hz, 2H), 2.30 (s, 3H). $^{13}$C NMR (126 MHz, Chloroform-d) δ 168.80, 138.70, 138.58, 135.43, 129.03, 128.27, 128.25, 127.77, 126.29, 123.23, 122.29, 120.53, 117.55, 108.63, 52.11, 44.43, 35.88, 27.74, 26.86, 21.01.

methyl 1-(2-(2H-tetrazol-5-yl)ethyl)-3-(4-methoxyphenethyl)-1H-indole-5-carboxylate (120d). The synthesis of 120d followed general procedure F to obtain the desired product as yellow solid (CH$_2$Cl$_2$:MeOH=15:1, 70% yield). Low resolution mass spectrometry [M+Na]$^+$: 421.2. $^1$H NMR (500 MHz, Chloroform-d) δ 8.15 (d, J=1.7 Hz, 1H), 7.70 (dd, J=8.7, 1.7 Hz, 1H), 7.16 (d, J=8.7 Hz, 1H), 7.04-7.00 (m, 2H), 6.79-6.75 (m, 2H), 6.74 (s, 1H), 4.51 (t, J=7.0 Hz, 2H), 3.84 (s, 3H), 3.73 (s, 3H), 3.46 (t, J=7.0 Hz, 2H), 2.92-2.86 (m, 2H), 2.85-2.80 (m, 2H). $^{13}$C NMR (126 MHz, Chloroform-d) δ 168.85, 157.77, 138.49, 133.84, 129.23, 127.73, 126.32, 123.15, 122.24, 120.41, 117.47, 113.71, 108.59, 55.21, 52.09, 44.25, 35.34, 26.90, 24.91.

methyl 1-(2-(2H-tetrazol-5-yl)ethyl)-3-(4-(trifluoromethyl)phenethyl)-1H-indole-5-carboxylate (120e). The synthesis of 120e followed general procedure F to obtain the desired product as yellow solid (CH$_2$Cl$_2$:MeOH=15:1, 30% yield). Low resolution mass spectrometry [M+Na]$^+$: 466.2. $^1$H NMR (500 MHz, DMSO-d$_6$) δ 8.10 (dd, J=1.7, 0.6 Hz, 1H), 7.72 (dd, J=8.7, 1.6 Hz, 1H), 7.62-7.57 (m, 2H), 7.49 (dd, J=8.7, 0.6 Hz, 1H), 7.45-7.41 (m, 2H), 7.23 (s, 1H), 4.59 (t, J=7.0 Hz, 2H), 3.83 (s, 3H), 3.37 (t, J=7.0 Hz, 2H), 3.01 (q, J=3.2 Hz, 4H). $^{13}$C NMR (126 MHz, DMSO-d$_6$) δ 167.09, 146.61, 138.20, 129.20, 127.47, 127.08, 124.97, 124.94, 122.14, 121.16, 120.12, 115.42, 109.51, 51.62, 43.40, 35.65, 25.86, 24.39.

methyl 1-(2-(2H-tetrazol-5-yl)ethyl)-3-(4-(trifluoromethoxy)phenethyl)-1H-indole-5-carboxylate (120f). The synthesis of 120f followed general procedure F to obtain the desired product as yellow solid (CH$_2$Cl$_2$:MeOH=15:1, 30% yield). Low resolution mass spectrometry [M+Na]$^+$: 482.2. $^1$H NMR (500 MHz, DMSO-d$_6$) δ 8.12 (d, J=1.6 Hz, 1H), 7.72 (dd, J=8.7, 1.7 Hz, 1H), 7.49 (d, J=8.7 Hz, 1H), 7.37-7.32 (m, 2H), 7.25-7.22 (m, 3H), 4.59 (t, J=7.0 Hz, 2H), 3.83 (s, 3H), 3.37 (t, J=7.0 Hz, 2H), 3.02-2.97 (m, 2H), 2.94 (dd, J=8.2, 5.8 Hz, 2H). $^{13}$C NMR (126 MHz, DMSO-d$_6$) δ 167.10, 146.57, 141.21, 138.21, 130.22, 130.11, 127.41, 127.09, 122.13, 121.17, 120.73, 120.10, 115.56, 109.51, 51.63, 43.40, 35.11, 26.10, 24.41.

methyl 1-(2-(2H-tetrazol-5-yl)ethyl)-3-(3-chlorophenethyl)-1H-indole-5-carboxylate (120g). The synthesis of 120g followed general procedure F to obtain the desired product as yellow solid (CH$_2$Cl$_2$:MeOH=15:1, 41% yield). This compound was used for the next step without further purification. Low resolution mass spectrometry [M+H]$^+$: 410.2.

methyl 1-(2-(2H-tetrazol-5-yl)ethyl)-3-(3,4-dichlorophenethyl)-1H-indole-5-carboxylate (120h). The synthesis of 120h followed general procedure F to obtain the desired product as yellow solid (CH$_2$Cl$_2$:MeOH=15:1, 55% yield). This compound was used for the next step without further purification. Low resolution mass spectrometry [M+Na]$^+$: 466.1.

methyl 1-(2-(2H-tetrazol-5-yl)ethyl)-3-(2-(naphthalen-2-yl)ethyl)-1H-indole-5-carboxylate (120i). The synthesis of 120i followed general procedure F to obtain the desired product as red solid (CH$_2$Cl$_2$:MeOH=15:1, 39% yield). Low resolution mass spectrometry [M+Na]$^+$: 448.4. $^1$H NMR (500 MHz, DMSO-d$_6$) δ 8.19 (d, J=1.6 Hz, 1H), 7.86 (dd, J=7.7, 1.6 Hz, 1H), 7.84 (dd, J=8.1, 2.2 Hz, 2H), 7.76-7.74 (m, 1H), 7.73 (dd, J=8.7, 1.6 Hz, 1H), 7.50 (d, J=8.7 Hz, 1H), 7.45 (tdd, J=8.5, 3.9, 1.7 Hz, 3H), 7.27 (s, 1H), 4.59 (t, J=7.1 Hz, 2H), 3.82 (s, 3H), 3.37 (t, J=7.1 Hz, 2H), 3.09 (s, 4H). $^{13}$C NMR (126 MHz, DMSO-d$_6$) δ 167.12, 139.39, 138.26, 133.16, 131.62, 127.63, 127.43, 127.39, 127.30, 127.13, 126.14, 125.87, 125.15, 122.15, 121.22, 120.09, 115.91, 109.53, 51.65, 43.39, 36.05, 26.16, 24.41.

methyl 1-(2-(2H-tetrazol-5-yl)ethyl)-3-(2-(naphthalen-1-yl)ethyl)-1H-indole-5-carboxylate (120j). The synthesis of 120j followed general procedure F to obtain the desired product as yellow solid (CH$_2$Cl$_2$:MeOH=15:1, 48% yield). This compound used for the next step without further purification. Low resolution mass spectrometry [M+Na]$^+$: 448.2.

methyl 1-(2-(2H-tetrazol-5-yl)ethyl)-3-(2-(thiazol-2-yl)ethyl)-1H-indole-5-carboxylate (120k). The synthesis of 120k followed general procedure F to obtain the desired product as yellow oil (CH$_2$Cl$_2$:MeOH=15:1, 59% yield). $^1$H NMR (500 MHz, Chloroform-d) δ 8.09 (d, J=1.6 Hz, 1H), 7.72 (dd, J=8.7, 1.6 Hz, 1H), 7.46 (d, J=3.4 Hz, 1H), 7.20 (d, J=3.4 Hz, 1H), 7.05 (d, J=8.7 Hz, 1H), 6.67 (s, 1H), 4.48 (dd, J=7.0, 5.7 Hz, 2H), 3.86 (s, 3H), 3.38 (t, J=6.3 Hz, 2H), 3.31 (t, J=7.0 Hz, 2H), 3.11 (t, J=6.9 Hz, 2H). $^{13}$C NMR (126 MHz, Chloroform-d) δ 171.06, 168.08, 141.14, 138.57, 127.34, 126.35, 123.45, 121.63, 121.31, 119.12, 115.87, 108.61, 51.94, 44.53, 33.84, 25.57, 25.55. Low resolution mass spectrometry [M]$^+$: 383.2.

methyl 1-(2-(2H-tetrazol-5-yl)ethyl)-3-(2-(pyridin-4-yl)ethyl)-1H-indole-5-carboxylate (120l). The synthesis of 120l followed general procedure F to obtain the desired product as yellow oil (CH$_2$Cl$_2$:MeOH=13:1, 51% yield). $^1$H NMR (500 MHz, Chloroform-d) δ 13.65 (s, 1H), 8.16 (dd, J=6.5, 3.2 Hz, 3H), 7.77 (dd, J=8.7, 1.6 Hz, 1H), 7.19 (d, J=8.6 Hz, 1H), 7.02 (d, J=5.2 Hz, 2H), 6.65 (s, 1H), 4.52 (t, J=6.7 Hz, 2H), 3.86 (s, 3H), 3.36 (t, J=6.7 Hz, 2H), 2.94 (dd, J=12.4, 5.6 Hz, 4H). $^{13}$C NMR (126 MHz, Chloroform-d) δ 168.03, 155.52, 153.79, 146.81, 138.41, 127.37, 126.99, 124.83, 123.26, 121.76, 121.15, 114.99, 108.87, 51.94, 44.48, 35.53, 29.25, 25.28. Low resolution mass spectrometry [M]$^+$: 377.2.

methyl 1-(2-(2H-tetrazol-5-yl)ethyl)-3-(2-(5-methylpyridin-2-yl)ethyl)-1H-indole-5-carboxylate (120m). The synthesis of 120m followed general procedure F to obtain the desired product as yellow oil (CH$_2$Cl$_2$:MeOH=15:1, 78% yield). Low resolution mass spectrometry [M+H]$^+$: 391.3. $^1$H NMR (500 MHz, Chloroform-d) δ 15.25 (s, 1H), 7.95 (dt, J=1.9, 0.9 Hz, 1H), 7.89 (d, J=1.6 Hz, 1H), 7.67 (dd, J=8.6, 1.6 Hz, 1H), 7.48 (ddd, J=7.9, 2.2, 0.8 Hz, 1H), 7.11-7.06 (m, 2H), 6.62 (s, 1H), 4.41 (t, J=6.6 Hz, 2H), 3.80 (s, 3H), 3.32 (t, J=6.7 Hz, 2H), 2.98 (d, J=5.9 Hz, 2H), 2.95 (d, J=5.9 Hz, 2H), 2.20 (s, 3H). $^{13}$C NMR (126 MHz, Chloroform-d) δ 167.80, 156.83, 155.51, 146.04, 139.60, 138.25, 131.97, 127.43, 126.79, 123.70, 122.85, 121.42, 120.79, 115.44, 108.66, 51.68, 44.74, 37.02, 25.41, 25.04, 17.82.

methyl 1-(2-(2H-tetrazol-5-yl)ethyl)-3-(2-([1,1'-biphenyl]-4-yl)ethyl)-1H-indole-5-carboxylate (120n). The synthesis of 120n followed general procedure F to obtain the desired product as yellow solid (CH$_2$Cl$_2$:MeOH=15:1, 55% yield). $^1$H NMR (500 MHz, DMSO-d$_6$) δ 8.16 (d, J=1.5 Hz, 1H), 7.73 (dd, J=8.7, 1.6 Hz, 1H), 7.63 (dt, J=6.3, 1.3 Hz, 2H), 7.56 (d, J=8.0 Hz, 2H), 7.50 (d, J=8.7 Hz, 1H), 7.45 (t, J=7.8 Hz, 2H), 7.36-7.30 (m, 3H), 7.26 (s, 1H), 4.60 (t, J=7.0 Hz, 2H), 3.81 (s, 3H), 3.39 (t, J=7.0 Hz, 2H), 3.05-2.99 (m, 2H), 2.99-2.93 (m, 2H). $^{13}$C NMR (126 MHz, DMSO-d$_6$) δ 167.12, 141.02, 140.14, 138.25, 137.77, 128.94, 128.85, 127.40, 127.15, 127.12, 126.52, 126.47, 122.13, 121.22, 120.08, 115.85, 109.52, 51.64, 43.40, 35.46, 26.25, 24.42. Low resolution mass spectrometry [M+Na]$^+$: 474.3.

methyl 1-(2-(2H-tetrazol-5-yl)ethyl)-3-(4-morpholinophenethyl)-1H-indole-5-carboxylate (120o). The synthesis of 120o followed general procedure F to obtain the desired product as yellow solid (CH$_2$Cl$_2$:MeOH=15:1, 65% yield). $^1$H NMR (500 MHz, Chloroform-d) δ 8.20 (d, J=1.6 Hz, 1H), 7.74 (dd, J=8.6, 1.7 Hz, 1H), 7.16 (d, J=8.7 Hz, 1H), 7.07-7.00 (m, 2H), 6.85-6.77 (m, 2H), 6.71 (s, 1H), 4.50 (t, J=6.9 Hz, 2H), 3.85 (s, 3H), 3.84-3.79 (m, 4H), 3.38 (t, J=6.9 Hz, 2H), 3.12-3.04 (m, 4H), 2.90 (dd, J=9.2, 6.1 Hz, 2H), 2.82 (dd, J=8.9, 5.7 Hz, 2H). $^{13}$C NMR (126 MHz, Chloroform-d) δ 168.63, 148.93, 138.47, 133.98, 129.11, 127.70, 126.31, 123.13, 122.20, 120.52, 117.31, 116.07, 108.58, 66.71, 52.04, 49.81, 44.30, 35.27, 26.74, 25.13. Low resolution mass spectrometry [M]$^+$: 461.3.

methyl 1-(2-(2H-tetrazol-5-yl)ethyl)-3-(2-cyclohexylethyl)-1H-indole-5-carboxylate (120p). The synthesis of 120p followed general procedure F to obtain the desired product as white solid (CH$_2$Cl$_2$:MeOH=15:1, 66% yield). This compound was used directly for the next step without further purification. Low resolution mass spectrometry [M+H]$^+$: 382.3.

methyl 1-(2-(2H-tetrazol-5-yl)ethyl)-3-(2-(tetrahydro-2H-pyran-4-yl)ethyl)-1H-indole-5-carboxylate (120q). The synthesis of 120q followed general procedure F to obtain the desired product as white solid (CH$_2$Cl$_2$:MeOH=15:1, 50% yield). $^1$H NMR (500 MHz, Chloroform-d) δ 8.18 (d, J=1.6 Hz, 1H), 7.74 (dd, J=8.6, 1.6 Hz, 1H), 7.18 (d, J=8.7 Hz, 1H), 6.76 (s, 1H), 4.55 (t, J=6.8 Hz, 2H), 3.88-3.81 (m, 5H), 3.45 (t, J=6.8 Hz, 2H), 3.32 (td, J=11.7, 2.0 Hz, 2H), 2.61 (dd, J=9.2, 6.3 Hz, 2H), 1.60-1.50 (m, 4H), 1.48-1.40 (m, 1H), 1.26-1.18 (m, 2H). $^{13}$C NMR (126 MHz, Chloroform-d) δ 168.59, 138.47, 127.74, 125.96, 123.13, 122.11, 120.51, 117.80, 108.53, 67.90, 52.00, 44.27, 36.83, 34.33, 32.76, 24.96, 21.41. Low resolution mass spectrometry [M]$^+$: 384.3.

methyl 1-(2-(2H-tetrazol-5-yl)ethyl)-3-(2-(2,3-dihydrobenzo[b][1,4]dioxin-6-yl)ethyl)-1H-indole-5-carboxylate (120r). The synthesis of 120r followed general procedure F to obtain the desired product as yellow solid (CH$_2$Cl$_2$:MeOH=15:1, 71% yield). Low resolution mass spectrometry [M+H]$^+$: 434.2. $^1$H NMR (500 MHz, DMSO-d$_6$) δ 8.16-8.08 (m, 1H), 7.72 (ddd, J=8.8, 4.4, 2.7 Hz, 1H), 7.49 (dd, J=8.4, 5.9 Hz, 1H), 7.23 (d, J=4.9 Hz, 1H), 6.77-6.71 (m, 2H), 6.67 (ddd, J=8.2, 5.5, 1.9 Hz, 1H), 4.59 (q, J=6.8 Hz, 2H), 4.19 (d, J=5.6 Hz, 4H), 3.88-3.80 (m, 3H), 3.37 (q, J=6.8 Hz, 2H), 2.92 (dd, J=9.9, 5.2 Hz, 2H), 2.79 (dt, J=9.6, 6.0 Hz, 2H). $^{13}$C NMR (126 MHz, DMSO-d$_6$) δ 167.15, 143.04, 141.50, 138.23, 134.77, 127.30, 127.13, 122.10, 121.24, 121.00, 120.05, 116.74, 116.67, 115.98, 109.49, 64.01, 63.92, 51.66, 43.36, 35.13, 26.46, 24.35.

1-(2-(2H-tetrazol-5-yl)ethyl)-3-phenethyl-1H-indole-5-carboxylic acid (5). The synthesis of 5 followed general procedure G to obtain the desired product as white solid (56% yield). Low resolution mass spectrometry [M+Na]$^+$: $^1$H NMR (500 MHz, DMSO-d$_6$) δ 12.44 (s, 1H), 8.18 (d, J=1.8 Hz, 1H), 7.73 (dd, J=8.5, 1.9 Hz, 1H), 7.47 (d, J=8.6 Hz, 1H), 7.31-7.23 (m, 4H), 7.21-7.16 (m, 1H), 4.58 (t, J=7.0 Hz, 2H), 3.37 (t, J=7.0 Hz, 2H), 3.02-2.94 (m, 2H), 2.93-2.89 (m, 2H). $^{13}$C NMR (126 MHz, DMSO-d$_6$) δ 168.26, 141.75, 138.13, 128.29, 128.26, 128.21, 127.10, 127.07, 125.80, 122.44, 121.26, 121.16, 115.74, 109.28, 43.38, 35.87, 26.38, 24.41. HPLC purity (water/CH$_3$CN): 95.78%, Rt: 12.61 min. HPLC purity (water/MeOH): 95.97%, Rt: 15.22 min.

1-(2-(2H-tetrazol-5-yl)ethyl)-3-(4-methylphenethyl)-1H-indole-5-carboxylic acid (7). The synthesis of 7 followed general procedure G to obtain the desired product as white solid (58% yield). Low resolution mass spectrometry [M+H]$^+$: 367.3. $^1$H NMR (500 MHz, DMSO-d$_6$) δ 12.45 (s, 1H), 8.16 (d, J=1.9 Hz, 1H), 7.72 (d, J=8.7 Hz, 1H), 7.46 (d, J=8.7 Hz, 1H), 7.19 (s, 1H), 7.12 (d, J=7.8 Hz, 2H), 7.07 (d, J=7.7 Hz, 2H), 4.58 (t, J=7.0 Hz, 2H), 3.37 (t, J=7.0 Hz, 2H), 2.97-2.90 (m, 2H), 2.86 (dd, J=9.2, 6.0 Hz, 2H), 2.26 (d, J=2.8 Hz, 3H). $^{13}$C NMR (126 MHz, DMSO-d$_6$) δ 168.25, 138.63, 138.12, 134.63, 128.78, 128.15, 127.08, 122.41, 121.25, 121.13, 115.78, 109.26, 43.37, 35.45, 26.50, 24.38, 20.62. (C spectrum DCM peak, H spectrum no DCM peak). HPLC purity (water/CH$_3$CN): 95.77%, Rt: 12.60 min. HPLC purity (water/MeOH): 95.98%, Rt: 15.21 min.

methyl 1-(2-(2H-tetrazol-5-yl)ethyl)-3-(4-methoxyphenethyl)-1H-indole-5-carboxylate (8). The synthesis of 8 followed general procedure G to obtain the desired product as white solid (65% yield). Low resolution mass spectrometry [M+H]$^+$. $^1$H NMR (500 MHz, DMSO-d$_6$) δ 12.45 (s, 1H), 8.16 (d, J=1.5 Hz, 1H), 7.72 (dd, J=8.7, 1.6 Hz, 1H), 7.47 (d, J=8.7 Hz, 1H), 7.18 (s, 1H), 7.16-7.12 (m, 2H), 6.84-6.81 (m, 2H), 4.58 (t, J=7.0 Hz, 2H), 3.71 (d, J=2.3 Hz, 3H), 3.37 (t, J=7.0 Hz, 2H), 2.96-2.91 (m, 2H), 2.87-2.83 (m, 2H). $^{13}$C NMR (126 MHz, DMSO-d$_6$) δ 168.26, 157.44, 138.12, 133.65, 129.20, 127.10, 127.08, 122.41, 121.27, 121.13, 115.79, 113.63, 109.25, 54.94, 43.37, 34.99, 26.67, 24.39. HPLC purity (water/CH$_3$CN): 95.78%, Rt: 12.62 min. HPLC purity (water/MeOH): 95.99%, Rt: 15.21 min.

1-(2-(2H-tetrazol-5-yl)ethyl)-3-(4-(trifluoromethyl)phenethyl)-1H-indole-5-carboxylic acid (9). The synthesis of 9 followed general procedure G to obtain the desired product as white solid (71% yield). Low resolution mass spectrometry [M+H]$^+$. $^1$H NMR (500 MHz, DMSO-d$_6$) δ 12.42 (s, 1H), 8.15 (d, J=1.5 Hz, 1H), 7.72 (dd, J=8.7, 1.6 Hz, 1H), 7.61 (d, J=8.0 Hz, 2H), 7.47 (d, J=8.7 Hz, 1H), 7.44 (d, J=8.0 Hz, 2H), 7.21 (s, 1H), 4.58 (t, J=7.0 Hz, 2H), 3.37 (t, J=7.0 Hz, 2H), 3.01 (s, 4H). $^{13}$C NMR (126 MHz, DMSO-d$_6$) δ 168.22, 146.65, 138.11, 129.17, 127.24, 127.03, 125.00, 124.97, 122.46, 121.26, 121.21, 115.27, 109.29, 43.40, 35.59, 25.90, 24.39. HPLC purity (water/CH$_3$CN): 95.78%, Rt: 12.62 min. HPLC purity (water/MeOH): 95.97%, Rt: 15.22 min.

1-(2-(2H-tetrazol-5-yl)ethyl)-3-(4-(trifluoromethoxy)phenethyl)-1H-indole-5-carboxylic acid (10). The synthesis of 10 followed general procedure G to obtain the desired product as white solid (60% yield). Low resolution mass spectrometry [M+Na]$^+$: 468.2. $^1$H NMR (500 MHz, DMSO-d) δ 12.44 (s, 1H), 8.15 (d, J=1.6 Hz, 1H), 7.72 (dd, J=8.7, 1.6 Hz, 1H), 7.47 (d, J=8.7 Hz, 1H), 7.37-7.32 (m, 2H), 7.24 (d, J=8.2 Hz, 2H), 7.20 (s, 1H), 4.58 (t, J=7.0 Hz, 2H), 3.37 (t, J=7.0 Hz, 2H), 3.00-2.92 (m, 4H). $^{13}$C NMR (126 MHz, DMSO-d$_6$) δ 168.23, 146.55, 141.25, 138.11, 130.19, 130.09, 127.17, 127.04, 122.44, 121.27, 121.18, 121.12, 120.83, 120.75, 115.43, 109.28, 43.38, 35.08, 26.15, 24.38. HPLC purity (water/CH$_3$CN): 95.77%, Rt: 12.61 min. HPLC purity (water/MeOH): 95.98%, Rt: 15.22 min.

1-(2-(2H-tetrazol-5-yl)ethyl)-3-(3-chlorophenethyl)-1H-indole-5-carboxylic acid (11). The synthesis of 11 followed general procedure G to obtain the desired product as white solid (76% yield). $^1$H NMR (500 MHz, DMSO-d$_6$) δ 12.43 (s, 1H), 8.19 (d, J=1.6 Hz, 1H), 7.72 (dd, J=8.6, 1.7 Hz, 1H), 7.47 (d, J=8.7 Hz, 1H), 7.34 (t, J=1.9 Hz, 1H), 7.31-7.27 (m, 1H), 7.23 (dt, J=8.2, 1.4 Hz, 1H), 7.22-7.16 (m, 2H), 4.58 (t, J=7.0 Hz, 2H), 3.36 (t, J=7.0 Hz, 2H), 3.01-2.96 (m, 2H), 2.95-2.89 (m, 2H). $^{13}$C NMR (126 MHz, DMSO-d$_6$) δ 168.25, 144.33, 138.11, 132.84, 129.98, 128.20, 127.17, 127.11, 127.03, 125.80, 122.45, 121.33, 121.19, 115.44, 109.28, 43.38, 35.39, 26.00, 24.42.

1-(2-(2H-tetrazol-5-yl)ethyl)-3-(3,4-dichlorophenethyl)-1H-indole-5-carboxylic acid (12). The synthesis of 12 followed general procedure G to obtain the desired product as white solid (83% yield). $^1$H NMR (500 MHz, DMSO-d$_6$) δ 12.43 (s, 1H), 8.16 (d, J=1.6 Hz, 1H), 7.72 (dd, J=8.6, 1.7 Hz, 1H), 7.54 (d, J=2.0 Hz, 1H), 7.48 (dd, J=10.7, 8.4 Hz, 2H), 7.22-7.17 (m, 2H), 4.58 (t, J=7.1 Hz, 2H), 3.36 (t, J=7.1 Hz, 2H), 2.98 (dd, J=7.3, 2.6 Hz, 2H), 2.92 (dd, J=7.4, 2.6 Hz, 2H). $^{13}$C NMR (126 MHz, DMSO-d$_6$) δ 168.26, 143.00, 138.11, 130.71, 130.43, 130.20, 128.90, 128.38, 127.27, 127.03, 122.48, 121.37, 121.21, 115.23, 109.29, 43.38, 34.80, 25.83, 24.40. HPLC purity (water/CH$_3$CN): 98.84%, Rt: 13.14 min. HPLC purity (water/MeOH): 98.90%, Rt: 15.62 min.

1-(2-(2H-tetrazol-5-yl)ethyl)-3-(2-(naphthalen-2-yl)ethyl)-1H-indole-5-carboxylic acid (13). The synthesis of 13 followed general procedure G to obtain the desired product as white solid (82% yield). Low resolution mass spectrometry [M+Na]$^+$: 434.1. $^1$H NMR (500 MHz, DMSO-d$_6$) δ 12.44 (s, 1H), 8.24 (d, J=1.5 Hz, 1H), 7.85 (ddd, J=11.5, 6.4, 2.5 Hz, 3H), 7.79-7.71 (m, 2H), 7.49-7.42 (m, 4H), 7.25 (s, 1H), 4.58 (t, J=7.1 Hz, 2H), 3.37 (t, J=7.0 Hz, 2H), 3.09 (s, 4H). $^{13}$C NMR (126 MHz, DMSO-d$_6$) δ 168.26, 139.41, 138.16, 133.17, 131.61, 127.64, 127.43, 127.37, 127.32, 127.16, 127.09, 126.10, 125.89, 125.16, 122.46, 121.29, 121.19, 115.75, 109.31, 43.39, 36.03, 26.21, 24.40. HPLC purity (water/CH$_3$CN): 95.78%, Rt: 12.61 min. HPLC purity (water/MeOH): 95.98%, Rt: 15.22 min.

1-(2-(2H-tetrazol-5-yl)ethyl)-3-(2-(naphthalen-1-yl)ethyl)-1H-indole-5-carboxylic acid (14). The synthesis of 14 followed general procedure G to obtain the desired product as white solid (80% yield). $^1$H NMR (500 MHz, DMSO-d$_6$) δ 12.43 (s, 1H), 8.21 (d, J=1.4 Hz, 1H), 8.16-8.11 (m, 1H), 7.94 (dd, J=8.0, 1.5 Hz, 1H), 7.79 (d, J=7.9 Hz, 1H), 7.74 (dd, J=8.6, 1.6 Hz, 1H), 7.59-7.48 (m, 3H), 7.45-7.37 (m, 2H), 7.31 (s, 1H), 4.60 (t, J=7.1 Hz, 2H), 3.41-3.36 (m, 4H), 3.09 (dd, J=9.4, 6.5 Hz, 2H). $^{13}$C NMR (126 MHz, DMSO-d$_6$) δ 168.25, 138.18, 137.74, 133.46, 131.33, 128.67, 127.24, 127.08, 126.51, 125.99, 125.92, 125.62, 125.55, 123.52, 122.47, 121.22, 115.89, 109.34, 43.42, 32.98, 25.73, 24.40. HPLC purity (water/CH$_3$CN): 98.98%, Rt: 12.87 min. HPLC purity (water/MeOH): 99.88%, Rt: 15.54 min.

1-(2-(2H-tetrazol-5-yl)ethyl)-3-(2-(thiazol-2-yl)ethyl)-1H-indole-5-carboxylic acid (15). The synthesis of 15 followed general procedure G to obtain the desired product as light yellow solid (52% yield). $^1$H NMR (500 MHz, DMSO-d$_6$) δ 8.17 (d, J=1.5 Hz, 1H), 7.73 (dd, J=8.6, 1.6 Hz, 1H), 7.69 (d, J=3.3 Hz, 1H), 7.54 (d, J=3.3 Hz, 1H), 7.48 (d, J=8.7 Hz, 1H), 7.25 (s, 1H), 4.57 (t, J=7.1 Hz, 2H), 3.36-3.30 (m, 4H), 3.14 (dd, J=8.5, 6.8 Hz, 2H). $^{13}$C NMR (126 MHz, DMSO-d$_6$) δ 169.45, 168.24, 142.02, 138.15, 127.55, 126.95, 122.51, 121.29, 121.17, 119.29, 114.57, 109.41, 43.55, 33.27, 24.80, 24.58. HPLC purity (water/CH$_3$CN): 99.53%, Rt: 7.41 min. HPLC purity (water/MeOH): 99.81%, Rt: 10.74 min.

1-(2-(2H-tetrazol-5-yl)ethyl)-3-(2-(pyridin-4-yl)ethyl)-1H-indole-5-carboxylic acid (16). The synthesis of 16 followed general procedure G to obtain the desired product as white solid (34% yield). Low resolution mass spectrometry [M]$^+$: 363.2. $^1$H NMR (500 MHz, DMSO-d$_6$) δ 8.45 (d, J=4.9 Hz, 2H), 8.17 (s, 1H), 7.82-7.75 (m, 1H), 7.33-7.25 (m, 3H), 7.15 (s, 1H), 4.38 (t, J=7.7 Hz, 2H), 3.06 (t, J=7.8 Hz, 2H), 3.02-2.94 (m, 4H). $^{13}$C NMR (126 MHz, DMSO-d$_6$) δ 173.98, 150.81, 149.40, 136.94, 126.68, 126.23, 123.95, 123.12, 120.22, 113.75, 108.03, 45.31, 35.01, 26.95, 25.56. HPLC purity (water/CH$_3$CN): 98.48%, Rt: 7.18 min. HPLC purity (water/MeOH): 99.73%, Rt: 9.83 min.

1-(2-(2H-tetrazol-5-yl)ethyl)-3-(2-(5-methylpyridin-2-yl)ethyl)-1H-indole-5-carboxylic acid (17). The synthesis of 17 followed general procedure G to obtain the desired product as white solid (19% yield). Low resolution mass spectrometry [M+Na]$^+$: 421.2. $^1$H NMR (500 MHz, DMSO-d$_6$) δ 12.43 (s, 1H), 8.38-8.30 (m, 1H), 8.12 (d, J=1.5 Hz, 1H), 7.71 (dd, J=8.7, 1.6 Hz, 1H), 7.50-7.43 (m, 2H), 7.18 (s, 1H), 7.13 (d, J=7.8 Hz, 1H), 4.57 (t, J=7.0 Hz, 2H), 3.36 (t, J=7.0 Hz, 2H), 3.06-3.02 (m, 2H), 3.02-2.99 (m, 2H), 2.25 (s, 3H). $^{13}$C NMR (126 MHz, DMSO-d$_6$) δ 168.24, 157.90, 153.80, 149.09, 138.12, 136.77, 130.12, 127.09, 122.41, 122.20, 121.24, 121.12, 115.71, 109.26, 43.39, 37.76, 24.61, 24.40, 17.55. HPLC purity (water/CH₃CN): 95.78%, Rt: 12.62 min. HPLC purity (water/MeOH): 95.97%, Rt: 15.22 min.

1-(2-(2H-tetrazol-5-yl)ethyl)-3-(2-([1,1'-biphenyl]-4-yl)ethyl)-1H-indole-5-carboxylic acid (18). The synthesis of 18 followed general procedure G to obtain the desired product as white solid (50% yield). ¹H NMR (500 MHz, DMSO-d₆) δ 12.45 (s, 1H), 8.20 (d, J=1.5 Hz, 1H), 7.73 (dd, J=8.7, 1.6 Hz, 1H), 7.64 (dd, J=8.3, 1.3 Hz, 2H), 7.59-7.55 (m, 2H), 7.49-7.43 (m, 3H), 7.36-7.31 (m, 3H), 7.24 (s, 1H), 4.59 (t, J=7.0 Hz, 2H), 3.38 (t, J=7.0 Hz, 2H), 3.04-3.00 (m, 2H), 2.96 (dd, J=8.6, 5.7 Hz, 2H). ¹³C NMR (126 MHz, DMSO-d₆) δ 168.26, 141.05, 140.15, 138.15, 137.77, 128.91, 128.86, 127.16, 127.12, 127.10, 126.54, 126.49, 122.45, 121.30, 121.17, 115.70, 109.30, 43.42, 35.44, 26.29, 24.44. HPLC purity (water/CH₃CN): 95.76%, Rt: 12.61 min. HPLC purity (water/MeOH): 95.98%, Rt: 15.21 min.

1-(2-(2H-tetrazol-5-yl)ethyl)-3-(4-morpholinophenethyl)-1H-indole-5-carboxylic acid (19). The synthesis of 19 followed general procedure G to obtain the desired product as white solid (82% yield). ¹H NMR (500 MHz, DMSO-d₆) δ 12.43 (s, 1H), 8.15 (d, J=1.5 Hz, 1H), 7.72 (dd, J=8.7, 1.6 Hz, 1H), 7.46 (d, J=8.6 Hz, 1H), 7.19 (s, 1H), 7.12-7.06 (m, 2H), 6.88-6.81 (m, 2H), 4.58 (t, J=7.0 Hz, 2H), 3.72 (dd, J=5.6, 3.9 Hz, 4H), 3.37 (t, J=7.0 Hz, 2H), 3.06-3.02 (m, 4H), 2.92 (dd, J=9.4, 6.3 Hz, 2H), 2.82 (dd, J=9.4, 6.2 Hz, 2H). ¹³C NMR (126 MHz, DMSO-d₆) δ 168.28, 149.31, 138.13, 132.53, 128.78, 127.12, 127.08, 122.41, 121.29, 121.11, 115.92, 115.24, 109.27, 66.15, 48.83, 43.39, 35.02, 26.68, 24.42. HPLC purity (water/CH₃CN): 99.09%, Rt: 8.70 min. HPLC purity (water/MeOH): 98.98%, Rt: 12.45 min.

1-(2-(2H-tetrazol-5-yl)ethyl)-3-(2-cyclohexylethyl)-1H-indole-5-carboxylic acid (20). The synthesis of 20 followed general procedure G to obtain the desired product as white solid (67% yield). ¹H NMR (500 MHz, DMSO-d₆) δ 12.44 (s, 1H), 8.14 (d, J=1.5 Hz, 1H), 7.72 (dd, J=8.6, 1.6 Hz, 1H), 7.46 (d, J=8.7 Hz, 1H), 7.14 (s, 1H), 4.58 (t, J=7.0 Hz, 2H), 3.37 (t, J=7.0 Hz, 2H), 2.67 (t, J=7.9 Hz, 2H), 1.76 (dd, J=12.5, 3.6 Hz, 2H), 1.69-1.60 (m, 3H), 1.49 (q, J=7.3 Hz, 2H), 1.26-1.12 (m, 4H), 0.92 (qd, J=12.1, 3.3 Hz, 2H). ¹³C NMR (126 MHz, DMSO-d₆) δ 168.26, 138.16, 127.15, 126.76, 122.35, 121.19, 121.00, 116.47, 109.25, 43.38, 37.42, 36.63, 32.75, 26.20, 25.77, 24.36, 21.53.

1-(2-(2H-tetrazol-5-yl)ethyl)-3-(2-(tetrahydro-2H-pyran-4-yl)ethyl)-1H-indole-5-carboxylic acid (21). The synthesis of 21 followed general procedure G to obtain the desired product as white solid (45% yield). ¹H NMR (500 MHz, DMSO-d₆) δ 12.43 (s, 1H), 8.15 (d, J=1.6 Hz, 1H), 7.72 (dd, J=8.6, 1.6 Hz, 1H), 7.47 (d, J=8.7 Hz, 1H), 7.15 (s, 1H), 4.59 (t, J=6.8 Hz, 2H), 3.83 (ddd, J=11.4, 4.5, 1.8 Hz, 2H), 3.38 (t, J=6.8 Hz, 2H), 3.27 (td, J=11.7, 2.1 Hz, 2H), 2.69 (t, J=7.7 Hz, 2H), 1.66-1.59 (m, 2H), 1.54 (q, J=7.3 Hz, 2H), 1.47 (ddd, J=10.8, 7.0, 3.8 Hz, 1H), 1.18 (qd, J=12.0, 4.4 Hz, 2H). ¹³C NMR (126 MHz, DMSO-d₆) δ 168.26, 138.16, 127.12, 126.89, 122.37, 121.18, 121.04, 116.10, 109.29, 67.03, 43.41, 36.80, 33.87, 32.67, 24.36, 21.00. Low resolution mass spectrometry [M]⁺: 363.2. HPLC purity (water/CH₃CN): 99.07%, Rt: 9.82 min. HPLC purity (water/MeOH): 99.43%, Rt: 13.84 min.

1-(2-(2H-tetrazol-5-yl)ethyl)-3-(2-(2,3-dihydrobenzo[b][1,4]dioxin-6-yl)ethyl)-1H-indole-5-carboxylic acid (22). The synthesis of 22 followed general procedure G to obtain the desired product as white solid (62% yield). ¹H NMR (500 MHz, DMSO-d₆) δ 12.43 (s, 1H), 8.14 (d, J=1.5 Hz, 1H), 7.72 (dd, J=8.6, 1.6 Hz, 1H), 7.46 (d, J=8.6 Hz, 1H), 7.20 (s, 1H), 6.75-6.71 (m, 2H), 6.66 (dd, J=8.2, 2.1 Hz, 1H), 4.58 (t, J=7.1 Hz, 2H), 4.19 (s, 4H), 3.37 (t, J=7.1 Hz, 2H), 2.91 (dd, J=9.4, 6.4 Hz, 2H), 2.79 (dd, J=9.4, 6.5 Hz, 2H). ¹³C NMR (126 MHz, DMSO-d₆) δ 168.26, 143.06, 141.50, 138.12, 134.80, 127.09, 127.06, 122.41, 121.33, 121.12, 120.99, 116.70, 116.66, 115.84, 109.24, 64.02, 63.92, 43.37, 35.15, 26.52, 24.40.

Scheme 6.

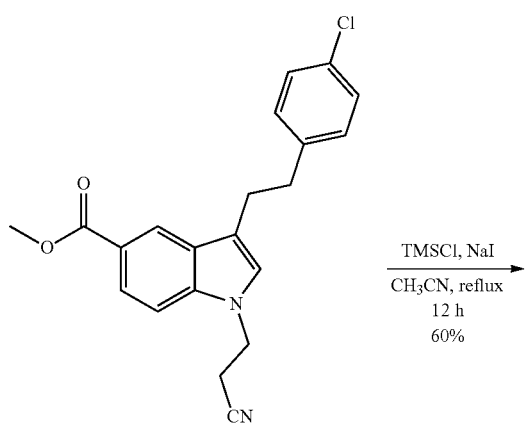

A

120b

-continued
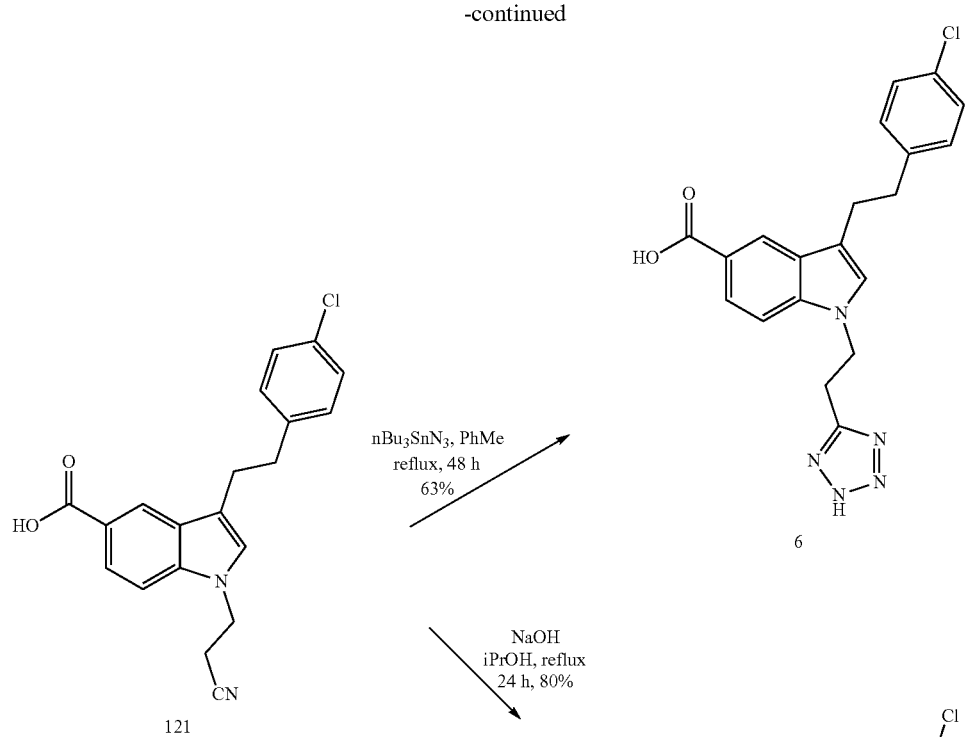
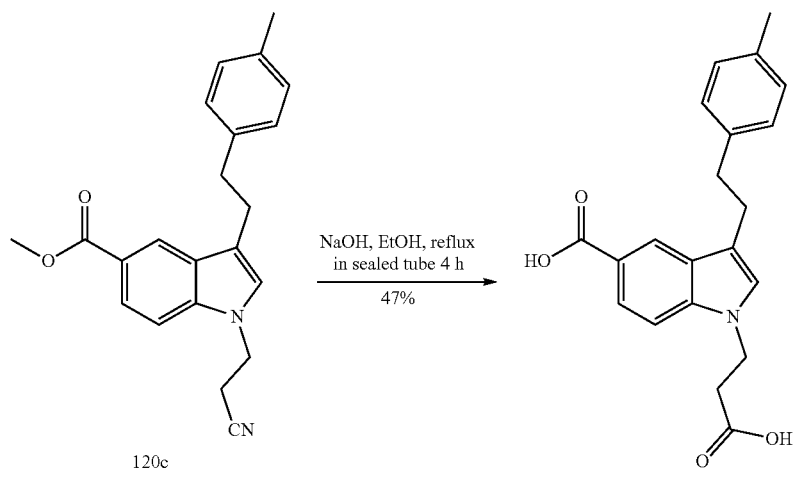

3-(4-chlorophenethyl)-1-(2-cyanoethyl)-1H-indole-5-carboxylic acid (121). Compound 120b (860 mg, 2.34 mmol) was dissolved in 20 mL anhydrous CH$_3$CN, and TMSCl (0.580 mL, 4.68 mmol) and NaI (701.1 mg, 4.68 mmol) were added. The reaction mixture was brought to reflux for 48 h. The reaction was then quenched with H$_2$O, and dissolved in EtOAc. The combined organic layers were washed with H$_2$O, 5% Na$_2$S$_2$O$_3$, and brine, and evaporated in vacuo. The residue was subjected to flash column chromatography (100:1 CH$_2$Cl$_2$/MeOH) to obtain the desired product as white solid (0.5 g, 60% yield). R$_f$=0.5 (40:1 CH$_2$Cl$_2$/MeOH). $^1$H NMR (CD$_3$OD, 300 MHz): δ 8.26 (s, 1H), 7.87 (d, J=7.5 Hz, 1H), 7.48 (d, J=8.4 Hz, 1H), 7.21 (d, J=8.4 Hz, 2H), 7.13 (d, J=8.4 Hz, 2H), 7.09 (s, 1H), 4.46 (t, J=6.6 Hz, 2H), 3.06-2.99 (m, 4H), 2.92 (t, J=6.6 Hz, 2H). $^{13}$C NMR (DMSO-d$_6$, 75 MHz): δ 168.9, 141.4, 138.9, 131.1, 130.9, 128.78, 127.8, 123.2, 122.1, 122.0, 119.5, 116.4, 110.4, 41.8, 35.7, 26.9, 19.2. LRMS (ESI) m/z=353.3 [M+H]$^+$.

1-(2-(2H-tetrazol-5-yl)ethyl)-3-(4-chlorophenethyl)-1H-indole-5-carboxylic acid (6). The synthesis of 5 followed general procedure G to obtain the desired product as white solid (0.083 g, 63% yield). $^1$H NMR (500 MHz, DMSO-d$_6$) δ 12.50 (s, 1H), 8.21 (d, J=1.5 Hz, 1H), 7.76 (dd, J=8.6, 1.6 Hz, 1H), 7.52 (d, J=8.6 Hz, 1H), 7.34-7.24 (m, 5H), 3.01 (td, J=6.0, 3.1 Hz, 2H), 2.95 (ddd, J=8.7, 6.6, 1.9 Hz, 2H). $^{13}$C NMR (126 MHz, DMSO-d$_6$) δ 168.18, 140.70, 138.51, 130.42, 130.25, 128.09, 127.59, 127.34, 122.78, 121.69, 121.31, 116.13, 109.68, 34.96, 26.13. HPLC purity (water/CH$_3$CN): 95.80%, Rt: 12.59 min. HPLC purity (water/MeOH): 96.00%, Rt: 15.22 min.

1-(2-carboxyethyl)-3-(4-chlorophenethyl)-1H-indole-5-carboxylic acid (23). To a solution of 121 (164.4 mg, 0.465 mmol) in i-PrOH (30 mL) was added NaOH (8 mL, 3 M aqueous solution). The resulting mixture was refluxing for 12 h. Upon completion, the reaction was cooled down to room temperature and evaporated to dryness. The residue was dissolved in water and extracted with EtOAc (3 times). Then the aqueous layer was acidified with 3 M HCl and stirred for additional 3 h. The mixture was filtered and the filter cake was wash with water and dried with lyophilization to provide the desired product as white solid (139.3 mg, 80% yield). $^1$H NMR (500 MHz, DMSO-d$_6$) δ 12.40 (s, 2H), 8.23-8.09 (m, 1H), 7.74 (dq, J=8.7, 1.9 Hz, 1H), 7.51 (dd, J=8.7, 1.4 Hz, 1H), 7.33-7.24 (m, 5H), 4.36 (t, J=6.7 Hz, 2H), 2.99 (dd, J=8.8, 5.4 Hz, 2H), 2.96-2.91 (m, 2H), 2.72 (td, J=6.8, 1.8 Hz, 2H). $^{13}$C NMR (126 MHz, DMSO-d$_6$) δ 172.37, 168.35, 140.82, 138.20, 130.43, 130.27, 128.35, 128.26, 128.12, 127.39, 127.03, 122.41, 121.26, 121.08, 115.18, 109.57, 41.50, 35.14, 34.71, 26.26.

1-(2-carboxyethyl)-3-(4-methylphenethyl)-1H-indole-5-carboxylic acid (24). Compound 24 was synthesized using the same procedure as 23 to obtain the desired product as white solid. $^1$H NMR (500 MHz, DMSO-d$_6$) δ 12.40 (s, 2H), 8.18 (q, J=1.5 Hz, 1H), 7.73 (dt, J=8.7, 1.5 Hz, 1H), 7.51 (dd, J=8.7, 2.4 Hz, 1H), 7.25 (d, J=2.4 Hz, 1H), 7.14 (dd, J=8.0, 2.4 Hz, 2H), 7.11-7.02 (m, 2H), 4.36 (td, J=6.9, 2.3 Hz, 2H), 3.03-2.93 (m, 2H), 2.89 (dt, J=9.1, 4.6 Hz, 2H), 2.73 (td, J=6.9, 2.4 Hz, 2H), 2.26 (d, J=2.3 Hz, 3H). $^{13}$C NMR (126 MHz, DMSO-d$_6$) δ 172.47, 168.44, 138.78, 138.25, 134.72, 128.87, 128.25, 127.31, 127.11, 122.43, 121.32, 121.06, 115.62, 109.59, 41.51, 35.59, 34.71, 26.69, 20.70.

Scheme 7.

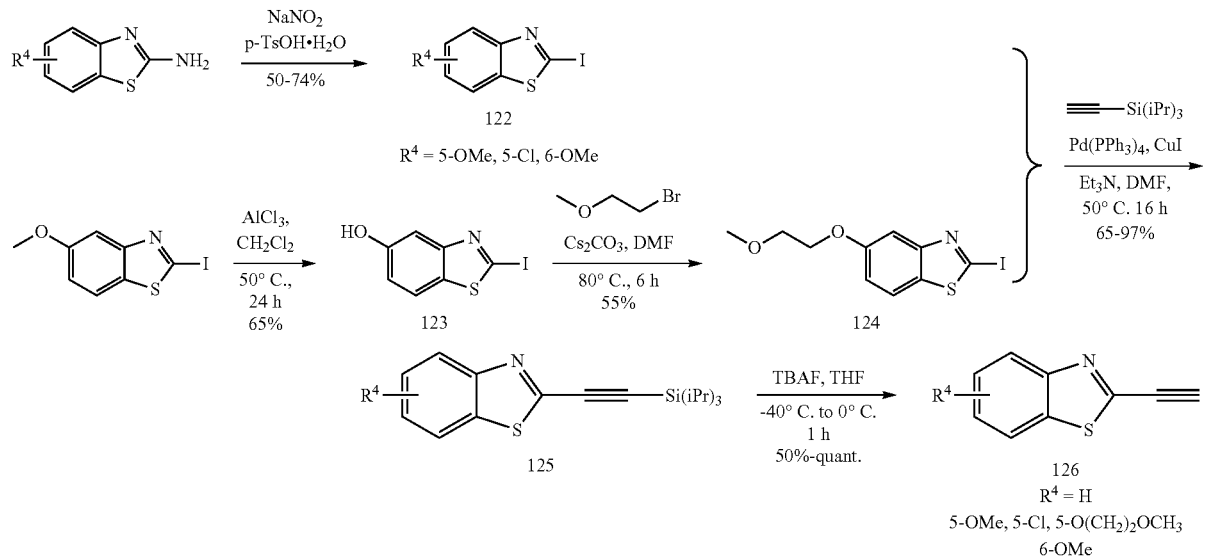

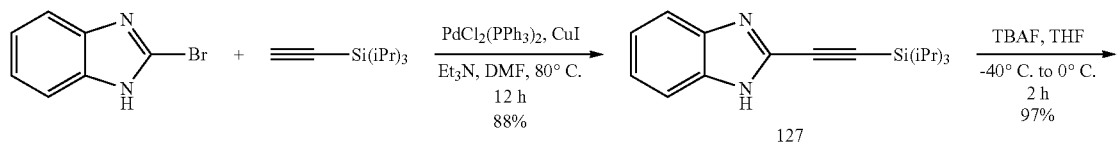

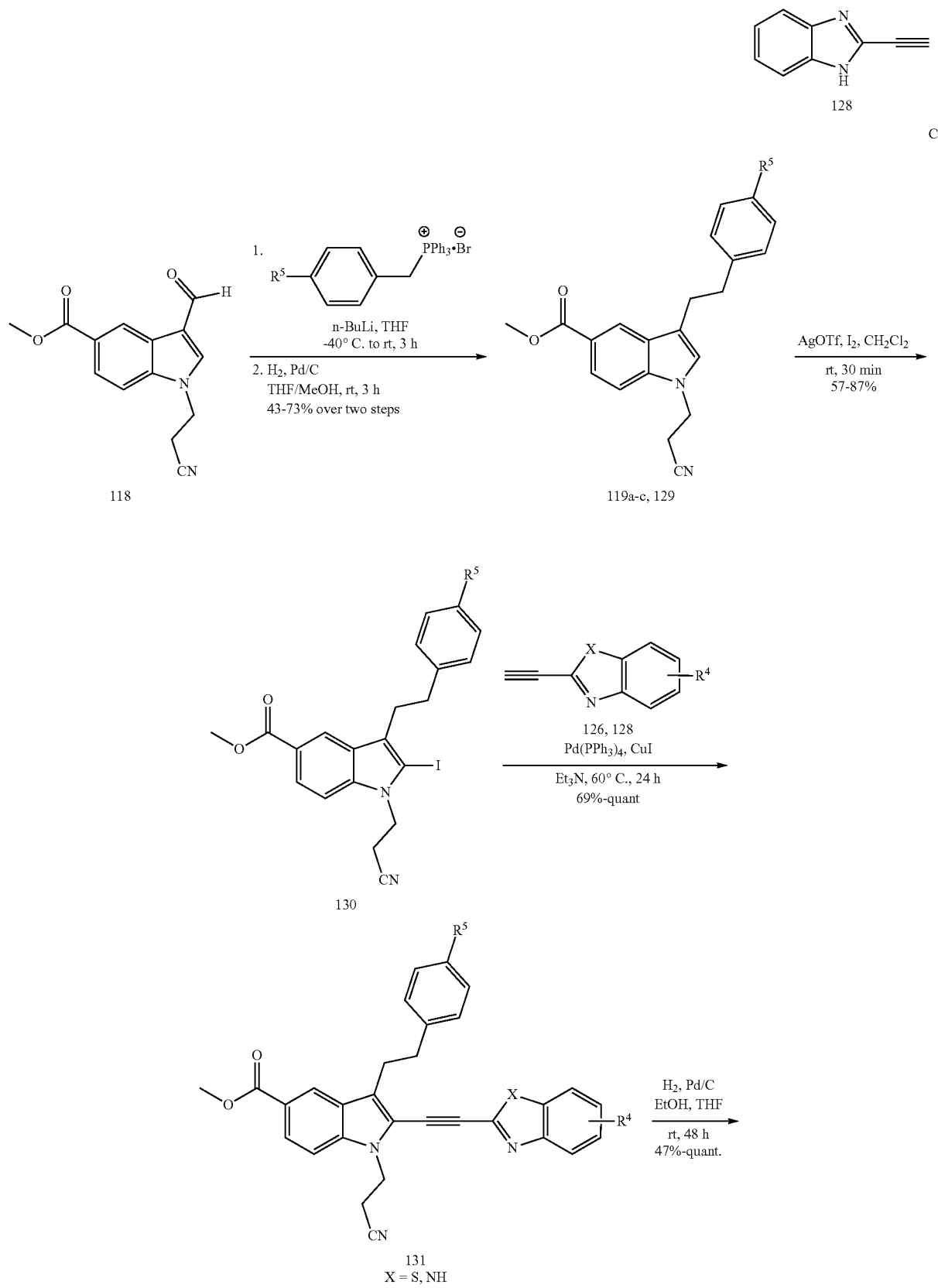

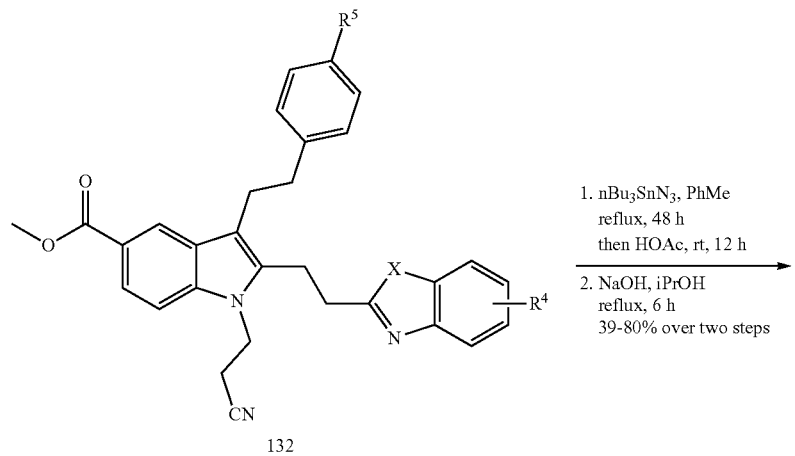
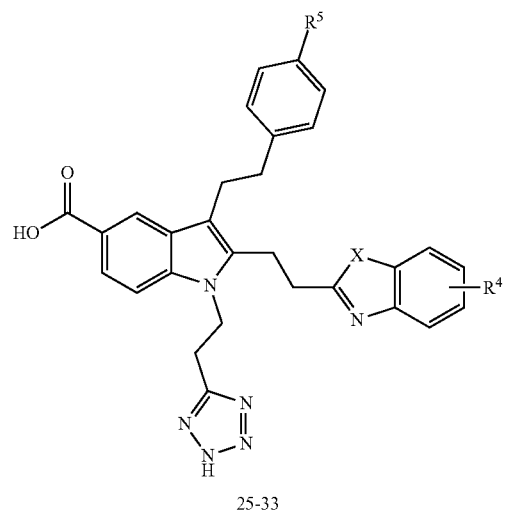
25-33
25 R⁵ = H, R⁴ = H, X = S     30. R⁵ = Cl, R⁴ = 5-Cl, X = S
26 R⁵ = F, R⁴ = H, X = S     31. R⁵ = Cl, R⁴ = 5-OMe, X = S
27 R⁵ = Cl, R⁴ = H, X = S    32. R⁵ = Cl, R⁴ = 5-O(CH₂)₂OCH₃, X = S
28 R⁵ = CH₃, R⁴ = H, X = S   33. R⁵ = Cl, R⁴ = 6-OMe, X = S
29. R⁵ = Cl, R⁴ = H, X = NH
D
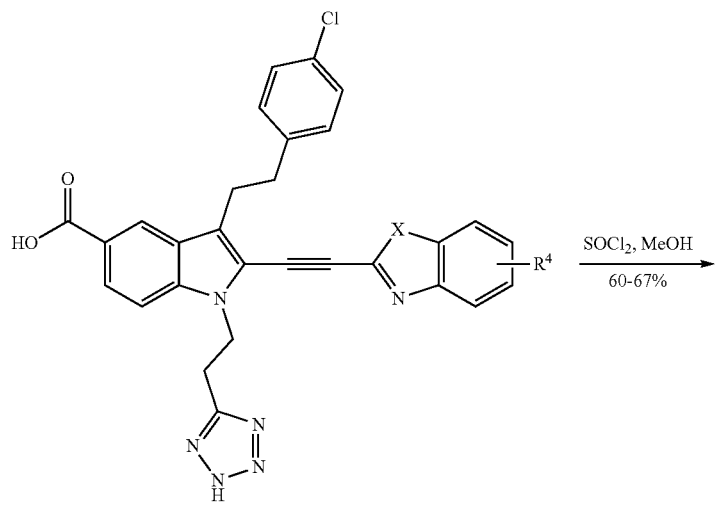
29, 31

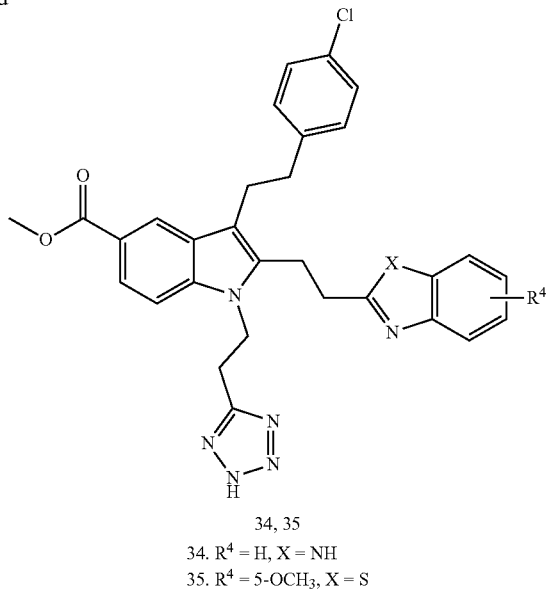

34, 35
34. R⁴ = H, X = NH
35. R⁴ = 5-OCH₃, X = S

Synthesis of substituted 2-iodo benzothiazoles from 2-aminobenzothiazoles (122). In a 100 mL round bottom flask, substituted benzo[d]thiazol-2-amine (0.83 mmol) and p-toluenesulfonic acid monohydrate (473.6 mg, 2.49 mmo) were suspended in 10 mL anhydrous MeCN and cooled down to 0° C. Then NaNO₂ (114.8 mg, 1.66 mmol) and KI (358.56 mg, 2.16 mmol) were dissolved in 20 mL H₂O and added to the mixture via addition funnel. The reaction was allowed to warm up to room temperature and stirred overnight. After 16 h, the reaction was quenched with 10% aqueous Na₂S₂O₃ solution, extracted two times with ethyl acetate and concentrated under vacuum. The crude product was purified via flash column chromatography.

2-Iodo-5-methoxybenzo[d]thiazole (122a). Yellow solid (hexanes:ethyl acetate=6:1, 121.4 mg, 50% yield). ¹H-NMR (CDCl₃, 300 MHz) δ 7.66 (d, J=9.0 Hz, 1H), 7.49 (d, J=2.4 Hz, 1H), 7.01 (dd, J=2.4, 8.7 Hz, 1H), 3.85 (s, 3H). ¹³C-NMR (CDCl₃, 75 MHz) δ 159.18, 155.54, 131.23, 120.80, 115.96, 106.38, 105.20, 55.87.

5-Chloro-2-iodobenzo[d]thiazole (122b). The reaction was run for 3 d instead of 16 h to afford the desired product as white solid (hexanes:ethyl acetate=6:1, 74% yield). ¹H-NMR (CDCl₃, 300 MHz) δ 8.01 (d, J=1.8 Hz, 1H), 7.75 (d, J=8.7 Hz, 1H), 7.38 (dd, J=2.1 Hz, 8.4 Hz, 1H). ¹³C-NMR (CDCl₃, 75 MHz) δ 155.08, 137.67, 132.82, 126.38, 122.60, 121.28, 107.72.

2-iodo-6-methoxybenzo[d]thiazole (122c). Light red solid (hexanes:ethyl acetate=20:1, 72% yield). Low resolution mass spectrometry [M+H]⁺: 292.0. ¹H NMR (500 MHz, DMSO-d₆) δ 7.89 (dt, J=9.0, 1.3 Hz, 1H), 7.70-7.65 (m, 1H), 7.11-7.05 (m, 1H), 3.82 (s, 3H). ¹³C NMR (126 MHz, DMSO-d₆) δ 157.55, 148.79, 139.83, 122.27, 115.63, 106.43, 104.12, 55.74.

2-Iodobenzo[d]thiazol-5-ol (123). Compound 122a (2.45 g, 8.41 mmol) was placed in a 100 mL oven-dried round bottom flask. The flask was evacuated and flushed three times with argon. Subsequently 30 mL anhydrous DCE was added via syringe. To this stirring solution was added portionwise AlCl₃ (5.61 g, 42.08 mmol). The mixture was heated to 50° C. for 24 h. Upon completion, the reaction was cooled down to room temperature and the solids were removed via filtration. The filtrate was treated with saturated aqueous NaHCO₃-solution, extracted two times with ethyl acetate and concentrated under vacuum. The crude product was purified via flash column chromatography (hexanes:ethyl acetate=5:1 to 2:1) to isolate the desired product as pale yellow solid (1.53 g, 65% yield). ¹H-NMR (CD₃OD, 300 MHz) δ 7.74-7.67 (m, 1H), 7.35-7.29 (m, 1H), 6.98-6.91 (m, 1H). ¹³C-NMR (CD₃OD, 75 MHz) δ 157.08, 155.36, 129.62, 120.93, 115.70, 108.27, 106.70.

2-Iodo-5-(2-methoxyethoxy)benzo[d]thiazole (124). In a 25 mL round bottom flask, compound 123 (75 mg, 0.27 mmol) was dissolved in 5 mL anhydrous DMF. Cs₂CO₃ (263.9 mg, 0.81 mmol) and 1-bromo-2-methoxy-ethane (0.038 mL, 0.40 mmol) were added. The mixture was heated to 80° C. for 6 h and cooled to room temperature upon completion. It was quenched with brine, extracted two times with ethyl acetate and concentrated under vacuum. The crude product was purified via flash column chromatography (hexanes:ethyl acetate=3:1) to isolate the desired product as white solid (49.7 mg, 55% yield). ¹H-NMR (CDCl₃, 300 MHz) δ 7.67 (d, J=9.0 Hz, 1H), 7.50 (d, J=2.4 Hz, 1H), 7.12-7.03 (m, 1H), 4.16 (t, J=4.8 Hz, 2H), 3.77 (t, J=4.5 Hz, 2H), 3.45 (s, 3H). ¹³C-NMR (CDCl₃, 75 MHz) δ 158.33, 155.44, 131.48, 120.83, 116.49, 106.38, 105.99, 71.09, 67.94, 59.49.

Sonogashira coupling at the 2ⁿᵈ position of diverse heterocycles (125). 2-halobenzo[d]thiazole (0.23 mmol), Pd(PPh₃)₄ (26.98 mg, 0.023 mmol), CuI (6.6 mg, 0.035 mmo) were placed in a 20 mL oven-dried scintillation vial. The vile was evacuated and flushed three times with argon. Then ethynyltriisopropylsilane (0.15 mL, 0.70 mmol), anhydrous Et₃N (1 mL), DMF (1 mL) were added via syringe. The vial was sealed and stirred at 50° C. for 16 h. Upon completion, the reaction was quenched with brine, extracted two times with Et₂O and concentrated under vacuum. The crude product was purified via flash column chromatography to offer the desired product.

2-((Triisopropylsilyl)ethynyl)benzo[d]thiazole (125a). Colorless liquid (hexanes:ethyl acetate=40:1, 87% yield). ¹H-NMR (CDCl₃, 300 MHz) δ 8.05 (d, J=8.4 Hz, 1H), 7.84 (d, J=8.4 Hz, 1H), 7.54-7.47 (m, 1H), 7.46-7.40 (m, 1H), 1.16 (s, 18H). $^{13}$C-NMR (CDCl$_3$, 75 MHz) δ 152.98, 148.69, 135.47, 126.90, 126.52, 123.96, 121.48, 101.02, 98.98, 18.83, 11.39.

5-Methoxy-2-((triisopropylsilyl)ethynyl)benzo[d]thiazole (125b). Colorless liquid (hexanes:ethyl acetate=20:1, 65% yield). $^1$H-NMR (CDCl$_3$, 300 MHz) δ 7.65 (d, J=8.7 Hz, 1H), 7.51 (d, J=2.4 Hz, 1H), 7.07 (dd, J=2.4, 8.7 Hz, 1H), 3.81 (s, 3H), 1.15 (s, 18H). $^{13}$C-NMR (CDCl$_3$, 75 MHz) δ 159.60, 154.34, 149.62, 127.36, 121.62, 117.15, 105.76, 100.64, 99.16, 55.77, 18.81, 11.40.

5-Chloro-2-((triisopropylsilyl)ethynyl)benzo[d]thiazole (125c). Colorless liquid (hexanes:ethyl acetate=30:1, 97% yield). $^1$H-NMR (CDCl$_3$, 300 MHz) δ 8.02 (d, J=2.1 Hz, 1H), 7.73 (d, J=8.4 Hz, 1H), 7.40 (dd, J=2.1, 8.7 Hz, 1H), 1.16 (s, 18H). $^{13}$C-NMR (CDCl$_3$, 75 MHz) δ 153.84, 150.39, 133.69, 133.07, 127.05, 123.61, 122.16, 102.25, 98.60, 18.81, 11.38.

5-(2-methoxyethoxy)-2-((triisopropylsilyl)ethynyl)benzo[d]thiazole (125d). Colorless liquid (hexanes:ethyl acetate=7:1, 76% yield). $^1$H-NMR (CDCl$_3$, 300 MHz) δ 7.66 (d, J=9.0 Hz, 1H), 7.53 (d, J=2.4 Hz, 1H), 7.13 (dd, J=2.4, 9.0 Hz, 1H), 4.18 (t, J=4.6 Hz, 2H), 3.78 (t, J=4.6 Hz, 2H), 3.45 (s, 3H), 1.15 (s, 18H). $^{13}$C-NMR (CDCl$_3$, 75 MHz) δ 158.76, 154.06, 149.67, 127.53, 121.69, 117.75, 106.44, 101.02, 99.00, 71.10, 67.88, 59.48, 18.82, 11.39.

6-methoxy-2-((triisopropylsilyl)ethynyl)benzo[d]thiazole (125e). Brown solid (hexanes:ethyl acetate=20:1, 95% yield). Low resolution mass spectrometry [M+H]$^+$: 346.2. $^1$H NMR (500 MHz, Chloroform-d) δ 7.92 (d, J=9.0 Hz, 1H), 7.25 (d, J=2.5 Hz, 1H), 7.09 (dd, J=9.0, 2.5 Hz, 1H), 3.86 (s, 3H), 1.19-1.13 (m, 21H). $^{13}$C NMR (126 MHz, Chloroform-d) δ 158.75, 147.24, 145.80, 136.82, 124.22, 116.45, 103.31, 99.82, 98.88, 55.78, 18.62, 11.20.

Deprotection of the silyl group using TBAF to synthesized 126. Compound 122 or 124 (0.20 mmol) was dissolved in 5 mL THF and cooled down to −40° C. 1 M TBAF solution (0.41 mL, 0.41 mmol) was added dropwise via a syringe. The reaction was allowed to warm up and completed within 1 h. It was quenched with brine, extracted two times with ethyl acetate and concentrated under vacuum. The crude product was purified via flash column chromatography to offer the desired product.

2-Ethynylbenzo[d]thiazole (126a). Brown semi solid (hexanes:ethyl acetate=20:1, quantitative yield). $^1$H-NMR (CDCl$_3$, 300 MHz) δ 8.06 (d, J=7.5 Hz, 1H), 7.84 (d, J=8.1 Hz, 1H), 7.55-7.41 (m, 2H), 3.60 (s, 1H). $^{13}$C-NMR (CDCl$_3$, 75 MHz) δ 152.62, 147.68, 135.22, 126.97, 126.76, 123.95, 121.49, 84.71, 76.87, 18.02, 12.62.

2-Ethynyl-5-methoxybenzo[d]thiazole (126b). White solid (hexanes:ethyl acetate=10:1, 50% yield). $^1$H-NMR (CDCl$_3$, 300 MHz) δ 7.70 (d, J=8.7 Hz, 1H), 7.52 (d, J=2.4 Hz, 1H), 7.11 (d, J=2.4, 9.0 Hz, 1H), 3.88 (s, 3H), 3.57 (s, 1H). $^{13}$C-NMR (CDCl$_3$, 75 MHz) δ 159.71, 154.25, 148.57, 127.31, 121.74, 117.57, 105.86, 83.89, 77.10, 55.84.

5-Chloro-2-ethynylbenzo[d]thiazole (126c). Brown solid (hexanes:ethyl acetate=20:1 to 15:1, 87% yield). $^1$H-NMR (CDCl$_3$, 300 MHz) δ 8.00 (d, J=1.5 Hz, 1H), 7.72 (d, J=8.7 Hz, 1H), 7.39 (dd, J=2.1, 8.7 Hz, 1H), 3.63 (s, 1H). $^{13}$C-NMR (CDCl$_3$, 75 MHz) δ 153.61, 149.39, 133.58, 133.23, 127.36, 123.75, 122.29, 85.04, 76.63.

2-Ethynyl-5-(2-methoxyethoxy)benzo[d]thiazole (126d). Brown solid (hexanes:ethyl acetate=3:1 to 2:1, 93% yield). $^1$H-NMR (CDCl$_3$, 300 MHz) δ 7.65 (d, J=9.0 Hz, 1H), 7.48 (d, J=1.5 Hz, 1H), 7.12 (dd, J=1.8, 8.7 Hz, 1H), 4.15 (t, J=4.5 Hz, 2H), 3.75 (t, J=4.5 Hz, 2H), 3.58 (s, 1H), 3.42 (s, 3H). $^{13}$C-NMR (CDCl$_3$, 75 MHz) δ 158.79, 154.09, 148.56, 127.49, 121.78, 117.98, 106.59, 84.11, 77.02, 71.05, 67.88, 59.41.

2-ethynyl-6-methoxybenzo[d]thiazole (126e). Brown solid (hexanes:ethyl acetate=15:1, 68% yield). Low resolution mass spectrometry [M+H]$^+$: 190.1. $^1$H NMR (500 MHz, Chloroform-d) δ 7.94 (dd, J=9.0, 0.9 Hz, 1H), 7.28 (dd, J=2.6, 1.2 Hz, 1H), 7.16-7.10 (m, 1H), 3.92-3.85 (m, 3H), 3.55 (s, 1H). $^{13}$C NMR (126 MHz, Chloroform-d) δ 159.00, 147.19, 144.74, 136.82, 124.46, 116.74, 103.35, 83.31.

2-((Triisopropylsilyl)ethynyl)-1H-benzo[d]imidazole (127). 2-bromo benzo[d]imidazole (45.32 mg, 0.23 mmol), Pd(PPh$_3$)$_3$Cl$_2$ (16.14 mg, 0.023 mmol), CuI (6.6 mg, 0.035 mmo) were placed in a 20 mL oven-dried scintillation vile. The vile was evacuated and flushed three times with argon. Then ethynyltriisopropylsilane (0.15 mL, 0.70 mmol), anhydrous Et$_3$N (1 mL), DMF (1 mL) were added via syringe. The vile was sealed and stirred at 80° C. for 12 h. Upon completion, the reaction was quenched with brine, extracted two times with Et$_2$O and concentrated under vacuum. The crude product was purified via flash column chromatography (hexanes:ethyl acetate=8:1 to 7:1) to offer the desired product as white solid (88% yield). $^1$H-NMR (CDCl$_3$, 300 MHz) δ 11.23 (brs, 1H), 7.67 (dd, J=3.0, 6.0 Hz, 2H), 7.28 (dd, J=3.0, 6.0 Hz, 2H), 1.01 (s, 18H). $^{13}$C-NMR (CDCl$_3$, 75 MHz) δ 138.15, 135.37, 123.71, 115.69, 115.65, 96.58, 96.48, 18.66, 11.27.

2-Ethynyl-1H-benzo[d]imidazole (128). Compound 127 (59.64 mg, 0.20 mmol) was dissolved in 5 mL THF and cooled down to −40° C. 1 M TBAF solution (0.41 mL, 0.41 mmol) was added dropwise via a syringe. The reaction was allowed to warm up and completed within 1 h. It was quenched with brine, extracted two times with ethyl acetate and concentrated under vacuum. The crude product was purified via flash column chromatography (hexanes:ethyl acetate=1:1) to offer the desired product as white solid (97% yield). $^1$H-NMR (DMSO-d$_6$, 300 MHz) δ 13.16 (brs, 1H), 7.54 (s, 2H), 7.31-7.18 (m, 2H), 4.65 (s, 1H). $^{13}$C NMR (DMSO-d$_6$, 75 MHz): δ 134.7, 124.0, 123.8, 123.4, 83.9, 75.8.

Methyl 1-(2-cyanoethyl)-3-(4-fluorophenethyl)-1H-indole-5-carboxylate (129). The synthesis of 129 followed general procedures B and D to obtain the desired product as white solid (43% yield over two steps) using the Wittig salt, (4-fluorobenzyl) triphenylphosphonium bromide. $^1$H-NMR (CDCl$_3$, 300 MHz) δ 8.31 (s, 1H), 7.94 (d, J=8.4 Hz, 1H), 7.27 (d, J=8.7 Hz, 1H), 7.17-7.05 (m, 2H), 7.05-7.01 (m, 2H), 6.92 (s, 1H), 4.35 (t, J=6.3 Hz, 2H), 3.93 (s, 3H), 3.10-2.89 (m, 4H), 2.76 (t, J=6.6 Hz, 2H). $^{13}$C-NMR (CDCl$_3$, 75 MHz) δ 168.20, 163.18, 159.96, 138.48, 137.67, 137.63, 130.16, 130.05, 128.20, 126.24, 123.86, 122.60, 121.88, 117.88, 117.38, 115.40, 115.12, 108.63, 52.19, 42.20, 35.76, 27.22, 19.42. MS (ESI) m/z=351.2 [M+H]$^+$.

Methyl 1-(2-cyanoethyl)-2-iodo-3-phenethyl-1H-indole-5-carboxylate (130a). The synthesis of 130a followed general procedure E to obtain the desired product as white solid (hexanes:ethyl acetate=7:1 to 6:1 to 5:1 to 4:1, 70% yield). $^1$H-NMR (CDCl$_3$, 300 MHz) δ 8.26 (s, 1H), 7.91 (d, J=8.7 Hz, 1H), 7.36 (d, J=8.7 Hz, 1H), 7.30-7.14 (m, 5H), 4.46 (t, J=7.2 Hz, 2H), 3.95 (s, 3H), 3.09-2.98 (m, 2H), 2.95-2.85 (m, 2H), 2.72 (t, J=7.2 Hz, 2H). $^{13}$C-NMR (CDCl$_3$, 75 MHz) δ 167.84, 141.47, 140.22, 128.93, 128.62, 127.91, 126.37, 124.10, 124.05, 122.40, 121.54, 116.98, 109.29, 87.18, 52.32, 43.05, 36.55, 29.87, 18.77.

Methyl 1-(2-cyanoethyl)-3-(4-fluorophenethyl)-2-iodo-1H-indole-5-carboxylate (130b).

The synthesis of 130b followed general procedure E to obtain the desired product as white solid (hexanes:ethyl acetate=3:1 to 2:1, 74% yield). $^1$H-NMR (CDCl$_3$, 300 MHz) δ $^{13}$C-NMR (CDCl$_3$, 75 MHz) δ 8.19 (d, J=0.9 Hz, 1H), 7.91 (dd, J=1.5, 8.7 Hz, 1H), 7.36 (d, J=8.7 Hz, 1H), 7.12-7.03 (m, 2H), 6.93 (t, J=8.7 Hz, 2H), 4.49 (t, J=6.9 Hz, 2H), 3.95 (s, 3H), 3.02 (t, J=7.6 Hz, 2H), 2.88 (t, J=7.5 Hz, 2H), 2.75 (t, J=7.2 Hz, 2H). $^{13}$C-NMR (CDCl$_3$, 75 MHz) δ 167.79, 140.20, 137.05, 137.01, 130.40, 130.30, 127.88, 124.17, 123.78, 122.47, 121.51, 116.82, 115.42, 115.14, 109.22, 87.21, 52.30, 43.06, 35.66, 29.97, 18.78.

Methyl 3-(4-chlorophenethyl)-1-(2-cyanoethyl)-2-iodo-1H-indole-5-carboxylate (130c). The synthesis of 130c followed general procedure E to obtain the desired product as pale yellow solid (hexanes:ethyl acetate=3:1 to 2:1, 87% yield). $^1$H NMR (500 MHz, DMSO-d$_6$) δ 8.06 (d, J=1.2 Hz, 1H), 7.72 (d, J=1.2 Hz, 2H), 7.26 (d, J=8.4 Hz, 2H), 7.14 (d, J=8.4 Hz, 2H), 4.55 (t, J=6.6 Hz, 2H), 3.86 (s, 3H), 2.97 (dt, J=16.2, 6.8 Hz, 4H), 2.83 (dd, J=8.5, 6.7 Hz, 2H). $^{13}$C NMR (126 MHz, DMSO-d$_6$) δ 166.81, 140.07, 139.76, 130.59, 130.37, 128.40, 128.21, 128.05, 127.07, 122.42, 121.64, 120.98, 120.21, 118.09, 110.49, 91.37, 51.81, 42.30, 35.07, 28.90, 18.12.

Methyl 1-(2-cyanoethyl)-2-iodo-3-(4-methylphenethyl)-1H-indole-5-carboxylate (130d). The synthesis of 130d followed general procedure E to obtain the desired product as white solid (hexanes:ethyl acetate=4:1 to 3:1, 57% yield). $^1$H-NMR (CDCl$_3$, 300 MHz) δ 8.25 (d, J=0.9 Hz, 1H), 7.91 (dd, J=1.5, 8.7 Hz, 1H), 7.36 (d, J=8.7 Hz, 1H), 7.14-7.06 (m, 4H), 4.52 (t, J=7.2 Hz, 2H), 3.95 (s, 3H), 3.06-2.99 (m, 2H), 2.90-2.82 (m, 2H), 2.76 (t, J=7.2 Hz, 2H), 2.33 (s, 3H). $^{13}$C-NMR (CDCl$_3$, 75 MHz) δ 167.85, 140.17, 138.44, 135.83, 129.27, 128.73, 127.96, 124.33, 124.13, 122.43, 121.62, 116.85, 109.12, 86.91, 52.30, 43.09, 36.13, 30.01, 21.29, 18.75. MS (ESI) m/z=495.2 [M+Na]$^+$.

Methyl 2-(benzo[d]thiazol-2-ylethynyl)-1-(2-cyanoethyl)-3-phenethyl-1H-indole-5-carboxylate (131a). The synthesis of compound 131a followed general procedure C to obtain the desired product as dark yellow solid (CH$_2$Cl$_2$ to hexanes:ethyl acetate=2:1 to 1:1, 69% yield). $^1$H-NMR (CDCl$_3$, 300 MHz) δ 8.35 (s, 1H), 8.11 (dd, J=0.9, 8.1 Hz, 1H), 8.05 (dd, J=1.5, 8.7 Hz, 1H), 7.91 (dd, J=0.9 Hz, 8.1 Hz, 1H), 7.60-7.53 (m, 1H), 7.53-7.46 (m, 1H), 7.38 (d, J=8.7 Hz, 1H), 7.28-7.21 (m, 2H), 7.20-7.13 (m, 3H), 4.60 (t, J=6.9 Hz, 2H), 3.96 (s, 3H), 3.29 (t, J=7.8 Hz, 2H), 3.06 (t, J=7.8 Hz, 2H), 2.87 (t, J=6.9 Hz, 2H), $^{13}$C-NMR (CDCl$_3$, 75 MHz) δ 167.70, 153.28, 147.54, 141.34, 139.38, 135.71, 128.88, 128.59, 127.75, 127.25, 126.81, 126.77, 126.40, 126.38, 124.04, 123.40, 123.16, 121.64, 118.60, 116.99, 109.29, 92.64, 85.63, 52.33, 40.64, 36.92, 27.73, 19.10.

Methyl 2-(benzo[d]thiazol-2-ylethynyl)-1-(2-cyanoethyl)-3-(4-fluorophenethyl)-1H-indole-5-carboxylate (131b). The synthesis of compound 131b followed general procedure C to obtain the desired product as yellow solid (DCM to hexanes:ethyl acetate=3:1 to 2:1 to 1:1, 77% yield). $^1$H-NMR (CDCl$_3$, 300 MHz) δ 8.29 (s, 1H), 8.12 (d, J=7.8 Hz, 1H), 8.06 (d, J=8.4 Hz, 1H), 7.92 (d, J=7.5 Hz, 1H), 7.63-7.44 (m, 2H), 7.37 (d, J=8.4 Hz, 1H), 7.16-7.05 (m, 2H), 7.01-6.87 (m, 2H), 4.60 (t, J=5.7 Hz, 2H), 3.96 (s, 3H), 3.26 (t, J=6.6 Hz, 2H), 3.04 (t, J=6.6 Hz, 2H), 2.89 (t, J=6.0 Hz, 2H). $^{13}$C-NMR (CDCl$_3$, 75 MHz) δ 167.68, 153.29, 147.43, 139.38, 137.00, 135.68, 130.37, 130.26, 127.37, 126.88, 126.72, 126.43, 124.06, 123.33, 123.20, 121.67, 118.69, 116.99, 115.47, 115.19, 109.35, 92.64, 85.52, 52.35, 40.64, 36.06, 27.84, 19.12.

Methyl 2-(benzo[d]thiazol-2-ylethynyl)-3-(4-chlorophenethyl)-1-(2-cyanoethyl)-1H-indole-5-carboxylate (131c). The synthesis of compound 131c followed general procedure C to obtain the desired product as dark yellow solid (CH$_2$Cl$_2$ to hexanes:ethyl acetate=3:1 to 2:1 to 1:1, 85% yield). $^1$H-NMR (CDCl$_3$, 300 MHz) δ 8.29 (d, J=1.5 Hz, 1H), 8.15-8.10 (m, 1H), 8.06 (dd, J=1.5, 8.7, 1H), 7.95-7.90 (m, 1H), 7.62-7.47 (m, 2H), 7.38 (d, J=8.7 Hz, 1H), 7.23-7.17 (m, 2H), 0.12-7.05 (m, 2H), 4.61 (t, J=6.9 Hz, 2H), 3.97 (s, 3H), 3.27 (t, J=7.5 Hz, 2H), 3.04 (t, J=7.5 Hz, 2H), 2.89 (t, J=6.9 Hz, 2H). $^{13}$C-NMR (CDCl$_3$, 75 MHz) δ 167.65, 153.29, 147.38, 139.78, 139.36, 135.70, 132.18, 130.29, 128.88, 128.68, 127.35, 127.30, 127.20, 126.89, 126.70, 126.44, 123.29, 123.38, 121.67, 118.70, 116.95, 109.35, 92.72, 85.44, 52.38, 40.65, 36.22, 27.60, 19.11.

Methyl 2-(benzo[d]thiazol-2-ylethynyl)-1-(2-cyanoethyl)-3-(4-methylphenethyl)-1H-indole-5-carboxylate (131d). The synthesis of compound 131d followed general procedure C to obtain the desired product as brown solid (CH$_2$Cl$_2$ to hexanes:ethyl acetate=3:1 to 2:1 to 1:1, 90% yield). $^1$H-NMR (CDCl$_3$, 300 MHz) δ 8.34 (d, J=1.5 Hz, 1H), 8.15-8.09 (m, 1H), 8.05 (dd, J=1.8, 8.7 Hz, 1H), 7.95-7.89 (m, 1H), 7.60-7.46 (m, 2H), 7.38 (d, J=9.0 Hz, 1H), 7.12-7.04 (m, 4H), 4.60 (t, J=6.9 Hz, 2H), 3.96 (s, 3H), 3.26 (t, J=7.2 Hz, 2H), 3.02 (t, J=7.6 Hz, 2H), 2.88 (t, J=6.9 Hz, 2H), 2.27 (s, 3H). $^{13}$C-NMR (CDCl$_3$, 75 MHz) δ 167.72, 153.29, 147.58, 139.37, 138.34, 135.84, 129.31, 128.75, 127.94, 127.26, 126.81, 126.38, 124.03, 123.44, 123.11, 121.65, 118.56, 117.05, 109.29, 92.67, 85.72, 52.35, 40.63, 36.55, 27.89, 21.28, 19.09.

Methyl 2-((1H-benzo[d]imidazol-2-yl)ethynyl)-3-(4-chlorophenethyl)-1-(2-cyanoethyl)-1H-indole-5-carboxylate (131e). The synthesis of compound 131e followed general procedure C to obtain the desired product as orange solid (CH$_2$Cl$_2$ to hexanes:ethyl acetate=1:1 to 1:2). It was further purified by using recrystallization technique in EtOH (73% yield). $^1$H-NMR (CDCl$_3$, 300 MHz) δ 11.08 (brs, 1H), 8.19 (s, 1H), 8.01 (d, J=9.0 Hz, 1H), 7.88-7.80 (m, 1H), 7.56-7.46 (m, 1H), 7.40-7.31 (m, 2H), 7.21 (d, J=9.0 Hz, 1H), 7.19 (d, J=8.4 Hz, 2H), 6.93 (d, J=8.4 Hz, 2H), 4.35 (t, J=6.0 Hz, 2H), 3.96 (s, 3H), 3.09 (t, J=7.2 Hz, 2H), 2.89 (t, J=7.2 Hz, 2H), 2.70 (t, J=6.0 Hz, 2H). $^{13}$C-NMR (CDCl$_3$, 75 MHz) δ 167.22, 139.90, 138.97, 134.58, 131.92, 130.29, 128.55, 128.81, 126.67, 126.24, 126.16, 125.11, 123.70, 123.18, 123.11, 119.07, 117.68, 109.03, 98.81, 89.71, 82.08, 52.41, 40.29, 36.08, 27.27, 19.13.

Methyl 2-((5-chlorobenzo[d]thiazol-2-yl)ethynyl)-3-(4-chlorophenethyl)-1-(2-cyanoethyl)-1H-indole-5-carboxylate (131f). The synthesis of compound 131f followed general procedure C to obtain the desired product as brown solid (CH$_2$Cl$_2$ to hexanes:ethyl acetate=3:1 to 2:1, 72% yield). $^1$H-NMR (CDCl$_3$, 300 MHz) δ 8.27 (s, 1H), 8.11-8.01 (m, 2H), 7.81 (d, J=8.7 Hz, 1H), 7.45 (dd, J=1.5, 8.7 Hz, 1H), 7.36 (d, J=8.7 Hz, 1H), 7.17 (d, J=8.1 Hz, 2H), 7.06 (d, J=8.4 Hz, 2H), 4.58 (t, J=6.6 Hz, 2H), 3.95 (s, 3H), 3.25 (t, J=7.3 Hz, 2H), 3.02 (t, J=7.3 Hz, 2H), 2.87 (t, J=6.6 Hz, 2H). $^{13}$C-NMR (CDCl$_3$, 75 MHz) δ 167.57, 154.13, 149.15, 139.72, 139.41, 133.89, 133.48, 133.46, 132.22, 130.27, 128.67, 127.56, 127.35, 126.66, 123.68, 122.33, 118.51, 109.37, 92.42, 52.37, 40.66, 36.20, 27.61, 19.09.

Methyl 3-(4-chlorophenethyl)-1-(2-cyanoethyl)-2-((5-methoxybenzo[d]thiazol-2-yl)ethynyl)-1H-indole-5-carboxylate (131g). The synthesis of compound 131g followed general procedure C to obtain the desired product as yellow solid (CH$_2$Cl$_2$ to hexanes:ethyl acetate=2:1 to 1:1, quantitative yield). $^1$H-NMR (CDCl$_3$, 300 MHz) δ 8.27 (s, 1H), 8.04 (d, J=8.4 Hz, 1H), 7.76 (d, J=9.0 Hz, 1H), 7.56 (s, 1H), 7.37 (d, J=8.4 Hz, 1H), 7.23-7.02 (m, 5H), 4.59 (t, J=6.6 Hz, 2H), 3.96 (s, 3H), 3.91 (s, 3H), 3.25 (t, J=7.6 Hz, 2H), 3.02 (t, J=7.2 Hz, 2H), 2.88 (t, J=6.0 Hz, 2H). $^{13}$C-NMR (CDCl$_3$, 75 MHz) δ 167.66, 159.87, 154.66, 148.31, 139.78, 139.34, 132.16, 130.28, 127.05, 126.70, 126.40, 123.36, 123.26, 123.19, 121.85, 118.76, 117.62, 116.98, 109.33, 105.69, 92.83, 85.26, 55.90, 52.38, 40.64, 36.20, 27.58, 19.10.

Methyl 3-(4-chlorophenethyl)-1-(2-cyanoethyl)-2-((5-(2-methoxyethoxy)benzo[d]thiazol-2-yl)ethynyl)-1H-indole-5-carboxylate (131h). The synthesis of compound 131h followed general procedure C to obtain the desired product as yellow solid (CH$_2$Cl$_2$ to hexanes:ethyl acetate=2:1 to 1:1 to 1:2, 66% yield). $^1$H-NMR (CDCl$_3$, 300 MHz) δ 8.26 (s, 1H), 8.03 (dd, J=1.2, 8.7 Hz, 1H), 7.73 (d, J=9.0 Hz, 1H), 7.56 (d, J=2.1 Hz, 1H), 7.35 (d, J=8.7 Hz, 1H), 7.23-7.14 (m, 3H), 7.06 (d, J=8.1 Hz, 2H), 4.57 (t, J=6.6 Hz, 2H), 4.21 (t, J=4.5 Hz, 2H), 3.95 (s, 3H), 3.81 (t, J=4.5 Hz, 2H), 3.47 (s, 3H), 3.24 (t, J=7.3 Hz, 2H), 3.01 (t, J=7.3 Hz, 2H), 2.86 (t, J=6.6 Hz, 2H). $^{13}$C-NMR (CDCl$_3$, 75 MHz) δ 167.62, 159.01, 154.57, 148.28, 138.79, 139.33, 132.16, 130.26, 128.65, 127.03, 126.69, 126.37, 123.22, 123.20, 121.85, 118.75, 118.06, 116.95, 109.32, 106.52, 92.83, 85.26, 71.10, 67.97, 59.51, 52.34, 40.62, 36.19, 27.56, 19.07.

methyl 3-(4-chlorophenethyl)-1-(2-cyanoethyl)-2-((6-methoxybenzo[d]thiazol-2-yl)ethynyl)-1H-indole-5-carboxylate (131i). The synthesis of compound 131i followed general procedure C to obtain the desired product as yellow solid (CH$_2$Cl$_2$: MeOH=13:1, 86% yield). Low resolution mass spectrometry [M+Na]$^+$: 576.2. $^1$H NMR (500 MHz, DMSO-d$_6$) δ 8.22 (d, J=1.5 Hz, 1H), 8.01 (d, J=9.0 Hz, 1H), 7.89 (dd, J=8.8, 1.6 Hz, 1H), 7.79-7.74 (m, 2H), 7.27-7.24 (m, 2H), 7.22 (dd, J=9.0, 2.6 Hz, 1H), 7.21-7.18 (m, 2H), 4.65 (t, J=6.4 Hz, 2H), 3.88 (d, J=1.0 Hz, 6H), 3.24 (t, J=7.4 Hz, 2H), 3.08 (t, J=6.4 Hz, 2H), 2.99 (t, J=7.4 Hz, 2H). $^{13}$C NMR (126 MHz, DMSO-d$_6$) δ 166.68, 158.54, 147.06, 144.04, 140.03, 138.90, 136.87, 130.69, 130.38, 128.11, 125.81, 125.41, 124.91, 123.92, 122.25, 121.91, 118.79, 118.27, 117.02, 110.81, 104.44, 92.14, 84.77, 55.86, 54.91, 51.95, 35.34, 26.69, 18.24.

Methyl 2-(2-(benzo[d]thiazol-2-yl)ethyl)-1-(2-cyanoethyl)-3-phenethyl-1H-indole-5-carboxylate (132a). The synthesis of compound 132a followed general procedure D to obtain the desired product as yellow solid (hexanes:ethyl acetate=5:1 to 4:1 to 3:1 to 2:1, 47% yield). $^1$H-NMR (300 MHz, CDCl$_3$) δ 8.35 (s, 1H), 8.00 (d, J=8.1 Hz, 1H), 7.95 (d, J=8.4 Hz, 1H), 7.83 (d, J=8.1 Hz, 1H), 7.48 (t, J=7.6 Hz, 1H), 7.38 (t, J=7.5 Hz, 1H), 7.29-7.16 (m, 4H), 7.07 (d, J=7.2 Hz, 2H), 4.41 (t, J=7.0 Hz, 2H), 3.96 (s, 3H), 3.14 (t, J=7.8 Hz, 2H), 3.06 (t, J=6.8 Hz, 2H), 3.02-2.89 (m, 4H), 2.70 (t, J=6.9 Hz, 2H). $^{13}$C-NMR (75 MHz, CDCl$_3$) δ 169.38, 168.24, 153.31, 141.97, 138.45, 136.01, 135.34, 128.92, 128.66, 128.18, 126.43, 126.34, 125.33, 123.64, 122.92, 122.25, 122.04, 121.85, 117.02, 114.72, 108.60, 52.21, 39.33, 36.98, 34.36, 27.15, 23.91, 18.68.

Methyl 2-(2-(benzo[d]thiazol-2-yl)ethyl)-1-(2-cyanoethyl)-3-(4-fluorophenethyl)-1H-indole-5-carboxylate (132b). The synthesis of compound 132b followed general procedure D to obtain the desired product as yellow solid (hexanes:ethyl acetate=5:1 to 4:1 to 3:1 to 2:1, 84% yield). 8.28 (s, 1H), 7.99 (d, J=8.4 Hz, 1H), 7.95 (d, J=8.7 Hz, 1H), 7.82 (d, J=7.8 Hz, 1H), 7.48 (t, J=7.2 Hz, 1H), 7.37 (t, J=7.5 Hz, 1H), 7.25 (d, J=8.7, Hz, 1H), 7.05-6.98 (m, 2H), 6.97-6.87 (m, 2H), 4.41 (t, J=6.7 Hz, 2H), 3.95 (s, 3H), 3.18 (t, J=7.3 Hz, 2H), 3.08-3.00 (m, 4H), 2.96-2.90 (m, 2H), 2.71 (t, J=6.7 Hz, 2H). $^{13}$C-NMR (CDCl$_3$, 75 MHz) δ 169.22, 168.21, 160.03, 153.34, 138.44, 137.63, 136.06, 135.33, 130.33, 130.22, 128.11, 126.47, 125.38, 123.65, 122.93, 122.26, 121.99, 122.89, 117.08, 115.51, 115.23, 114.51, 108.68, 52.21, 39.32, 36.18, 34.45, 27.18, 23.89, 18.73.

Methyl 2-(2-(benzo[d]thiazol-2-yl)ethyl)-3-(4-chlorophenethyl)-1-(2-cyanoethyl)-1H-indole-5-carboxylate (132c). The synthesis of compound 132c followed general procedure D to obtain the desired product as pale yellow solid (hexanes:ethyl acetate=4:1 to 3:1 to 2:1, 50% yield). $^1$H-NMR (CDCl$_3$, 300 MHz) δ 8.28 (s, 1H), 8.00 (d, J=8.1 Hz, 1H), 7.95 (d, J=8.7 Hz, 1H), 7.84 (d, J=8.1 Hz, 1H), 7.49 (t, J=7.6 Hz, 1H), 7.38 (t, J=7.6 Hz, 1H), 7.26-7.16 (m, 3H), 6.99 (d, J=8.1 Hz, 2H), 4.42 (t, J=6.9 Hz, 2H), 3.96 (s, 3H), 3.20 (t, J=7.6 Hz, 2H), 3.09-2.98 (m 4H), 2.96-2.89 (m, 2H), 2.72 (t, J=6.9 Hz, 2H). $^{13}$C-NMR (CDCl$_3$, 75 MHz) δ 169.18, 168.19, 153.33, 141.98, 140.38, 138.43, 136.06, 135.33, 132.08, 130.26, 128.71, 128.08, 125.38, 123.68, 122.93, 122.30, 121.96, 121.89, 117.03, 114.40, 108.66, 52.24, 39.33, 36.34, 34.44, 26.98, 18.72.

Methyl 2-(2-(benzo[d]thiazol-2-yl)ethyl)-1-(2-cyanoethyl)-3-(4-methylphenethyl)-1H-indole-5-carboxylate (132d). The synthesis of compound 132d followed general procedure D to obtain the desired product as pale yellow solid (hexanes:ethyl acetate=3:1 to 2:1, 80% yield). $^1$H-NMR (CDCl$_3$, 300 MHz) δ 8.37 (d, J=0.9 Hz, 1H), 8.01 (d, J=8.1 Hz, 1H), 7.96 (dd, J=1.5, 8.4 Hz, 1H), 7.83 (d, J=7.5 Hz, 1H), 7.53-7.44 (m, 1H), 7.43-7.34 (m, 1H), 7.25 (d, J=8.7 Hz, 1H), 7.07 (d, J=7.8 Hz, 2H), 6.97 (d, J=8.1 Hz, 2H), 4.41 (t, J=6.9 Hz, 2H), 3.97 (s, 3H), 3.19 (t, J=7.6 Hz, 2H), 3.10-3.00 (m, 2H), 2.97-2.87 (m, 4H), 2.70 (t, J=6.9 Hz, 2H), 2.31 (s, 3H). $^{13}$C-NMR (CDCl$_3$, 75 MHz) δ 169.49, 168.28, 153.35, 138.94, 138.48, 136.06, 135.78, 135.36, 129.37, 128.81, 128.22, 126.44, 125.34, 123.60, 122.92, 122.19, 122.06, 121.88, 117.15, 114.84, 108.65, 52.22, 39.33, 36.60, 34.32, 27.31, 23.87, 21.34, 18.69.

Methyl 2-(2-(1H-benzo[d]imidazol-2-yl)ethyl)-3-(4-chlorophenethyl)-1-(2-cyanoethyl)-1H-indole-5-carboxylate (132e). The synthesis of compound 132e followed general procedure D to obtain the desired product as white solid (hexanes:acetone=2:1 to 1:1, 71% yield). $^1$H-NMR (Acetone-d$_6$, 300 MHz) δ 11.27 (brs, 1H), 8.17 (d, J=1.5 Hz, 1H), 7.87-7.78 (m, 1H), 7.60 (dd, J=1.5, 8.7 Hz, 1H), 7.42 (brs, 2H), 7.27-7.20 (m, 2H), 7.20-7.11 (m, 4H), 4.71 (t, J=6.7 Hz, 2H), 3.87 (s, 3H), 3.44-3.36 (m, 2H), 3.20-3.09 (m, 2H), 3.08-2.98 (m, 4H), 2.90-2.83 (m, 2H). $^{13}$C-NMR (CDCl$_3$, 75 MHz) δ 168.37, 153.12, 142.20, 140.49, 138.44, 136.43, 132.15, 131.83, 130.35, 129.14, 128.89, 128.58, 128.11, 126.29, 123.50, 122.88, 122.02, 117.37, 114.95, 114.27, 114.15, 108.73, 52.24, 38.86, 36.67, 29.77, 26.90, 23.13, 18.55.

Methyl 2-(2-(5-chlorobenzo[d]thiazol-2-yl)ethyl)-3-(4-chlorophenethyl)-1-(2-cyanoethyl)-1H-indole-5-carboxylate (132f). The synthesis of compound 132f followed general procedure D to obtain the desired product as yellow solid (hexanes:ethyl acetate=2:1, 83% yield). $^1$H-NMR (300 MHz, CDCl$_3$) δ 8.26 (s, 1H), 8.01-7.90 (m, 2H), 7.72 (d, J=8.4 Hz, 1H), 7.34 (dd, J=1.8, 8.4 Hz, 1H), 7.23 (s, 1H), 7.19 (d, J=8.1 Hz, 2H), 6.96 (d, J=8.1 Hz, 2H), 4.41 (t, J=6.6 Hz, 2H), 3.95 (s, 3H), 3.17 (t, J=4.6 Hz, 2H), 3.04-2.95 (m, 4H), 2.95-2.87 (m, 2H), 2.72 (t, J=6.9 Hz, 2H). $^{13}$C-NMR (75 MHz, CDCl$_3$) δ 171.18, 168.13, 154.15, 140.33, 138.43, 135.84, 133.55, 132.52, 132.12, 130.24, 128.71, 125.88, 123.74, 122.82, 122.55, 122.38, 121.98, 116.95, 114.45, 108.63, 52.20, 39.34, 36.25, 34.40, 26.94, 23.69, 18.72.

Methyl 3-(4-chlorophenethyl)-1-(2-cyanoethyl)-2-(2-(5-methoxybenzo[d]thiazol-2-yl)ethyl)-1H-indole-5-carboxylate (132g). The synthesis of compound 132g followed general procedure D to obtain the desired product as yellow solid (hexanes:ethyl acetate=1:1, quantitative yield). ¹H-NMR (300 MHz, CDCl₃) δ 8.26 (s, 1H), 7.93 (d, J=8.7 Hz, 1H), 7.66 (d, J=8.7 Hz, 1H), 7.45 (s, 1H), 7.28-7.14 (m, 3H), 7.06-6.93 (m, 3H), 4.41 (t, J=6.9 Hz, 2H), 3.94 (s, 3H), 3.88 (s, 3H), 3.21-3.12 (m, 2H), 3.07-2.97 (m, 4H), 2.92-2.85 (m, 2H), 2.71 (t, J=6.9 Hz, 2H). ¹³C-NMR (75 MHz, CDCl₃) δ 170.43, 168.18, 159.27, 154.51, 140.37, 138.40, 136.02, 132.07, 130.24, 128.07, 128.07, 126.95, 123.67, 122.28, 122.08, 121.97, 117.02, 115.50, 114.39, 108.63, 105.39, 55.85, 52.23, 39.32, 36.30, 34.43, 26.94, 23.95, 18.71.

Methyl 3-(4-chlorophenethyl)-1-(2-cyanoethyl)-2-(2-(5-(2-methoxyethoxy)benzo[d]thiazol-2-yl)ethyl)-1H-indole-5-carboxylate (132h). The synthesis of compound 132h followed general procedure D to obtain the desired product as pale yellow solid (hexanes:ethyl acetate=1:1 to 1:2 to 1:3, 85%). ¹H-NMR (300 MHz, CDCl₃) δ 8.24 (s, 1H), 7.92 (d, J=8.4 Hz, 1H), 7.64 (d, J=9.0 Hz, 1H), 7.47 (s, 1H), 7.23-7.13 (m, 3H), 7.05 (d, J=8.4 Hz, 1H), 6.97 (d, J=8.1 Hz, 2H), 4.39 (t, J=6.4 Hz, 2H), 4.17 (t, J=3.9 Hz, 2H), 3.93 (s, 3H), 3.79 (t, J=4.0 Hz, 2H), 3.46 (s, 3H), 3.16 (t, J=4.2 Hz, 2H), 3.05-2.93 (m, 4H), 2.93-2.84 (m, 2H), 2.69 (t, J=6.6 Hz, 2H). ¹³C-NMR (75 MHz, CDCl₃) δ 170.47, 168.16, 158.40, 154.47, 140.38, 138.42, 136.05, 132.04, 130.30, 130.24, 128.89, 128.68, 128.06, 127.23, 123.64, 122.26, 122.26, 122.08, 121.93, 117.06, 115.98, 114.38, 108.66, 106.25, 71.17, 67.93, 59.48, 52.19, 39.31, 36.31, 34.42, 26.91, 23.94, 18.68.

methyl 3-(4-chlorophenethyl)-1-(2-cyanoethyl)-2-(2-(6-methoxybenzo[d]thiazol-2-yl)ethyl)-1H-indole-5-carboxylate (132i). The synthesis of compound 132i followed general procedure D to obtain the desired product as brown solid (CH₂Cl₂:MeOH=13:1, 68% yield). ¹H NMR (500 MHz, Chloroform-d) δ 8.17 (t, J=1.1 Hz, 1H), 7.85 (dd, J=8.6, 1.6 Hz, 1H), 7.76 (d, J=8.9 Hz, 1H), 7.20-7.17 (m, 1H), 7.15 (d, J=8.6 Hz, 1H), 7.13-7.09 (m, 2H), 7.00-6.95 (m, 1H), 6.92-6.88 (m, 2H), 4.31 (t, J=7.0 Hz, 2H), 3.86 (s, 3H), 3.77 (s, 3H), 3.08 (dd, J=8.9, 6.5 Hz, 2H), 2.95-2.88 (m, 4H), 2.82 (t, J=7.3 Hz, 2H), 2.62 (t, J=7.0 Hz, 2H). ¹³C NMR (126 MHz, Chloroform-d) δ 167.92, 166.20, 157.62, 147.56, 140.14, 138.17, 136.40, 135.87, 131.82, 130.00, 128.44, 127.85, 123.40, 123.09, 122.04, 121.69, 116.76, 115.43, 114.15, 108.39, 104.20, 55.78, 51.96, 39.08, 36.10, 34.05, 26.70, 23.67, 18.46.

1-(2-(2H-tetrazol-5-yl)ethyl)-2-(2-(benzo[d]thiazol-2-yl)ethyl)-3-phenethyl-1H-indole-5-carboxylic acid (25). The synthesis of compound 25 followed general procedures F and G to obtain the desired product as pale yellow solid (59% yield over two steps). ¹H-NMR (500 MHz, DMSO-d₆) δ: 12.46 (brs, 1H), 8.16 (s, 1H), 8.04 (d, J=8.5 Hz, 1H), 7.94 (d, J=7.5 Hz, 1H), 7.72 (d, J=9.0 Hz, 1H), 7.51-7.44 (m, 2H), 7.40 (t, J=8.0 Hz, 1H), 7.22 (t, J=7.5 Hz, 2H), 7.15 (t, J=7.5 Hz, 1H), 7.08 (d, J=7.0 Hz, 2H), 4.60 (t, J=7.5 Hz, 2H), 3.12 (s, 4H), 2.92 (t, J=7.5 Hz, 2H), 2.76 (t, J=7.5 Hz, 2H). ¹³C-NMR (125 MHz, DMSO-d₆) δ: 170.33, 168.74, 153.12, 142.11, 138.51, 136.94, 135.24, 128.78, 128.66, 127.46, 126.52, 126.26, 125.36, 122.69, 122.65, 122.54, 121.05, 113.27, 109.99, 109.68, 41.45, 36.98, 33.99, 26.78, 24.28, 23.51

1-(2-(2H-tetrazol-5-yl)ethyl)-2-(2-(benzo[d]thiazol-2-yl)ethyl)-3-(4-fluorophenethyl)-1H-indole-5-carboxylic acid (26). The synthesis of compound 26 followed general procedures F and G to obtain the desired product as pale yellow solid (72% yield over two steps). ¹H-NMR (500 MHz, DMSO-d₆) δ: 12.46 (brs, 1H), 8.10 (s, 1H), 8.04 (d, J=8.0 Hz, 1H), 7.94 (d, J=8.5 Hz, 1H), 7.70 (d, J=8.5 Hz, 1H), 7.51-7.45 (m, 2H), 7.39 (t, J=8.5 Hz, 1H), 7.11-7.06 (m, 2H), 7.05-6.99 (m, 2H), 4.61 (t, J=7.5 Hz, 2H), 3.30 (t, J=7.5 Hz, 2H), 3.15 (s, 4H), 2.90 (t, J=7.5 Hz, 2H), 2.74 (t, J=7.5 Hz, 2H). ¹³C-NMR (125 MHz, DMSO-d₆) δ:170.30, 168.72, 162.07, 160.15, 153.13, 138.49, 138.18, 136.98, 135.24, 130.56, 130.50, 127.45, 126.53, 125.36, 122.66, 122.54, 121.96, 121.08, 115.35, 115.19, 113.09, 109.68, 41.48, 36.06, 34.01, 26.74, 24.50, 23.47.

1-(2-(2H-tetrazol-5-yl)ethyl)-2-(2-(benzo[d]thiazol-2-yl)ethyl)-3-(4-chlorophenethyl)-1H-indole-5-carboxylic acid (27). The synthesis of compound 27 followed general procedures F and G to obtain the desired product as white solid (49% yield over two steps). ¹H-NMR (500 MHz, DMSO-d₆) δ: 12.45 (brs, 1H), 8.11 (s, 1H), 8.04 (dd, J=1.5, 8.0 Hz, 1H), 7.94 (dd, J=1.5, 8.0 Hz, 1H), 7.71 (dd, J=1.5, 8.5 Hz, 1H), 7.51-7.43 (m, 2H), 7.40 (td, J=2.0, 8.0 Hz, 1H), 7.27 (dd, J=3.0, 8.0 Hz, 2H), 7.09 (dd, J=3.0, 8.0 Hz, 2H), 4.60 (t, J=6.0 Hz, 2H), 3.15 (s, 4H), 2.90 (t, J=6.5 Hz, 2H), 2.74 (t, J=6.5 Hz, 2H). ¹³C-NMR (125 MHz, DMSO-d₆) δ: 170.54, 168.99, 153.37, 141.31, 138.73, 137.24, 135.49, 131.18, 130.92, 129.03, 128.91, 128.79, 127.65, 126.78, 125.62, 122.96, 122.92, 122.21, 113.21, 109.93, 41.75, 36.45, 34.23, 26.76, 24.76, 23.69.

1-(2-(2H-tetrazol-5-yl)ethyl)-2-(2-(benzo[d]thiazol-2-yl)ethyl)-3-(4-methylphenethyl)-1H-indole-5-carboxylic acid (28). The synthesis of compound 28 followed general procedures F and G to obtain the desired product as pale yellow solid (40% yield over two steps). ¹H-NMR (500 MHz, DMSO-d₆) δ: 12.50 (brs, 2H), 8.14 (d, J=1.5 Hz, 1H), 8.04 (d, J=8.0 Hz, 1H), 7.94 (d, J=8.0 Hz, 1H), 7.72 (dd, J=1.0, 8.5 Hz, 1H), 7.45 (q, J=8.0 Hz, 2H), 7.39 (t, J=8.0 Hz, 1H), 7.02 (d, J=8.0 Hz, 2H), 6.96 (d, J=8.0 Hz, 2H), 4.60 (t, J=7.5 Hz, 2H), 3.30 (t, J=7.5 Hz, 2H), 3.19-3.12 (m, 2H), 3.12-3.05 (m, 2H), 2.90 (t, J=7.5 Hz, 2H), 2.72 (t, J=7.5 Hz, 2H), 2.23 (s, 3H). ¹³C-NMR (125 MHz, DMSO-d₆) δ: 169.85, 168.27, 152.66, 138.55, 138.03, 136.44, 134.75, 134.67, 128.76, 128.19, 128.16, 126.99, 126.03, 124.86, 122.19, 122.17, 122.05, 121.46, 120.59, 112.82, 109.18, 41.03, 36.08, 33.47, 26.46, 24.06, 22.97, 20.61.

2-(2-(1H-benzo[d]imidazol-2-yl)ethyl)-1-(2-(2H-tetrazol-5-yl)ethyl)-3-(4-chlorophen ethyl)-1H-indole-5-carboxylic acid (29). The synthesis of compound 29 followed general procedures F and G to obtain the desired product as yellow solid (39% yield over two steps). ¹H-NMR (500 MHz, DMSO-d₆) δ: 15.49 (brs, 1H), 12.50, (brs, 1H), 8.11 (d, J=27.0 Hz, 1H), 7.78 (dd, J=3.0, 5.5 Hz, 2H), 7.71 (t, J=7.2 Hz, 1H), 7.53-7.46 (m, 3H), 7.26 (d, J=8.5 Hz, 1H), 7.23-7.12 (m, 4H), 4.72 (t, J=7.0 Hz, 2H), 3.39-3.26 (m, 4H), 3.22 (t, J=7.5 Hz, 2H), 2.96-2.88 (m, 2H), 2.78-2.70 (m, 2H). ¹³C-NMR (125 MHz, DMSO-d₆) δ: 168.67, 153.30, 142.00, 140.96, 138.66, 138.62, 135.69, 131.79, 130.79, 128.87, 128.53, 128.44, 128.37, 127.35, 127.32, 126.27, 125.70, 125.67, 122.88, 122.04, 121.17, 114.27, 113.75, 109.86, 41.40, 37.13, 27.58, 26.28, 24.61, 21.90.

1-(2-(2H-tetrazol-5-yl)ethyl)-2-(2-(5-chlorobenzo[d]thiazol-2-yl)ethyl)-3-(4-chlorophen ethyl)-1H-indole-5-carboxylic acid (30). The synthesis of compound 30 followed general procedures F and G to obtain the desired product as yellow solid (50% yield over two steps). ¹H-NMR (500 MHz, DMSO-d₆) δ: 8.11 (d, J=1.5 Hz, 1H), 8.07 (d, J=8.5 Hz, 1H), 8.01 (d, J=2.0 Hz, 1H), 7.71 (dd, J=1.5, 8.5 Hz, 1H), 7.48-7.42 (m, 2H), 7.26 (d, J=8.5 Hz, 2H), 7.08 (d, J=8.5 Hz, 2H), 4.57 (t, J=7.5 Hz, 2H), 3.25 (t, J=7.5 Hz, 2H), 3.20-3.12 (m, 4H), 2.89 (t, J=7.5 Hz, 2H), 2.73 (t, J=7.5 Hz, 2H). ¹³C-NMR (125 MHz, DMSO-d₆) δ: 173.09, 168.74, 154.88, 154.04, 141.04, 138.51, 136.85, 134.05, 131.32, 130.93, 130.63, 128.53, 127.36, 125.48, 124.04, 122.69, 122.17, 121.92, 121.07, 122.92, 109.71, 41.92, 36.17, 34.03, 26.42, 25.02, 23.43.

1-(2-(2H-tetrazol-5-yl)ethyl)-3-(4-chlorophenethyl)-2-(2-(5-methoxybenzo[d]thiazol-2-yl)ethyl)-1H-indole-5-carboxylic acid (31). The synthesis of compound 31 followed general procedures F and G to obtain the desired product as yellow solid (69% yield over two steps). $^1$H-NMR (500 MHz, DMSO-d$_6$) δ: 12.46 (brs, 2H), 8.11 (s, 1H), 7.89 (d, J=8.5 Hz, 1H), 7.71 (d, J=8.5 Hz, 1H), 7.49-7.44 (m, 2H), 7.26 (d, J=8.5 Hz, 2H), 7.09 (d, J=8.5 Hz, 2H), 7.03 (dd, J=2.5, 8.5 Hz, 1H), 4.60 (t, J=7.5 Hz, 2H), 3.82 (s, 3H), 3.16-3.10 (m, 4H), 2.90 (t, J=7.5 Hz, 2H), 2.73 (t, J=7.5 Hz, 2H). $^{13}$C-NMR (125 MHz, DMSO-d$_6$) δ:171.42, 168.72, 158.93, 154.49, 141.06, 138.49, 137.00, 130.94, 130.66, 128.53, 127.42, 126.88, 122.79, 122.70, 121.98, 121.08, 114.92, 112.99, 109.99, 109.68, 105.73, 55.91, 41.47, 36.17, 34.05, 26.47, 23.54.

1-(2-(2H-tetrazol-5-yl)ethyl)-3-(4-chlorophenethyl)-2-(2-(5-(2-methoxyethoxy)benzo [d]thiazol-2-yl)ethyl)-1H-indole-5-carboxylic acid (32). The synthesis of compound 32 followed general procedures F and G to obtain the desired product as pale yellow solid (80% yield over two steps). $^1$H-NMR (500 MHz, DMSO-d$_6$) δ: 12.44 (brs, 1H), 8.11 (s, 1H), 7.88 (d, J=8.5 Hz, 1H), 7.71 (dd, J=1.0, 8.5 Hz, 1H), 7.48 (d, J=2.0 Hz, 1H), 7.45 (d, J=9.0 Hz, 1H), 7.26 (d, J=8.0 Hz, 2H), 7.09 (d, J=8.0 Hz, 2H), 7.04 (dd, J=2.5, 9.0 Hz, 1H), 4.60 (t, J=7.5 Hz, 2H), 4.16 (t, J=4.5 Hz, 2H), 3.69 (t, J=4.5 Hz, 2H), 3.32 (s, 3H), 3.30 (t, J=7.5 Hz, 2H), 3.14 (s, 4H), 2.90 (t, J=7.5 Hz, 2H), 2.73 (t, J=7.5 Hz, 2H). $^{13}$C-NMR (125 MHz, DMSO-d$_6$) δ: 171.48, 168.75, 158.08, 154.40, 141.02, 138.49, 136.96, 130.93, 130.64, 128.53, 127.41, 126.97, 122.84, 122.70, 121.92, 121.06, 115.31, 113.01, 109.99, 109.67, 106.37, 70.79, 67.80, 58.62, 41.46, 36.13, 33.99, 26.43, 24.41, 23.54.

1-(2-(2H-tetrazol-5-yl)ethyl)-3-(4-chlorophenethyl)-2-(2-(6-methoxybenzo[d]thiazol-2-yl)ethyl)-1H-indole-5-carboxylic acid (33). The synthesis of compound 33 followed general procedures F and G to obtain the desired product as light yellow solid (67% yield). $^1$H NMR (500 MHz, DMSO-d$_6$) δ 12.45 (s, 1H), 8.11 (d, J=1.6 Hz, 1H), 7.82 (d, J=8.9 Hz, 1H), 7.71 (dd, J=8.6, 1.6 Hz, 1H), 7.61 (d, J=2.6 Hz, 1H), 7.46 (d, J=8.6 Hz, 1H), 7.30-7.24 (m, 2H), 7.12-7.08 (m, 2H), 7.07 (dd, J=8.9, 2.6 Hz, 1H), 4.63-4.55 (m, 2H), 3.81 (s, 3H), 3.32-3.28 (m, 2H), 3.11 (tt, J=8.1, 4.1 Hz, 4H), 2.90 (dd, J=8.8, 6.6 Hz, 2H), 2.74 (t, J=7.7 Hz, 2H). $^{13}$C NMR (126 MHz, DMSO-d$_6$) δ 168.29, 167.02, 157.00, 147.05, 140.63, 138.02, 136.60, 136.20, 130.48, 130.24, 128.10, 126.96, 122.66, 122.23, 121.49, 120.63, 115.20, 112.50, 109.23, 104.75, 55.65, 41.02, 35.75, 33.40, 26.06, 24.03, 23.05.

Synthesis of 34 and 35. Compound 29 or 31 (0.097 mmol) was dissolved in 15 mL anhydrous MeOH and cooled down to 0° C. SOCl$_2$ (0.045 mL, 0.43 mmol) was added via syringe. The mixture was warmed up to room temperature and refluxed for 24 h. Upon completion, the reaction was quenched with sat. aqueous NH$_4$Cl-solution and extracted two times with DCM. The organic solvent was subsequently removed and the crude product purified via flash column chromatography.

Methyl 2-(2-(1H-benzo[d]imidazol-2-yl)ethyl)-1-(2-(2H-tetrazol-5-yl)ethyl)-3-(4-chloro phenethyl)-1H-indole-5-carboxylate (34). The reaction was run for 48 h. The pale yellow solid was isolated (CH$_2$Cl$_2$:MeOH=15:1 to 10:1, 60% yield). $^1$H-NMR (300 MHz, CD$_3$OD) δ: 8.15 (d, J=1.0 Hz, 1H), 7.80 (td, J=1.2, 8.1 Hz, 1H), 7.59-7.52 (m, 2H), 7.37 (t, J=8.5 Hz, 1H), 7.34-7.27 (m, 2H), 7.12 (d, J=8.0 Hz, 2H), 6.94 (m, 2H), 4.61-4.52 (m, 2H), 3.90 (s, 3H), 3.14-2.91 (m, 4H), 2.90-2.67 (m, 4H). $^{13}$C-NMR (125 MHz, CD$_3$OD) δ: 168.77, 166.42, 153.54, 141.92, 139.13, 135.89, 131.54, 130.05, 128.46, 128.03, 128.01, 125.72, 123.60, 122.67, 121.22, 120.97, 114.04, 108.94, 51.13, 41.81, 36.74, 28.23, 26.34, 24.76, 22.19.

Methyl 1-(2-(2H-tetrazol-5-yl)ethyl)-3-(4-chlorophenethyl)-2-(2-(5-methoxybenzo[d]thiazol-2-yl)ethyl)-1H-indole-5-carboxylate (35). The reaction was run for 24 h. The pale yellow solid was isolated (hexanes:acetone=1:1, 67% yield). $^1$H-NMR (500 MHz, DMSO-d$_6$) δ: 8.04 (d, J=1.5 Hz, 1H), 7.88 (d, J=9.0 Hz, 1H), 7.71 (dd, J=1.5, 9.0 Hz, 1H), 7.50-7.45 (m, 2H), 7.25 (d, J=8.5 Hz, 2H), 7.07 (d, J=8.0 Hz, 2H), 7.03 (dd, J=2.0, 9.0 Hz, 1H), 4.60 (t, J=7.0 Hz, 2H), 3.84 (s, 3H), 3.82 (s, 3H), 3.30 (t, J=7.5 Hz, 2H), 3.14 (s, 4H), 2.91 (t, J=7.5 Hz, 2H), 2.73 (t, J=7.5 Hz, 2H). $^{13}$C-NMR (125 MHz, DMSO-d$_6$) δ: 171.39, 167.61, 158.93, 154.49, 141.04, 138.58, 137.28, 130.97, 130.70, 128.51, 127.48, 126.88, 122.78, 122.38, 120.98, 120.87, 114.93, 113.11, 109.87, 105.73, 55.91, 52.12, 41.52, 36.21, 34.02, 26.40, 24.53, 23.54.

Scheme 8.

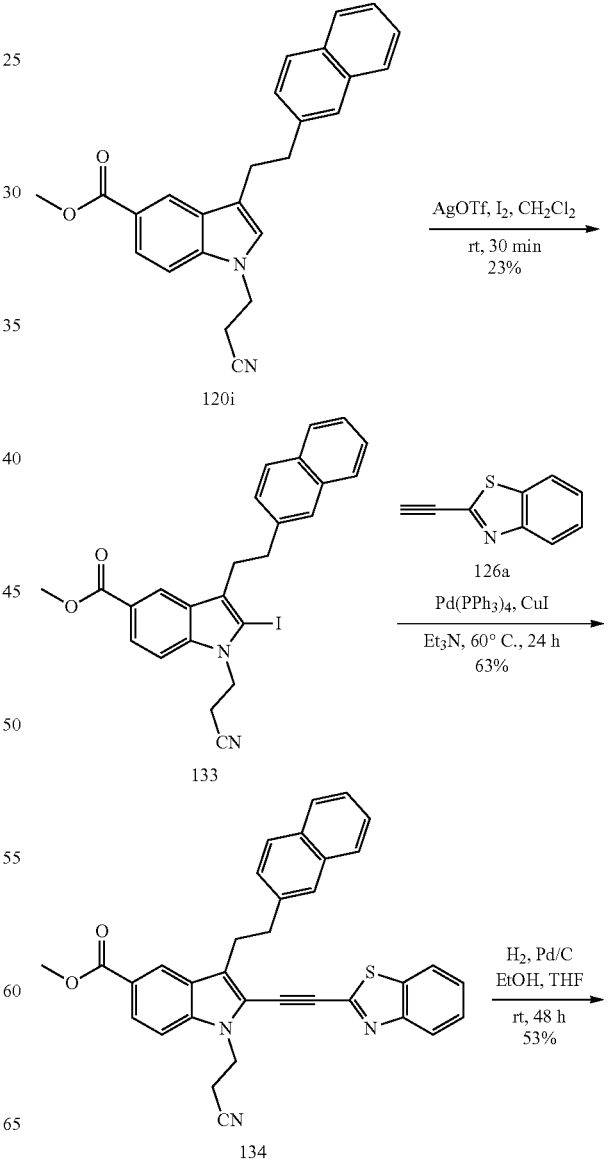

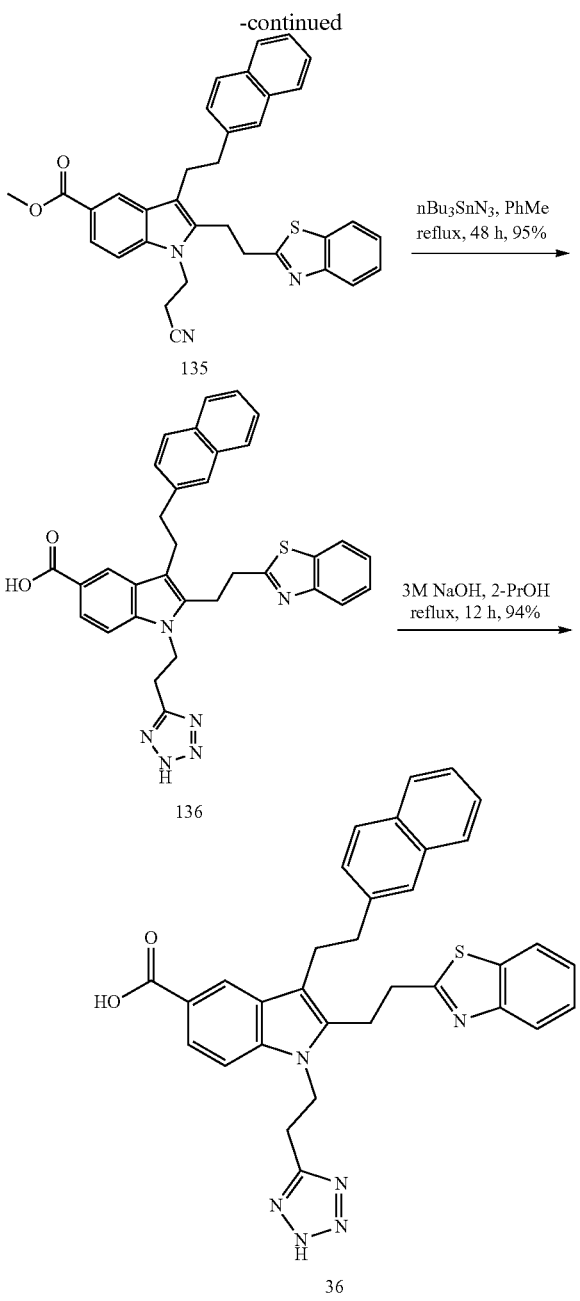

methyl 1-(2-cyanoethyl)-2-iodo-3-(2-(naphthalen-2-yl)ethyl)-1H-indole-5-carboxylate (133). The synthesis of compound 133 followed general procedure E to obtain the desired product as white solid (hexanes:ethyl acetate=3:1, 23% yield). Low resolution mass spectrometry [M+H]+: 531.1. ¹H NMR (500 MHz, DMSO-d₆) δ 8.17-8.13 (m, 1H), 7.87-7.84 (m, 1H), 7.83-7.79 (m, 2H), 7.75-7.70 (m, 2H), 7.69-7.67 (m, 1H), 7.48-7.42 (m, 2H), 7.38 (dd, J=8.3, 1.8 Hz, 1H), 4.56 (t, J=6.6 Hz, 2H), 3.82 (s, 3H), 3.11 (dd, J=9.4, 6.5 Hz, 2H), 3.00 (dd, J=9.1, 6.4 Hz, 2H), 2.95 (t, J=6.6 Hz, 2H). ¹³C NMR (126 MHz, DMSO-d₆) δ 166.80, 139.82, 138.82, 133.15, 131.67, 127.67, 127.45, 127.43, 127.29, 127.10, 126.32, 125.88, 125.18, 122.44, 122.02, 120.97, 120.25, 118.16, 110.52, 91.26, 51.79, 42.33, 36.04, 28.93, 18.16.

methyl 2-(benzo[d]thiazol-2-ylethynyl)-1-(2-cyanoethyl)-3-(2-(naphthalen-2-yl)ethyl)-1H-indole-5-carboxylate (134). The synthesis of compound 134 followed general procedure C to obtain the desired product as yellow solid (CH₂Cl₂: MeOH=15:1, 63% yield). ¹H NMR (500 MHz, DMSO-d₆) δ 8.29 (dd, J=1.6, 0.7 Hz, 1H), 8.19 (ddd, J=8.0, 1.4, 0.7 Hz, 1H), 8.12 (ddd, J=8.1, 1.3, 0.7 Hz, 1H), 7.89 (dd, J=8.8, 1.6 Hz, 1H), 7.82-7.79 (m, 2H), 7.78-7.75 (m, 2H), 7.72-7.70 (m, 1H), 7.65-7.61 (m, 1H), 7.58 (ddd, J=8.3, 7.2, 1.3 Hz, 1H), 7.43 (dd, J=8.4, 1.8 Hz, 1H), 7.41-7.37 (m, 2H), 4.66 (t, J=6.4 Hz, 2H), 3.84 (s, 3H), 3.37 (dd, J=8.4, 6.7 Hz, 2H), 3.19 (t, J=7.6 Hz, 2H), 3.06 (t, J=6.4 Hz, 2H). ¹³C NMR (126 MHz, DMSO-d₆) δ 166.63, 152.60, 146.96, 139.01, 138.69, 135.04, 133.12, 131.69, 128.79, 128.69, 127.72, 127.42, 127.35, 127.28, 127.23, 126.72, 126.42, 126.32, 125.81, 125.79, 125.16, 125.03, 123.29, 122.36, 122.34, 121.94, 118.52, 118.31, 110.86, 92.24, 85.66, 51.91, 40.24, 36.29, 26.69, 18.27.

methyl 2-(2-(benzo[d]thiazol-2-yl)ethyl)-1-(2-cyanoethyl)-3-(2-(naphthalen-2-yl)ethyl)-1H-indole-5-carboxylate (135). The synthesis of compound 135 followed general procedure D to provide the desired product as brown solid (CH₂Cl₂: MeOH=15:1, 53% yield). ¹H NMR (500 MHz, Acetone-d₆) δ 8.31 (dd, J=1.7, 0.6 Hz, 1H), 7.98-7.93 (m, 2H), 7.85 (dd, J=8.6, 1.6 Hz, 1H), 7.84-7.81 (m, 1H), 7.79 (d, J=8.5 Hz, 1H), 7.78-7.75 (m, 2H), 7.64-7.61 (m, 1H), 7.49 (ddd, J=8.3, 7.2, 1.2 Hz, 1H), 7.44-7.40 (m, 2H), 7.40-7.35 (m, 2H), 4.70 (t, J=6.9 Hz, 2H), 3.87 (s, 3H), 3.42-3.35 (m, 2H), 3.25-3.16 (m, 4H), 3.10 (dd, J=8.7, 6.5 Hz, 2H), 2.99 (t, J=6.9 Hz, 2H). ¹³C NMR (126 MHz, Acetone-d₆) δ 170.47, 168.14, 154.28, 140.52, 139.54, 137.77, 136.24, 134.63, 133.09, 128.73, 128.69, 128.41, 128.35, 128.28, 127.42, 126.82, 126.66, 125.96, 125.74, 123.39, 123.35, 122.60, 122.45, 121.85, 118.53, 114.72, 110.23, 51.90, 39.95, 37.91, 34.67, 27.32, 24.15, 18.96.

methyl 1-(2-(2H-tetrazol-5-yl)ethyl)-2-(2-(benzo[d]thiazol-2-yl)ethyl)-3-(2-(naphthalen-2-yl)ethyl)-1H-indole-5-carboxylate (136). The synthesis of compound 136 followed general procedure F to obtain the desired product as brown solid (CH₂Cl₂:MeOH=15:1, 95% yield). ¹H NMR (500 MHz, Chloroform-d) δ 8.30 (d, J=1.5 Hz, 1H), 7.98 (dt, J=8.1, 0.9 Hz, 1H), 7.85 (dd, J=8.6, 1.6 Hz, 1H), 7.77 (dt, J=7.9, 1.0 Hz, 1H), 7.74 (dd, J=7.8, 1.8 Hz, 1H), 7.69 (d, J=8.4 Hz, 1H), 7.66 (dd, J=8.0, 1.7 Hz, 1H), 7.47-7.44 (m, 1H), 7.42 (ddd, J=8.3, 7.2, 1.2 Hz, 1H), 7.38-7.31 (m, 3H), 7.23 (d, J=8.6 Hz, 1H), 7.19 (dd, J=8.4, 1.7 Hz, 1H), 4.53-4.45 (m, 2H), 3.88 (s, 3H), 3.39-3.32 (m, 2H), 3.08-3.00 (m, 6H), 2.86 (dd, J=9.6, 6.3 Hz, 2H). ¹³C NMR (126 MHz, Chloroform-d) δ 169.98, 152.34, 139.19, 138.62, 135.40, 134.61, 133.43, 131.89, 127.80, 127.52, 127.30, 126.57, 126.31, 125.84, 125.17, 125.14, 123.07, 122.14, 121.57, 121.50, 121.23, 114.03, 108.59, 51.82, 41.65, 36.97, 33.68, 26.62, 23.98, 21.45.

1-(2-(2H-tetrazol-5-yl)ethyl)-2-(2-(benzo[d]thiazol-2-yl)ethyl)-3-(2-(naphthalen-2-yl)ethyl)-1H-indole-5-carboxylic acid (36). The synthesis of compound 36 followed general procedure G to obtain the desired product as yellow solid (94% yield) was synthesized following the above general procedure. ¹H NMR (500 MHz, DMSO-d₆) δ 12.47 (s, 1H), 8.23 (d, J=1.6 Hz, 1H), 8.03 (dd, J=8.0, 1.1 Hz, 1H), 7.96-7.92 (m, 1H), 7.87-7.83 (m, 1H), 7.79 (dd, J=11.7, 7.5 Hz, 2H), 7.73 (dd, J=8.6, 1.6 Hz, 1H), 7.60 (d, J=1.6 Hz, 1H), 7.50-7.46 (m, 2H), 7.45-7.38 (m, 3H), 7.34 (dd, J=8.4, 1.7 Hz, 1H), 4.61 (dd, J=8.6, 6.3 Hz, 2H), 3.30 (t, J=7.6 Hz, 2H), 3.17 (d, J=4.0 Hz, 4H), 3.03 (dd, J=9.4, 6.2 Hz, 2H), 2.92 (dd, J=9.4, 6.3 Hz, 2H). ¹³C NMR (126 MHz, DMSO-d₆) δ 169.86, 168.32, 152.67, 139.33, 138.09, 136.50, 134.82, 133.12, 131.59, 127.69, 127.46, 127.32, 127.29, 127.02, 126.11, 126.07, 125.90, 125.18, 124.91, 122.28, 122.21, 122.09, 121.53, 120.65, 112.92, 109.27, 41.05, 36.79, 33.59, 26.13, 24.08, 23.07. HPLC purity (water/CH₃CN): 98.49%, Rt: 14.34 min. HPLC purity (water/MeOH): 99.99%, Rt: 16.37 min.

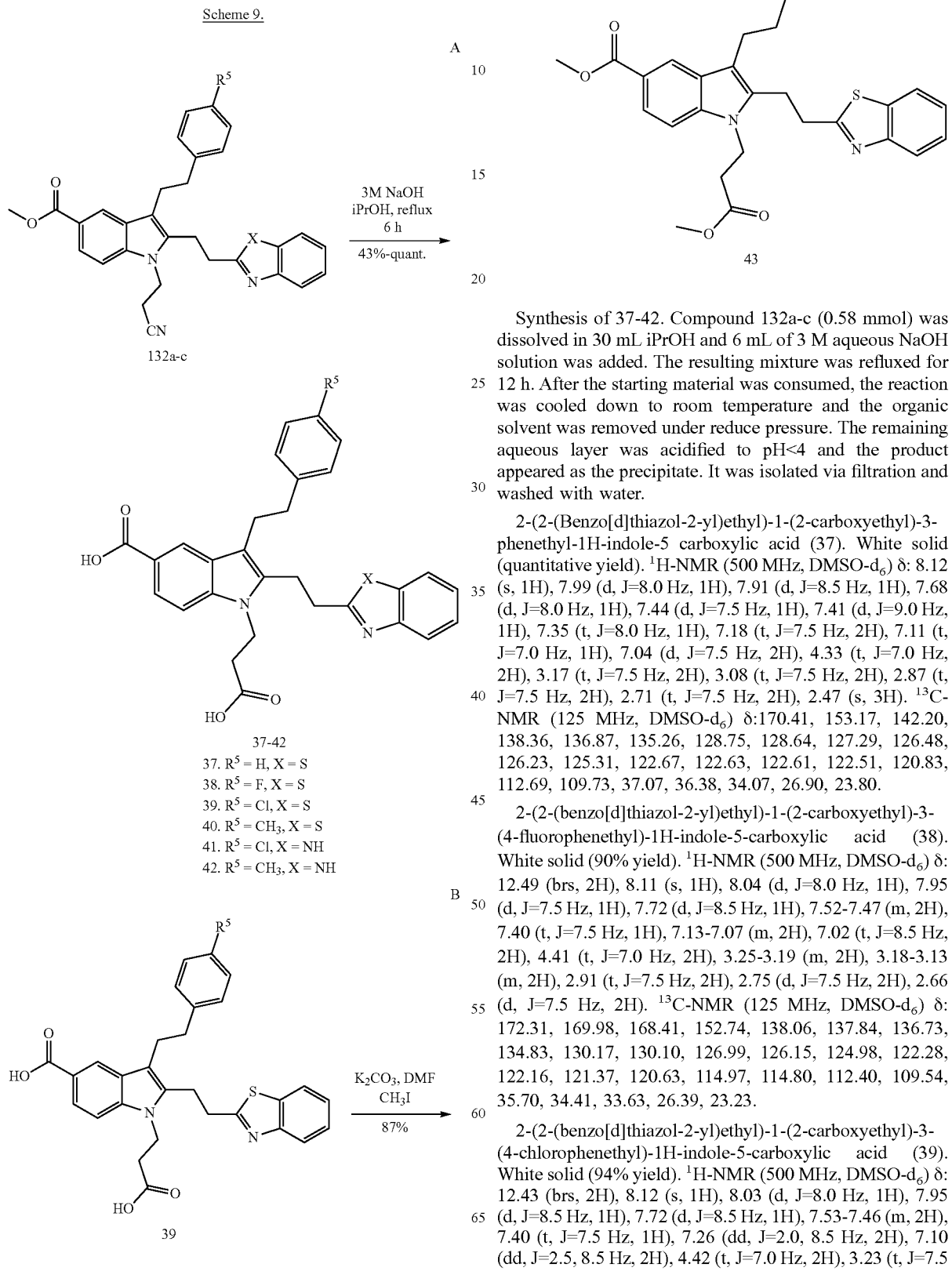

Scheme 9.

37-42
37. R⁵ = H, X = S
38. R⁵ = F, X = S
39. R⁵ = Cl, X = S
40. R⁵ = CH₃, X = S
41. R⁵ = Cl, X = NH
42. R⁵ = CH₃, X = NH

Synthesis of 37-42. Compound 132a-c (0.58 mmol) was dissolved in 30 mL iPrOH and 6 mL of 3 M aqueous NaOH solution was added. The resulting mixture was refluxed for 12 h. After the starting material was consumed, the reaction was cooled down to room temperature and the organic solvent was removed under reduce pressure. The remaining aqueous layer was acidified to pH<4 and the product appeared as the precipitate. It was isolated via filtration and washed with water.

2-(2-(Benzo[d]thiazol-2-yl)ethyl)-1-(2-carboxyethyl)-3-phenethyl-1H-indole-5 carboxylic acid (37). White solid (quantitative yield). $^1$H-NMR (500 MHz, DMSO-$d_6$) δ: 8.12 (s, 1H), 7.99 (d, J=8.0 Hz, 1H), 7.91 (d, J=8.5 Hz, 1H), 7.68 (d, J=8.0 Hz, 1H), 7.44 (d, J=7.5 Hz, 1H), 7.41 (d, J=9.0 Hz, 1H), 7.35 (t, J=8.0 Hz, 1H), 7.18 (t, J=7.5 Hz, 2H), 7.11 (t, J=7.0 Hz, 1H), 7.04 (d, J=7.5 Hz, 2H), 4.33 (t, J=7.0 Hz, 2H), 3.17 (t, J=7.5 Hz, 2H), 3.08 (t, J=7.5 Hz, 2H), 2.87 (t, J=7.5 Hz, 2H), 2.71 (t, J=7.5 Hz, 2H), 2.47 (s, 3H). $^{13}$C-NMR (125 MHz, DMSO-$d_6$) δ:170.41, 153.17, 142.20, 138.36, 136.87, 135.26, 128.75, 128.64, 127.29, 126.48, 126.23, 125.31, 122.67, 122.63, 122.61, 122.51, 120.83, 112.69, 109.73, 37.07, 36.38, 34.07, 26.90, 23.80.

2-(2-(benzo[d]thiazol-2-yl)ethyl)-1-(2-carboxyethyl)-3-(4-fluorophenethyl)-1H-indole-5-carboxylic acid (38). White solid (90% yield). $^1$H-NMR (500 MHz, DMSO-$d_6$) δ: 12.49 (brs, 2H), 8.11 (s, 1H), 8.04 (d, J=8.0 Hz, 1H), 7.95 (d, J=7.5 Hz, 1H), 7.72 (d, J=8.5 Hz, 1H), 7.52-7.47 (m, 2H), 7.40 (t, J=7.5 Hz, 1H), 7.13-7.07 (m, 2H), 7.02 (t, J=8.5 Hz, 2H), 4.41 (t, J=7.0 Hz, 2H), 3.25-3.19 (m, 2H), 3.18-3.13 (m, 2H), 2.91 (t, J=7.5 Hz, 2H), 2.75 (d, J=7.5 Hz, 2H), 2.66 (d, J=7.5 Hz, 2H). $^{13}$C-NMR (125 MHz, DMSO-$d_6$) δ: 172.31, 169.98, 168.41, 152.74, 138.06, 137.84, 136.73, 134.83, 130.17, 130.10, 126.99, 126.15, 124.98, 122.28, 122.16, 121.37, 120.63, 114.97, 114.80, 112.40, 109.54, 35.70, 34.41, 33.63, 26.39, 23.23.

2-(2-(benzo[d]thiazol-2-yl)ethyl)-1-(2-carboxyethyl)-3-(4-chlorophenethyl)-1H-indole-5-carboxylic acid (39). White solid (94% yield). $^1$H-NMR (500 MHz, DMSO-$d_6$) δ: 12.43 (brs, 2H), 8.12 (s, 1H), 8.03 (d, J=8.0 Hz, 1H), 7.95 (d, J=8.5 Hz, 1H), 7.72 (d, J=8.5 Hz, 1H), 7.53-7.46 (m, 2H), 7.40 (t, J=7.5 Hz, 1H), 7.26 (dd, J=2.0, 8.5 Hz, 2H), 7.10 (dd, J=2.5, 8.5 Hz, 2H), 4.42 (t, J=7.0 Hz, 2H), 3.23 (t, J=7.5

Hz, 2H), 3.17-3.12 (m, 2H), 2.91 (t, J=7.5 Hz, 2H), 2.75 (t, J=7.5 Hz, 2H), 2.66 (t, J=7.5 Hz, 2H). $^{13}$C-NMR (125 MHz, DMSO-d$_6$) δ: 172.64, 170.33, 168.76, 153.16, 141.10, 138.48, 137.14, 135.25, 130.92, 130.66, 128.53, 127.37, 126.52, 125.36, 122.68, 122.62, 122.53, 121.82, 121.00, 112.73, 109.92, 36.24, 34.83, 34.03, 26.54, 23.64.

2-(2-(benzo[d]thiazol-2-yl)ethyl)-1-(2-carboxyethyl)-3-(4-methylphenethyl)-1H-indole-5-carboxylic acid (40). White solid (78% yield). $^1$H-NMR (500 MHz, DMSO-d$_6$) δ:12.54 (brs, 1H), 8.14 (s, 1H), 8.04 (d, J=8.0 Hz, 1H), 7.95 (d, J=8.0 Hz, 1H), 7.72 (dd, J=1.5, 8.5 Hz, 1H), 7.52-7.45 (m, 2H), 7.42-7.37 (m, 1H), 7.02 (d, J=8.0 Hz, 2H), 6.96 (d, J=7.5 Hz, 2H), 4.40 (t, J=7.0 Hz, 2H), 3.23 (t, J=7.5 Hz, 2H), 3.09 (t, J=7.5 Hz, 2H), 2.89 (t, J=7.5 Hz, 2H), 2.72 (t, J=7.5 Hz, 2H), 2.63 (t, J=7.5 Hz, 2H), 2.23 (s, 3H). $^{13}$C-NMR (125 MHz, DMSO-d$_6$) δ: 172.37, 169.97, 168.43, 152.72, 138.64, 138.02, 136.60, 134.81, 134.70, 128.85, 128.81, 128.22, 126.95, 126.08, 124.91, 122.24, 122.16, 122.11, 121.42, 120.55, 112.54, 109.45, 36.20, 34.69, 33.56, 26.57, 23.21, 23.19, 20.67.

2-(2-(1H-benzo[d]imidazol-2-yl)ethyl)-1-(2-carboxyethyl)-3-(4-chlorophenethyl)-1H-indole-5-carboxylic acid (41). White solid (quantitative yield). $^1$H-NMR (500 MHz, DMSO-d$_6$) δ: 15.06 (brs, 1H), 12.45 (brs, 1H), 8.12 (dd, J=1.5, 22.0 Hz, 1H), 7.79 (dd, J=3.0, 6.0 Hz, 2H), 7.74 (ddd, J=1.5, 4.0, 8.5 Hz, 1H), 7.54-7.50 (m, 3H), 7.29-7.09 (m, 5H), 4.48 (t, J=7.5 Hz, 2H), 3.21 (t, J=7.5 Hz, 2H), 2.94-2.88 (m, 2H), 2.77-2.70 (m, 2H), 2.68 (t, J=7.5 Hz, 2H). $^{13}$C-NMR (125 MHz, DMSO-d$_6$) δ: 172.65, 168.72, 153.33, 142.00, 140.96, 138.60, 138.57, 135.81, 131.55, 130.77, 128.85, 128.55, 128.42, 127.32, 126.26, 125.85, 122.82, 121.90, 121.13, 114.25, 113.49, 113.24, 110.06, 37.15, 36.41, 34.86, 27.45, 26.30, 21.85.

2-(2-(1H-benzo[d]imidazol-2-yl)ethyl)-1-(2-carboxyethyl)-3-(4-methylphenethyl)-1H-indole-5-carboxylic acid (42). White solid (43% yield). $^1$H-NMR (500 MHz, DMSO-d$_6$) δ:15.04 (brs, 1H), 12.48 (brs, 1H), 8.11 (s, 1H), 7.80 (dd, J=3.0, 6.0 Hz, 2H), 7.74 (dd, J=1.5, 8.5 Hz, 1H), 7.55-7.50 (m, 3H), 7.05 (d, J=8.0 Hz, 2H), 7.01 (d, J=7.5 Hz, 2H), 4.47 (t, J=7.5 Hz, 2H), 3.19 (t, J=7.5 Hz, 2H), 2.89 (t, J=7.5 Hz, 2H), 2.72-2.63 (m, 4H), 2.20 (s, 3H). $^{13}$C-NMR (125 MHz, DMSO-d$_6$) δ: 172.17, 169.07, 168.24, 152.88, 138.48, 138.11, 135.29, 134.66, 131.01, 130.99, 128.66, 128.64, 128.24, 126.86, 125.42, 121.41, 120.66, 113.76, 113.09, 36.28, 34.37, 26.97, 25.97, 23.33, 21.30, 20.56.

Methyl 2-(2-(benzo[d]thiazol-2-yl)ethyl)-3-(4-chlorophenethyl)-1-(3-methoxy-3-oxo propyl)-1H-indole-5-carboxylate (43). Compound 39 (60 mg, 0.11 mmol) was dissolved in 10 mL DMF. K$_2$CO$_3$ (38.8 mg, 0.28 mmol) and MeI (0.017 ml, 0.28 mmol) were added to the solution. The reaction was stirred for 12 h and the organic solvent was removed. The crude product was purified via flash column chromatography (hexanes:acetone=3:2). The pale yellow solid was isolated as the desired product (55 mg, 87% yield). $^1$H-NMR (500 MHz, CD$_3$OD) δ: 8.09 (d, J=1.5 Hz, 1H), 7.90 (d, J=8.5 Hz, 1H), 7.87 (d, J=8.0 Hz, 1H), 7.79 (dd, J=1.5, 8.5 Hz, 1H), 7.47 (ddd, J=1.2, 7.5, 8.5 Hz, 1H), 7.39-7.33 (m, 2H), 7.12 (d, J=8.5 Hz, 2H), 6.89 (d, J=8.0 Hz, 2H), 4.42 (t, J=7.0 Hz, 2H), 3.89 (s, 3H), 3.57 (s, 3H), 3.16-3.12 (m, 2H), 3.10-3.07 (m, 2H), 2.89 (t, J=7.0 Hz, 2H), 2.77 (t, J=7.0 Hz, 2H), 2.69 (t, J=7.0 Hz, 2H). $^{13}$C-NMR (125 MHz, CD$_3$OD) δ:173.02, 172.22, 169.96, 154.00, 141.89, 140.17, 137.65, 136.29, 132.74, 131.36, 131.33, 129.29, 128.88, 127.42, 126.35, 123.67, 123.16, 122.90, 122.29, 114.55, 110.27, 52.36, 52.24, 40.25, 37.19, 35.38, 34.78, 27.58, 24.90.

Scheme 10.

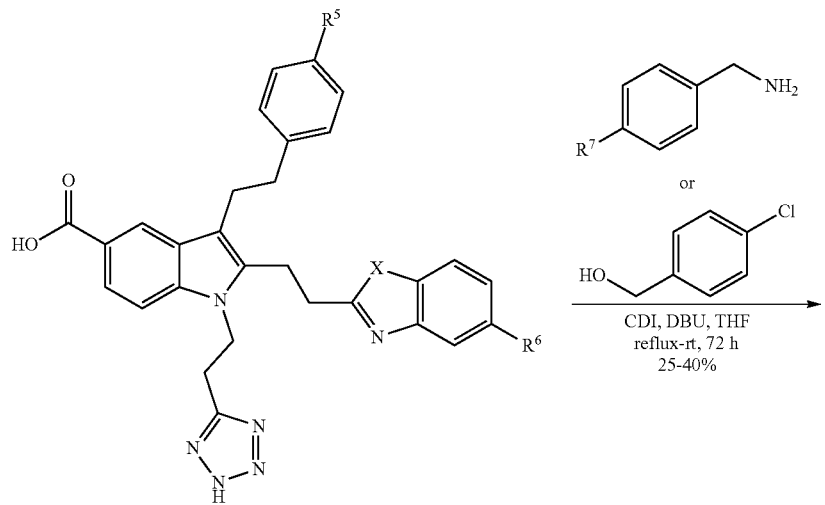

26, 32

-continued
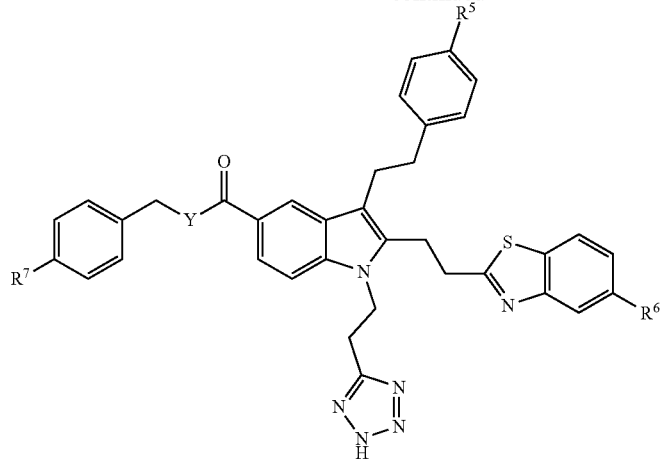
44-46, 70
44. $R^5$ = F, $R^6$ = H, $R^7$ = F, Y = NH
45. $R^5$ = F, $R^6$ = H, $R^7$ = Cl, Y = NH
46. $R^5$ = Cl, $R^6$ = ⁓O⁓O⁓ , $R^7$ = Cl, Y = NH
70. $R^5$ Cl, $R^6$ = $OCH_3$, $R^7$ = Cl, Y = O
B
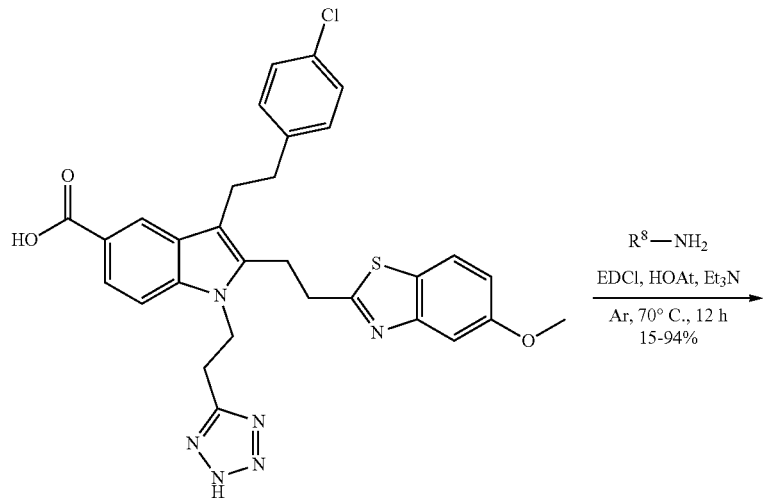
31
$R^8$—$NH_2$
EDCl, HOAt, $Et_3N$
Ar, 70° C., 12 h
15-94%
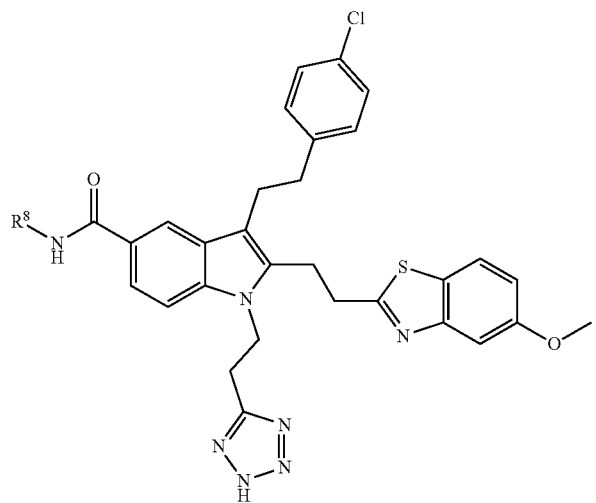
47-69

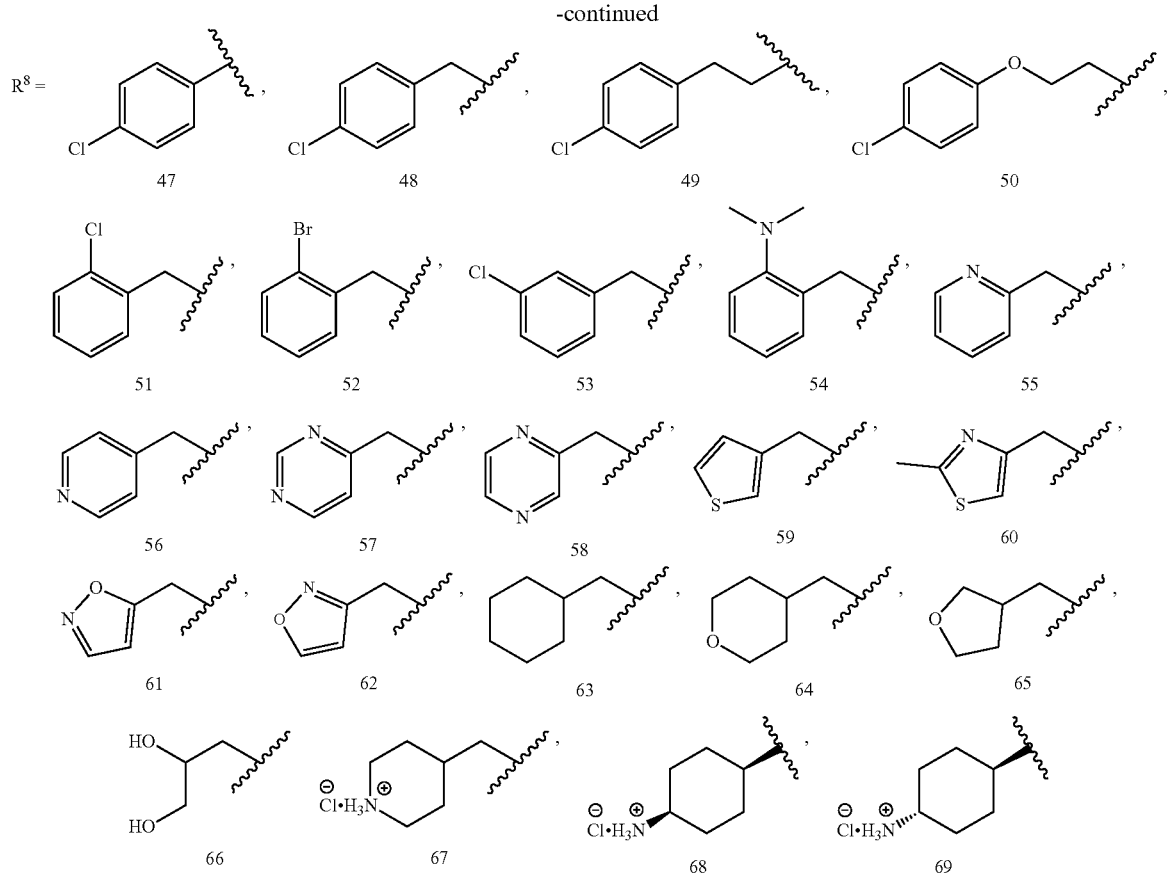

Synthesis of 44-46, and 70. Compound 26, or 32 (0.28 mmol), and CDI (137.67 mg, 0.85 mmol) were placed in a 50 mL oven-dried round bottom flask. The mixture was dissolved in anhydrous 20 mL anhydrous THF. The resulting solution was refluxed for 24 h until TLC shows no starting material. The reaction was allowed to cool down to room temperature and benzyl amines (0.99 mmol) was added, followed by DBU (1M in THF, 0.99 mL, 0.99 mmol). The mixture was stirred for 48 h at room temperature. It was subsequently quenched with sat. aqueous NH$_4$C-solution and extracted two times with DCM. After removal of the organic solvent, the crude product was purified via flash column chromatography to offer the desired product.

1-(2-(2H-tetrazol-5-yl)ethyl)-2-(2-(benzo[d]thiazol-2-yl)ethyl)-N-(4-fluorobenzyl)-3-(4-fluoro-phenethyl)-1H-indole-5-carboxamide (44). White solid (CH$_2$Cl$_2$:MeOH=30:1 to 20:1, 27% yield). $^1$H-NMR (500 MHz, Acetone-d$_6$) δ: 8.23 (s, 2H), 7.96 (d, J=7.5 Hz, 1H), 7.94 (d, J=8.0 Hz, 1H), 7.78 (dd, J=1.5, 8.5 Hz, 1H), 7.51-7.36 (m, 5H), 7.14-7.09 (m, 2H), 7.06 (d, J=8.5 Hz, 1H), 6.97 (t, J=9.0 Hz, 2H), 4.74 (t, J=7.0 Hz, 2H), 4.61 (d, J=5.5 Hz, 2H), 3.48 (t, J=7.5 Hz, 2H), 3.22 (s, 4H), 2.97 (t, J=7.5 Hz, 2H), 2.84 (t, J=7.5 Hz, 2H). $^{13}$C-NMR (125 MHz, Acetone-d$_6$) δ: 169.79, 167.52, 162.75, 162.23, 160.82, 160.30, 153.86, 153.31, 138.11, 138.08, 137.83, 136.31, 135.27, 130.19, 130.13, 129.46, 129.38, 127.57, 125.97, 124.88, 122.40, 121.74, 120.79, 118.06, 114.88, 114.78, 114.71, 114.61, 113.05, 108.98, 42.40, 41.27, 35.84, 33.82, 26.59, 24.30, 23.35.

1-(2-(2H-tetrazol-5-yl)ethyl)-2-(2-(benzo[d]thiazol-2-yl)ethyl)-N-(4-chlorobenzyl)-3-(4-fluoro-phenethyl)-1H-indole-5-carboxamide (45). White solid (CH$_2$Cl$_2$:MeOH=30:1 to 25:1 to 20:1, 25% yield). $^1$H-NMR (500 MHz, CD$_3$CN) δ: 7.94 (d, J=1.0 Hz, 1H), 7.93-7.88 (m, 2H), 7.59 (dd, J=1.5, 8.5 Hz, 1H), 7.55 (t, J=6.0 Hz, 1H), 7.47 (ddd, J=1.0, 7.0, 8.5 Hz, 1H), 7.40-7.31 (m, 4H), 7.28 (d, J=8.5 Hz, 1H), 7.05-7.01 (m, 2H), 6.92 (t, J=9.0 Hz, 2H), 4.58-4.50 (m, 4H), 3.33 (t, J=7.0 Hz, 2H), 3.17-3.11 (m, 2H), 3.10-3.04 (m, 2H), 2.85 (t, J=7.5 Hz, 2H), 2.73 (t, J=7.5 Hz, 2H). $^{13}$C-NMR (125 MHz, CD$_3$CN) δ: 170.19, 167.97, 162.15, 160.23, 153.77, 153.11, 138.87, 138.15, 138.12, 137.73, 136.38, 135.20, 132.03, 130.19, 130.12, 129.12, 128.31, 127.44, 126.10, 125.49, 124.96, 122.23, 121.86, 120.58, 117.88, 114.77, 114.61, 113.23, 109.09, 42.43, 41.29, 35.69, 33.66, 26.36, 24.23, 23.33.

1-(2-(2H-tetrazol-5-yl)ethyl)-N-(4-chlorobenzyl)-3-(4-chlorophenethyl)-2-(2-(5-(2-methoxy-ethoxy)benzo[d]thiazol-2-yl)ethyl)-1H-indole-5-carboxamide (46). Pale yellow solid (CH$_2$Cl$_2$:MeOH=20:1 to 15:1. 30% yield). $^1$H-NMR (500 MHz, CD$_3$CN) δ: 7.93 (s, 1H), 7.73 (d, J=8.5 Hz, 1H), 7.59 (dd, J=1.5, 9.0 Hz, 1H), 7.54 (t, J=6.9 Hz, 1H), 7.41 (d, J=2.5 Hz, 1H), 7.38-7.30 (m, 4H), 7.28 (d, J=8.5 Hz, 1H), 7.18 (d, J=8.5 Hz, 2H), 7.03-6.97 (m, 2H), 4.56-4.50 (m, 4H), 4.16-4.11 (m, 2H), 3.73-3.68 (m, 2H), 3.36 (s, 3H), 3.32 (t, J=7.5 Hz, 2H), 3.13-3.04 (m, 4H), 2.84 (t, J=7.5 Hz, 2H), 2.71 (t, J=7.5 Hz, 2H). $^{13}$C-NMR (125 MHz, CD$_3$CN) δ:171.45, 167.98, 158.18, 154.40, 153.77, 141.00, 138.86, 137.71, 136.39, 132.03, 131.03, 130.21, 129.13, 128.32, 128.22, 128.10, 127.42, 127.03, 125.49, 122.18, 120.60, 117.87, 115.00, 113.13, 109.11, 105.91, 70.66, 67.74, 58.08, 42.44, 41.30, 35.80, 33.68, 26.09, 24.21, 23.42.

4-Chlorobenzyl 1-(2-(2H-tetrazol-5-yl)ethyl)-3-(4-chlorophenethyl)-2-(2-(5-methoxy benzo-[d]thiazol-2-yl)ethyl)-

1H-indole-5-carboxylate (70). White solid (CH$_2$Cl$_2$:MeOH=30:1 to 20:1 to 15:1, 40% yield). $^1$H-NMR (500 MHz, DMSO-d$_6$) δ: 8.09 (s, 1H), 7.89 (d, J=8.5 Hz, 1H), 7.73 (d, J=8.5 Hz, 1H), 7.54-7.44 (m, 6H), 7.23 (d, J=8.0 Hz, 2H), 7.06 (d, J=8.5 Hz, 2H), 7.04-7.00 (m, 1H), 5.35 (s, 2H), 4.59 (t, J=7.0 Hz, 2H), 3.82 (s, 3H), 3.15 (s, 4H), 2.90 (t, J=7.5 Hz, 2H), 2.72 (t, J=7.5 Hz, 2H). $^{13}$C-NMR (125 MHz, Acetone-d$_6$) δ: 170.79, 166.62, 159.08, 154.67, 140.88, 138.81, 136.88, 136.12, 133.20, 131.13, 130.21, 129.66, 128.49, 128.15, 127.63, 126.89, 122.44, 121.90, 121.07, 120.95, 114.66, 113.26, 109.21, 105.23, 64.86, 55.02, 41.51, 36.13, 33.80, 26.30, 24.50, 23.43.

1-(2-(2H-tetrazol-5-yl)ethyl)-3-(4-chlorophenethyl)-N-(4-chlorophenyl)-2-(2-(5-methoxybenzo[d]thiazol-2-yl)ethyl)-1H-indole-5-carboxamide (47). The synthesis of compound 47 followed general procedure H to obtain the desired product as brown solid (CH$_2$Cl$_2$:MeOH=15:1, 61% yield). $^1$H NMR (500 MHz, DMSO-d$_6$) δ 10.21 (s, 1H), 8.18 (d, J=1.8 Hz, 1H), 7.89 (d, J=8.8 Hz, 1H), 7.87-7.81 (m, 2H), 7.75 (dd, J=8.6, 1.7 Hz, 1H), 7.51 (d, J=8.7 Hz, 1H), 7.48 (d, J=2.6 Hz, 1H), 7.44-7.38 (m, 2H), 7.31-7.25 (m, 2H), 7.16-7.10 (m, 2H), 7.03 (dd, J=8.8, 2.5 Hz, 1H), 4.67-4.59 (m, 2H), 3.83 (s, 3H), 3.32 (t, J=7.4 Hz, 2H), 3.16 (h, J=2.6 Hz, 4H), 2.92 (dd, J=9.1, 6.4 Hz, 2H), 2.79 (dd, J=8.9, 6.5 Hz, 2H). $^{13}$C NMR (125 MHz, DMSO-d$_6$) δ 170.98, 166.40, 158.47, 154.05, 140.73, 138.55, 137.43, 136.43, 130.47, 130.25, 128.40, 128.07, 126.82, 126.80, 126.42, 125.43, 122.34, 121.91, 120.92, 118.61, 114.47, 112.52, 109.19, 105.25, 55.45, 35.63, 33.61, 26.12, 24.07, 23.14. HPLC purity (water/CH$_3$CN): 98.24%, Rt: 15.83 min. HPLC purity (water/MeOH): 99.42%, Rt: 16.93 min.

1-(2-(2H-tetrazol-5-yl)ethyl)-N-(4-chlorobenzyl)-3-(4-chlorophenethyl)-2-(2-(5-methoxybenzo-[d]thiazol-2-yl)ethyl)-1H-indole-5-carboxamide (48). The synthesis of compound 48 followed general procedure H to obtain the desired product as brown solid (CH$_2$Cl$_2$:MeOH=15:1, 71% yield). $^1$H NMR (500 MHz, DMSO-d$_6$) δ 8.94 (t, J=6.0 Hz, 1H), 8.14 (d, J=1.7 Hz, 1H), 7.88 (d, J=8.8 Hz, 1H), 7.70 (dd, J=8.6, 1.7 Hz, 1H), 7.47 (d, J=2.5 Hz, 1H), 7.45 (d, J=8.6 Hz, 1H), 7.39 (d, J=8.6 Hz, 2H), 7.36 (d, J=8.7 Hz, 2H), 7.28 (d, J=8.4 Hz, 2H), 7.11 (d, J=8.4 Hz, 2H), 7.03 (dd, J=8.8, 2.5 Hz, 1H), 4.62-4.56 (m, 2H), 4.50 (d, J=5.9 Hz, 2H), 3.82 (s, 3H), 3.29 (d, J=7.5 Hz, 2H), 3.13 (d, J=2.2 Hz, 4H), 2.88 (dd, J=9.1, 6.4 Hz, 2H), 2.77 (dd, J=9.0, 6.4 Hz, 2H). $^{13}$C NMR (125 MHz, DMSO-d$_6$) δ 170.99, 167.08, 158.46, 154.04, 140.73, 139.25, 137.22, 136.16, 131.13, 130.43, 130.21, 129.03, 128.17, 128.06, 126.83, 126.42, 122.34, 120.62, 117.95, 114.47, 112.31, 109.05, 105.23, 55.44, 41.98, 40.97, 35.55, 33.64, 26.08, 24.05, 23.12. HPLC purity (water/CH$_3$CN): 98.87%, Rt: 15.48 min. HPLC purity (water/MeOH): 98.53%, Rt: 16.83 min.

1-(2-(2H-tetrazol-5-yl)ethyl)-N,3-bis(4-chlorophenethyl)-2-(2-(5-methoxybenzo[d]thiazol-2-yl)ethyl)-1H-indole-5-carboxamide (49). The synthesis of compound 49 followed general procedure H to obtain the desired product as brown solid (CH$_2$Cl$_2$:MeOH=15:1, 40% yield). $^1$H NMR (500 MHz, DMSO-d$_6$) δ 8.41 (t, J=5.6 Hz, 1H), 8.03 (d, J=1.7 Hz, 1H), 7.89 (d, J=8.8 Hz, 1H), 7.62 (dd, J=8.6, 1.7 Hz, 1H), 7.47 (d, J=2.5 Hz, 1H), 7.43 (d, J=8.6 Hz, 1H), 7.36-7.32 (m, 2H), 7.30-7.27 (m, 4H), 7.14-7.10 (m, 2H), 7.03 (dd, J=8.8, 2.5 Hz, 1H), 4.65-4.51 (m, 2H), 3.82 (s, 3H), 3.50 (dt, J=7.7, 6.1 Hz, 2H), 3.28 (d, J=6.4 Hz, 2H), 3.13 (p, J=3.2 Hz, 4H), 2.87 (td, J=7.1, 4.3 Hz, 4H), 2.76 (dd, J=9.1, 6.4 Hz, 2H). $^{13}$C NMR (125 MHz, DMSO-d$_6$) δ 171.00, 158.46, 154.04, 140.75, 138.78, 137.09, 136.07, 130.67, 130.59, 130.45, 130.20, 128.18, 128.08, 126.75, 126.42, 125.60, 122.34, 120.51, 117.80, 114.47, 112.24, 108.98, 105.24, 55.44, 40.95, 40.66, 35.55, 34.57, 33.66, 26.12, 24.05, 23.12. HPLC purity (water/CH$_3$CN): 98.75%, Rt: 15.61 min. HPLC purity (water/MeOH): 99.32%, Rt: 16.90 min.

1-(2-(2H-tetrazol-5-yl)ethyl)-3-(4-chlorophenethyl)-N-(2-(4-chlorophenoxy)ethyl)-2-(2-(5-methoxybenzo[d]thiazol-2-yl)ethyl)-1H-indole-5-carboxamide (50). The synthesis of compound 50 followed general procedure H to obtain the desired product as brown solid (CH$_2$Cl$_2$:MeOH=15:1, 63% yield). $^1$H NMR (500 MHz, DMSO-d$_6$) δ 8.59 (t, J=5.6 Hz, 1H), 8.09 (d, J=1.7 Hz, 1H), 7.89 (d, J=8.8 Hz, 1H), 7.66 (dd, J=8.7, 1.7 Hz, 1H), 7.47 (d, J=2.5 Hz, 1H), 7.44 (d, J=8.6 Hz, 1H), 7.34-7.30 (m, 2H), 7.30-7.26 (m, 2H), 7.13-7.08 (m, 2H), 7.05-7.00 (m, 3H), 4.58 (t, J=7.4 Hz, 2H), 4.14 (t, J=6.0 Hz, 2H), 3.82 (s, 3H), 3.65 (q, J=5.8 Hz, 2H), 3.29 (t, J=7.4 Hz, 2H), 3.12 (d, J=4.7 Hz, 4H), 2.88 (dd, J=9.1, 6.4 Hz, 2H), 2.76 (dd, J=9.0, 6.5 Hz, 2H). $^{13}$C NMR (126 MHz, DMSO-d$_6$) δ 171.02, 167.44, 158.47, 157.36, 154.05, 140.76, 137.19, 136.15, 130.46, 130.24, 129.27, 128.09, 126.78, 126.43, 125.21, 124.29, 122.37, 120.59, 117.98, 116.27, 114.49, 112.30, 109.02, 105.23, 66.59, 55.45, 54.93, 41.00, 35.57, 33.66, 26.12, 24.11, 23.13. HPLC purity (water/CH$_3$CN): 97.15%, Rt: 14.17 min. HPLC purity (water/MeOH): 97.17%, Rt: 16.18 min.

1-(2-(2H-tetrazol-5-yl)ethyl)-N-(2-chlorobenzyl)-3-(4-chlorophenethyl)-2-(2-(5-methoxybenzo[d]thiazol-2-yl)ethyl)-1H-indole-5-carboxamide (51). The synthesis of compound 51 followed general procedure H to obtain the desired product as brown solid (CH$_2$Cl$_2$:MeOH=15:1, 38% yield). $^1$H NMR (500 MHz, Chloroform-d) δ 7.80 (s, 1H), 7.63 (d, J=8.8 Hz, 1H), 7.48 (d, J=2.5 Hz, 1H), 7.38 (dd, J=6.4, 2.9 Hz, 1H), 7.34 (d, J=8.6 Hz, 1H), 7.31 (dd, J=6.6, 2.5 Hz, 1H), 7.15 (dt, J=5.7, 2.3 Hz, 2H), 7.07 (d, J=7.9 Hz, 2H), 7.05-6.97 (m, 3H), 6.84 (d, J=7.9 Hz, 2H), 4.67 (d, J=5.7 Hz, 2H), 4.45 (t, J=7.4 Hz, 2H), 3.83 (s, 3H), 3.34 (t, J=7.3 Hz, 2H), 3.09 (dd, J=9.3, 6.1 Hz, 2H), 2.99 (dd, J=9.2, 6.2 Hz, 2H), 2.80 (t, J=7.4 Hz, 2H), 2.68 (t, J=7.4 Hz, 2H). $^{13}$C NMR (125 MHz, Chloroform-d) δ 170.75, 169.44, 159.19, 154.01, 140.25, 138.00, 135.86, 135.36, 133.55, 131.70, 130.08, 129.89, 129.61, 129.00, 128.32, 127.56, 127.11, 126.49, 124.74, 121.90, 120.51, 118.49, 115.46, 113.75, 108.95, 104.94, 55.64, 42.37, 41.72, 36.22, 33.97, 26.53, 24.86, 24.16. HPLC purity (water/CH$_3$CN): 98.68%, Rt: 15.44 min. HPLC purity (water/MeOH): 98.46%, Rt: 16.79 min.

1-(2-(2H-tetrazol-5-yl)ethyl)-N-(2-bromobenzyl)-3-(4-chlorophenethyl)-2-(2-(5-methoxybenzo[d]thiazol-2-yl)ethyl)-1H-indole-5-carboxamide (52). The synthesis of compound 52 followed general procedure H to obtain the desired product as white solid (CH$_2$Cl$_2$:MeOH=15:1, 46% yield). $^1$H NMR (500 MHz, Chloroform-d) δ 7.81 (d, J=1.7 Hz, 1H), 7.65 (d, J=8.8 Hz, 1H), 7.55-7.50 (m, 2H), 7.41 (dd, J=7.7, 1.7 Hz, 1H), 7.34 (dd, J=8.6, 1.8 Hz, 1H), 7.22 (td, J=7.5, 1.3 Hz, 1H), 7.13-7.08 (m, 3H), 7.05-7.00 (m, 2H), 6.91 (t, J=6.0 Hz, 1H), 6.89-6.85 (m, 2H), 4.68 (d, J=5.8 Hz, 2H), 4.47 (t, J=7.3 Hz, 2H), 3.86 (s, 3H), 3.42-3.34 (m, 2H), 3.10 (dd, J=9.4, 6.1 Hz, 2H), 2.99 (dd, J=9.3, 6.2 Hz, 2H), 2.82 (t, J=7.3 Hz, 2H), 2.72 (t, J=7.3 Hz, 2H). $^{13}$C NMR (125 MHz, Chloroform-d) δ 170.83, 169.26, 159.28, 153.96, 140.27, 138.03, 137.03, 135.77, 132.93, 131.77, 130.24, 130.13, 129.33, 128.38, 127.79, 127.56, 126.43, 124.86, 123.73, 121.95, 120.49, 118.58, 115.62, 113.79, 108.95, 104.88, 55.70, 44.74, 41.80, 36.24, 33.94, 26.61, 24.91, 24.30. HPLC purity (water/CH$_3$CN): 97.83%, Rt: 15.56 min. HPLC purity (water/MeOH): 98.41%, Rt: 16.85 min.

1-(2-(2H-tetrazol-5-yl)ethyl)-N-(3-chlorobenzyl)-3-(4-chlorophenethyl)-2-(2-(5-methoxybenzo[d]thiazol-2-yl)ethyl)-1H-indole-5-carboxamide (53). The synthesis of compound 53 followed general procedure H to obtain the desired product as brown solid (CH$_2$Cl$_2$:MeOH=15:1, 42% yield). $^1$H NMR (500 MHz, Chloroform-d) δ 7.80 (d, J=1.7 Hz, 1H), 7.64 (d, J=8.8 Hz, 1H), 7.50 (d, J=2.4 Hz, 1H), 7.38 (dd, J=8.6, 1.7 Hz, 1H), 7.28 (d, J=1.7 Hz, 1H), 7.18 (d, J=1.4 Hz, 3H), 7.09-7.06 (m, 2H), 7.04 (d, J=8.6 Hz, 1H), 7.01 (dd, J=8.8, 2.5 Hz, 2H), 6.86-6.83 (m, 2H), 4.57 (d, J=5.8 Hz, 2H), 4.47-4.42 (m, 2H), 3.84 (s, 3H), 3.38-3.33 (m, 2H), 3.08 (dd, J=9.4, 6.1 Hz, 2H), 2.99 (dd, J=9.4, 6.2 Hz, 2H), 2.81 (t, J=7.3 Hz, 2H), 2.70 (t, J=7.2 Hz, 2H). $^{13}$C NMR (125 MHz, Chloroform-d) δ 170.84, 169.42, 159.26, 153.93, 140.30, 138.04, 135.81, 134.50, 131.72, 130.16, 130.02, 128.34, 127.67, 127.55, 126.43, 125.84, 124.77, 121.95, 120.64, 118.52, 115.56, 113.79, 108.97, 104.89, 55.69, 43.74, 41.74, 36.24, 33.92, 26.53, 24.86, 24.25. HPLC purity (water/CH$_3$CN): 98.53%, Rt: 15.50 min. HPLC purity (water/MeOH): 98.78%, Rt: 16.48 min.

1-(2-(2H-tetrazol-5-yl)ethyl)-3-(4-chlorophenethyl)-N-(2-(dimethylamino)benzyl)-2-(2-(5-methoxybenzo[d]thiazol-2-yl)ethyl)-1H-indole-5-carboxamide (54). The synthesis of compound 54 followed general procedure H to obtain the desired product as brown solid (CH$_2$Cl$_2$:MeOH=13:1, 78% yield). $^1$H NMR (500 MHz, Chloroform-d) δ 8.16 (s, 1H), 7.80 (d, J=1.8 Hz, 1H), 7.63 (d, J=8.8 Hz, 1H), 7.48 (d, J=2.5 Hz, 1H), 7.36 (dd, J=8.6, 1.7 Hz, 1H), 7.30 (dd, J=7.6, 1.6 Hz, 1H), 7.28-7.23 (m, 1H), 7.16 (dd, J=8.2, 1.3 Hz, 1H), 7.12 (d, J=8.6 Hz, 1H), 7.10-7.07 (m, 2H), 7.04-6.99 (m, 2H), 6.86 (d, J=8.4 Hz, 2H), 4.78 (d, J=4.5 Hz, 2H), 4.54-4.48 (m, 2H), 3.85 (s, 3H), 3.43-3.38 (m, 2H), 3.13 (dd, J=9.3, 6.3 Hz, 2H), 3.00 (dd, J=9.2, 6.3 Hz, 2H), 2.82 (t, J=7.4 Hz, 2H), 2.71 (s, 8H). $^{13}$C NMR (125 MHz, Chloroform-d) δ 170.61, 169.14, 159.11, 154.16, 153.52, 152.06, 140.16, 137.99, 136.00, 131.75, 131.41, 129.96, 129.61, 128.58, 128.36, 127.52, 126.60, 125.00, 124.22, 121.84, 120.59, 119.85, 118.05, 115.34, 113.50, 109.09, 105.04, 55.63, 44.68, 42.35, 41.95, 36.16, 34.06, 26.50, 24.95, 24.05. HPLC purity (water/CH$_3$CN): 97.13%, Rt: 13.88 min. HPLC purity (water/MeOH): 97.76%, Rt: 15.07 min.

1-(2-(2H-tetrazol-5-yl)ethyl)-3-(4-chlorophenethyl)-2-(2-(5-methoxybenzo[d]thiazol-2-yl)ethyl)-N-(pyridin-2-ylmethyl)-1H-indole-5-carboxamide (55). The synthesis of compound 55 followed general procedure H to obtain the desired product as brown solid (CH$_2$Cl$_2$:MeOH=13:1, 75% yield). $^1$H NMR (500 MHz, DMSO-d$_6$) δ 9.00 (t, J=6.0 Hz, 1H), 8.52 (ddd, J=4.8, 1.9, 0.9 Hz, 1H), 8.18 (d, J=1.7 Hz, 1H), 7.89 (d, J=8.8 Hz, 1H), 7.78-7.71 (m, 2H), 7.49-7.44 (m, 2H), 7.34 (d, J=7.9 Hz, 1H), 7.30-7.24 (m, 3H), 7.14-7.09 (m, 2H), 7.03 (dd, J=8.8, 2.5 Hz, 1H), 4.60 (dd, J=9.0, 6.2 Hz, 4H), 3.82 (s, 3H), 3.33-3.28 (m, 2H), 3.14 (h, J=2.5 Hz, 4H), 2.89 (dd, J=9.1, 6.3 Hz, 2H), 2.78 (dd, J=9.1, 6.4 Hz, 2H). $^{13}$C NMR (125 MHz, DMSO-d$_6$) δ 170.99, 167.19, 159.31, 158.46, 154.04, 148.76, 140.75, 137.24, 136.65, 136.15, 130.43, 130.22, 128.06, 126.42, 125.13, 122.34, 121.96, 120.90, 120.68, 118.01, 114.47, 112.34, 109.06, 105.24, 55.44, 35.56, 33.65, 26.11, 24.05, 23.13. HPLC purity (water/CH$_3$CN): 98.77%, Rt: 13.16 min. HPLC purity (water/MeOH): 98.31%, Rt: 15.70 min.

1-(2-(2H-tetrazol-5-yl)ethyl)-3-(4-chlorophenethyl)-2-(2-(5-methoxybenzo[d]thiazol-2-yl)ethyl)-N-(pyridin-4-ylmethyl)-1H-indole-5-carboxamide (56). The synthesis of compound 56 followed general procedure H to obtain the desired product as brown solid (CH$_2$Cl$_2$:MeOH=13:1, 40% yield). $^1$H NMR (500 MHz, Methanol-d$_4$) δ 8.43-8.34 (m, 2H), 8.03 (d, J=1.7 Hz, 1H), 7.65 (dd, J=8.6, 1.8 Hz, 1H), 7.59 (d, J=8.8 Hz, 1H), 7.40-7.35 (m, 2H), 7.31-7.25 (m, 2H), 7.08-7.03 (m, 2H), 6.91 (dd, J=8.8, 2.5 Hz, 1H), 6.87-6.82 (m, 2H), 4.58 (s, 2H), 4.53-4.47 (m, 2H), 3.74 (s, 3H), 3.28-3.24 (m, 2H), 3.03-2.93 (m, 4H), 2.77 (t, J=7.4 Hz, 2H), 2.65 (t, J=7.5 Hz, 2H). $^{13}$C NMR (125 MHz, Methanol-d$_4$) δ 173.40, 171.47, 160.72, 155.31, 151.88, 149.84, 142.05, 139.59, 137.33, 132.71, 131.31, 129.30, 129.03, 128.00, 125.94, 123.99, 123.15, 121.85, 119.78, 116.22, 114.75, 110.23, 105.79, 56.10, 43.61, 42.90, 37.10, 34.82, 27.55, 25.81, 25.04. HPLC purity (water/CH$_3$CN): 97.76%, Rt: 13.01 min. HPLC purity (water/MeOH): 98.09%, Rt: 14.89 min.

1-(2-(2H-tetrazol-5-yl)ethyl)-3-(4-chlorophenethyl)-2-(2-(5-methoxybenzo[d]thiazol-2-yl)ethyl)-N-(pyrimidin-4-ylmethyl)-1H-indole-5-carboxamide (57). The synthesis of compound 57 followed general procedure H to obtain the desired product as brown solid (CH$_2$Cl$_2$:MeOH=13:1, 60% yield). $^1$H NMR (500 MHz, DMSO-d$_6$) δ 9.12 (d, J=1.4 Hz, 1H), 9.08 (t, J=5.9 Hz, 1H), 8.73 (d, J=5.2 Hz, 1H), 8.18 (s, 1H), 7.89 (d, J=8.8 Hz, 1H), 7.72 (d, J=8.3 Hz, 1H), 7.50-7.40 (m, 3H), 7.31-7.26 (m, 2H), 7.14-7.09 (m, 2H), 7.03 (dd, J=8.8, 2.5 Hz, 1H), 4.60 (dd, J=15.1, 6.5 Hz, 4H), 3.82 (s, 3H), 3.31 (t, J=7.4 Hz, 2H), 3.14 (dt, J=6.0, 3.1 Hz, 4H), 2.90 (dd, J=9.1, 6.4 Hz, 2H), 2.78 (dd, J=9.0, 6.5 Hz, 2H). $^{13}$C NMR (125 MHz, DMSO-d$_6$) δ 170.99, 168.11, 167.44, 158.46, 158.05, 157.26, 154.04, 140.73, 137.33, 136.25, 130.44, 130.22, 128.07, 126.86, 126.42, 124.75, 122.34, 120.66, 118.52, 118.09, 114.47, 112.37, 109.12, 105.24, 55.44, 54.89, 44.28, 35.56, 33.64, 26.10, 24.07, 23.13. HPLC purity (water/CH$_3$CN): 99.09%, Rt: 13.92 min. HPLC purity (water/MeOH): 98.19%, Rt: 16.14 min.

1-(2-(2H-tetrazol-5-yl)ethyl)-3-(4-chlorophenethyl)-2-(2-(5-methoxybenzo[d]thiazol-2-yl)ethyl)-N-(pyrazin-2-ylmethyl)-1H-indole-5-carboxamide (58). The synthesis of compound 58 followed general procedure H to obtain the desired product as white solid (CH$_2$Cl$_2$:MeOH=13:1, 78% yield). $^1$H NMR (500 MHz, Chloroform-d) δ 8.59-8.56 (m, 1H), 8.43-8.38 (m, 2H), 7.88 (d, J=1.7 Hz, 1H), 7.73 (t, J=5.4 Hz, 1H), 7.61 (d, J=8.8 Hz, 1H), 7.50-7.45 (m, 2H), 7.08 (dd, J=10.7, 8.4 Hz, 3H), 6.98 (dd, J=8.8, 2.5 Hz, 1H), 6.85-6.81 (m, 2H), 4.74 (d, J=5.3 Hz, 2H), 4.48 (t, J=7.3 Hz, 2H), 3.81 (s, 3H), 3.36 (t, J=7.4 Hz, 2H), 3.05 (dd, J=9.5, 6.1 Hz, 2H), 2.94 (dd, J=9.4, 6.2 Hz, 2H), 2.79 (t, J=7.4 Hz, 2H), 2.68 (t, J=7.4 Hz, 2H). $^{13}$C NMR (125 MHz, Chloroform-d) δ 170.78, 169.39, 159.16, 153.92, 152.67, 143.89, 143.75, 143.34, 140.20, 137.96, 135.89, 131.68, 130.00, 128.33, 127.53, 126.42, 124.66, 121.89, 120.63, 118.66, 115.40, 113.64, 108.96, 104.92, 55.64, 43.14, 41.73, 36.13, 33.91, 26.52, 24.77, 24.06. HPLC purity (water/CH$_3$CN): 98.24%, Rt: 15.83 min. HPLC purity (water/MeOH): 99.42%, Rt: 16.93 min.

1-(2-(2H-tetrazol-5-yl)ethyl)-3-(4-chlorophenethyl)-2-(2-(5-methoxybenzo[d]thiazol-2-yl)ethyl)-N-(thiophen-3-ylmethyl)-1H-indole-5-carboxamide (59). The synthesis of compound 59 followed general procedure H to obtain the desired product as brown solid (CH$_2$Cl$_2$:MeOH=15:1, 54% yield). $^1$H NMR (500 MHz, Chloroform-d) δ 7.74 (d, J=1.7 Hz, 1H), 7.63 (d, J=8.8 Hz, 1H), 7.49 (d, J=2.5 Hz, 1H), 7.34 (d, J=8.5 Hz, 1H), 7.22 (dd, J=5.0, 3.0 Hz, 1H), 7.15-7.12 (m, 1H), 7.06 (d, J=8.3 Hz, 2H), 7.04-6.98 (m, 3H), 6.86 (d, J=5.3 Hz, 1H), 6.82 (d, J=8.0 Hz, 2H), 4.60 (d, J=5.6 Hz, 2H), 4.43 (s, 2H), 3.83 (s, 3H), 3.33 (q, J=7.5, 6.1 Hz, 2H), 3.08 (dd, J=9.4, 6.2 Hz, 2H), 2.98 (dd, J=9.3, 6.2 Hz, 2H), 2.79 (t, J=7.3 Hz, 2H), 2.68 (t, J=7.3 Hz, 2H). $^{13}$C NMR (125 MHz, Chloroform-d) δ 170.82, 169.31, 159.22, 154.00, 140.28, 138.84, 137.96, 135.84, 131.71, 130.13, 128.32, 127.52, 127.33, 126.49, 124.92, 122.42, 121.93, 120.64, 118.33, 115.48, 113.67, 109.00, 104.96, 55.67, 41.80, 39.63, 36.24, 33.98, 26.50, 24.89, 24.20. HPLC purity (water/CH$_3$CN): 98.71%, Rt: 15.02 min. HPLC purity (water/MeOH): 98.75%, Rt: 16.12 min.

1-(2-(2H-tetrazol-5-yl)ethyl)-3-(4-chlorophenethyl)-2-(2-(5-methoxybenzo[d]thiazol-2-yl)ethyl)-N-((2-methylthiazol-4-yl)methyl)-1H-indole-5-carboxamide (60). The synthesis of compound 60 followed general procedure H to obtain the desired product as brown solid (CH$_2$Cl$_2$:MeOH=13:1, 41% yield). $^1$H NMR (500 MHz, Chloroform-d) δ 7.89 (d, J=1.7 Hz, 1H), 7.75 (t, J=5.1 Hz, 1H), 7.60 (d, J=8.8 Hz, 1H), 7.47-7.40 (m, 2H), 7.08 (dd, J=8.8, 2.5 Hz, 3H), 7.02 (s, 1H), 6.97 (dd, J=8.8, 2.5 Hz, 1H), 6.82-6.73 (m, 2H), 4.54 (d, J=5.0 Hz, 2H), 4.50 (t, J=7.0 Hz, 2H), 3.83 (s, 3H), 3.40 (t, J=7.0 Hz, 2H), 3.01 (dd, J=8.9, 5.8 Hz, 2H), 2.93 (dd, J=8.8, 5.8 Hz, 2H), 2.73-2.66 (m, 2H), 2.58 (t, J=7.5 Hz, 2H), 2.52 (s, 3H). $^{13}$C NMR (125 MHz, Chloroform-d) δ 170.65, 169.02, 167.05, 159.06, 154.15, 151.74, 140.17, 137.90, 136.06, 131.65, 129.81, 128.30, 127.48, 126.63, 124.42, 121.82, 121.02, 118.59, 115.80, 115.26, 113.46, 109.00, 105.06, 55.62, 41.89, 40.41, 36.03, 34.06, 26.29, 24.56, 23.90, 18.92. HPLC purity (water/CH$_3$CN): 98.70%, Rt: 14.20 min. HPLC purity (water/MeOH): 98.75%, Rt: 15.89 min.

1-(2-(2H-tetrazol-5-yl)ethyl)-3-(4-chlorophenethyl)-N-(isoxazol-5-ylmethyl)-2-(2-(5-methoxybenzo[d]thiazol-2-yl)ethyl)-1H-indole-5-carboxamide (61). The synthesis of compound 61 followed general procedure H to obtain the desired product as brown solid (CH$_2$Cl$_2$:MeOH=12:1, 37% yield). $^1$H NMR (500 MHz, Chloroform-d) δ 8.09 (d, J=1.8 Hz, 1H), 7.83 (d, J=1.8 Hz, 1H), 7.64 (d, J=8.8 Hz, 1H), 7.51 (d, J=2.4 Hz, 1H), 7.44 (dd, J=8.6, 1.7 Hz, 1H), 7.36 (t, J=5.9 Hz, 1H), 7.11-7.06 (m, 2H), 7.04 (d, J=8.6 Hz, 1H), 7.00 (dd, J=8.8, 2.5 Hz, 1H), 6.85-6.81 (m, 2H), 6.20 (d, J=1.8 Hz, 1H), 4.72 (d, J=5.8 Hz, 2H), 4.47 (t, J=7.5 Hz, 2H), 3.83 (s, 3H), 3.37 (t, J=7.4 Hz, 2H), 3.08-3.02 (m, 2H), 2.96 (dd, J=9.1, 5.8 Hz, 2H), 2.78 (t, J=7.3 Hz, 2H), 2.67 (t, J=7.3 Hz, 2H). $^{13}$C NMR (125 MHz, Chloroform-d) δ 170.95, 169.22, 168.47, 159.30, 153.83, 150.48, 140.25, 138.09, 135.78, 131.72, 130.12, 128.35, 127.50, 126.36, 124.42, 121.98, 120.66, 118.80, 115.59, 113.84, 108.93, 104.84, 101.75, 55.70, 41.70, 36.17, 35.81, 33.83, 26.51, 24.83, 24.24. HPLC purity (water/CH$_3$CN): 97.89%, Rt: 14.32 min. HPLC purity (water/MeOH): 98.90%, Rt: 15.55 min.

1-(2-(2H-tetrazol-5-yl)ethyl)-3-(4-chlorophenethyl)-N-(isoxazol-3-ylmethyl)-2-(2-(5-methoxybenzo[d]thiazol-2-yl)ethyl)-1H-indole-5-carboxamide (62). The synthesis of compound 62 followed general procedure H to obtain the desired product as brown solid (CH$_2$Cl$_2$:MeOH=15:1, 94% yield). $^1$H NMR (500 MHz, DMSO-d$_6$) δ 8.98 (t, J=5.9 Hz, 1H), 8.84 (d, J=1.7 Hz, 1H), 8.13 (d, J=1.7 Hz, 1H), 7.89 (d, J=8.8 Hz, 1H), 7.69 (dd, J=8.6, 1.7 Hz, 1H), 7.47 (d, J=2.5 Hz, 1H), 7.46 (d, J=8.7 Hz, 1H), 7.31-7.26 (m, 2H), 7.14-7.08 (m, 2H), 7.03 (dd, J=8.8, 2.5 Hz, 1H), 6.51 (d, J=1.7 Hz, 1H), 4.62-4.54 (m, 4H), 3.82 (s, 3H), 3.31-3.28 (m, 2H), 3.12 (tt, J=7.9, 4.1 Hz, 4H), 2.88 (dd, J=9.1, 6.3 Hz, 2H), 2.77 (dd, J=9.1, 6.4 Hz, 2H). $^{13}$C NMR (126 MHz, DMSO-d$_6$) δ 170.99, 167.29, 161.51, 159.83, 158.46, 154.04, 140.74, 137.28, 136.22, 130.45, 130.22, 128.08, 126.81, 126.42, 124.82, 122.34, 120.68, 118.06, 114.47, 112.35, 109.09, 105.23, 104.16, 55.44, 40.97, 35.55, 34.67, 33.64, 26.11, 24.03, 23.11. HPLC purity (water/CH$_3$CN): 98.78%, Rt: 14.22 min. HPLC purity (water/MeOH): 99.02%, Rt: 16.08 min.

1-(2-(2H-tetrazol-5-yl)ethyl)-3-(4-chlorophenethyl)-N-(cyclohexylmethyl)-2-(2-(5-methoxybenzo[d]thiazol-2-yl)ethyl)-1H-indole-5-carboxamide (63). The synthesis of compound 63 followed general procedure H to obtain the desired product as brown solid (CH$_2$Cl$_2$:MeOH=15:1, 86% yield). $^1$H NMR (500 MHz, Chloroform-d) δ 7.69 (d, J=1.7 Hz, 1H), 7.64 (d, J=8.8 Hz, 1H), 7.51 (d, J=2.5 Hz, 1H), 7.28 (dd, J=8.6, 1.7 Hz, 1H), 7.13-7.10 (m, 2H), 7.06 (d, J=8.6 Hz, 1H), 7.01 (dd, J=8.8, 2.4 Hz, 1H), 6.89-6.85 (m, 2H), 6.41 (t, J=5.8 Hz, 1H), 4.50 (t, J=7.4 Hz, 2H), 3.86 (s, 3H), 3.39 (t, J=7.6 Hz, 2H), 3.30 (t, J=6.4 Hz, 2H), 3.13 (dd, J=9.3, 6.3 Hz, 2H), 3.02 (dd, J=9.3, 6.2 Hz, 2H), 2.82 (t, J=7.4 Hz, 2H), 2.71 (t, J=7.2 Hz, 2H), 1.79-1.68 (m, 4H), 1.61-1.55 (m, 1H), 1.25-1.12 (m, 4H), 0.98 (qd, J=12.0, 3.1 Hz, 2H). $^{13}$C NMR (125 MHz, Chloroform-d) δ 170.75, 169.69, 159.21, 154.09, 140.35, 137.88, 135.81, 131.75, 130.14, 128.35, 127.52, 126.53, 125.45, 121.90, 120.50, 118.07, 115.46, 113.61, 109.00, 105.01, 55.68, 46.73, 41.95, 38.10, 36.29, 34.06, 30.99, 26.56, 26.37, 25.85, 25.00, 24.24. HPLC purity (water/CH$_3$CN): 98.75%, Rt: 15.80 min. HPLC purity (water/MeOH): 98.77%, Rt: 16.66 min.

1-(2-(2H-tetrazol-5-yl)ethyl)-3-(4-chlorophenethyl)-2-(2-(5-methoxybenzo[d]thiazol-2-yl)ethyl)-N-((tetrahydro-2H-pyran-4-yl)methyl)-1H-indole-5-carboxamide (64). The synthesis of compound 64 followed general procedure H to obtain the desired product as white solid (CH$_2$Cl$_2$:MeOH=13:1, 34% yield). $^1$H NMR (500 MHz, DMSO-d$_6$) δ 8.34 (t, J=5.9 Hz, 1H), 8.06 (d, J=1.7 Hz, 1H), 7.88 (d, J=8.8 Hz, 1H), 7.64 (dd, J=8.6, 1.7 Hz, 1H), 7.47 (d, J=2.5 Hz, 1H), 7.42 (d, J=8.7 Hz, 1H), 7.30-7.25 (m, 2H), 7.12-7.09 (m, 2H), 7.03 (dd, J=8.8, 2.5 Hz, 1H), 4.62-4.54 (m, 2H), 3.85 (ddd, J=11.2, 4.7, 2.0 Hz, 2H), 3.82 (s, 3H), 3.28 (ddd, J=7.5, 5.2, 1.8 Hz, 4H), 3.18 (t, J=6.4 Hz, 2H), 3.12 (dp, J=5.3, 2.5 Hz, 4H), 2.88 (dd, J=9.0, 6.4 Hz, 2H), 2.76 (dd, J=8.9, 6.5 Hz, 2H), 1.82 (td, J=7.3, 3.7 Hz, 1H), 1.61 (ddd, J=12.7, 4.0, 1.9 Hz, 2H), 1.23-1.17 (m, 2H). $^{13}$C NMR (125 MHz, DMSO-d$_6$) δ 171.00, 167.14, 158.46, 154.04, 140.75, 137.07, 136.03, 130.43, 130.22, 128.06, 126.78, 126.42, 125.63, 122.34, 120.54, 117.83, 114.46, 112.23, 108.89, 105.24, 66.82, 55.44, 44.95, 41.02, 35.57, 35.06, 33.65, 30.65, 26.06, 24.13, 23.14. HPLC purity (water/CH$_3$CN): 95.68%, Rt: 14.33 min. HPLC purity (water/MeOH): 98.98%, Rt: 16.33 min.

1-(2-(2H-tetrazol-5-yl)ethyl)-3-(4-chlorophenethyl)-2-(2-(5-methoxybenzo[d]thiazol-2-yl)ethyl)-N-((tetrahydrofuran-3-yl)methyl)-1H-indole-5-carboxamide (65). The synthesis of compound 65 followed general procedure H to obtain the desired product as white solid (CH$_2$Cl$_2$:MeOH=13:1, 15% yield). $^1$H NMR (500 MHz, Chloroform-d) δ 7.78 (d, J=1.6 Hz, 1H), 7.66 (d, J=8.7 Hz, 1H), 7.53 (d, J=2.5 Hz, 1H), 7.37 (dd, J=8.5, 1.6 Hz, 1H), 7.12 (dq, J=8.9, 2.4 Hz, 3H), 7.02 (dd, J=8.8, 2.3 Hz, 1H), 6.90-6.85 (m, 2H), 6.78 (t, J=5.8 Hz, 1H), 4.52 (t, J=7.3 Hz, 2H), 3.93-3.88 (m, 1H), 3.87 (s, 3H), 3.80 (dd, J=8.8, 6.7 Hz, 1H), 3.72 (td, J=8.2, 6.9 Hz, 1H), 3.63 (dd, J=8.8, 4.8 Hz, 1H), 3.48 (t, J=6.3 Hz, 2H), 3.41 (t, J=7.4 Hz, 2H), 3.12 (dd, J=9.3, 6.2 Hz, 2H), 3.01 (dd, J=9.3, 6.2 Hz, 2H), 2.84 (t, J=7.3 Hz, 2H), 2.73 (t, J=7.2 Hz, 2H), 2.65-2.57 (m, 1H), 2.07 (dtd, J=13.3, 8.1, 5.3 Hz, 1H), 1.68 (dtd, J=12.7, 7.7, 5.7 Hz, 1H). $^{13}$C NMR (126 MHz, Chloroform-d) δ 169.73, 159.33, 140.31, 137.97, 135.75, 131.76, 130.14, 128.37, 127.54, 125.21, 121.97, 120.54, 118.37, 115.68, 113.73, 108.97, 104.81, 71.44, 67.79, 55.72, 43.35, 41.85, 39.07, 36.23, 33.90, 29.96, 26.60, 24.92, 24.24. HPLC purity (water/CH$_3$CN): 95.30%, Rt: 14.16 min. HPLC purity (water/MeOH): 97.14%, Rt: 16.20 min.

1-(2-(2H-tetrazol-5-yl)ethyl)-3-(4-chlorophenethyl)-N-(2,3-dihydroxypropyl)-2-(2-(5-methoxybenzo[d]thiazol-2-yl)ethyl)-1H-indole-5-carboxamide (66). The synthesis of compound 66 followed general procedure H to obtain the desired product as brown solid (CH$_2$Cl$_2$:MeOH=12:1, 50% yield for two steps). $^1$H NMR (500 MHz, DMSO-d$_6$) δ 8.34 (t, J=5.8 Hz, 1H), 8.11 (s, 1H), 7.89 (d, J=8.8 Hz, 1H), 7.67 (d, J=8.6 Hz, 1H), 7.51-7.46 (m, 1H), 7.44 (d, J=8.6 Hz, 1H), 7.30 (d, J=7.9 Hz, 2H), 7.12 (d, J=7.9 Hz, 2H), 7.04 (dd, J=8.9, 2.5 Hz, 1H), 4.92-4.80 (m, 1H), 4.60 (d, J=7.5 Hz, 3H), 3.83 (s, 3H), 3.67 (s, 1H), 3.47-3.41 (m, 1H), 3.37 (s, 2H), 3.30 (t, J=7.5 Hz, 2H), 3.24 (dd, J=13.1, 6.3 Hz, 1H), 3.16-3.07 (m, 4H), 2.89 (d, J=7.7 Hz, 2H), 2.79 (d, J=7.7 Hz, 2H). $^{13}$C NMR (126 MHz, DMSO-d$_6$) δ 171.02, 167.67, 158.47, 154.05, 140.78, 137.15, 136.10, 130.45, 130.24, 128.09, 126.78, 126.43, 125.39, 122.36, 120.65, 117.96, 114.48, 112.30, 108.97, 105.23, 70.75, 63.94, 55.45, 43.03, 35.57, 33.66, 26.12, 24.05, 23.12. HPLC purity (water/CH$_3$CN): 98.67%, Rt: 13.14 min. HPLC purity (water/MeOH): 98.93%, Rt: 15.82 min.

4-((1-(2-(2H-tetrazol-5-yl)ethyl)-3-(4-chlorophenethyl)-2-(2-(5-methoxybenzo[d]thiazol-2-yl)ethyl)-1H-indole-5-carboxamido)methyl)piperidin-1-ium (67). The synthesis of compound 67 followed general procedure H to obtain the crude product without column chromatography. The crude product which was dissolved in CH$_2$Cl$_2$ (10 mL/mmol), and HCl in 1,4-dioxane (4.0 M, 3.0 eq) was added at 0° C. The resulting mixture was stirred for additional 12 h at room temperature. The reaction mixture was filtered, and the filter cake was washed with EtOAc, CH$_2$Cl$_2$, and ethyl ether. Then, the cake was dissolved in water and filtered, and the desired product was isolated via lyophilization (light brown solid, 0.101 g, 35% yield two steps). $^1$H NMR (500 MHz, Methanol-d$_4$) δ 8.02 (d, J=1.6 Hz, 1H), 7.78 (d, J=8.8 Hz, 1H), 7.66 (dd, J=8.6, 1.7 Hz, 1H), 7.41 (d, J=2.4 Hz, 1H), 7.35 (d, J=8.6 Hz, 1H), 7.18 (d, J=7.9 Hz, 2H), 7.08 (dd, J=8.8, 2.5 Hz, 1H), 6.99 (d, J=8.0 Hz, 2H), 4.63 (t, J=7.1 Hz, 2H), 3.88 (s, 3H), 3.45 (dt, J=13.0, 3.3 Hz, 2H), 3.42-3.36 (m, 4H), 3.13 (s, 4H), 3.02 (td, J=12.9, 2.8 Hz, 2H), 2.91 (t, J=7.4 Hz, 2H), 2.81 (t, J=7.4 Hz, 2H), 2.04 (dq, J=15.1, 3.7, 3.1 Hz, 3H), 1.53 (dtd, J=16.3, 12.8, 11.9, 3.7 Hz, 2H). $^{13}$C NMR (125 MHz, Methanol-d$_4$) δ 174.62, 171.55, 161.15, 153.16, 142.01, 139.47, 136.88, 132.75, 131.36, 129.34, 128.93, 126.46, 123.60, 121.91, 119.68, 116.87, 114.94, 110.13, 104.88, 56.24, 45.57, 45.07, 42.51, 37.06, 35.64, 34.36, 27.92, 27.52, 25.39, 24.94. HPLC purity (water/CH$_3$CN): 98.41%, Rt: 12.90 min. HPLC purity (water/MeOH): 98.56%, Rt: 14.95 min.

(1s,4s)-4-(1-(2-(2H-tetrazol-5-yl)ethyl)-3-(4-chlorophenethyl)-2-(2-(5-methoxybenzo[d]thiazol-2-yl)ethyl)-1H-indole-5-carboxamido)cyclohexan-1-aminium (cis) (68). The synthesis of compound 68 followed general procedure H to obtain the crude product without column chromatography. The crude product which was dissolved in CH$_2$Cl$_2$ (10 mL/mmol), and HCl in 1,4-dioxane (4.0 M, 3.0 eq) was added at 0° C. The resulting mixture was stirred for additional 12 h at room temperature. The reaction mixture was filtered, and the filter cake was washed with EtOAc, CH$_2$Cl$_2$, and ethyl ether. Then, the cake was dissolved in water and filtered, and the desired product was isolated via lyophilization (light brown solid, 0.093 g, 32% yield). $^1$H NMR (500 MHz, Methanol-d$_4$) δ 7.99 (dd, J=1.7, 0.6 Hz, 1H), 7.89 (d, J=8.9 Hz, 1H), 7.65 (dd, J=8.6, 1.7 Hz, 1H), 7.43 (d, J=2.4 Hz, 1H), 7.35 (dd, J=8.7, 0.6 Hz, 1H), 7.18 (dd, J=9.0, 2.4 Hz, 1H), 7.17-7.11 (m, 2H), 7.01-6.91 (m, 2H), 4.67-4.60 (m, 2H), 4.08 (dt, J=6.4, 3.5 Hz, 1H), 3.89 (s, 3H), 3.35 (td, J=7.9, 5.4 Hz, 3H), 3.23 (dd, J=8.6, 6.4 Hz, 2H), 3.13 (dd, J=8.7, 6.4 Hz, 2H), 2.88 (t, J=7.0 Hz, 2H), 2.80 (t, J=6.9 Hz, 2H), 2.04-1.81 (m, 8H). $^{13}$C NMR (125 MHz, Methanol-d$_4$) δ 176.84, 171.37, 161.90, 155.56, 149.26, 142.00, 139.52, 136.20, 131.45, 129.36, 128.84, 126.87, 125.90, 124.40, 122.25, 120.10, 118.04, 115.27, 110.16, 103.22, 56.46, 49.18, 49.05, 48.88, 47.47, 42.55, 37.08, 33.55, 28.03, 27.54, 27.48, 25.37, 24.79. HPLC purity (water/CH$_3$CN): 98.50%, Rt: 12.86 min. HPLC purity (water/MeOH): 98.29%, Rt: 14.96 min.

(1r,4r)-4-(1-(2-(2H-tetrazol-5-yl)ethyl)-3-(4-chlorophenethyl)-2-(2-(5-methoxybenzo[d]thiazol-2-yl)ethyl)-1H-indole-5-carboxamido)cyclohexan-1-aminium (trans) (69). The synthesis of compound 69 followed general procedure H to obtain the crude product without column chromatography. The crude product which was dissolved in CH$_2$Cl$_2$ (10 mL/mmol), and HCl in 1,4-dioxane (4.0 M, 3.0 eq) was added at 0° C. The resulting mixture was stirred for additional 12 h at room temperature. The reaction mixture was filtered, and the filter cake was washed with EtOAc, CH$_2$Cl$_2$, and ethyl ether. Then, the cake was dissolved in water and filtered, and the desired product was isolated via lyophilization (brown solid, 0.123 g, 43% yield). $^1$H NMR (500 MHz, Methanol-d4) δ 7.98-7.90 (m, 2H), 7.63 (dd, J=8.6, 1.7 Hz, 1H), 7.43 (d, J=2.4 Hz, 1H), 7.35 (d, J=8.6 Hz, 1H), 7.23 (dd, J=9.1, 2.4 Hz, 1H), 7.16-7.09 (m, 2H), 6.98-6.85 (m, 2H), 4.63 (t, J=7.1 Hz, 2H), 3.89 (s, 4H), 3.35 (t, J=7.0 Hz, 2H), 3.31-3.28 (m, 2H), 3.19-3.08 (m, 3H), 2.85 (t, J=6.9 Hz, 2H), 2.78 (t, J=6.9 Hz, 2H), 2.10 (dt, J=8.9, 4.6 Hz, 4H), 1.61-1.50 (m, 4H). $^{13}$C NMR (125 MHz, Methanol-d$_4$) δ 178.29, 170.86, 162.38, 155.51, 146.69, 141.96, 139.58, 135.79, 132.79, 131.46, 129.37, 128.79, 126.52, 125.02, 124.91, 122.36, 120.02, 118.81, 115.46, 110.30, 102.11, 56.61, 50.73, 42.59, 37.06, 33.02, 31.23, 30.80, 27.45, 25.34, 24.70. HPLC purity (water/CH$_3$CN): 97.59%, Rt: 12.86 min. HPLC purity (water/MeOH): 97.92%, Rt: 14 min.

Scheme 11.

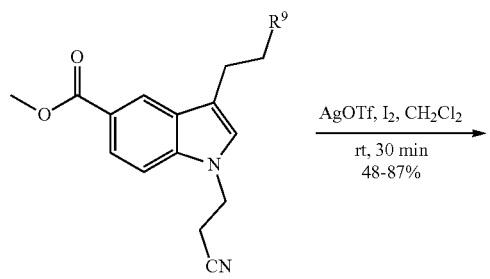

A 119b, c, n, o

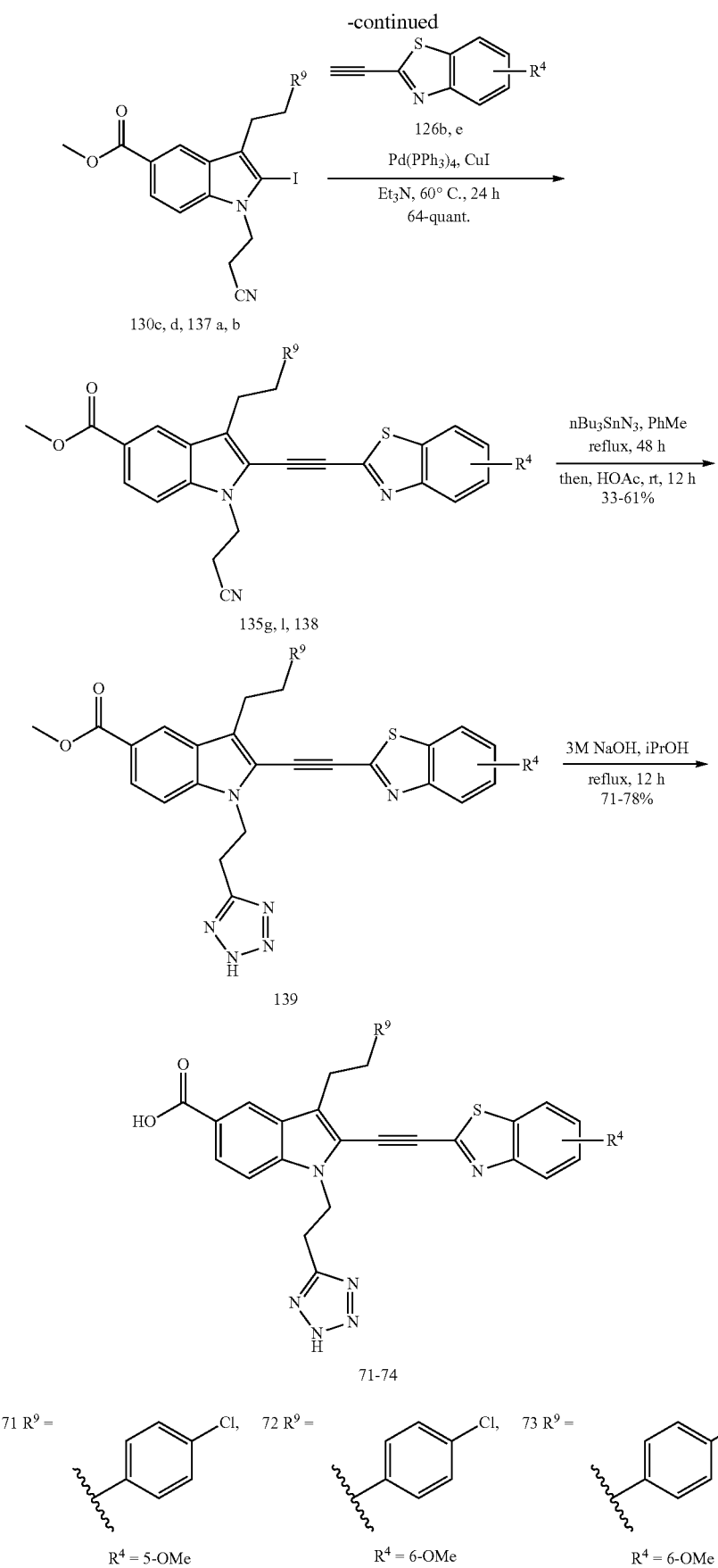

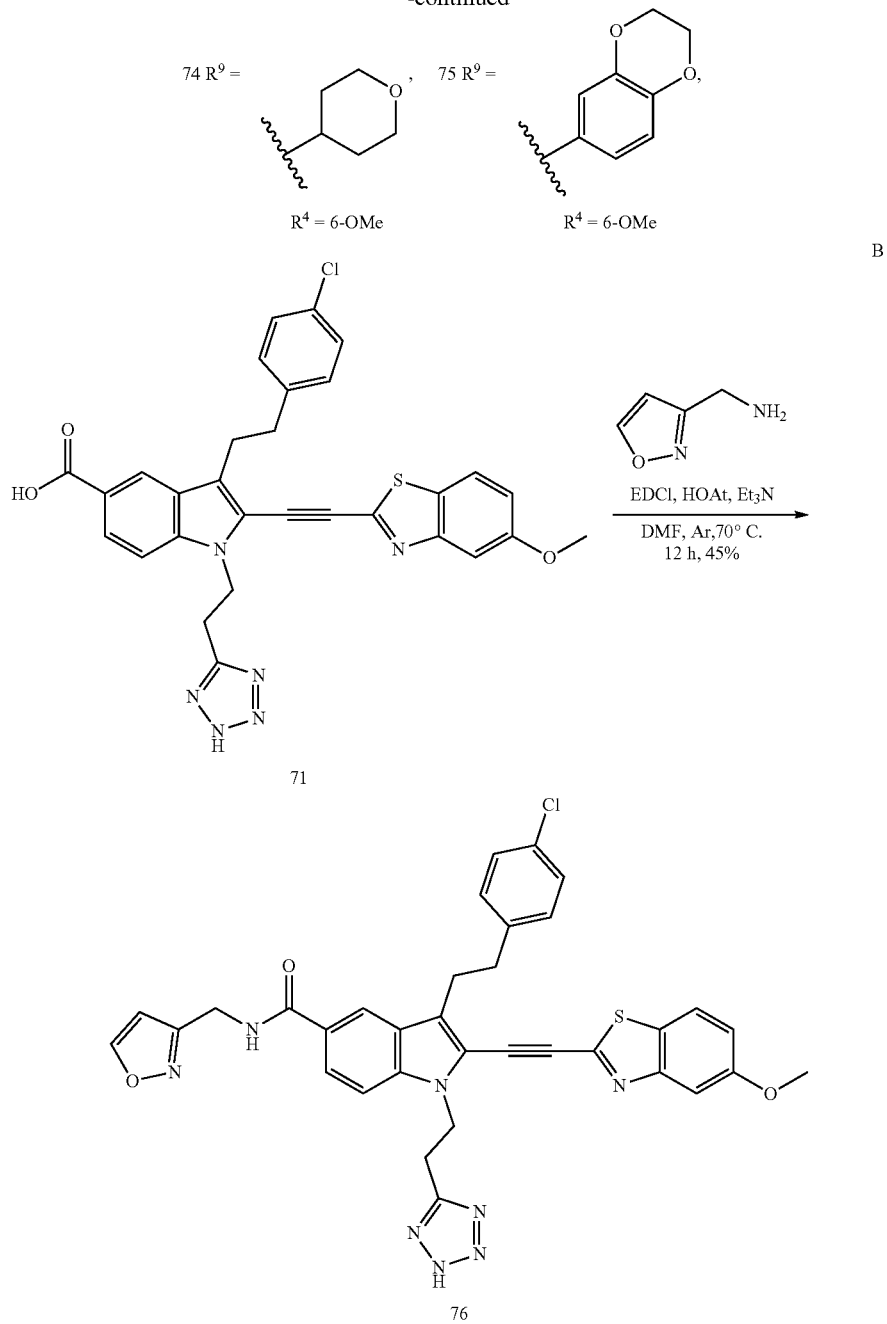

methyl 1-(2-cyanoethyl)-2-iodo-3-(2-(tetrahydro-2H-pyran-4-yl)ethyl)-1H-indole-5-carboxylate (137a). The synthesis of compound 137a followed general procedure E to obtain the desired product as brown solid (hexanes:acetone=14:1, 63% yield). Low resolution mass spectrometry [M+Na]$^+$: 489.1. $^1$H NMR (500 MHz, DMSO-d$_6$) δ 8.17 (s, 1H), 7.73 (d, J=1.3 Hz, 2H), 4.56 (t, J=6.6 Hz, 2H), 3.86 (s, 3H), 3.85-3.82 (m, 2H), 3.26 (td, J=11.7, 2.1 Hz, 2H), 2.98 (t, J=6.6 Hz, 2H), 2.74 (dd, J=8.5, 6.8 Hz, 2H), 1.69 (dq, J=12.8, 1.9 Hz, 2H), 1.57-1.44 (m, 3H), 1.25-1.16 (m, 2H). $^{13}$C NMR (126 MHz, DMSO-d$_6$) δ 166.85, 139.88, 127.04, 122.88, 122.44, 120.94, 120.01, 118.18, 110.60, 90.80, 67.04, 51.88, 42.30, 37.11, 34.01, 32.81, 23.75, 18.12. Low resolution mass spectrometry [M+Na]$^+$: 489.1.

methyl 1-(2-cyanoethyl)-3-(2-(2,3-dihydrobenzo[b][1,4]dioxin-6-yl)ethyl)-2-iodo-1H-indole-5-carboxylate (137b). The synthesis of compound 137b followed general procedure E to obtain the desired product as white solid (hexanes:acetone=6:1, 48% yield). Low resolution mass spectrometry [M+Na]$^+$: 539.1. $^1$H NMR (500 MHz, Chloroform-d) δ 8.21 (d, J=1.6 Hz, 1H), 7.91 (dd, J=8.6, 1.6 Hz, 1H), 7.35 (d, J=8.7 Hz, 1H), 6.77 (d, J=8.7 Hz, 1H), 6.67-6.62 (m, 2H), 4.52 (t, J=7.3 Hz, 2H), 4.23 (s, 4H), 3.95 (s, 3H), 3.00 (dd, J=9.1, 6.6 Hz, 2H), 2.79 (t, J=7.8 Hz, 2H), 2.75 (t, J=7.3 Hz, 2H). $^{13}$C NMR (126 MHz, Chloroform-d) δ 167.63, 143.31, 142.00, 139.98, 134.63, 127.81, 124.06, 123.98, 122.31, 121.66, 121.43, 117.37, 117.09, 116.59, 108.92, 86.77, 64.48, 64.40, 52.06, 42.95, 35.62, 29.81, 18.51.

methyl 1-(2-cyanoethyl)-2-((6-methoxybenzo[d]thiazol-2-yl)ethynyl)-3-(4-methylphenethyl)-1H-indole-5-carboxylate (138a). The synthesis of compound 138a followed general procedure C to obtain the desired product as yellow solid (CH$_2$Cl$_2$:MeOH=15:1, 85% yield). Low resolution mass spectrometry [M+H]$^+$: 534.2. $^1$H NMR (500 MHz, DMSO-d$_6$) δ 8.24 (d, J=1.5 Hz, 1H), 8.00 (d, J=9.0 Hz, 1H), 7.89 (dd, J=8.8, 1.6 Hz, 1H), 7.79-7.74 (m, 2H), 7.22 (dd, J=9.0, 2.6 Hz, 1H), 7.09 (d, J=8.0 Hz, 2H), 7.04 (d, J=7.7 Hz, 2H), 4.65 (t, J=6.4 Hz, 2H), 3.88 (d, J=1.2 Hz, 6H), 3.21 (dd, J=8.5, 6.8 Hz, 2H), 3.08 (t, J=6.4 Hz, 2H), 2.95 (t, J=7.6 Hz, 2H), 2.20 (s, 3H). $^{13}$C NMR (126 MHz, DMSO-d$_6$) δ 166.68, 158.52, 147.05, 144.09, 138.91, 137.95, 136.84, 134.86, 131.50, 131.42, 128.81, 128.78, 128.28, 125.86, 125.82, 124.86, 123.88, 122.23, 121.86, 118.67, 118.28, 116.99, 110.77, 104.45, 92.16, 84.90, 55.85, 51.93, 35.73, 27.00, 20.62, 18.24.

methyl 1-(2-cyanoethyl)-2-((6-methoxybenzo[d]thiazol-2-yl)ethynyl)-3-(2-(tetrahydro-2H-pyran-4-yl)ethyl)-1H-indole-5-carboxylate (138b). The synthesis of compound 138b followed general procedure C to obtain the desired product as yellow solid (CH$_2$Cl$_2$:MeOH=13:1, 64% yield). Low resolution mass spectrometry [M+H]$^+$: 528.3. $^1$H NMR (500 MHz, DMSO-d$_6$) δ 8.32 (dd, J=1.6, 0.7 Hz, 1H), 8.00 (d, J=9.0 Hz, 1H), 7.91 (dd, J=8.8, 1.6 Hz, 1H), 7.79-7.75 (m, 2H), 7.22 (dd, J=9.0, 2.6 Hz, 1H), 4.67 (t, J=6.4 Hz, 2H), 3.88 (s, 3H), 3.87 (s, 3H), 3.82 (ddd, J=11.4, 4.5, 1.8 Hz, 2H), 3.24 (td, J=11.7, 2.0 Hz, 2H), 3.12 (t, J=6.4 Hz, 2H), 3.00 (t, J=7.5 Hz, 2H), 1.72 (ddd, J=12.6, 3.9, 1.9 Hz, 2H), 1.65 (q, J=7.2 Hz, 2H), 1.54 (ddt, J=10.8, 7.3, 3.8 Hz, 1H), 1.28-1.17 (m, 2H). $^{13}$C NMR (126 MHz, DMSO-d$_6$) δ 166.67, 158.54, 147.06, 144.05, 138.98, 136.80, 126.67, 125.79, 124.94, 123.89, 122.03, 121.88, 118.57, 118.31, 117.02, 110.90, 104.50, 92.28, 85.18, 67.04, 55.85, 51.97, 37.17, 33.71, 32.71, 21.30, 18.24.

methyl 1-(2-cyanoethyl)-3-(2-(2,3-dihydrobenzo[b][1,4]dioxin-6-yl)ethyl)-2-((6-methoxybenzo[d]thiazol-2-yl)ethynyl)-1H-indole-5-carboxylate (138c). The synthesis of compound 138c followed general procedure C to obtain the desired product as yellow solid (CH$_2$Cl$_2$:MeOH=13:1, 77% yield). Low resolution mass spectrometry [M+H]$^+$: 578.3. $^1$H NMR (500 MHz, DMSO-d$_6$) δ 8.22 (d, J=1.5 Hz, 1H), 8.01 (d, J=9.0 Hz, 1H), 7.89 (dd, J=8.7, 1.6 Hz, 1H), 7.79-7.75 (m, 2H), 7.22 (dd, J=9.0, 2.6 Hz, 1H), 6.72-6.68 (m, 2H), 6.63 (d, J=2.0 Hz, 1H), 4.66 (t, J=6.4 Hz, 2H), 4.13 (s, 4H), 3.88 (d, J=0.8 Hz, 6H), 3.18 (dd, J=8.5, 6.8 Hz, 2H), 3.08 (t, J=6.4 Hz, 2H), 2.87 (t, J=7.6 Hz, 2H). $^{13}$C NMR (126 MHz, DMSO-d$_6$) δ 166.70, 158.52, 147.05, 144.09, 143.07, 141.66, 138.90, 136.86, 134.08, 131.50, 131.42, 128.78, 128.69, 125.91, 125.83, 124.86, 123.88, 122.33, 121.86, 121.13, 118.64, 118.28, 116.99, 116.93, 116.70, 110.76, 104.45, 92.18, 84.91, 63.95, 63.86, 55.85, 51.92, 35.45, 27.08, 18.24.

methyl 1-(2-(2H-tetrazol-5-yl)ethyl)-3-(4-chlorophenethyl)-2-((5-methoxybenzo[d]thiazol-2-yl)ethynyl)-1H-indole-5-carboxylate (139a). The synthesis of compound 139a followed general procedure F to obtain the desired product as yellow solid (42% yield). $^1$H NMR (500 MHz, DMSO-d$_6$) δ 8.16 (d, J=1.5 Hz, 1H), 8.06 (d, J=8.9 Hz, 1H), 7.84 (dd, J=8.7, 1.7 Hz, 1H), 7.65 (d, J=2.5 Hz, 1H), 7.54 (d, J=8.8 Hz, 1H), 7.28-7.24 (m, 2H), 7.22 (dd, J=8.9, 2.5 Hz, 1H), 7.20-7.16 (m, 2H), 4.73 (t, J=6.8 Hz, 2H), 3.88 (s, 3H), 3.87 (s, 3H), 3.41 (t, J=6.8 Hz, 2H), 3.20 (t, J=7.4 Hz, 2H), 2.96 (t, J=7.4 Hz, 2H). $^{13}$C NMR (126 MHz, DMSO-d$_6$) δ 166.67, 159.26, 154.09, 140.05, 138.84, 130.69, 130.38, 128.12, 126.93, 125.70, 125.54, 124.85, 122.62, 122.30, 121.63, 118.53, 116.88, 110.29, 105.50, 91.82, 85.16, 55.65, 51.92, 42.73, 35.40, 26.70, 24.13.

methyl 1-(2-(2H-tetrazol-5-yl)ethyl)-3-(4-chlorophenethyl)-2-((6-methoxybenzo[d]thiazol-2-yl)ethynyl)-1H-indole-5-carboxylate (139b). The synthesis of compound 139b followed general procedure F to obtain the desired product as yellow solid (56% yield). Low resolution mass spectrometry [M]$^-$: 595.1. $^1$H NMR (500 MHz, DMSO-d$_6$) δ 8.15 (d, J=1.6 Hz, 1H), 8.00 (d, J=9.0 Hz, 1H), 7.83 (dd, J=8.7, 1.7 Hz, 1H), 7.77 (d, J=2.6 Hz, 1H), 7.53 (d, J=8.8 Hz, 1H), 7.26 (d, J=8.4 Hz, 2H), 7.22 (dd, J=8.9, 2.6 Hz, 1H), 7.19 (d, J=8.4 Hz, 2H), 4.73 (t, J=6.8 Hz, 2H), 3.88 (s, 3H), 3.87 (s, 3H), 3.41 (t, J=6.8 Hz, 2H), 3.19 (t, J=7.4 Hz, 2H), 2.96 (t, J=7.4 Hz, 2H). $^{13}$C NMR (126 MHz, DMSO-d$_6$) δ 166.66, 158.50, 147.04, 144.01, 140.04, 138.77, 136.87, 130.66, 130.35, 128.08, 125.70, 125.21, 124.73, 123.87, 122.20, 121.59, 118.64, 116.95, 110.21, 104.41, 91.70, 84.64, 55.84, 51.88, 42.68, 35.38, 26.67, 24.11.

methyl 1-(2-(2H-tetrazol-5-yl)ethyl)-2-((6-methoxybenzo[d]thiazol-2-yl)ethynyl)-3-(4-methylphenethyl)-1H-indole-5-carboxylate (139c). The synthesis of compound 139c followed general procedure F to obtain the desired product as yellow solid (48% yield). Low resolution mass spectrometry [M+H]$^+$: 577.2. H NMR (500 MHz, DMSO-d$_6$) δ 8.20 (d, J=1.7 Hz, 1H), 8.00 (d, J=9.0 Hz, 1H), 7.84 (dd, J=8.7, 1.6 Hz, 1H), 7.78 (d, J=2.6 Hz, 1H), 7.54 (d, J=8.8 Hz, 1H), 7.22 (dd, J=9.0, 2.6 Hz, 1H), 7.09 (d, J=8.0 Hz, 2H), 7.04 (d, J=7.8 Hz, 2H), 4.73 (t, J=6.8 Hz, 2H), 3.88 (s, 3H), 3.87 (s, 3H), 3.41 (t, J=6.8 Hz, 2H), 3.17 (dd, J=8.6, 6.7 Hz, 2H), 2.92 (t, J=7.7 Hz, 2H), 2.21 (s, 3H). $^{13}$C NMR (126 MHz, DMSO-d$_6$) δ 166.70, 158.50, 147.04, 144.09, 138.80, 137.99, 136.87, 134.84, 128.81, 128.27, 125.72, 125.69, 124.73, 123.86, 122.23, 121.56, 118.56, 116.96, 110.23, 104.44, 91.75, 84.80, 55.85, 51.89, 42.67, 27.01, 24.14, 20.62.

methyl 1-(2-(2H-tetrazol-5-yl)ethyl)-2-((6-methoxybenzo[d]thiazol-2-yl)ethynyl)-3-(2-(tetrahydro-2H-pyran-4-yl)ethyl)-1H-indole-5-carboxylate (139d). The synthesis of compound 139d followed general procedure F to obtain the desired product as yellow solid (33% yield). Low resolution mass spectrometry [M+H]$^+$: 571.2. $^1$H NMR (500 MHz, DMSO-d$_6$) δ 8.30-8.26 (m, 1H), 7.99 (d, J=9.0 Hz, 1H), 7.87 (dd, J=8.7, 1.6 Hz, 1H), 7.78 (d, J=2.6 Hz, 1H), 7.59 (d, J=8.7 Hz, 1H), 7.22 (dd, J=9.0, 2.6 Hz, 1H), 4.74 (t, J=6.7 Hz, 2H), 3.87 (s, 6H), 3.84-3.78 (m, 2H), 3.43 (t, J=6.7 Hz, 2H), 3.30-3.24 (m, 2H), 2.94 (t, J=7.4 Hz, 2H), 1.70 (ddd, J=12.7, 4.0, 1.9 Hz, 2H), 1.61 (q, J=7.2 Hz, 2H), 1.53-1.43 (m, 1H), 1.27-1.15 (m, 2H). $^{13}$C NMR (126 MHz, DMSO-d$_6$) δ 166.70, 158.51, 147.04, 144.02, 138.91, 136.83, 126.38, 125.70, 124.81, 123.86, 122.01, 121.57, 118.46, 116.98, 110.40, 104.47, 91.68, 84.91, 66.99, 55.85, 51.94, 42.80, 40.12, 39.95, 37.19, 33.51, 32.71, 24.09, 21.20.

methyl 1-(2-(2H-tetrazol-5-yl)ethyl)-3-(2-(2,3-dihydrobenzo[b][1,4]dioxin-6-yl)ethyl)-2-((6-methoxybenzo[d]thiazol-2-yl)ethynyl)-1H-indole-5-carboxylate (139e). The synthesis of compound 139e followed general procedure F to obtain the desired product as yellow solid (61% yield).

Low resolution mass spectrometry [M+H]⁺: 621.3. ¹H NMR (500 MHz, DMSO-d₆) δ 8.20-8.17 (m, 1H), 8.01 (d, J=9.0 Hz, 1H), 7.85 (dd, J=8.8, 1.6 Hz, 1H), 7.78 (d, J=2.5 Hz, 1H), 7.55 (d, J=8.8 Hz, 1H), 7.23 (dd, J=9.0, 2.6 Hz, 1H), 6.73-6.69 (m, 2H), 6.63 (dd, J=8.2, 2.0 Hz, 1H), 4.74 (t, J=6.9 Hz, 2H), 4.14 (s, 4H), 3.88 (d, J=4.5 Hz, 6H), 3.42 (t, J=6.9 Hz, 2H), 3.15 (dd, J=8.6, 6.7 Hz, 2H), 2.84 (dd, J=8.5, 6.8 Hz, 2H). $^{13}$C NMR (126 MHz, DMSO-d₆) δ 166.71, 158.49, 147.04, 144.06, 143.05, 141.64, 138.78, 136.87, 134.12, 125.73, 124.72, 123.84, 122.31, 121.56, 121.12, 118.53, 116.94, 116.90, 116.70, 110.19, 104.42, 91.74, 84.80, 63.95, 63.85, 55.84, 51.86, 42.65, 35.50, 27.07.

1-(2-(2H-tetrazol-5-yl)ethyl)-3-(4-chlorophenethyl)-2-((5-methoxybenzo[d]thiazol-2-yl)ethynyl)-1H-indole-5-carboxylic acid (71). The synthesis of compound 71 followed general procedure G to obtain the desired product as yellow solid (72% yield). ¹H NMR (500 MHz, DMSO-d₆) δ 12.67 (s, 1H), 8.24 (d, J=1.6 Hz, 1H), 8.06 (d, J=8.9 Hz, 1H), 7.84 (dd, J=8.8, 1.6 Hz, 1H), 7.65 (d, J=2.5 Hz, 1H), 7.52 (d, J=8.8 Hz, 1H), 7.27 (d, J=8.4 Hz, 2H), 7.21 (td, J=8.7, 2.3 Hz, 3H), 4.73 (t, J=6.8 Hz, 2H), 3.88 (s, 3H), 3.41 (t, J=6.8 Hz, 2H), 3.19 (t, J=7.5 Hz, 2H), 2.97 (t, J=7.5 Hz, 2H). $^{13}$C NMR (126 MHz, DMSO-d₆) δ 206.48, 167.79, 159.26, 154.10, 147.84, 140.06, 138.78, 130.65, 130.33, 128.14, 126.92, 125.66, 125.48, 125.21, 122.79, 122.62, 122.35, 118.32, 116.85, 110.08, 105.50, 91.76, 85.31, 55.65, 54.91, 35.36, 30.70, 26.70.

1-(2-(2H-tetrazol-5-yl)ethyl)-3-(4-chlorophenethyl)-2-((6-methoxybenzo[d]thiazol-2-yl)ethynyl)-1H-indole-5-carboxylic acid (72). The synthesis of compound 72 followed general procedure G to obtain the desired product as light yellow solid (74% yield). Low resolution mass spectrometry [M+H]⁺: 583.1. ¹H NMR (500 MHz, DMSO-d₆) δ 12.68 (s, 1H), 8.23 (d, J=1.5 Hz, 1H), 8.00 (d, J=8.9 Hz, 1H), 7.83 (dd, J=8.7, 1.6 Hz, 1H), 7.77 (d, J=2.6 Hz, 1H), 7.51 (d, J=8.8 Hz, 1H), 7.27 (d, J=8.4 Hz, 2H), 7.23 (d, J=2.5 Hz, 1H), 7.20 (d, J=8.4 Hz, 2H), 4.72 (t, J=6.8 Hz, 2H), 3.88 (s, 3H), 3.41 (t, J=6.8 Hz, 2H), 3.18 (t, J=7.5 Hz, 2H), 2.96 (t, J=7.5 Hz, 2H). $^{13}$C NMR (126 MHz, DMSO-d₆) δ 167.78, 158.50, 147.05, 144.07, 140.07, 138.71, 136.87, 130.64, 130.31, 128.11, 125.66, 125.16, 125.10, 123.87, 122.74, 122.27, 118.43, 116.96, 110.02, 104.42, 91.64, 84.79, 55.86, 42.68, 35.35, 26.68, 24.13.

1-(2-(2H-tetrazol-5-yl)ethyl)-2-((6-methoxybenzo[d]thiazol-2-yl)ethynyl)-3-(4-methylphenethyl)-1H-indole-5-carboxylic acid (73). The synthesis of compound 73 followed general procedure G to obtain the desired product as light yellow solid (71% yield). Low resolution mass spectrometry [M+H]⁺: 563.2. ¹H NMR (500 MHz, DMSO-d₆) δ 12.67 (s, 1H), 8.24 (d, J=1.6 Hz, 1H), 8.00 (d, J=9.0 Hz, 1H), 7.84 (dd, J=8.6, 1.6 Hz, 1H), 7.77 (d, J=2.6 Hz, 1H), 7.51 (d, J=8.7 Hz, 1H), 7.22 (dd, J=9.0, 2.6 Hz, 1H), 7.10 (d, J=7.7 Hz, 2H), 7.05 (d, J=7.7 Hz, 2H), 4.73 (t, J=6.9 Hz, 2H), 3.88 (s, 3H), 3.41 (t, J=6.8 Hz, 2H), 3.16 (dd, J=8.9, 6.6 Hz, 2H), 2.92 (t, J=7.7 Hz, 2H), 2.21 (s, 3H). $^{13}$C NMR (126 MHz, DMSO-d₆) δ 167.80, 158.49, 147.05, 144.13, 138.72, 138.03, 136.86, 134.84, 128.84, 128.23, 125.69, 125.64, 125.08, 123.85, 122.70, 122.29, 118.33, 116.94, 110.01, 104.44, 91.70, 84.94, 55.85, 42.66, 35.79, 27.06, 24.13, 20.63.

1-(2-(2H-tetrazol-5-yl)ethyl)-2-((6-methoxybenzo[d]thiazol-2-yl)ethynyl)-3-(2-(tetrahydro-2H-pyran-4-yl)ethyl)-1H-indole-5-carboxylic acid (74). The synthesis of compound 74 followed general procedure G to obtain the desired product as light yellow solid (76% yield). Low resolution mass spectrometry [M+H]⁺: 557.2. ¹H NMR (500 MHz, DMSO-d₆) δ 12.69 (s, 1H), 8.27 (d, J=1.5 Hz, 1H), 7.99 (d, J=9.0 Hz, 1H), 7.86 (dd, J=8.8, 1.6 Hz, 1H), 7.78 (d, J=2.6 Hz, 1H), 7.56 (d, J=8.8 Hz, 1H), 7.22 (dd, J=9.0, 2.6 Hz, 1H), 4.74 (t, J=6.7 Hz, 2H), 3.88 (s, 3H), 3.84-3.79 (m, 2H), 3.43 (t, J=6.7 Hz, 2H), 3.30-3.25 (m, 2H), 2.93 (t, J=7.4 Hz, 2H), 1.70 (ddd, J=12.6, 4.0, 1.8 Hz, 2H), 1.62 (q, J=7.2 Hz, 2H), 1.48 (ddt, J=11.0, 7.5, 3.9 Hz, 1H), 1.26-1.16 (m, 2H). $^{13}$C NMR (126 MHz, DMSO-d₆) δ 167.79, 158.50, 147.05, 144.08, 138.81, 136.83, 126.34, 125.69, 125.13, 123.85, 122.68, 122.12, 118.22, 116.97, 110.15, 104.48, 91.61, 85.05, 67.00, 55.85, 42.79, 37.20, 33.53, 32.72, 24.05, 21.25.

1-(2-(2H-tetrazol-5-yl)ethyl)-3-(2-(2,3-dihydrobenzo[b][1,4]dioxin-6-yl)ethyl)-2-((6-methoxybenzo[d]thiazol-2-yl)ethynyl)-1H-indole-5-carboxylic acid (75). The synthesis of compound 75 followed general procedure G to obtain the desired product as light yellow solid (75% yield). ¹H NMR (500 MHz, DMSO-d₆) δ 12.66 (s, 1H), 8.20 (d, J=1.5 Hz, 1H), 8.00 (d, J=9.0 Hz, 1H), 7.84 (dd, J=8.7, 1.6 Hz, 1H), 7.77 (d, J=2.6 Hz, 1H), 7.51 (d, J=8.8 Hz, 1H), 7.22 (dd, J=9.0, 2.6 Hz, 1H), 6.73 (d, J=2.1 Hz, 1H), 6.69 (d, J=8.2 Hz, 1H), 6.61 (dd, J=8.2, 2.1 Hz, 1H), 4.73 (t, J=6.9 Hz, 2H), 4.14 (s, 4H), 3.88 (s, 3H), 3.41 (t, J=6.9 Hz, 2H), 3.13 (dd, J=8.8, 6.7 Hz, 2H), 2.84 (dd, J=8.7, 6.8 Hz, 2H). $^{13}$C NMR (126 MHz, DMSO-d₆) δ 167.81, 158.48, 147.05, 144.12, 143.09, 141.65, 138.70, 136.87, 134.15, 125.71, 125.69, 125.07, 123.83, 122.69, 122.38, 121.11, 118.31, 116.93, 116.84, 116.69, 109.97, 104.42, 91.69, 84.95, 63.95, 63.86, 55.85, 42.64, 35.52, 27.13, 24.13.

1-(2-(2H-tetrazol-5-yl)ethyl)-3-(4-chlorophenethyl)-N-(isoxazol-3-ylmethyl)-2-((5-methoxybenzo[d]thiazol-2-yl)ethynyl)-1H-indole-5-carboxamide (76). To a solution of 71 (0.059 g, 0.1 mmol), isoxazol-3-methylamine hydrochloride (0.027 mg, 0.2 mmol), HOAT (0.027 mg, 0.2 mmol) and EDCI (0.039 mg, 0.2 mmol) in DMF (5.0 mL) was added Et₃N (56 μM, 0.4 mmol). The resulting mixture was stirred at rt for 12 h. Upon completion, the solvent was removed under vacuum. The residue was dissolved in DCM, and washed with water. The organic layer was concentrated under vacuum. Light yellow solid (CH₂Cl₂:MeOH=12:1, 0.03 g, 45% yield) was isolated by column chromatography. ¹H NMR (500 MHz, DMSO-d₆) δ 9.08 (t, J=5.9 Hz, 1H), 8.85 (d, J=1.7 Hz, 1H), 8.28 (d, J=1.6 Hz, 1H), 8.05 (d, J=8.8 Hz, 1H), 7.83 (dd, J=8.7, 1.7 Hz, 1H), 7.64 (d, J=2.5 Hz, 1H), 7.52 (d, J=8.9 Hz, 1H), 7.29 (d, J=8.4 Hz, 2H), 7.21 (dd, J=8.8, 2.7 Hz, 3H), 6.53 (d, J=1.7 Hz, 1H), 4.72 (t, J=6.9 Hz, 2H), 4.60 (d, J=5.9 Hz, 2H), 3.88 (s, 3H), 3.39 (t, J=6.9 Hz, 2H), 3.21-3.16 (m, 2H), 3.01 (dd, J=8.5, 6.8 Hz, 2H). $^{13}$C NMR (126 MHz, DMSO-d₆) δ 166.73, 161.37, 159.89, 159.24, 154.09, 147.88, 140.12, 138.14, 130.63, 130.26, 128.16, 126.90, 125.96, 125.46, 125.22, 123.88, 122.57, 119.62, 118.02, 116.79, 109.95, 105.50, 104.17, 91.64, 85.55, 55.63, 42.74, 35.17, 34.71, 26.76, 24.30.

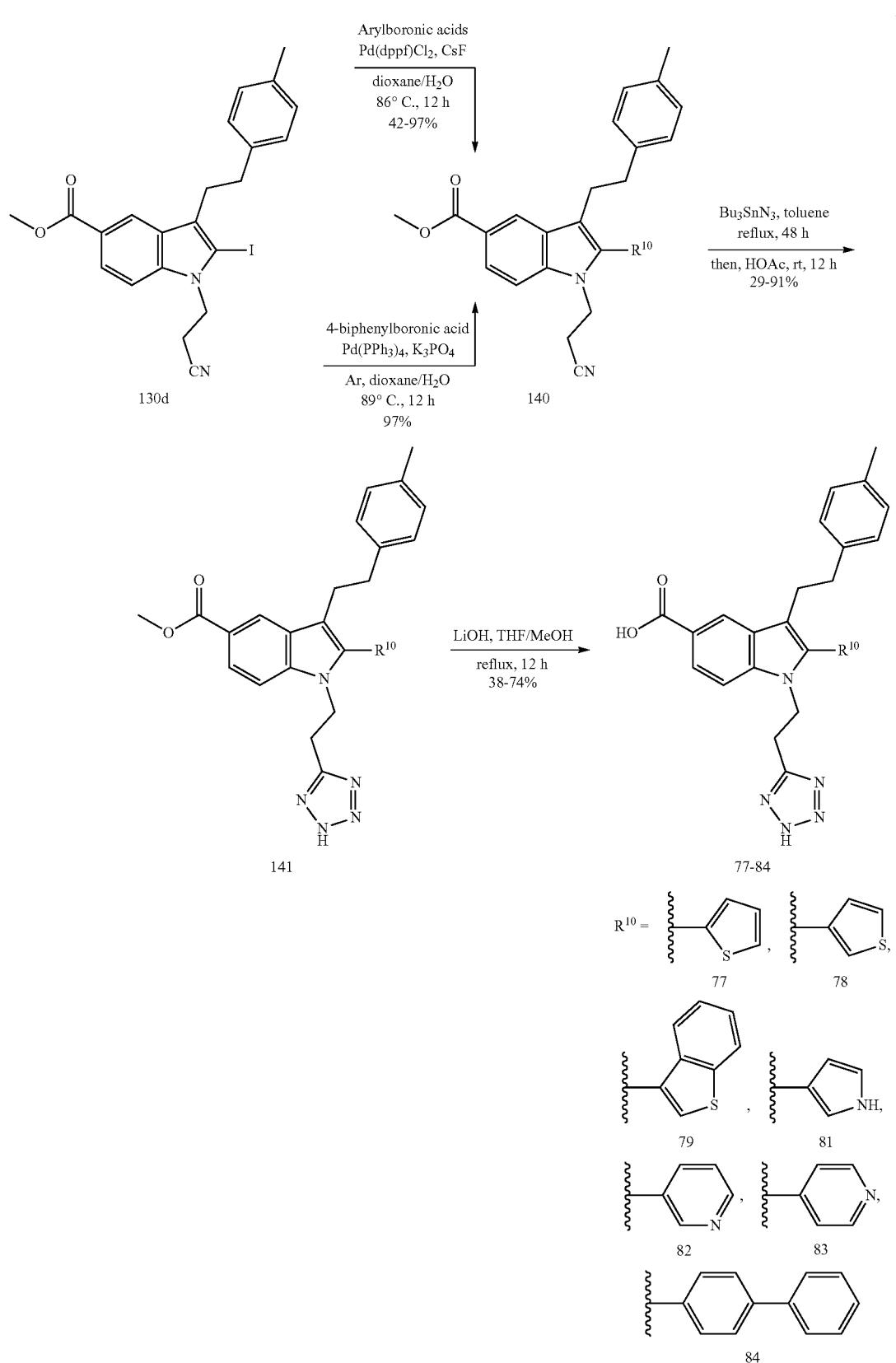

-continued
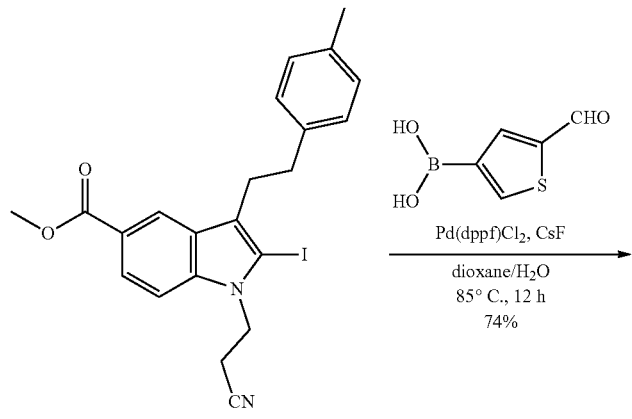
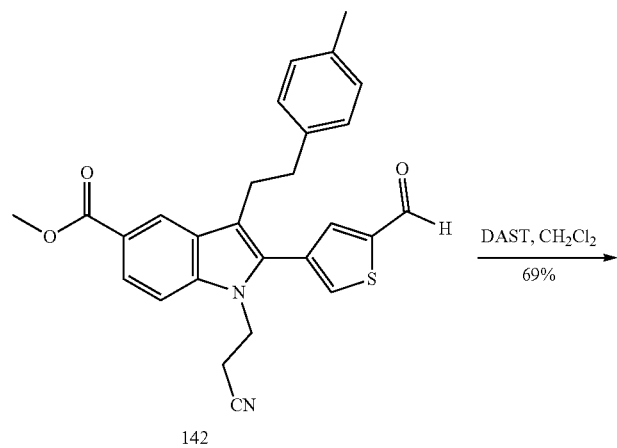
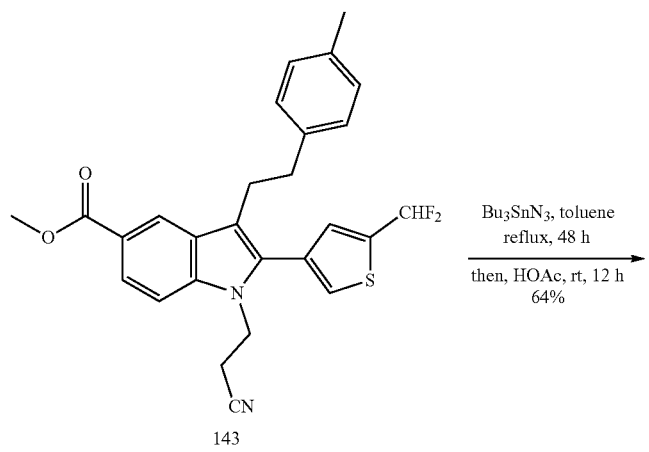

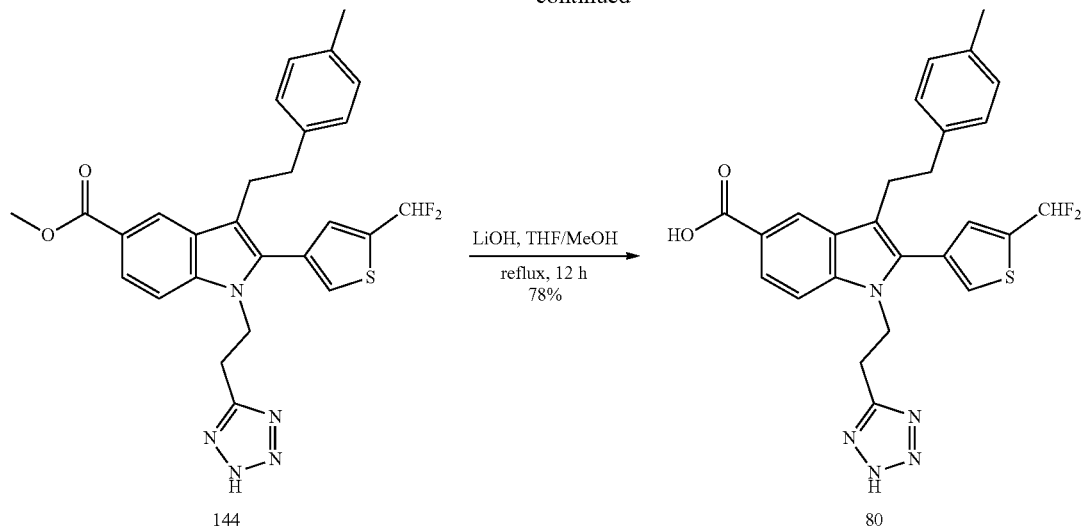

methyl 1-(2-cyanoethyl)-3-(4-methylphenethyl)-2-(thiophen-2-yl)-1H-indole-5-carboxylate (140a). The synthesis of compound 140a followed general procedure I to obtain the desired product as brown solid (hexanes:ethyl acetate=3:1, 82% yield). Low resolution mass spectrometry [M+Na]$^+$: 451.2. $^1$H NMR (500 MHz, Chloroform-d) δ 8.56 (d, J=1.6 Hz, 1H), 8.19 (dd, J=8.7, 1.6 Hz, 1H), 7.68 (dd, J=5.2, 1.2 Hz, 1H), 7.53 (d, J=8.7 Hz, 1H), 7.32 (dd, J=5.2, 3.4 Hz, 1H), 7.21 (d, J=7.7 Hz, 2H), 7.15-7.10 (m, 2H), 7.06 (dd, J=3.5, 1.2 Hz, 1H), 4.55 (t, J=7.3 Hz, 2H), 4.14 (s, 3H), 3.20-3.14 (m, 2H), 3.07 (dd, J=9.3, 6.3 Hz, 2H), 2.77 (t, J=7.2 Hz, 2H), 2.48 (s, 3H). $^{13}$C NMR (126 MHz, Chloroform-d) δ 167.69, 138.56, 138.43, 135.23, 130.25, 130.13, 130.10, 128.81, 128.27, 128.25, 127.55, 127.28, 124.14, 122.37, 122.11, 118.74, 116.74, 108.81, 51.81, 39.46, 36.63, 26.84, 20.88, 18.28.

methyl 1-(2-cyanoethyl)-3-(4-methylphenethyl)-2-(thiophen-3-yl)-1H-indole-5-carboxylate (140b). The synthesis of compound 140b followed general procedure I to obtain the desired product as brown solid (hexanes:ethyl acetate=3:1, 84% yield). $^1$H NMR (500 MHz, Chloroform-d) δ 8.31 (dd, J=1.6, 0.6 Hz, 1H), 7.90 (dd, J=8.6, 1.6 Hz, 1H), 7.35 (dd, J=4.9, 2.9 Hz, 1H), 7.25 (dd, J=8.5, 0.6 Hz, 1H), 6.96-6.91 (m, 2H), 6.88 (dd, J=3.0, 1.3 Hz, 1H), 6.82 (dd, J=4.9, 1.3 Hz, 1H), 6.81-6.76 (m, 2H), 4.23 (t, J=7.1 Hz, 2H), 3.88 (s, 3H), 2.85 (ddd, J=8.4, 6.6, 1.8 Hz, 2H), 2.82-2.76 (m, 2H), 2.44 (t, J=7.2 Hz, 2H), 2.21 (s, 3H). $^{13}$C NMR (126 MHz, Chloroform-d) δ 167.95, 138.57, 138.45, 135.35, 133.31, 130.36, 128.87, 128.71, 128.45, 127.72, 126.54, 126.49, 123.82, 122.29, 122.10, 116.77, 116.65, 108.70, 51.95, 39.57, 36.46, 26.78, 20.99, 18.20. Low resolution mass spectrometry [M+Na]$^+$: 451.2.

methyl 2-(benzo[b]thiophen-3-yl)-1-(2-cyanoethyl)-3-(4-methylphenethyl)-1H-indole-5-carboxylate (140c). The synthesis of compound 140c followed general procedure I to obtain the desired product as brown solid (hexanes:ethyl acetate=3:1, 42% yield). $^1$H NMR (500 MHz, DMSO-d$_6$) δ 8.30-8.24 (m, 1H), 8.12 (dt, J=8.1, 0.9 Hz, 1H), 7.86 (dd, J=8.7, 1.7 Hz, 1H), 7.81-7.74 (m, 2H), 7.45 (ddd, J=8.2, 6.9, 1.3 Hz, 1H), 7.39 (ddd, J=8.1, 7.0, 1.1 Hz, 1H), 7.31 (dt, J=8.0, 1.1 Hz, 1H), 6.93-6.86 (m, 2H), 6.80-6.72 (m, 2H), 4.50 (dt, J=14.8, 6.2 Hz, 1H), 4.05 (dt, J=14.9, 6.9 Hz, 1H), 3.89 (s, 3H), 3.00-2.89 (m, 1H), 2.75-2.65 (m, 5H), 2.17 (s, 3H). $^{13}$C NMR (126 MHz, DMSO-d$_6$) δ 167.09, 139.08, 138.64, 138.36, 138.16, 134.62, 132.07, 130.05, 128.64, 127.98, 127.02, 125.37, 124.99, 124.86, 123.18, 122.72, 122.29, 121.31, 121.00, 118.14, 116.47, 110.54, 51.81, 36.00, 26.55, 20.57, 18.08.

methyl 1-(2-cyanoethyl)-3-(4-methylphenethyl)-2-(1H-pyrrol-3-yl)-1H-indole-5-carboxylate (140d). The synthesis of compound 140d followed general procedure I to obtain the desired product as white solid (hexanes:ethyl acetate=2:1, 97% yield). $^1$H NMR (500 MHz, Chloroform-d) δ 8.57 (s, 1H), 8.37 (dd, J=1.7, 0.6 Hz, 1H), 7.96 (dd, J=8.6, 1.6 Hz, 1H), 7.33 (dd, J=8.7, 0.6 Hz, 1H), 7.07-7.02 (m, 2H), 7.00-6.95 (m, 2H), 6.91 (td, J=2.7, 2.0 Hz, 1H), 6.56 (dt, J=2.6, 1.7 Hz, 1H), 6.16 (td, J=2.7, 1.6 Hz, 1H), 4.42 (dd, J=7.9, 6.9 Hz, 2H), 3.97 (s, 3H), 3.02-2.95 (m, 2H), 2.93-2.86 (m, 2H), 2.57 (dd, J=7.8, 6.9 Hz, 2H), 2.31 (s, 3H). $^{13}$C NMR (126 MHz, Chloroform-d) δ 168.25, 139.05, 138.39, 135.24, 133.97, 128.86, 128.46, 127.97, 123.20, 121.94, 121.65, 118.94, 118.74, 117.14, 115.79, 112.23, 110.07, 108.44, 51.93, 39.46, 36.78, 26.90, 21.03, 18.18. Low resolution mass spectrometry [M+Na]$^+$: 434.2.

methyl 1-(2-cyanoethyl)-3-(4-methylphenethyl)-2-(pyridin-3-yl)-1H-indole-5-carboxylate (140e). The synthesis of compound 140e followed general procedure I to obtain the desired product as brown solid (hexanes:ethyl acetate=2:1, 46% yield). Low resolution mass spectrometry [M+H]$^+$: 424.2. $^1$H NMR (500 MHz, Chloroform-d) δ 8.67 (dd, J=4.7, 1.9 Hz, 1H), 8.44 (d, J=1.6 Hz, 1H), 8.37-8.33 (m, 1H), 8.02 (dd, J=8.6, 1.6 Hz, 1H), 7.37 (d, J=8.7 Hz, 1H), 7.35-7.29 (m, 2H), 6.97 (d, J=7.7 Hz, 2H), 6.78 (d, J=7.8 Hz, 2H), 4.28 (t, J=7.0 Hz, 2H), 3.97 (s, 3H), 2.96-2.90 (m, 2H), 2.88 (dd, J=8.2, 5.3 Hz, 2H), 2.52 (t, J=7.0 Hz, 2H), 2.29 (s, 3H). $^{13}$C NMR (126 MHz, Chloroform-d) δ 167.72, 150.84, 149.85, 138.59, 138.06, 138.04, 135.38, 134.74, 128.81, 128.34, 127.66, 126.51, 124.19, 123.31, 122.49, 122.43, 117.26, 116.40, 108.92, 51.93, 39.42, 36.23, 26.55, 20.92, 18.08.

methyl 1-(2-cyanoethyl)-3-(4-methylphenethyl)-2-(pyridin-4-yl)-1H-indole-5-carboxylate (140f). The synthesis of compound 140f followed general procedure I to obtain the desired product as brown solid (hexanes:ethyl acetate=2:1, 68% yield). Low resolution mass spectrometry [M+H]$^+$: 424.2. $^1$H NMR (500 MHz, DMSO-d$_6$) δ 8.69 (d, J=5.2 Hz, 2H), 8.27 (d, J=1.5 Hz, 1H), 7.86 (dd, J=8.5, 1.5 Hz, 1H), 7.78 (d, J=8.7 Hz, 1H), 7.30-7.24 (m, 2H), 6.97 (d, J=7.7 Hz, 2H), 6.83 (d, J=7.7 Hz, 2H), 4.40 (t, J=6.5 Hz, 2H), 3.88 (s, 3H), 2.91 (dd, J=8.4, 6.7 Hz, 2H), 2.75 (dt, J=9.5, 7.0 Hz, 4H), 2.23 (s, 3H). $^{13}$C NMR (126 MHz, DMSO-d$_6$) δ 166.97, 149.85, 138.71, 138.06, 138.00, 136.01, 134.78, 128.71, 128.12, 126.91, 125.12, 123.16, 121.51, 121.35, 118.12, 115.64, 110.76, 51.83, 35.96, 26.13, 20.59, 17.77.

methyl 2-([1,1'-biphenyl]-4-yl)-1-(2-cyanoethyl)-3-(4-methylphenethyl)-1H-indole-5-carboxylate (140g). The synthesis of compound 140g followed general procedure K to obtain the desired compound as brown solid (hexane:ethyl acetate=3:1, 97% yield). Low resolution mass spectrometry [M+H]$^+$: 521.3. $^1$H NMR (500 MHz, DMSO-d$_6$) δ 8.28-8.20 (m, 1H), 7.87-7.73 (m, 6H), 7.52 (dd, J=8.3, 7.1 Hz, 2H), 7.45-7.36 (m, 3H), 7.03-6.96 (m, 2H), 6.93-6.88 (m, 2H), 4.40 (t, J=6.6 Hz, 2H), 3.88 (s, 3H), 2.90 (dd, J=8.9, 6.3 Hz, 2H), 2.79 (q, J=7.3, 6.6 Hz, 4H), 2.23 (s, 3H). $^{13}$C NMR (126 MHz, DMSO-d$_6$) δ 167.09, 140.18, 139.28, 138.41, 138.39, 138.26, 134.71, 131.08, 129.30, 129.06, 128.73, 128.11, 127.83, 127.08, 126.73, 122.61, 121.17, 121.02, 118.22, 114.69, 110.50, 51.78, 39.27, 36.14, 26.35, 20.61, 17.79.

methyl 1-(2-(2H-tetrazol-5-yl)ethyl)-3-(4-methylphenethyl)-2-(thiophen-2-yl)-1H-indole-5-carboxylate (141a). The synthesis of compound 141a followed general procedure F to obtain the desired product as brown solid (CH$_2$Cl$_2$:MeOH=15:1, 45% yield). Low resolution mass spectrometry [M+Na]$^+$: 494.2. $^1$H NMR (500 MHz, DMSO-d$_6$) δ 8.19 (d, J=1.6 Hz, 1H), 7.82 (dd, J=5.2, 1.2 Hz, 1H), 7.79 (d, J=8.8 Hz, 1H), 7.53 (s, 1H), 7.23 (dd, J=5.2, 3.5 Hz, 1H), 7.10-7.05 (m, 1H), 7.04-7.01 (m, 2H), 6.95 (d, J=7.8 Hz, 2H), 4.51 (t, J=7.5 Hz, 2H), 3.87 (s, 3H), 3.16 (s, 2H), 2.95-2.89 (m, 2H), 2.77 (dd, J=9.3, 6.3 Hz, 2H), 2.24 (s, 3H). $^{13}$C NMR (126 MHz, DMSO-d$_6$) δ 167.01, 138.45, 138.29, 134.76, 130.87, 130.00, 128.97, 128.80, 128.78, 128.11, 128.08, 127.78, 126.50, 122.98, 121.36, 120.86, 116.83, 109.98, 51.77, 36.45, 26.64, 26.25, 20.61, 13.49.

methyl 1-(2-(2H-tetrazol-5-yl)ethyl)-3-(4-methylphenethyl)-2-(thiophen-3-yl)-1H-indole-5-carboxylate (141b). The synthesis of compound 141b followed general procedure F to obtain the desired product as brown solid (CH$_2$Cl$_2$:MeOH=15:1, 91% yield). $^1$H NMR (500 MHz, Chloroform-d) δ 8.27 (dd, J=1.7, 0.6 Hz, 1H), 7.77 (dd, J=8.7, 1.6 Hz, 1H), 7.34 (dd, J=4.9, 3.0 Hz, 1H), 7.23 (dd, J=8.7, 0.6 Hz, 1H), 7.02-6.96 (m, 2H), 6.91 (dd, J=3.0, 1.3 Hz, 1H), 6.88-6.84 (m, 2H), 6.83 (dd, J=4.9, 1.2 Hz, 1H), 4.52-4.45 (m, 2H), 3.91 (s, 3H), 3.26 (t, J=7.1 Hz, 2H), 2.90-2.83 (m, 2H), 2.78 (dd, J=9.0, 6.4 Hz, 2H), 2.28 (s, 3H). $^{13}$C NMR (126 MHz, Chloroform-d) δ 168.98, 138.70, 138.56, 135.40, 133.86, 130.40, 128.92, 128.50, 128.34, 127.49, 126.46, 126.09, 123.56, 122.23, 120.98, 116.12, 108.98, 52.27, 42.06, 36.57, 26.73, 24.42, 21.01. Low resolution mass spectrometry [M+Na]$^+$: 494.2.

methyl 1-(2-(2H-tetrazol-5-yl)ethyl)-2-(benzo[b]thiophen-3-yl)-3-(4-methylphenethyl)-1H-indole-5-carboxylate (141c). The synthesis of compound 141c followed general procedure F to obtain the desired product as brown solid (CH$_2$Cl$_2$:MeOH=15:1, 37% yield). $^1$H NMR (500 MHz, Chloroform-d) δ 8.37-8.34 (m, 1H), 7.85-7.80 (m, 2H), 7.33 (ddd, J=8.1, 6.2, 2.0 Hz, 1H), 7.28-7.25 (m, 3H), 6.95 (s, 1H), 6.92-6.88 (m, 2H), 6.74 (d, J=8.1 Hz, 2H), 4.54-4.46 (m, 1H), 4.21 (dt, J=14.6, 7.3 Hz, 1H), 3.94 (s, 3H), 3.21-3.09 (m, 2H), 2.97 (td, J=8.5, 8.0, 4.0 Hz, 1H), 2.79-2.70 (m, 3H), 2.23 (s, 3H). $^{13}$C NMR (126 MHz, Chloroform-d) δ 168.89, 139.73, 138.93, 138.58, 138.38, 135.30, 132.32, 128.83, 128.51, 128.28, 127.67, 125.90, 124.88, 123.66, 122.90, 122.48, 122.40, 121.12, 117.45, 109.11, 52.27, 42.36, 36.46, 26.75, 24.59, 20.99. Low resolution mass spectrometry [M+Na]$^+$: 544.2.

methyl 1-(2-(2H-tetrazol-5-yl)ethyl)-3-(4-methylphenethyl)-2-(1H-pyrrol-3-yl)-1H-indole-5-carboxylate (141d). The synthesis of compound 141d followed general procedure F to obtain the desired product as brown solid (CH$_2$Cl$_2$:MeOH=13:1, 29% yield). $^1$H NMR (500 MHz, DMSO-d6) δ 11.20 (s, 1H), 8.14 (d, J=1.6 Hz, 1H), 7.72 (dd, J=8.6, 1.6 Hz, 1H), 7.48 (d, J=8.6 Hz, 1H), 7.07-7.04 (m, 2H), 7.01 (d, J=8.1 Hz, 2H), 6.94 (td, J=2.6, 1.8 Hz, 1H), 6.79 (dt, J=2.7, 1.8 Hz, 1H), 6.15 (td, J=2.5, 1.6 Hz, 1H), 4.56-4.49 (m, 2H), 3.86 (s, 3H), 3.20-3.13 (m, 2H), 2.93-2.87 (m, 2H), 2.79 (dd, J=9.7, 6.1 Hz, 2H), 2.25 (s, 3H). $^{13}$C NMR (126 MHz, DMSO-d$_6$) δ 167.26, 138.77, 138.12, 135.30, 134.64, 128.78, 128.12, 127.19, 121.72, 120.49, 120.22, 118.85, 118.45, 113.27, 111.20, 109.36, 108.83, 51.68, 41.28, 36.48, 26.82, 23.90, 20.64. Low resolution mass spectrometry [M+Na]$^+$: 477.3.

methyl 1-(2-(2H-tetrazol-5-yl)ethyl)-3-(4-methylphenethyl)-2-(pyridin-3-yl)-1H-indole-5-carboxylate (141e). The synthesis of compound 141e followed general procedure F to obtain the desired product as brown solid (CH$_2$Cl$_2$:MeOH=13:1, 31% yield). Low resolution mass spectrometry [M+H]$^+$: 467.0. H NMR (500 MHz, DMSO-d$_6$) δ 8.66 (dd, J=4.7, 1.8 Hz, 1H), 8.36 (dd, J=2.2, 0.9 Hz, 1H), 8.24 (d, J=1.6 Hz, 1H), 7.82 (dd, J=8.7, 1.7 Hz, 1H), 7.60 (d, J=8.7 Hz, 1H), 7.51 (dt, J=7.8, 2.0 Hz, 1H), 7.47 (ddd, J=7.8, 4.7, 1.0 Hz, 1H), 6.97 (d, J=7.6 Hz, 2H), 6.84-6.79 (m, 2H), 4.44 (t, J=7.2 Hz, 2H), 3.88 (s, 3H), 3.08 (t, J=7.2 Hz, 2H), 2.83 (dd, J=8.6, 6.4 Hz, 2H), 2.74 (dd, J=8.6, 6.4 Hz, 2H), 2.23 (s, 3H). $^{13}$C NMR (126 MHz, DMSO-d$_6$) δ 167.05, 150.23, 149.54, 138.44, 138.08, 137.65, 135.41, 134.74, 128.71, 128.05, 126.78, 126.44, 123.47, 122.82, 121.34, 120.90, 115.34, 110.10, 51.79, 41.62, 36.10, 26.24, 23.79, 20.60.

methyl 1-(2-(2H-tetrazol-5-yl)ethyl)-3-(4-methylphenethyl)-2-(pyridin-4-yl)-1H-indole-5-carboxylate (141f). The synthesis of compound 141f followed general procedure F to obtain the desired product as brown solid (CH$_2$Cl$_2$:MeOH=13:1, 53% yield). Low resolution mass spectrometry [M+H]$^+$: 467.3. $^1$H NMR (500 MHz, DMSO-d$_6$) δ 8.68-8.61 (m, 2H), 8.24 (t, J=1.1 Hz, 1H), 7.83 (dd, J=8.7, 1.6 Hz, 1H), 7.62 (d, J=8.7 Hz, 1H), 7.14-7.11 (m, 2H), 6.99-6.95 (m, 2H), 6.83 (d, J=8.0 Hz, 2H), 4.51-4.46 (m, 2H), 3.88 (s, 3H), 3.07 (t, J=7.1 Hz, 2H), 2.87 (dd, J=8.5, 6.5 Hz, 2H), 2.73 (dd, J=8.4, 6.6 Hz, 2H), 2.24 (s, 3H). $^{13}$C NMR (126 MHz, DMSO-d$_6$) δ 167.00, 149.80, 138.64, 138.17, 138.03, 135.95, 134.77, 128.72, 128.10, 126.83, 124.66, 123.07, 121.52, 121.06, 115.31, 110.26, 51.81, 41.67, 36.05, 26.14, 23.72, 20.60.

methyl 1-(2-(2H-tetrazol-5-yl)ethyl)-2-([1,1'-biphenyl]-4-yl)-3-(4-methylphenethyl)-1H-indole-5-carboxylate (141g). The synthesis of compound 141g followed general procedure F to obtain the desired product as pale white solid (CH$_2$Cl$_2$:MeOH=15:1, 59% yield). Low resolution mass spectrometry [M+H]$^+$: 542.2. $^1$H NMR (500 MHz, DMSO-d$_6$) δ 8.21 (d, J=1.6 Hz, 1H), 7.81-7.77 (m, 5H), 7.57 (d, J=8.7 Hz, 1H), 7.52 (dd, J=8.4, 7.1 Hz, 2H), 7.44-7.39 (m, 1H), 7.31-7.26 (m, 2H), 7.00 (d, J=7.8 Hz, 2H), 6.92-6.88 (m, 2H), 4.53-4.44 (m, 2H), 3.88 (s, 3H), 3.12 (t, J=7.2 Hz, 2H), 2.87 (dd, J=9.0, 6.2 Hz, 2H), 2.78 (dd, J=9.0, 6.3 Hz, 2H), 2.23 (s, 3H). $^{13}$C NMR (126 MHz, DMSO-d$_6$) δ 167.11, 140.02, 139.29, 138.39, 138.33, 138.31, 134.71, 130.68, 129.49, 129.05, 128.73, 128.09, 127.82, 126.98, 126.72, 126.69, 122.50, 121.18, 120.73, 114.40, 109.95, 51.76, 41.58, 36.22, 26.38, 23.79, 20.61.

1-(2-(2H-tetrazol-5-yl)ethyl)-3-(4-methylphenethyl)-2-(thiophen-2-yl)-1H-indole-5-carboxylic acid (77). The synthesis of compound 77 followed general procedure J to obtain the desired product as white solid (38% yield). $^1$H NMR (500 MHz, DMSO-$d_6$) δ 12.57 (s, 1H), 8.23 (s, 1H), 7.82 (d, J=5.1 Hz, 1H), 7.79 (d, J=8.7 Hz, 1H), 7.52 (d, J=8.7 Hz, 1H), 7.26-7.21 (m, 1H), 7.06 (d, J=3.5 Hz, 1H), 7.03 (d, J=7.7 Hz, 2H), 6.96 (d, J=7.6 Hz, 2H), 4.52 (t, J=7.4 Hz, 2H), 3.18 (t, J=7.5 Hz, 2H), 2.91 (dd, J=9.8, 6.2 Hz, 2H), 2.78 (dd, J=9.5, 6.3 Hz, 2H), 2.24 (s, 3H). $^{13}$C NMR (126 MHz, DMSO-$d_6$) δ 168.12, 138.33, 134.76, 130.61, 130.10, 129.95, 128.93, 128.83, 128.80, 128.04, 127.79, 126.48, 123.33, 122.01, 121.46, 116.77, 109.76, 41.54, 36.45, 26.71, 24.01, 20.62.

1-(2-(2H-tetrazol-5-yl)ethyl)-3-(4-methylphenethyl)-2-(thiophen-3-yl)-1H-indole-5-carboxylic acid (78). The synthesis of compound 78 followed general procedure J to obtain the desired product as white solid (73% yield). $^1$H NMR (500 MHz, Methanol-$d_4$) δ 8.29 (d, J=1.6 Hz, 1H), 7.88 (dd, J=8.6, 1.6 Hz, 1H), 7.51 (dd, J=4.9, 3.0 Hz, 1H), 7.40 (d, J=8.6 Hz, 1H), 6.97 (d, J=7.7 Hz, 2H), 6.94 (dd, J=3.0, 1.3 Hz, 1H), 6.83 (dd, J=4.9, 1.3 Hz, 1H), 6.82-6.77 (m, 2H), 4.50 (t, J=6.9 Hz, 2H), 3.16 (t, J=6.9 Hz, 2H), 2.92-2.86 (m, 2H), 2.81 (t, J=6.9 Hz, 2H), 2.26 (s, 3H). $^{13}$C NMR (126 MHz, Methanol-$d_4$) δ 171.33, 155.56, 140.23, 140.01, 136.38, 135.26, 132.13, 129.87, 129.84, 129.54, 128.92, 127.31, 127.28, 124.56, 123.20, 122.82, 116.78, 110.17, 43.04, 37.68, 28.14, 25.20, 21.09. Low resolution mass spectrometry [M+H]$^+$: 458.3. HPLC purity (water/CH$_3$CN): 99.86%, Rt: 13.66 min. HPLC purity (water/MeOH): 99.99%, Rt: 15.94 min.

1-(2-(2H-tetrazol-5-yl)ethyl)-2-(benzo[b]thiophen-3-yl)-3-(4-methylphenethyl)-1H-indole-5-carboxylic acid (79). The synthesis of compound 79 followed general procedure J to obtain the desired product as brown solid (51% yield). $^1$H NMR (500 MHz, DMSO-$d_6$) δ 12.54 (s, 1H), 8.28 (d, J=1.6 Hz, 1H), 8.11 (dt, J=8.2, 0.9 Hz, 1H), 7.80 (dd, J=8.7, 1.6 Hz, 1H), 7.55 (s, 2H), 7.47-7.42 (m, 1H), 7.38 (ddd, J=8.0, 6.9, 1.1 Hz, 1H), 7.33 (dt, J=8.0, 1.0 Hz, 1H), 6.91 (d, J=7.8 Hz, 2H), 6.79-6.74 (m, 2H), 4.56 (dt, J=14.3, 6.9 Hz, 1H), 4.16 (dt, J=14.7, 7.4 Hz, 1H), 3.04 (h, J=7.9 Hz, 2H), 2.95-2.86 (m, 1H), 2.73-2.63 (m, 3H), 2.18 (s, 3H). $^{13}$C NMR (126 MHz, DMSO-$d_6$) δ 168.24, 139.09, 138.44, 138.36, 138.24, 134.61, 131.86, 129.29, 128.67, 127.94, 126.90, 125.70, 124.95, 124.81, 123.17, 122.92, 122.35, 121.81, 121.42, 116.07, 109.74, 54.92, 36.09, 26.66, 20.59, 14.09. HPLC purity (water/CH$_3$CN): 99.15%, Rt: 14.37 min. HPLC purity (water/MeOH): 99.85%, Rt: 16.40 min.

1-(2-(2H-tetrazol-5-yl)ethyl)-3-(4-methylphenethyl)-2-(1H-pyrrol-3-yl)-1H-indole-5-carboxylic acid (81). The synthesis of compound 81 followed general procedure J to obtain the desired product as white solid (45% yield). $^1$H NMR (500 MHz, DMSO-$d_6$) δ 12.42 (s, 1H), 11.19 (s, 1H), 8.17 (d, J=1.5 Hz, 1H), 7.71 (dd, J=8.6, 1.6 Hz, 1H), 7.45 (d, J=8.6 Hz, 1H), 7.06 (d, J=7.8 Hz, 2H), 7.02 (d, J=8.1 Hz, 2H), 6.93 (q, J=2.5 Hz, 1H), 6.79 (q, J=2.0 Hz, 1H), 6.15 (td, J=2.5, 1.5 Hz, 1H), 4.55-4.49 (m, 2H), 3.19-3.13 (m, 2H), 2.89 (dd, J=10.1, 5.8 Hz, 2H), 2.80 (dd, J=10.0, 6.1 Hz, 2H), 2.25 (s, 3H). $^{13}$C NMR (126 MHz, DMSO-$d_6$) δ 168.39, 138.82, 138.02, 135.04, 134.64, 128.80, 128.09, 127.14, 122.03, 121.29, 120.59, 118.82, 118.40, 113.14, 111.29, 109.14, 108.83, 41.28, 36.49, 26.93, 20.65. HPLC purity (water/CH$_3$CN): 99.84%, Rt: 12.56 min. HPLC purity (water/MeOH): 99.99%, Rt: 15.31 min.

1-(2-(2H-tetrazol-5-yl)ethyl)-3-(4-methylphenethyl)-2-(pyridin-3-yl)-1H-indole-5-carboxylic acid (82). The synthesis of compound 82 followed general procedure J to obtain the desired product as brown solid (56.0% yield). $^1$H NMR (500 MHz, DMSO-$d_6$) δ 8.66 (s, 1H), 8.36 (s, 1H), 8.27 (s, 1H), 7.85-7.78 (m, 1H), 7.57 (d, J=8.7 Hz, 1H), 7.52-7.45 (m, 2H), 6.97 (d, J=7.5 Hz, 2H), 6.82 (d, J=7.6 Hz, 2H), 4.44 (t, J=7.1 Hz, 2H), 3.09 (t, J=7.2 Hz, 2H), 2.82 (dd, J=8.9, 6.2 Hz, 2H), 2.74 (t, J=7.6 Hz, 2H), 2.23 (s, 3H). $^{13}$C NMR (126 MHz, DMSO-$d_6$) δ 168.17, 150.23, 149.48, 138.35, 138.11, 137.64, 135.17, 134.74, 128.73, 128.02, 126.75, 123.15, 122.03, 121.44, 115.25, 109.88, 41.58, 36.10, 26.33, 23.74, 20.61.

1-(2-(2H-tetrazol-5-yl)ethyl)-3-(4-methylphenethyl)-2-(pyridin-4-yl)-1H-indole-5-carboxylic acid (83). The synthesis of compound 83 followed general procedure J to obtain the desired product as brown solid (68% yield). $^1$H NMR (500 MHz, DMSO-$d_6$) δ 12.60 (s, 1H), 8.64 (d, J=4.9 Hz, 2H), 8.27 (d, J=1.5 Hz, 1H), 7.83 (dd, J=8.6, 1.6 Hz, 1H), 7.59 (d, J=8.7 Hz, 1H), 7.14-7.09 (m, 2H), 6.98 (d, J=7.7 Hz, 2H), 6.86-6.82 (m, 2H), 4.48 (t, J=7.1 Hz, 2H), 3.08 (t, J=7.1 Hz, 2H), 2.86 (dd, J=8.7, 6.4 Hz, 2H), 2.74 (dd, J=8.7, 6.5 Hz, 2H), 2.24 (s, 3H). $^{13}$C NMR (126 MHz, DMSO-$d_6$) δ 168.11, 149.78, 138.56, 138.25, 138.06, 135.73, 134.77, 128.74, 128.06, 126.79, 124.67, 123.40, 122.18, 121.61, 115.23, 110.05, 41.66, 36.04, 26.23, 23.71, 20.60.

1-(2-(2H-tetrazol-5-yl)ethyl)-2-([1,1'-biphenyl]-4-yl)-3-(4-methylphenethyl)-1H-indole-5-carboxylic acid (84). The synthesis of compound 84 followed general procedure J to obtain the desired product as white solid (63% yield). Low resolution mass spectrometry [M+H]$^+$: 528.3. $^1$H NMR (500 MHz, DMSO-$d_6$) δ 12.53 (s, 1H), 8.25 (s, 1H), 7.78 (d, J=7.4 Hz, 5H), 7.53 (q, J=8.1, 7.6 Hz, 3H), 7.42 (t, J=7.4 Hz, 1H), 7.28 (d, J=7.8 Hz, 2H), 7.00 (d, J=7.6 Hz, 2H), 6.91 (d, J=7.5 Hz, 2H), 4.49 (t, J=7.3 Hz, 2H), 3.12 (t, J=7.3 Hz, 2H), 2.87 (dd, J=9.3, 6.0 Hz, 2H), 2.78 (dd, J=9.2, 6.2 Hz, 2H), 2.23 (s, 3H). $^{13}$C NMR (126 MHz, DMSO-$d_6$) δ 168.23, 139.97, 139.31, 138.34, 138.24, 138.15, 134.70, 130.67, 129.58, 129.05, 128.75, 128.05, 127.81, 126.94, 126.72, 126.68, 122.82, 121.84, 121.28, 114.29, 109.74, 41.57, 36.22, 26.48, 23.71, 20.62.

methyl 1-(2-cyanoethyl)-2-(5-formylthiophen-3-yl)-3-(4-methylphenethyl)-1H-indole-5-carboxylate (142). The synthesis of compound 142 followed general procedure I to obtain the desired product as brown solid (hexanes:acetone=5:1, 74% yield). Low resolution mass spectrometry [M+H]$^+$: 479.1. $^1$H NMR (500 MHz, Chloroform-d) δ 9.84 (d, J=1.2 Hz, 1H), 8.45 (dd, J=1.7, 0.6 Hz, 1H), 8.03 (dd, J=8.6, 1.6 Hz, 1H), 7.35 (dd, J=8.7, 0.6 Hz, 1H), 7.28 (t, J=1.4 Hz, 1H), 7.13 (d, J=1.5 Hz, 1H), 7.03-6.94 (m, 2H), 6.75 (d, J=8.0 Hz, 2H), 4.29 (t, J=6.8 Hz, 2H), 3.98 (s, 3H), 2.92 (d, J=2.6 Hz, 4H), 2.58 (t, J=6.8 Hz, 2H), 2.30 (s, 3H). $^{13}$C NMR (126 MHz, Chloroform-d) δ 182.64, 167.82, 144.23, 138.54, 138.35, 137.70, 135.65, 135.54, 131.88, 131.79, 128.96, 128.76, 127.58, 124.40, 122.60, 122.57, 117.22, 116.59, 108.92, 52.07, 39.61, 36.10, 26.87, 21.03, 18.31. Low resolution mass spectrometry [M+Na]$^+$: 479.1.

methyl 1-(2-cyanoethyl)-2-(5-(difluoromethyl)thiophen-3-yl)-3-(4-methylphenethyl)-1H-indole-5-carboxylate (143). methyl 1-(2-cyanoethyl)-2-(5-formylthiophen-3-yl)-3-(4-methylphenethyl)-1H-indole-5-carboxylate (0.677 g, 1.483 mmol, 1.0 eq) was dissolved in CH$_2$Cl$_2$ (dry, 10 mL). DAST (0.717 g, 3.0 eq) was added dropwise to the above solution at 0° C. After the addition, the ice bath was removed, and the reaction was stirred at room temperature overnight. The mixture was diluted with CH$_2$Cl$_2$, and washed with water, brine. The organic layer was dried with anhydrous Na$_2$SO$_4$ and concentrated under vacuum. The desired product (brown solid, hexanes:ethyl acetate=2:1, 0.50 g, 69% yield) was purified via flash column chromatography. 1H NMR (500 MHz, Chloroform-d) δ 8.44 (d, J=1.5 Hz, 1H), 8.01 (dd, J=8.6, 1.6 Hz, 1H), 7.34 (d, J=8.7 Hz, 1H), 7.06 (d, J=1.4 Hz, 1H), 7.01 (d, J=7.7 Hz, 2H), 6.93-6.68 (m, 4H), 4.26 (t, J=6.9 Hz, 2H), 3.97 (s, 3H), 2.92 (dd, J=7.3, 4.4 Hz, 4H), 2.53 (t, J=6.9 Hz, 2H), 2.31 (s, 3H). 13C NMR (126 MHz, Chloroform-d) δ 167.77, 138.43, 138.28, 136.97, 135.33, 132.31, 130.22, 129.36, 129.31, 129.26, 129.00, 128.98, 128.97, 128.80, 128.54, 127.46, 123.99, 122.31, 122.19, 116.84, 116.68, 112.97, 111.08, 109.19, 108.86, 51.88, 39.42, 36.08, 26.71, 20.84, 18.11. Low resolution mass spectrometry [M+Na]$^+$: 501.2.

methyl 1-(2-(2H-tetrazol-5-yl)ethyl)-2-(5-(difluoromethyl)thiophen-3-yl)-3-(4-methylphenethyl)-1H-indole-5-carboxylate (144). The synthesis of compound 144 followed general procedure F to obtain the desired product as yellow solid (CH$_2$Cl$_2$:MeOH=15:1, 64% yield). $^1$H NMR (500 MHz, DMSO-d$_6$) δ 8.21 (d, J=1.7 Hz, 1H), 7.79 (dd, J=8.6, 1.6 Hz, 1H), 7.67 (d, J=1.4 Hz, 1H), 7.55 (d, J=8.7 Hz, 1H), 7.31 (t, J=55.0 Hz, 1H), 7.25 (q, J=1.8 Hz, 1H), 7.00 (d, J=7.7 Hz, 2H), 6.87 (d, J=7.9 Hz, 2H), 4.48 (dd, J=8.0, 6.4 Hz, 2H), 3.87 (s, 3H), 3.12 (dd, J=7.9, 6.6 Hz, 2H), 2.86 (dd, J=8.6, 6.5 Hz, 2H), 2.75 (dd, J=8.6, 6.5 Hz, 2H), 2.24 (s, 3H). $^{13}$C NMR (126 MHz, DMSO-d$_6$) δ 167.07, 138.31, 138.26, 134.76, 132.81, 130.26, 130.16, 129.49, 128.74, 128.16, 126.69, 122.75, 121.24, 120.82, 115.23, 111.69, 109.97, 51.80, 41.62, 36.11, 26.48, 23.85, 20.60. Low resolution mass spectrometry [M+Na]$^+$: 544.2.

1-(2-(2H-tetrazol-5-yl)ethyl)-2-(5-(difluoromethyl)thiophen-3-yl)-3-(4-methylphenethyl)-1H-indole-5-carboxylic acid (80). The synthesis of compound 80 followed general procedure J to obtain the desired product as white solid (76% yield). $^1$H NMR (500 MHz, DMSO-d$_6$) δ 12.55 (s, 1H), 8.24 (d, J=1.6 Hz, 1H), 7.79 (dd, J=8.6, 1.6 Hz, 1H), 7.66 (d, J=1.4 Hz, 1H), 7.53 (d, J=8.7 Hz, 1H), 7.31 (t, J=55.0 Hz, 1H), 7.24 (q, J=1.9 Hz, 1H), 7.01 (d, J=7.7 Hz, 2H), 6.91-6.86 (d, J=7.7 Hz, 2H), 4.51-4.43 (m, 2H), 3.12 (t, J=7.3 Hz, 2H), 2.85 (dd, J=8.8, 6.3 Hz, 2H), 2.76 (dd, J=8.9, 6.6 Hz, 2H), 2.24 (s, 3H). $^{13}$C NMR (126 MHz, DMSO-d$_6$) δ 168.19, 138.30, 138.21, 134.75, 132.57, 130.28, 130.25, 129.41, 128.76, 128.13, 126.64, 123.07, 121.91, 121.33, 115.12, 113.56, 111.69, 109.75, 41.60, 36.11, 26.57, 23.82, 20.60. Low resolution mass spectrometry [M+H]$^+$: HPLC purity (water/CH$_3$CN): 99.21%, Rt: 13.84 min. HPLC purity (water/MeOH): 99.69%, Rt: 15.81 min.

Scheme 13.

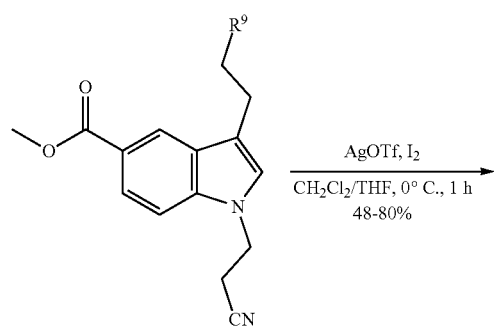

119m, n, o

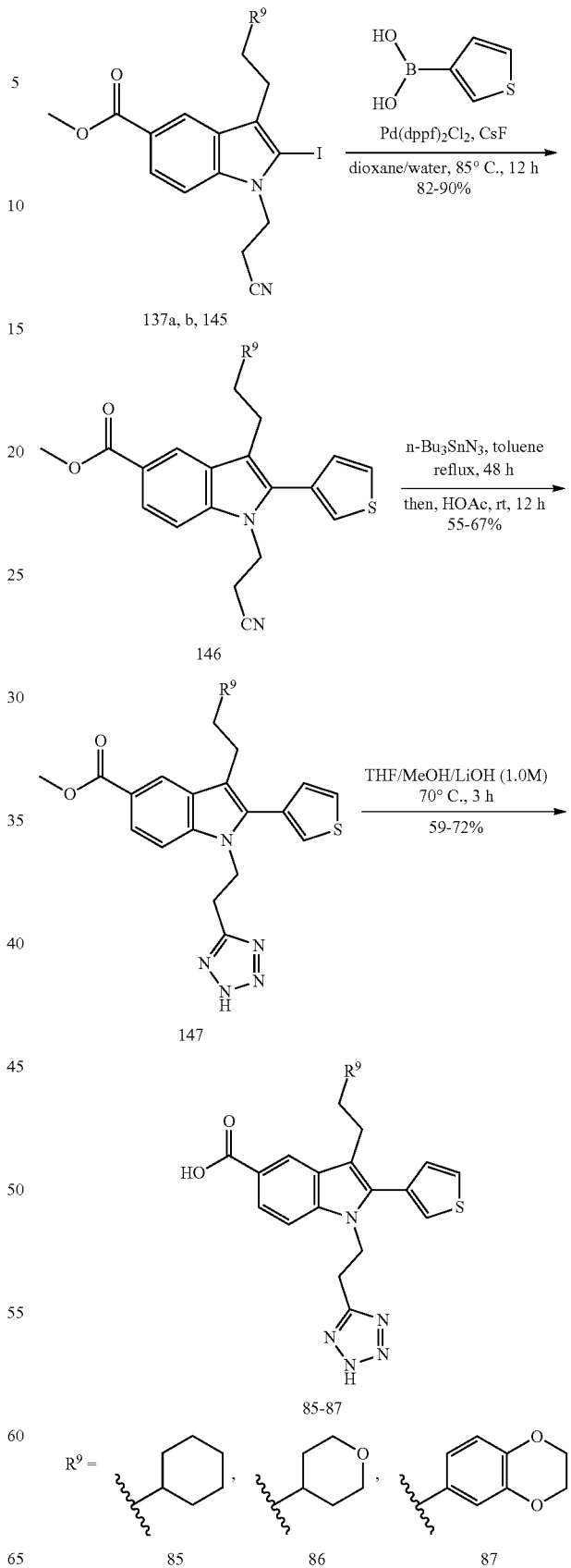

methyl 1-(2-cyanoethyl)-3-(2-cyclohexylethyl)-2-iodo-1H-indole-5-carboxylate (145). The synthesis of compound 145 followed general procedure E to obtain the desired product as brown solid (hexanes:ethyl acetate=3:1, 80% yield). Low resolution mass spectrometry [M+Na]$^+$: 487.2. $^1$H NMR (500 MHz, DMSO-d$_6$) δ 8.15 (t, J=1.1 Hz, 1H), 7.73 (t, J=1.1 Hz, 2H), 4.55 (t, J=6.6 Hz, 2H), 3.86 (s, 3H), 2.97 (t, J=6.5 Hz, 2H), 2.77-2.67 (m, 2H), 1.86-1.76 (m, 2H), 1.68 (dd, J=11.6, 4.3 Hz, 2H), 1.64-1.57 (m, 1H), 1.47-1.38 (m, 2H), 1.33-1.10 (m, 4H), 0.95 (qd, J=11.9, 3.2 Hz, 2H). $^{13}$C NMR (126 MHz, DMSO-d$_6$) δ 166.82, 139.86, 127.05, 123.14, 122.38, 120.89, 119.98, 118.15, 110.54, 90.60, 51.85, 42.29, 37.58, 36.61, 32.84, 26.14, 25.74, 24.17, 18.10.

methyl 1-(2-cyanoethyl)-3-(2-cyclohexylethyl)-2-(thiophen-3-yl)-1H-indole-5-carboxylate (146a). The synthesis of compound 146a followed general procedure I to obtain the desired product as brown solid (hexanes:ethyl acetate=3:1, 84% yield). Low resolution mass spectrometry [M+H]$^+$: 421.2. $^1$H NMR (500 MHz, Chloroform-d) δ 8.40-8.35 (m, 1H), 7.96 (dd, J=8.6, 1.6 Hz, 1H), 7.53 (dd, J=4.9, 3.0 Hz, 1H), 7.41 (dd, J=3.0, 1.3 Hz, 1H), 7.34-7.29 (m, 1H), 7.15 (dd, J=5.0, 1.3 Hz, 1H), 4.36 (t, J=7.1 Hz, 2H), 3.95 (s, 3H), 2.72-2.65 (m, 2H), 2.57 (t, J=7.1 Hz, 2H), 1.68-1.57 (m, 5H), 1.47 (ddd, J=10.1, 8.0, 6.3 Hz, 2H), 1.24-1.09 (m, 4H), 0.84 (qd, J=11.6, 10.2, 4.9 Hz, 2H). $^{13}$C NMR (126 MHz, Chloroform-d) δ 167.93, 138.41, 132.63, 130.77, 128.81, 127.86, 126.74, 126.35, 123.68, 122.33, 121.91, 118.16, 116.82, 108.58, 51.88, 39.55, 38.76, 37.29, 33.12, 26.61, 26.28, 21.70, 18.17.

methyl 1-(2-cyanoethyl)-3-(2-(tetrahydro-2H-pyran-4-yl)ethyl)-2-(thiophen-3-yl)-1H-indole-5-carboxylate (146b). The synthesis of compound 146b followed general procedure I to obtain the desired product as white solid (hexanes:ethyl acetate=2:1, 90% yield). $^1$H NMR (500 MHz, DMSO-d$_6$) δ 8.25-8.21 (m, 1H), 7.83-7.78 (m, 3H), 7.73 (dd, J=8.7, 0.6 Hz, 1H), 7.31 (dd, J=4.7, 1.5 Hz, 1H), 4.40 (t, J=6.7 Hz, 2H), 3.87 (s, 3H), 3.76-3.68 (m, 2H), 3.14 (td, J=11.7, 1.8 Hz, 2H), 2.80 (t, J=6.7 Hz, 2H), 2.70 (t, J=7.5 Hz, 2H), 1.44 (dt, J=8.3, 6.4 Hz, 2H), 1.38-1.28 (m, 3H), 1.09-0.97 (m, 2H). $^{13}$C NMR (126 MHz, DMSO-d$_6$) δ 167.08, 138.38, 133.68, 130.40, 129.15, 127.20, 127.09, 126.86, 122.57, 120.87, 120.84, 118.37, 115.70, 110.39, 66.97, 51.81, 37.64, 33.60, 32.55, 20.50, 17.81. Low resolution mass spectrometry [M+Na]$^+$: 445.2.

methyl 1-(2-cyanoethyl)-3-(2-(2,3-dihydrobenzo[b][1,4]dioxin-6-yl)ethyl)-2-(thiophen-3-yl)-1H-indole-5-carboxylate (146c). The synthesis of compound 146c followed general procedure I to obtain the desired product as brown solid (hexanes:ethyl acetate=2:1, 82% yield). Low resolution mass spectrometry [M+H]$^+$: 473.2. $^1$H NMR (500 MHz, Chloroform-d) δ 8.35 (d, J=1.5 Hz, 1H), 7.99 (dd, J=8.6, 1.6 Hz, 1H), 7.47 (dd, J=4.9, 2.9 Hz, 1H), 7.34 (d, J=8.6 Hz, 1H), 7.06 (dd, J=3.0, 1.3 Hz, 1H), 6.95 (dd, J=4.9, 1.2 Hz, 1H), 6.71 (d, J=8.7 Hz, 1H), 6.47 (dt, J=4.1, 2.1 Hz, 2H), 4.34 (t, J=7.2 Hz, 2H), 4.21 (s, 4H), 3.97 (s, 3H), 2.92 (dd, J=8.5, 6.6 Hz, 2H), 2.80 (dd, J=8.5, 6.6 Hz, 2H), 2.54 (t, J=7.2 Hz, 2H). $^{13}$C NMR (126 MHz, Chloroform-d) δ 167.99, 143.21, 141.82, 138.49, 135.06, 133.38, 130.47, 128.75, 127.81, 126.70, 126.48, 123.94, 122.36, 122.24, 121.58, 117.24, 116.92, 116.77, 116.73, 108.72, 64.45, 64.39, 52.00, 39.69, 36.25, 26.79, 18.21.

methyl 1-(2-(2H-tetrazol-5-yl)ethyl)-3-(2-cyclohexylethyl)-2-(thiophen-3-yl)-1H-indole-5-carboxylate (147a). The synthesis of compound 147a followed general procedure F to obtain the desired product as yellow solid (CH$_2$Cl$_2$:MeOH=15:1, 67% yield). Low resolution mass spectrometry [M+H]$^+$: 464.3. $^1$H NMR (500 MHz, Chloroform-d) δ 8.24 (d, J=1.6 Hz, 1H), 7.73 (dd, J=8.6, 1.7 Hz, 1H), 7.39 (dd, J=4.9, 2.9 Hz, 1H), 7.25-7.21 (m, 2H), 7.00 (dd, J=4.9, 1.3 Hz, 1H), 4.52 (t, J=7.1 Hz, 2H), 3.89 (s, 3H), 3.30 (t, J=7.1 Hz, 2H), 2.61-2.55 (m, 2H), 1.61-1.52 (m, 5H), 1.39-1.33 (m, 2H), 1.10 (ddd, J=11.4, 7.7, 4.0 Hz, 4H), 0.78 (td, J=11.8, 3.2 Hz, 2H). $^{13}$C NMR (126 MHz, Chloroform-d) δ 169.04, 138.74, 133.26, 130.75, 128.57, 127.65, 126.62, 125.94, 123.50, 122.28, 120.77, 117.57, 108.94, 52.26, 42.06, 38.84, 37.29, 33.12, 26.62, 26.29, 24.38, 21.68.

methyl 1-(2-(2H-tetrazol-5-yl)ethyl)-3-(2-(tetrahydro-2H-pyran-4-yl)ethyl)-2-(thiophen-3-yl)-1H-indole-5-carboxylate (147b). The synthesis of compound 147b followed general procedure F to obtain the desired product as yellow solid (CH$_2$Cl$_2$:MeOH=13:1, 55% yield). $^1$H NMR (500 MHz, Chloroform-d) δ 8.26 (d, J=1.6 Hz, 1H), 7.80 (dd, J=8.7, 1.6 Hz, 1H), 7.44 (dd, J=4.9, 3.0 Hz, 1H), 7.25-7.18 (m, 2H), 7.00 (dd, J=4.9, 1.3 Hz, 1H), 4.53 (t, J=6.9 Hz, 2H), 3.90 (s, 3H), 3.86-3.79 (m, 2H), 3.29-3.19 (m, 4H), 2.68-2.59 (m, 2H), 1.45 (dt, J=8.8, 6.5 Hz, 2H), 1.41-1.36 (m, 2H), 1.34 (dt, J=10.7, 3.7 Hz, 1H), 1.18-1.09 (m, 2H). $^{13}$C NMR (126 MHz, Chloroform-d) δ 168.77, 138.70, 133.43, 130.76, 128.56, 127.52, 126.88, 126.01, 123.64, 122.15, 121.17, 116.91, 109.01, 68.03, 52.25, 42.15, 38.08, 34.26, 32.83, 24.53, 21.08. Low resolution mass spectrometry [M+H]$^+$: 488.2.

methyl 1-(2-(2H-tetrazol-5-yl)ethyl)-3-(2-(2,3-dihydrobenzo[b][1,4]dioxin-6-yl)ethyl)-2-(thiophen-3-yl)-1H-indole-5-carboxylate (147c). The synthesis of compound 147c followed general procedure F to obtain the desired product as yellow solid (CH$_2$Cl$_2$:MeOH=13:1, 64% yield). Low resolution mass spectrometry [M+H]$^+$: 516.2. $^1$H NMR (500 MHz, Chloroform-d) δ 8.23 (d, J=1.7 Hz, 1H), 7.76 (dd, J=8.6, 1.6 Hz, 1H), 7.38 (dd, J=4.9, 3.0 Hz, 1H), 7.14 (d, J=8.7 Hz, 1H), 6.80-6.76 (m, 2H), 6.74 (d, J=8.2 Hz, 1H), 6.52 (dd, J=8.2, 2.1 Hz, 1H), 6.31 (d, J=2.0 Hz, 1H), 4.50 (t, J=6.6 Hz, 2H), 4.20 (tt, J=5.0, 2.8 Hz, 4H), 3.93 (s, 3H), 3.20 (t, J=6.6 Hz, 2H), 2.89-2.81 (m, 2H), 2.77 (t, J=7.2 Hz, 2H). $^{13}$C NMR (126 MHz, Chloroform-d) δ 168.71, 142.66, 141.87, 138.74, 135.11, 133.82, 130.48, 128.50, 127.36, 126.53, 125.98, 123.71, 122.25, 122.06, 121.29, 117.25, 117.13, 115.99, 108.94, 64.57, 64.33, 52.19, 42.27, 36.04, 26.72, 24.81.

1-(2-(2H-tetrazol-5-yl)ethyl)-3-(2-cyclohexylethyl)-2-(thiophen-3-yl)-1H-indole-5-carboxylic acid (85). The synthesis of compound 85 followed general procedure J to obtain the desired product as white solid (59% yield). $^1$H NMR (500 MHz, DMSO-d$_6$) δ 12.51 (s, 1H), 8.18 (d, J=1.5 Hz, 1H), 7.79-7.73 (m, 2H), 7.63 (dd, J=2.9, 1.3 Hz, 1H), 7.50 (d, J=8.7 Hz, 1H), 7.18 (dd, J=5.0, 1.3 Hz, 1H), 4.48 (dd, J=8.3, 6.4 Hz, 2H), 3.12 (t, J=7.4 Hz, 2H), 2.68-2.59 (m, 2H), 1.60-1.52 (m, 5H), 1.39 (dt, J=9.1, 6.7 Hz, 2H), 1.15-1.04 (m, 4H), 0.79 (q, J=13.6, 12.3 Hz, 2H). $^{13}$C NMR (126 MHz, DMSO-d$_6$) δ 168.21, 138.17, 133.27, 130.64, 128.79, 126.97, 126.82, 126.35, 122.72, 121.60, 121.02, 115.62, 109.55, 41.53, 38.33, 36.47, 32.64, 26.13, 25.71, 23.78, 21.15.

1-(2-(2H-tetrazol-5-yl)ethyl)-3-(2-(tetrahydro-2H-pyran-4-yl)ethyl)-2-(thiophen-3-yl)-1H-indole-5-carboxylic acid (86). The synthesis of compound 86 followed general procedure J to obtain the desired product as white solid (72% yield). $^1$H NMR (500 MHz, Methanol-d$_4$) δ 8.31 (d, J=1.6 Hz, 1H), 7.87 (dd, J=8.7, 1.7 Hz, 1H), 7.61 (dd, J=5.0, 2.9 Hz, 1H), 7.39 (d, J=8.7 Hz, 1H), 7.36 (dd, J=3.1, 1.2 Hz, 1H), 7.07 (dd, J=4.9, 1.3 Hz, 1H), 4.57 (t, J=6.8 Hz, 2H), 3.86-3.73 (m, 2H), 3.27 (td, J=11.7, 1.9 Hz, 2H), 3.20 (t, J=6.8 Hz, 2H), 2.73 (t, J=7.5 Hz, 2H), 1.50 (q, J=7.2 Hz, 2H), 1.44-1.39 (m, 2H), 1.37 (tt, J=7.2, 3.7 Hz, 1H), 1.18-1.09 (m, 2H). $^{13}$C NMR (126 MHz, Methanol-d4) δ 171.23, 140.27, 134.85, 132.45, 129.93, 128.89, 127.79, 127.31, 124.62, 123.06, 122.82, 117.56, 110.22, 69.08, 43.06, 39.14, 35.33, 34.12, 25.11, 21.99. Low resolution mass spectrometry [M+Na]⁺: 474.2. HPLC purity (water/CH₃CN): 99.99%, Rt: 13.39 min. HPLC purity (water/MeOH): 99.99%, Rt: 14.74 min.

1-(2-(2H-tetrazol-5-yl)ethyl)-3-(2-(2,3-dihydrobenzo[b][1,4]dioxin-6-yl)ethyl)-2-(thiophen-3-yl)-1H-indole-5-carboxylic acid (87). The synthesis of compound 87 followed general procedure J to obtain the desired product as white solid (71% yield). ¹H NMR (500 MHz, DMSO-d₆) δ 12.50 (s, 1H), 8.19 (d, J=1.5 Hz, 1H), 7.79-7.73 (m, 2H), 7.53-7.49 (m, 2H), 7.10 (dd, J=4.9, 1.3 Hz, 1H), 6.67 (d, J=8.2 Hz, 1H), 6.54 (d, J=2.0 Hz, 1H), 6.47 (dd, J=8.2, 2.1 Hz, 1H), 4.50-4.45 (m, 2H), 4.18 (s, 4H), 3.12 (dd, J=8.4, 6.5 Hz, 2H), 2.83 (dd, J=9.3, 6.4 Hz, 2H), 2.67 (dd, J=9.3, 6.4 Hz, 2H). ¹³C NMR (126 MHz, DMSO-d₆) δ 168.23, 143.04, 141.53, 138.11, 134.60, 133.62, 130.46, 128.71, 126.93, 126.78, 126.38, 122.78, 121.73, 121.23, 120.91, 116.62, 114.70, 109.55, 64.01, 63.92, 41.53, 35.93, 26.64, 23.81.

Scheme 14.

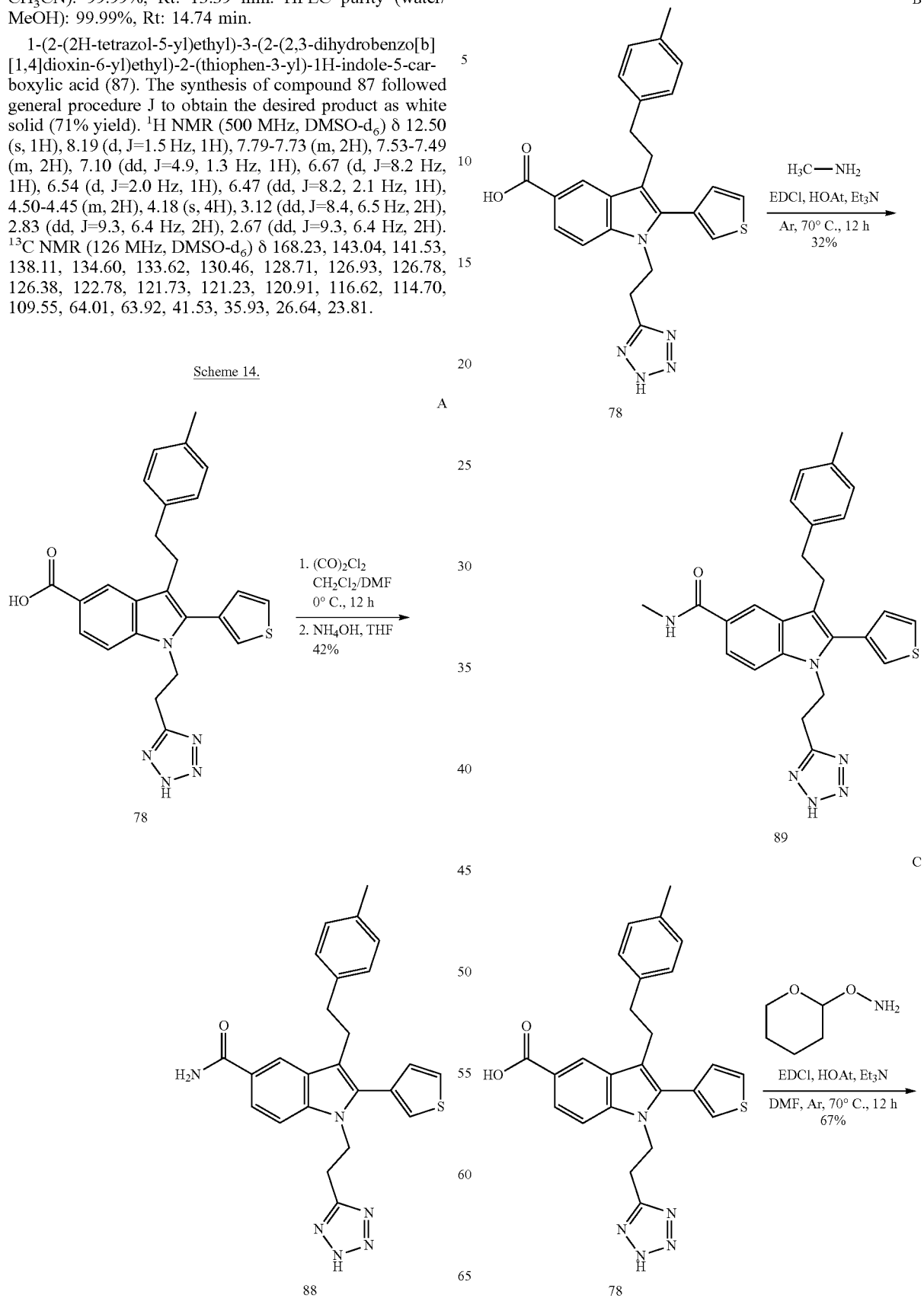

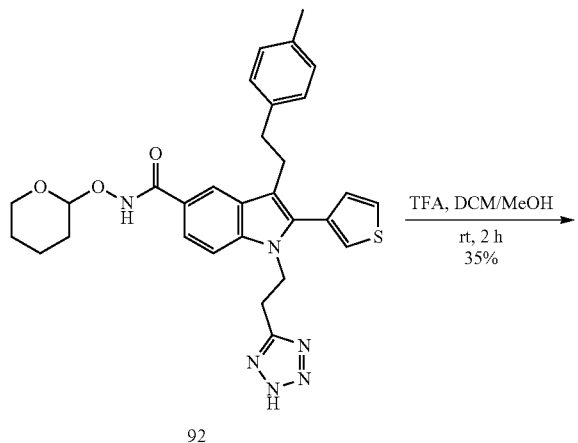

92

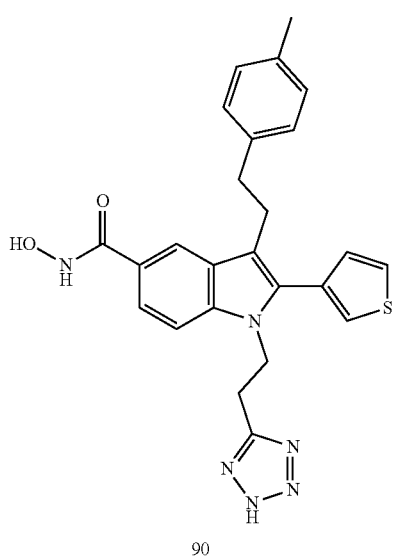

90

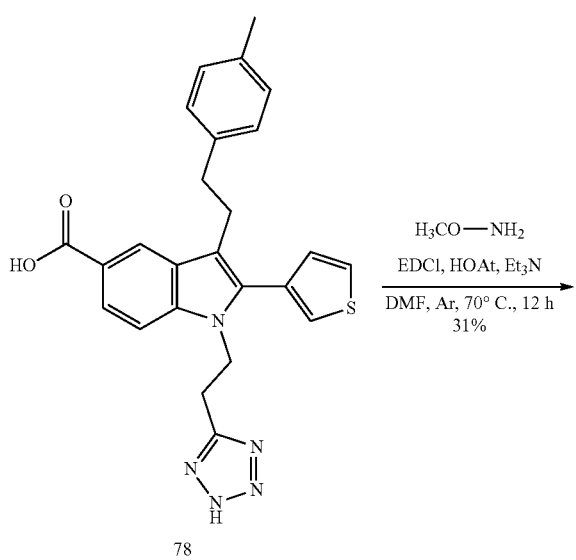

78

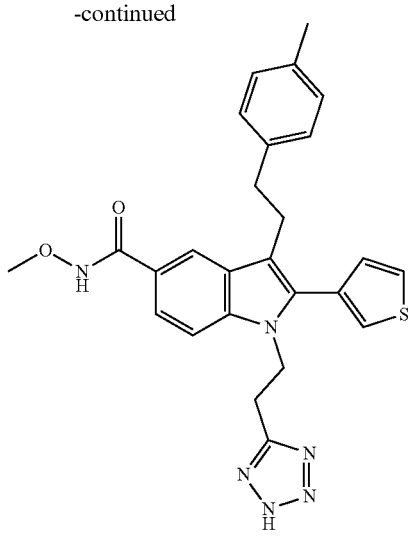

91

1-(2-(2H-tetrazol-5-yl)ethyl)-3-(4-methylphenethyl)-2-(thiophen-3-yl)-1H-indole-5-carboxamide (88). To a solution of 1-(2-(2H-tetrazol-5-yl)ethyl)-3-(4-methylphenethyl)-2-(thiophen-3-yl)-1H-indole-5-carboxylic acid (45.7 mg, 0.1 mmol) in dry DCM (4.0 mL) was added oxalyl chloride (0.4 mL) dropwise. Then two drops of DMF were added the above solution. The ice bath was removed, and the resulting mixture was stirred at room temperature for 12 h. Upon completion, the mixture was diluted with ethyl acetate. The organic layer was washed with water, brine and dried with $Mg_2SO_4$. The desired compound (brown solid, $CH_2Cl_2$:MeOH=12:1, 0.019 g, 42% yield) was isolated by column chromatography. $^1$H NMR (500 MHz, DMSO-$d_6$) δ 8.50 (s, 1H), 8.26-8.22 (m, 1H), 8.14 (s, 1H), 7.75 (dd, J=8.6, 1.7 Hz, 1H), 7.70 (dd, J=4.9, 2.9 Hz, 1H), 7.53 (d, J=8.6 Hz, 1H), 7.41 (dd, J=2.9, 1.3 Hz, 1H), 7.08-7.02 (m, 3H), 7.00-6.96 (m, 2H), 4.54 (t, J=6.9 Hz, 2H), 3.16 (t, J=6.9 Hz, 2H), 2.86-2.81 (m, 2H), 2.79 (dd, J=6.8, 2.7 Hz, 2H), 2.25 (s, 3H). $^{13}$C NMR (126 MHz, DMSO-$d_6$) δ 168.68, 165.44, 158.79, 154.41, 138.66, 137.30, 134.67, 133.12, 130.51, 128.73, 128.67, 128.11, 126.86, 126.73, 126.03, 125.52, 121.58, 118.87, 114.55, 109.23, 40.34, 36.13, 26.73, 25.66, 20.62.

1-(2-(2H-tetrazol-5-yl)ethyl)-N-methyl-3-(4-methylphenethyl)-2-(thiophen-3-yl)-1H-indole-5-carboxamide (89). The synthesis of compound 89 followed general procedure H to obtain the desired product as brown solid ($CH_2Cl_2$:MeOH=13:1, 32% yield). $^1$H NMR (500 MHz, Methanol-$d_4$) δ 8.09 (d, J=1.6 Hz, 1H), 7.68 (dd, J=8.6, 1.8 Hz, 1H), 7.52 (dd, J=4.9, 3.0 Hz, 1H), 7.40 (d, J=8.6 Hz, 1H), 6.97 (d, J=7.7 Hz, 2H), 6.94 (dd, J=3.0, 1.3 Hz, 1H), 6.85-6.80 (m, 3H), 4.50 (t, J=6.9 Hz, 2H), 3.16 (t, J=6.9 Hz, 2H), 2.97 (s, 3H), 2.92-2.88 (m, 2H), 2.85-2.81 (m, 2H), 2.26 (s, 3H). $^{13}$C NMR (126 MHz, Methanol-$d_4$) δ 171.97, 140.15, 139.38, 136.34, 135.20, 132.26, 129.86, 129.83, 129.61, 128.97, 127.28, 127.21, 126.71, 122.15, 120.01, 116.61, 110.29, 43.03, 37.64, 28.12, 27.05, 25.23, 21.09.

1-(2-(2H-tetrazol-5-yl)ethyl)-3-(4-methylphenethyl)-N-((tetrahydro-2H-pyran-2-yl)oxy)-2-(thiophen-3-yl)-1H-indole-5-carboxamide (92). The synthesis of compound 92 followed general procedure H to obtain the desired product as brown solid ($CH_2Cl_2$:MeOH=15:1, 67% yield). Low resolution mass spectrometry [M+H]$^+$: 557.2. $^1$H NMR (500 MHz, DMSO-$d_6$) δ 11.58 (s, 1H), 8.14 (d, J=1.6 Hz, 1H), 7.73 (dd, J=4.9, 2.9 Hz, 1H), 7.64 (dd, J=8.7, 1.7 Hz, 1H), 7.51 (d, J=8.6 Hz, 1H), 7.43 (dd, J=2.9, 1.3 Hz, 1H), 7.07 (dd, J=4.9, 1.3 Hz, 1H), 7.05 (d, J=7.8 Hz, 2H), 6.99-6.93 (m, 2H), 5.04 (d, J=3.3 Hz, 1H), 4.47 (dd, J=8.3, 6.4 Hz, 2H), 4.12 (ddd, J=12.1, 8.9, 3.8 Hz, 1H), 3.58-3.51 (m, 1H), 3.11 (dd, J=8.2, 6.6 Hz, 2H), 2.88-2.82 (m, 2H), 2.82-2.76 (m, 2H), 2.25 (s, 3H), 1.79-1.71 (m, 3H), 1.56 (q, J=6.4, 4.6 Hz, 3H). $^{13}$C NMR (126 MHz, DMSO-$d_6$) δ 165.32, 138.58, 137.46, 134.68, 133.40, 130.53, 128.75, 128.73, 128.09, 126.84, 126.59, 126.26, 123.24, 121.02, 118.46, 114.46, 109.54, 101.20, 61.57, 41.49, 36.08, 28.06, 26.71, 24.80, 23.82, 20.62, 18.53.

1-(2-(2H-tetrazol-5-yl)ethyl)-N-hydroxy-3-(4-methylphenethyl)-2-(thiophen-3-yl)-1H-indole-5-carboxamide (90). To a solution of 1-(2-(2H-tetrazol-5-yl)ethyl)-3-(4-methylphenethyl)-N-((tetrahydro-2H-pyran-2-yl)oxy)-2-(thiophen-3-yl)-1H-indole-5-carboxamide (0.15 g, 0.269 mmol) in DCM/MeOH (v/v=10/1, 5 mL) was added TFA (1.0 mL) at 0° C. The resultant mixture was stirred at 0° C. for 2 h. Upon completion, the mixture was diluted with $CH_2Cl_2$, and washed with water. The organic layer was concentrated under vacuum. The desired product (brown solid, $CH_2Cl_2$:MeOH=12:1, 0.045 g, 35% yield) was isolated using column chromatography. $^1$H NMR (500 MHz, DMSO-$d_6$) δ 11.18 (s, 1H), 8.89 (s, 1H), 8.13 (d, J=1.6 Hz, 1H), 7.73 (dd, J=4.9, 2.9 Hz, 1H), 7.64 (dd, J=8.6, 1.6 Hz, 1H), 7.51 (d, J=8.7 Hz, 1H), 7.44 (dd, J=2.9, 1.3 Hz, 1H), 7.08 (dd, J=4.9, 1.3 Hz, 1H), 7.05 (d, J=7.8 Hz, 2H), 6.98 (d, J=8.0 Hz, 2H), 4.46 (dd, J=8.4, 6.4 Hz, 2H), 3.11 (dd, J=8.4, 6.5 Hz, 2H), 2.82 (pd, J=10.0, 8.3, 3.5 Hz, 4H), 2.25 (s, 3H). $^{13}$C NMR (126 MHz, DMSO-$d_6$) δ 165.30, 138.67, 137.25, 134.66, 133.27, 130.60, 128.75, 128.09, 126.83, 126.62, 126.21, 123.77, 120.79, 117.95, 114.35, 109.55, 41.55, 36.10, 26.80, 23.92, 20.62.

1-(2-(2H-tetrazol-5-yl)ethyl)-N-methoxy-3-(4-methylphenethyl)-2-(thiophen-3-yl)-1H-indole-5-carboxamide (91). The synthesis of compound 91 followed general procedure H to obtain the desired product as brown solid ($CH_2Cl_2$:MeOH=12:1, 30% yield). $^1$H NMR (500 MHz, DMSO-$d_6$) δ 11.67 (s, 1H), 8.10 (d, J=1.7 Hz, 1H), 7.73 (dd, J=4.9, 2.9 Hz, 1H), 7.62 (dd, J=8.6, 1.7 Hz, 1H), 7.51 (d, J=8.6 Hz, 1H), 7.43 (dd, J=3.0, 1.3 Hz, 1H), 7.07 (dd, J=4.9, 1.3 Hz, 1H), 7.05 (d, J=7.7 Hz, 2H), 6.99-6.95 (m, 2H), 4.47 (dd, J=8.3, 6.4 Hz, 2H), 3.75 (s, 3H), 3.14-3.09 (m, 2H), 2.83 (dt, J=7.8, 1.9 Hz, 2H), 2.79 (dd, J=9.5, 4.7 Hz, 2H), 2.25 (s, 3H). $^{13}$C NMR (126 MHz, DMSO-$d_6$) δ 165.15, 138.62, 137.47, 134.70, 133.44, 130.52, 128.77, 128.74, 128.12, 126.88, 126.63, 126.30, 123.22, 120.81, 118.27, 114.47, 109.63, 63.29, 41.50, 36.11, 26.73, 23.81, 20.64.

Scheme 15

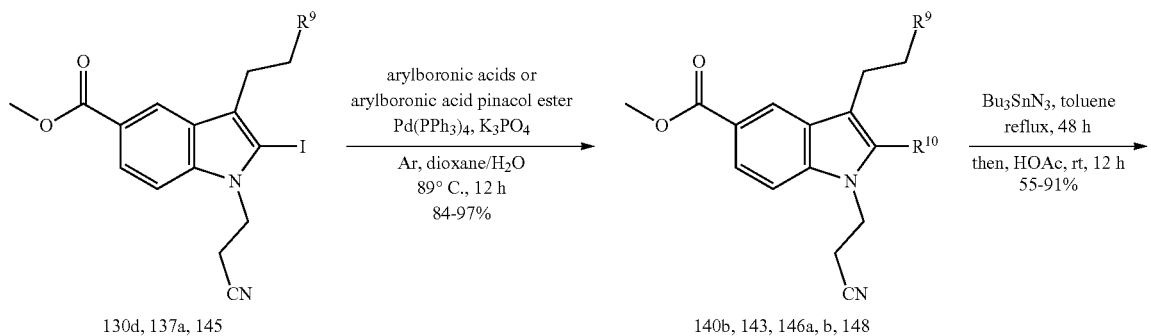

130d, 137a, 145 → 140b, 143, 146a, b, 148

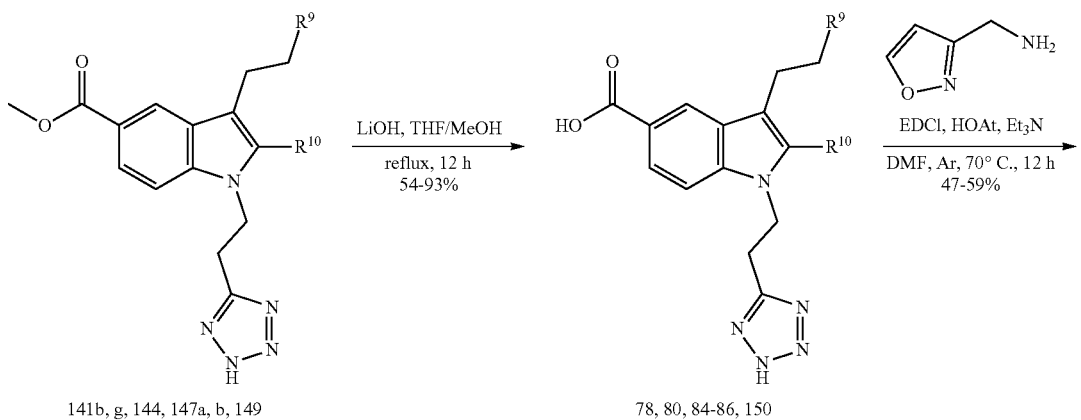

141b, g, 144, 147a, b, 149 → 78, 80, 84-86, 150

-continued
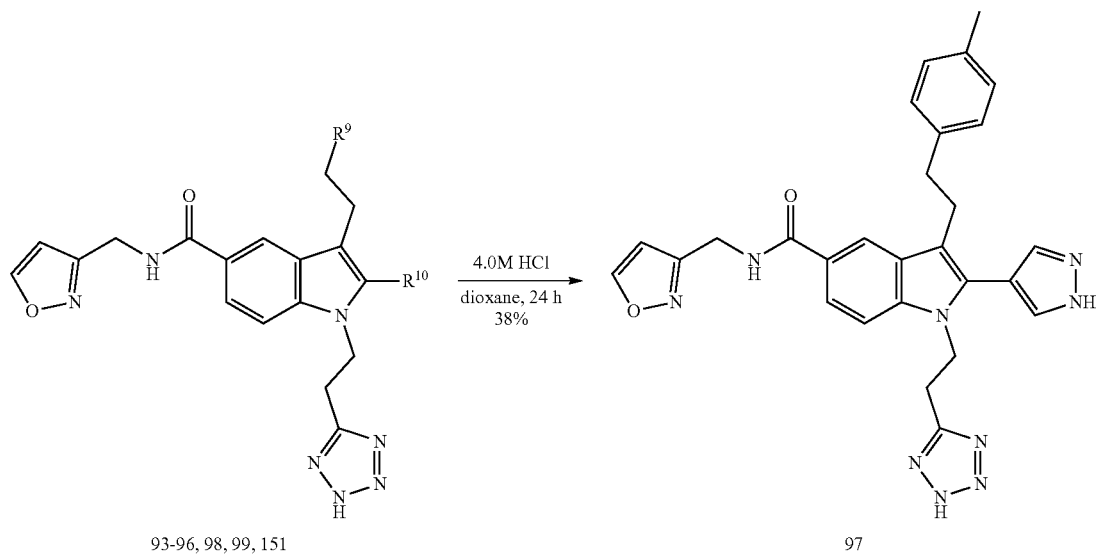
97
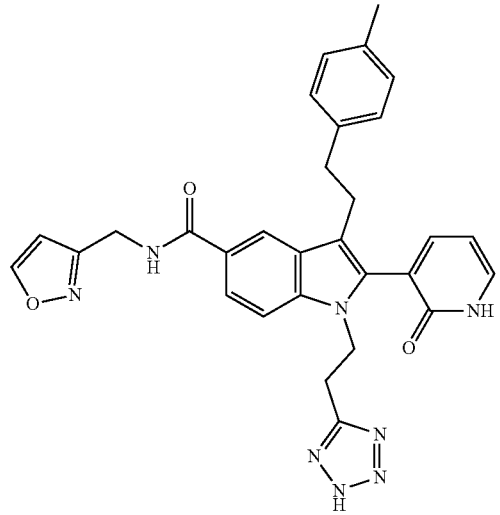
100
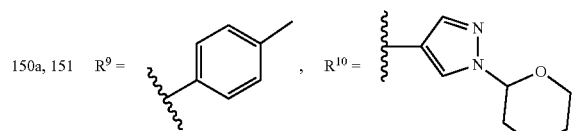
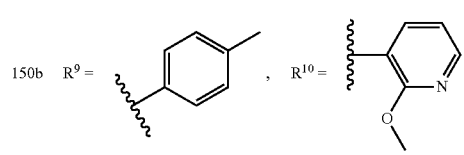
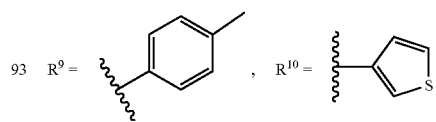
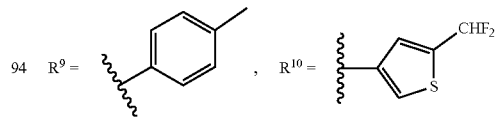

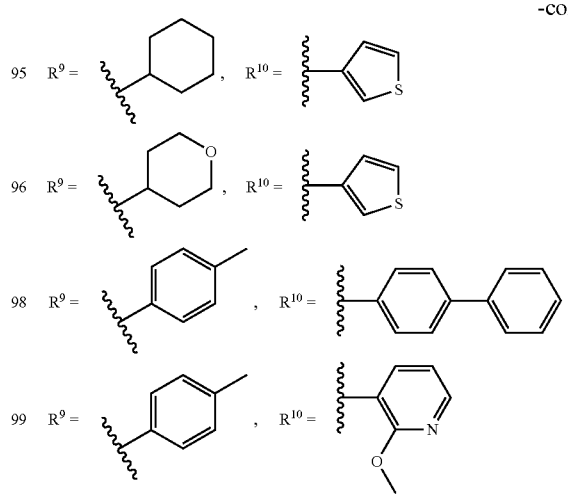

methyl 1-(2-cyanoethyl)-3-(4-methylphenethyl)-2-(1-(tetrahydro-2H-pyran-2-yl)-1H-pyrazol-4-yl)-1H-indole-5-carboxylate (148a). The synthesis of compound 148a followed general procedure K to obtain the desired compound as brown solid (hexanes:ethyl acetate=1:1, 93% yield). Low resolution mass spectrometry [M+H]$^+$: 497.3. $^1$H NMR (500 MHz, Chloroform-d) δ 8.43-8.37 (m, 1H), 7.99 (dd, J=8.6, 1.6 Hz, 1H), 7.36-7.32 (m, 2H), 7.04-7.00 (m, 2H), 6.97 (d, J=0.7 Hz, 1H), 6.85-6.81 (m, 2H), 5.35 (dd, J=8.6, 3.3 Hz, 1H), 4.32 (t, J=7.0 Hz, 2H), 4.14-4.07 (m, 1H), 3.97 (s, 3H), 3.77-3.70 (m, 1H), 2.97-2.86 (m, 4H), 2.56 (t, J=7.0 Hz, 2H), 2.31 (s, 3H), 2.12-2.04 (m, 3H), 1.75-1.64 (m, 3H). $^{13}$C NMR (126 MHz, Chloroform-d) δ 168.00, 139.97, 138.72, 138.59, 135.33, 129.99, 128.93, 128.79, 127.71, 123.80, 122.23, 122.10, 116.79, 116.77, 110.53, 108.69, 87.88, 67.93, 51.97, 39.41, 36.33, 30.57, 27.01, 24.96, 22.39, 21.05, 18.33.

methyl 1-(2-cyanoethyl)-2-(2-methoxypyridin-3-yl)-3-(4-methylphenethyl)-1H-indole-5-carboxylate (148b). The synthesis of compound 148b followed general procedure K to obtain the desired compound as brown solid (hexanes:ethyl acetate=3:1, 88% yield). Low resolution mass spectrometry [M+H]$^+$: 454.3. $^1$H NMR (500 MHz, Chloroform-d) δ 8.44-8.39 (m, 1H), 8.30 (dd, J=5.0, 2.0 Hz, 1H), 8.00 (dd, J=8.6, 1.6 Hz, 1H), 7.37-7.32 (m, 1H), 7.15 (dd, J=7.3, 2.0 Hz, 1H), 7.00 (d, J=7.6 Hz, 2H), 6.95 (dd, J=7.2, 5.0 Hz, 1H), 6.89-6.84 (m, 2H), 4.29-4.13 (m, 2H), 3.97 (s, 3H), 3.90 (s, 3H), 2.98 (ddd, J=13.7, 7.9, 6.1 Hz, 1H), 2.92-2.81 (m, 2H), 2.81-2.72 (m, 1H), 2.69-2.52 (m, 2H), 2.30 (s, 3H). $^{13}$C NMR (126 MHz, Chloroform-d) δ 167.99, 161.85, 148.34, 142.04, 138.54, 138.36, 135.35, 133.34, 128.92, 128.39, 127.83, 123.90, 122.52, 122.00, 116.93, 116.87, 116.76, 113.30, 108.64, 53.75, 51.97, 39.85, 36.35, 26.80, 21.02, 18.12.

methyl 1-(2-(2H-tetrazol-5-yl)ethyl)-3-(4-methylphenethyl)-2-(1-(tetrahydro-2H-pyran-2-yl)-1H-pyrazol-4-yl)-1H-indole-5-carboxylate (149a). The synthesis of compound 149a followed general procedure F to obtain the desired product as light yellow solid (CH$_2$Cl$_2$:MeOH=15:1, 62% yield). Low resolution mass spectrometry [M+H]$^+$: 540.3. $^1$H NMR (500 MHz, Chloroform-d) δ 8.37-8.33 (m, 1H), 7.87 (dd, J=8.6, 1.6 Hz, 1H), 7.25 (d, J=10 Hz, 1H), 7.02-6.99 (m, 2H), 6.83-6.78 (m, 3H), 5.34 (dd, J=9.2, 3.2 Hz, 1H), 4.42-4.36 (m, 2H), 4.16-4.06 (m, 1H), 3.92 (s, 3H), 3.75-3.68 (m, 1H), 3.20 (ddd, J=8.3, 6.8, 1.9 Hz, 2H), 2.87 (d, J=2.6 Hz, 4H), 2.30 (s, 3H), 2.12-2.01 (m, 3H), 1.72-1.63 (m, 3H). $^{13}$C NMR (126 MHz, Chloroform-d) δ 168.46, 140.16, 138.88, 138.73, 135.37, 129.72, 128.97, 128.76, 128.60, 127.31, 123.72, 122.17, 121.51, 116.35, 111.33, 108.94, 87.94, 68.27, 52.11, 42.08, 36.35, 30.34, 26.99, 24.88, 24.60, 22.45, 21.06.

methyl 1-(2-(2H-tetrazol-5-yl)ethyl)-2-(2-methoxypyridin-3-yl)-3-(4-methylphenethyl)-1H-indole-5-carboxylate (149b). The synthesis of compound 149b followed general procedure F to obtain the desired product as light yellow solid (CH$_2$Cl$_2$:MeOH=15:1, 63% yield). Low resolution mass spectrometry [M+H]$^+$: 497.2. $^1$H NMR (500 MHz, Chloroform-d) δ 8.31 (dd, J=1.7, 0.6 Hz, 1H), 8.19 (dd, J=5.0, 2.0 Hz, 1H), 7.79 (dd, J=8.6, 1.6 Hz, 1H), 7.26-7.22 (m, 1H), 7.01 (dd, J=7.2, 2.0 Hz, 1H), 6.99-6.95 (m, 2H), 6.88 (dd, J=7.2, 5.0 Hz, 1H), 6.84-6.80 (m, 2H), 4.42 (dt, J=14.8, 6.6 Hz, 1H), 4.32 (dt, J=14.9, 7.5 Hz, 1H), 3.91 (s, 3H), 3.85 (s, 3H), 3.30-3.23 (m, 2H), 2.96-2.87 (m, 1H), 2.81-2.75 (m, 2H), 2.75-2.67 (m, 1H), 2.28 (s, 3H). $^{13}$C NMR (126 MHz, Chloroform-d) δ 168.79, 161.61, 148.02, 141.46, 138.70, 138.45, 135.34, 133.53, 128.91, 128.27, 127.45, 123.62, 122.36, 120.98, 116.92, 116.40, 113.49, 108.97, 53.82, 52.18, 42.22, 36.29, 26.74, 24.25, 20.99.

1-(2-(2H-tetrazol-5-yl)ethyl)-3-(4-methylphenethyl)-2-(1-(tetrahydro-2H-pyran-2-yl)-1H-pyrazol-4-yl)-1H-indole-5-carboxylic acid (150a). The synthesis of compound 150a followed general procedure J to obtain the desired compound as white solid (54% yield). Low resolution mass spectrometry [M+H]$^+$: 526.3. $^1$H NMR (500 MHz, DMSO-d$_6$) δ 12.49 (s, 1H), 8.22 (d, J=1.6 Hz, 1H), 7.76 (dd, J=8.6, 1.6 Hz, 1H), 7.56 (s, 1H), 7.49 (d, J=8.7 Hz, 1H), 7.47 (s, 1H), 7.05 (d, J=7.7 Hz, 2H), 6.95-6.89 (m, 2H), 5.43 (dd, J=9.8, 2.2 Hz, 1H), 4.51-4.43 (m, 2H), 4.00-3.90 (m, 1H), 3.70-3.60 (m, 1H), 3.14 (t, J=7.4 Hz, 2H), 2.86-2.76 (m, 4H), 2.26 (s, 3H), 2.06 (ddd, J=12.7, 9.6, 3.0 Hz, 1H), 1.99-1.92 (m, 2H), 1.76-1.65 (m, 1H), 1.58 (dt, J=8.1, 3.8 Hz, 2H). $^{13}$C NMR (126 MHz, DMSO-d$_6$) δ 168.25, 139.07, 138.52, 138.23, 134.72, 130.44, 128.93, 128.80, 128.26, 126.76, 122.64, 121.63, 120.97, 114.47, 110.35, 109.48, 86.82, 66.75, 41.42, 36.08, 29.75, 26.80, 24.60, 23.94, 21.86, 20.62.

1-(2-(2H-tetrazol-5-yl)ethyl)-2-(2-methoxypyridin-3-yl)-3-(4-methylphenethyl)-1H-indole-5-carboxylic acid (150b). The synthesis of compound 150b followed general procedure J to obtain the desired compound as white solid (93% yield). Low resolution mass spectrometry [M+H]⁺: 483.3. ¹H NMR (500 MHz, DMSO-d$_6$) δ 13.37-11.61 (m, 1H), 8.31 (dd, J=5.0, 2.0 Hz, 1H), 8.24 (d, J=1.7 Hz, 1H), 7.79 (dd, J=8.6, 1.6 Hz, 1H), 7.54 (d, J=8.7 Hz, 1H), 7.25 (dd, J=7.2, 2.0 Hz, 1H), 7.06 (dd, J=7.2, 5.0 Hz, 1H), 6.98 (d, J=7.7 Hz, 2H), 6.89-6.81 (m, 2H), 4.50-4.39 (m, 1H), 4.20 (dt, J=14.7, 7.3 Hz, 1H), 3.81 (s, 3H), 3.17-3.04 (m, 2H), 2.87-2.79 (m, 1H), 2.75-2.62 (m, 3H), 2.23 (s, 3H). ¹³C NMR (126 MHz, DMSO-d$_6$) δ 168.25, 161.19, 147.93, 141.49, 138.28, 138.02, 134.64, 133.60, 128.73, 127.99, 126.84, 122.81, 121.64, 121.29, 116.98, 114.82, 113.16, 109.57, 53.37, 41.78, 35.92, 26.47, 23.83, 20.61.

1-(2-(2H-tetrazol-5-yl)ethyl)-N-(isoxazol-3-ylmethyl)-3-(4-methylphenethyl)-2-(thiophen-3-yl)-1H-indole-5-carboxamide (93). The synthesis of compound 93 followed general procedure H to obtain the desired product as brown solid (CH$_2$Cl$_2$:MeOH=13:1, 42% yield). ¹H NMR (500 MHz, DMSO-d$_6$) δ 9.11-8.97 (m, 1H), 8.85 (d, J=2.5 Hz, 1H), 8.25 (s, 1H), 7.80-7.67 (m, 2H), 7.51 (dd, J=8.7, 2.6 Hz, 1H), 7.43 (s, 1H), 7.10-7.01 (m, 3H), 6.96 (dd, J=7.9, 2.5 Hz, 2H), 6.53 (d, J=2.5 Hz, 1H), 4.62-4.58 (m, 2H), 4.49-4.44 (m, 2H), 3.14-3.09 (m, 2H), 2.85 (d, J=7.4 Hz, 2H), 2.80 (d, J=7.4 Hz, 2H), 2.24 (d, J=2.6 Hz, 3H). ¹³C NMR (126 MHz, DMSO-d$_6$) δ 167.19, 161.50, 159.87, 138.60, 137.43, 134.69, 133.38, 130.58, 128.76, 128.11, 126.85, 126.67, 126.26, 125.02, 121.26, 118.58, 114.50, 109.44, 104.21, 41.51, 36.09, 34.70, 26.71, 23.83, 20.63. HPLC purity (water/CH$_3$CN): 98.70%, Rt: 13.67 min. HPLC purity (water/MeOH): 99.73%, Rt: 15.53 min.

1-(2-(2H-tetrazol-5-yl)ethyl)-2-(5-(difluoromethyl)thiophen-3-yl)-N-(isoxazol-3-ylmethyl)-3-(4-methylphenethyl)-1H-indole-5-carboxamide (94). The synthesis of compound 94 followed general procedure H to obtain the desired product as brown solid (CH$_2$Cl$_2$:MeOH=13:1, 54% yield). ¹H NMR (500 MHz, Methanol-d4) δ 8.59 (d, J=1.7 Hz, 1H), 8.21 (d, J=1.7 Hz, 1H), 7.76 (dd, J=8.7, 1.7 Hz, 1H), 7.41 (d, J=8.6 Hz, 1H), 7.05 (d, J=1.4 Hz, 1H), 6.95 (t, J=55.5 Hz, 1H), 6.93 (d, J=7.8 Hz, 2H), 6.77 (q, J=1.8 Hz, 1H), 6.74-6.69 (m, 2H), 6.52 (d, J=1.7 Hz, 1H), 4.71 (s, 2H), 4.47 (t, J=6.8 Hz, 2H), 3.16 (t, J=6.8 Hz, 2H), 2.92-2.86 (m, 2H), 2.82 (dd, J=7.6, 5.4 Hz, 2H), 2.25 (s, 3H). ¹³C NMR (126 MHz, Methanol-d$_4$) δ 171.30, 162.62, 160.73, 139.89, 139.59, 138.38, 136.37, 134.24, 132.04, 129.90, 129.89, 129.86, 129.67, 128.79, 126.36, 122.69, 120.47, 117.06, 114.87, 113.00, 111.13, 110.53, 105.01, 43.06, 37.32, 36.38, 27.97, 25.12, 21.06. HPLC purity (water/CH$_3$CN): 99.64%, Rt: 13.92 min. HPLC purity (water/MeOH): 99.99%, Rt: 15.60 min.

1-(2-(2H-tetrazol-5-yl)ethyl)-3-(2-cyclohexylethyl)-N-(isoxazol-3-ylmethyl)-2-(thiophen-3-yl)-1H-indole-5-carboxamide (95). The synthesis of compound 95 followed general procedure H to obtain the desired product as brown solid (CH$_2$Cl$_2$:MeOH=13:1, 59% yield). HPLC purity (water/CH$_3$CN): 98.74%, Rt: 14.064 min. HPLC purity (water/MeOH): 98.78%, Rt: 15.905 min. ¹H NMR (500 MHz, DMSO-d$_6$) δ 9.00 (t, J=5.9 Hz, 1H), 8.84 (d, J=1.7 Hz, 1H), 8.16 (d, J=1.6 Hz, 1H), 7.76 (dd, J=4.9, 2.9 Hz, 1H), 7.73 (dd, J=8.7, 1.7 Hz, 1H), 7.62 (dd, J=2.9, 1.3 Hz, 1H), 7.48 (d, J=8.7 Hz, 1H), 7.18 (dd, J=4.9, 1.3 Hz, 1H), 6.51 (d, J=1.7 Hz, 1H), 4.58 (d, J=5.9 Hz, 2H), 4.48 (dd, J=8.3, 6.4 Hz, 2H), 3.14-3.07 (m, 2H), 2.65 (d, J=6.2 Hz, 2H), 1.61-1.50 (m, 5H), 1.40 (dt, J=9.1, 6.7 Hz, 2H), 1.15-1.03 (m, 4H), 0.80 (t, J=11.5 Hz, 2H). ¹³C NMR (126 MHz, DMSO-d$_6$) δ 167.15, 161.47, 159.83, 137.42, 133.03, 130.82, 128.82, 126.90, 126.76, 126.22, 124.86, 121.00, 118.62, 115.48, 109.32, 104.16, 41.50, 38.20, 36.50, 34.68, 32.63, 26.15, 25.73, 23.80, 21.20.

1-(2-(2H-tetrazol-5-yl)ethyl)-N-(isoxazol-3-ylmethyl)-3-(2-(tetrahydro-2H-pyran-4-yl)ethyl)-2-(thiophen-3-yl)-1H-indole-5-carboxamide (96). The synthesis of compound 96 followed general procedure H to obtain the desired product as brown solid (CH$_2$Cl$_2$:MeOH=12:1, 47% yield). ¹H NMR (500 MHz, DMSO-d$_6$) δ 9.01 (t, J=5.9 Hz, 1H), 8.84 (d, J=1.7 Hz, 1H), 8.17 (d, J=1.7 Hz, 1H), 7.76 (dd, J=4.9, 2.9 Hz, 1H), 7.73 (dd, J=8.7, 1.7 Hz, 1H), 7.64 (dd, J=2.9, 1.3 Hz, 1H), 7.49 (d, J=8.7 Hz, 1H), 7.19 (dd, J=4.9, 1.3 Hz, 1H), 6.52 (d, J=1.7 Hz, 1H), 4.58 (d, J=5.9 Hz, 2H), 4.48 (dd, J=8.2, 6.4 Hz, 2H), 3.76-3.67 (m, 2H), 3.18-3.09 (m, 4H), 2.67 (t, J=7.5 Hz, 2H), 1.49-1.41 (m, 2H), 1.37-1.27 (m, 3H), 1.10-0.98 (m, 2H). ¹³C NMR (126 MHz, DMSO-d$_6$) δ 167.15, 161.48, 159.86, 137.43, 133.18, 130.81, 128.87, 127.01, 126.71, 126.34, 124.90, 121.07, 118.59, 115.12, 109.38, 104.19, 66.98, 41.51, 37.61, 34.69, 33.66, 32.56, 23.81, 20.62. HPLC purity (water/CH$_3$CN): 99.99%, Rt: 11.47 min. HPLC purity (water/MeOH): 99.99%, Rt: 14.39 min.

1-(2-(2H-tetrazol-5-yl)ethyl)-2-([1,1'-biphenyl]-4-yl)-N-(isoxazol-3-ylmethyl)-3-(4-methylphenethyl)-1H-indole-5-carboxamide (98). The synthesis of compound 98 followed general procedure H to obtain the desired product as brown solid (CH$_2$Cl$_2$:MeOH=15:1, 49% yield). ¹H NMR (500 MHz, Chloroform-d) δ 8.34 (d, J=1.7 Hz, 1H), 7.85 (d, J=1.8 Hz, 1H), 7.69-7.58 (m, 4H), 7.48 (t, J=7.5 Hz, 2H), 7.43-7.36 (m, 2H), 7.22 (d, J=5.6 Hz, 1H), 7.14 (d, J=8.0 Hz, 3H), 6.94 (d, J=7.7 Hz, 2H), 6.82 (d, J=7.7 Hz, 2H), 6.41 (d, J=1.7 Hz, 1H), 4.79 (d, J=5.6 Hz, 2H), 4.45 (t, J=6.9 Hz, 2H), 3.19 (t, J=6.9 Hz, 2H), 2.82 (dd, J=8.6, 6.4 Hz, 2H), 2.72 (t, J=7.7 Hz, 2H), 2.24 (s, 3H). ¹³C NMR (126 MHz, Chloroform-d) δ 169.95, 160.09, 159.20, 141.50, 140.28, 138.94, 138.80, 138.24, 135.29, 130.71, 129.50, 128.95, 128.90, 128.57, 127.80, 127.78, 127.35, 127.18, 124.08, 121.03, 119.14, 115.52, 109.51, 104.00, 42.30, 36.80, 36.39, 26.68, 21.00.

1-(2-(2H-tetrazol-5-yl)ethyl)-N-(isoxazol-3-ylmethyl)-2-(2-methoxypyridin-3-yl)-3-(4-methylphenethyl)-1H-indole-5-carboxamide (99). The synthesis of compound 99 followed general procedure H to obtain the desired compound as gray solid (CH$_2$Cl$_2$:MeOH=15:1, 60% yield). Low resolution mass spectrometry [M+H]⁺: 563.3. ¹H NMR (500 MHz, DMSO-d$_6$) δ 9.04 (t, J=5.9 Hz, 1H), 8.85 (d, J=1.7 Hz, 1H), 8.30 (dd, J=5.0, 2.0 Hz, 1H), 7.77 (dd, J=8.6, 1.7 Hz, 1H), 7.53 (d, J=8.6 Hz, 1H), 7.23 (dd, J=7.2, 2.0 Hz, 1H), 7.05 (dd, J=7.2, 5.0 Hz, 1H), 6.99 (d, J=7.7 Hz, 2H), 6.91-6.85 (m, 2H), 6.53 (d, J=1.7 Hz, 1H), 4.60 (d, J=5.8 Hz, 2H), 4.43 (ddd, J=14.4, 8.1, 6.1 Hz, 1H), 4.19 (ddd, J=14.8, 8.2, 6.9 Hz, 1H), 3.81 (s, 3H), 3.16-3.04 (m, 2H), 2.86-2.79 (m, 1H), 2.78-2.71 (m, 2H), 2.68-2.61 (m, 1H), 2.23 (s, 3H). ¹³C NMR (126 MHz, DMSO-d$_6$) δ 167.20, 161.50, 161.20, 159.85, 147.84, 141.47, 138.40, 137.28, 134.60, 133.33, 128.70, 128.00, 126.71, 124.89, 121.25, 118.67, 116.94, 114.63, 113.29, 109.41, 104.18, 53.35, 41.78, 35.78, 34.69, 26.55, 23.89, 20.60.

1-(2-(2H-tetrazol-5-yl)ethyl)-N-(isoxazol-3-ylmethyl)-3-(4-methylphenethyl)-2-(1-(tetrahydro-2H-pyran-2-yl)-1H-pyrazol-4-yl)-1H-indole-5-carboxamide (151). The synthesis of compound 151 followed general procedure H to obtain the desired compound as gray solid (CH$_2$Cl$_2$:MeOH=15:1, 56% yield). Low resolution mass spectrometry [M+H]⁺: 606.3. ¹H NMR (500 MHz, Chloroform-d) δ 8.34 (d, J=1.6 Hz, 1H), 7.91 (d, J=1.8 Hz, 1H), 7.39 (d, J=1.8 Hz, 1H), 7.28-7.26 (m, 1H), 7.21 (t, J=5.7 Hz, 1H), 7.06 (d, J=8.6 Hz, 1H), 6.98 (s, 1H), 6.95 (d, J=7.5 Hz, 2H), 6.76 (d, J=8.0 Hz, 2H), 6.41 (d, J=1.7 Hz, 1H), 5.37-5.32 (m, 1H), 4.73 (d, J=5.6 Hz, 2H), 4.38 (t, J=7.0 Hz, 2H), 4.08 (dd, J=12.2, 3.2 Hz, 1H), 3.71 (td, J=11.6, 11.2, 3.0 Hz, 1H), 3.18 (t, J=7.0

Hz, 2H), 2.81-2.70 (m, 4H), 2.25 (s, 3H), 2.07 (q, J=5.8, 4.8 Hz, 3H), 1.74-1.61 (m, 3H). $^{13}$C NMR (126 MHz, Chloroform-d) δ 169.63, 160.42, 159.00, 139.88, 138.71, 138.17, 135.18, 130.33, 128.85, 128.68, 128.52, 127.44, 124.31, 120.91, 119.06, 115.84, 110.84, 109.21, 104.08, 87.72, 67.87, 42.00, 36.43, 35.98, 30.36, 29.26, 26.89, 24.87, 22.33, 20.95.

1-(2-(2H-tetrazol-5-yl)ethyl)-N-(isoxazol-3-ylmethyl)-3-(4-methylphenethyl)-2-(1H-pyrazol-4-yl)-1H-indole-5-carboxamide (97). 1-(2-(2H-tetrazol-5-yl)ethyl)-N-(isoxazol-3-ylmethyl)-3-(4-methylphenethyl)-2-(1-(tetrahydro-2H-pyran-2-yl)-1H-pyrazol-4-yl)-1H-indole-5-carboxamide (151) (0.072 g) was dissolved in 4.0 M HCl in dioxane (3.0 mL). The resulting mixture was stirred at room temperature for 1 day. Upon completion, the volatile was removed under vacuum. The residue was partitioned between DCM and water. The combined organic layers were concentrated under vacuum. Brown solid (CH$_2$Cl$_2$: MeOH=12:1, 0.032 g, 38% yield) was isolated by column chromatography. $^1$H NMR (500 MHz, Methanol-d$_4$) δ 8.60 (d, J=1.7 Hz, 1H), 8.18 (d, J=1.7 Hz, 1H), 7.72 (dd, J=8.7, 1.7 Hz, 1H), 7.42 (d, J=8.6 Hz, 1H), 7.22 (s, 2H), 7.00-6.95 (m, 2H), 6.83-6.79 (m, 2H), 6.53 (d, J=1.7 Hz, 1H), 4.71 (s, 2H), 4.50-4.42 (m, 2H), 3.16 (t, J=7.1 Hz, 2H), 2.88 (dt, J=11.1, 5.6 Hz, 4H), 2.27 (s, 3H). $^{13}$C NMR (126 MHz, Methanol-d$_4$) δ 171.53, 162.69, 160.72, 140.20, 139.70, 136.39, 131.98, 129.82, 129.74, 128.90, 125.97, 122.12, 120.15, 116.70, 111.44, 110.38, 105.02, 43.31, 37.55, 36.36, 28.22, 25.84, 21.08.

1-(2-(2H-tetrazol-5-yl)ethyl)-N-(isoxazol-3-ylmethyl)-3-(4-methylphenethyl)-2-(2-oxo-1,2-dihydropyridin-3-yl)-1H-indole-5-carboxamide (100). A mixture of 1-(2-(2H-tetrazol-5-yl)ethyl)-N-(isoxazol-3-ylmethyl)-2-(2-methoxypyridin-3-yl)-3-(4-methylphenethyl)-1H-indole-5-carboxamide (99) (28 mg, 0.05 mmol), 48% HBr (1.0 mL) in HOAc (3.0 mL) was heated at 75° C. for 36 h. The reaction mixture was cooled to room temperature, poured into a mixture of EtOAc and ice-water. The aqueous was extracted with EtOAc twice. The organic phase was combined together, concentrated under vacuum. Light brown solid (DCM:MeOH=12:1, 0.056 g, 28% yield) was isolated by column chromatography. $^1$H NMR (500 MHz, Methanol-d$_4$) δ 8.60 (d, J=1.7 Hz, 1H), 8.18 (d, J=1.6 Hz, 1H), 7.71 (dd, J=8.7, 1.7 Hz, 1H), 7.52 (dd, J=6.4, 2.1 Hz, 1H), 7.33 (d, J=8.7 Hz, 1H), 6.98 (d, J=7.7 Hz, 2H), 6.89-6.80 (m, 2H), 6.67 (dd, J=6.9, 2.1 Hz, 1H), 6.52 (d, J=1.7 Hz, 1H), 6.31 (t, J=6.7 Hz, 1H), 4.70 (s, 2H), 4.50 (ddd, J=15.0, 6.6, 5.3 Hz, 1H), 4.35 (ddd, J=15.0, 8.4, 6.7 Hz, 1H), 3.30-3.20 (m, 2H), 3.03 (dt, J=13.6, 6.6 Hz, 1H), 2.85 (t, J=7.3 Hz, 2H), 2.68 (dt, J=13.8, 8.0 Hz, 1H), 2.27 (s, 3H). $^{13}$C NMR (126 MHz, Methanol-d$_4$) δ 171.39, 164.01, 162.65, 160.72, 146.47, 140.14, 139.64, 137.30, 136.42, 135.21, 129.95, 129.63, 128.89, 126.03, 122.97, 122.50, 120.48, 117.18, 110.26, 108.16, 105.02, 43.61, 37.52, 36.35, 28.30, 25.22, 21.10.

Biochemical Assays

Protein Expression and Purification. Wild-type β-catenin (residues 138-781) were cloned into a pET-28b vector carrying a C-terminal 6×histidine (Novagen) and transformed into *E. coli* BL21 DE3 (Novagen). Cells were cultured in LB medium with 30 μg/mL kanamycin until the OD$_{600}$ was approximately 0.8, and then protein expression was induced with 400 μM of IPTG at 20° C. overnight. Cells were lysed by sonication. The proteins were purified by Ni-NTA affinity chromatography (30210, Qiagen) and dialyzed against a buffer containing 20 mM of Tris (pH 8.8), 100 mM NaCl, 10% glycerol, and 3 mM DTT. The purity of β-catenin was set to >95% as determined by SDS-PAGE gel analysis. Native non-denaturing gel electrophoresis experiment and the thermal-shift assay on an iCycler iQ Real Time Detection System (Bio-Rad) were performed for each purified protein. In the thermal shift assay, protein unfolding was evaluated through measuring the fluorescence changes of fluorescent dye Sypro Orange with purified β-catenin proteins. A temperature increment of 1° C./min was applied to monitor protein stability and detect protein aggregation. CD spectra were measured on a J-815 spectropolarimeter (Jasco). All spectra were recorded using a 1 mm path-length quartz cell. The CD spectra were averaged over three scans, and the wavelength was scanned from 260 to 190 nm in step of 1 nm. All spectra were recorded at room temperature, and the baseline was corrected by subtracting the CD spectra of a blank control containing all of the substances except protein. Samples were prepared at a concentration around 1-5 μM in a buffer of 10 mM potassium phosphate and 100 mM potassium fluoride at pH 7.0 to ensure that the transmission of light through the sample was not restricted. All proteins were stable, and no aggregation was observed under storage or assay conditions. Proteins were aliquoted and stored at −80° C. C-terminally fluorescein-labeled human Tcf4 (residues 7-51) was synthesized and HPLC purified with purity >95%. The structures were validated by LC/MS (liquid chromatography/mass spectrometry).

FP Assays. The procedures for the FP competitive inhibition assays have been described previously (Zhang, M.; Huang, Z.; Yu, B.; Ji, H. New homogeneous high-throughput assays for inhibitors of β-catenin/Tcf protein-protein interactions *Anal. Biochem.* 2012, 424, 57-63; Zhang, M.; Catrow, J. L.; Ji, H. High-throughput selectivity assays for small-molecule inhibitors of β-catenin/T-cell factor protein-protein interactions. *ACS Med. Chem. Lett.* 2013, 4, 306-311). Briefly, all of the tested compounds were prepared as 10 mM DMSO stocks. In the primary screen, the concentrations of the compounds and DMSO were set to 50 μM and 1% (v/v). Only the compounds which FP signal decreases were greater than 50% in the single-point β-catenin/Tcf assay were evaluated by counter screen. Compounds that were confirmed active in the competitive inhibition assay and inactive in the counter screen were further evaluated with the dose-response relationship. In the FP competitive inhibition assay, 10 nM human β-catenin and 2.5 nM of C-terminally fluorescein-labeled human Tcf4 were incubated in an assay buffer of 137 mM NaCl, 2.7 mM KCl, 10 mM Na$_2$HPO$_4$, 2 mM KH$_2$PO$_4$, 100 μg/mL of bovine γ-globulin, and 0.01% Triton-X100 for 15 min at 4° C. Bovine γ-globulin and Triton-X100 were included in the assay buffer to decrease the likelihood of compound acting by aggregate formation. Different concentrations of the tested compounds in the assay buffer were added to each test plate to make a final volume of 100 μL. Each assay plate was covered black and gently mixed on an orbital shaker at 4° C. for 1.5 h to reach equilibrium before the polarization values were read. The IC$_{50}$ value was determined by nonlinear least-square analysis of GraphPad Prism 5.0. The K$_i$ values were derived (Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and optimization of a binding assay for the XIAP BIR3 domain using fluorescence polarization. *Anal. Biochem.* 2004, 332, 261-273). Experiments were performed in triplicate and carried out in the presence of 1% DMSO.

TABLE 1

FP competitive inhibition assays to evaluate the inhibitory activities of new compounds for disruption of the β-catenin/Tcf protein-protein interaction. Each set of data was expressed as mean ± standard deviation (n = 3).

| Compound | Assay 1 | Assay 2 | Assay 3 | Assay 4 | Assay 5 |
|---|---|---|---|---|---|
| 1 | 990 ± 36 | | | | |
| 2 | 348 ± 1.3 | 780 ± 100 | | | |
| 3 | 250 ± 1.2 | | | | |
| 4 | 550 ± 56 | | | | |
| 5 | 62 ± 12 | | | | |
| 6 | 26 ± 2.3 | 19 ± 2.5 | | | |
| 7 | 27 ± 4.0 | | | | |
| 8 | 78 ± 10 | | | | |
| 9 | 31 ± 5.9 | | | | |
| 10 | 22 ± 3.1 | | | | |
| 11 | 27 ± 4.0 | 12 ± 2.2 | | | |
| 12 | 6.6 ± 0.44 | 41 ± 1.5 | | | |
| 13 | 6.5 ± 1.0 | | | | |
| 14 | 4.6 ± 0.36 | 3.5 ± 0.71 | | | |
| 15 | 29 ± 1.5 | >51 | | | |
| 16 | 18 ± 1.6 | 18 ± 0.67 | | | |
| 17 | 32 ± 3.9 | | | | |
| 18 | 1.1 ± 0.12 | 1.6 ± 0.23 | | | |
| 19 | >51 | | | | |
| 20 | 24 ± 1.7 | | | | |
| 21 | 6.6 ± 0.28 | 7.6 ± 0.65 | 10 ± 0.95 | 5.7 ± 1.1 | |
| 22 | 35 ± 1.2 | | | | |
| 23 | 94 ± 9.6 | | | | |
| 24 | 77 ± 4.5 | | | | |
| 25 | 11 ± 3.9 | 4.1 ± 0.88 | | | |
| 26 | 6.7 ± 1.1 | 2.7 ± 0.54 | | | |
| 27 | 3.3 ± 0.64 | 1.3 ± 0.38 | 5.6 ± 1.8 | | |
| 28 | 2.3 ± 0.54 | 0.87 ± 0.33 | | | |
| 29 | 11 ± 1.8 | 5.2 ± 1.7 | | | |
| 30 | 1.1 ± 0.27 | 1.6 ± 0.63 | 2.5 ± 1.5 | | |
| 31 | 2.0 ± 0.40 | 4.1 ± 0.60 | 4.1 ± 1.2 | 1.6 ± 0.12 | |
| 32 | 6.1 ± 1.5 | 7.5 ± 1.9 | 3.7 ± 1.3 | | |
| 33 | | | | | |
| 34 | | | | | |
| 35 | 4.1 ± 1.1 | | | | |
| 36 | 0.61 ± 0.065 | | | | |
| 37 | 28 ± 6.8 | | | | |
| 38 | 19 ± 2.8 | | | | |
| 39 | 7.9 ± 1.5 | 1.4 ± 0.45 | | | |
| 40 | 5.8 ± 1.3 | | | | |
| 41 | 36 ± 9.5 | 10 ± 2.2 | | | |
| 42 | 29 ± 3.3 | 2.0 ± 1.2 | | | |
| 43 | | | | | |
| 44 | 1.6 ± 0.37 | 0.35 ± 0.15 | 1.3 ± 0.37 | 0.92 ± 0.06 | |
| 45 | 0.97 ± 0.39 | 0.70 ± 0.02 | | | |
| 46 | 1.3 ± 0.40 | | | | |
| 47 | 7.4 ± 1.4 | 10 ± 0.66 | 2.1 ± 0.26 | 2.1 ± 0.27 | |
| 48 | 2.4 ± 0.56 | 3.2 ± 0.24 | | | |
| 49 | 0.75 ± 0.23 | 3.2 ± 0.24 | | | |
| 50 | 3.2 ± 0.28 | | | | |
| 51 | 3.6 ± 0.60 | 4.8 ± 0.84 | | | |
| 52 | 1.5 ± 0.17 | 2.6 ± 0.59 | | | |
| 53 | 2.7 ± 0.34 | 6.1 ± 1.2 | | | |
| 54 | 1.9 ± 0.14 | 3.0 ± 0.24 | | | |
| 55 | 2.9 ± 0.50 | 5.1 ± 0.42 | | | |
| 56 | 4.2 ± 0.43 | 1.9 ± 0.17 | | | |
| 57 | 3.6 ± 0.35 | 2.8 ± 0.17 | | | |
| 58 | 2.0 ± 0.29 | 7.6 ± 0.94 | | | |
| 59 | 0.83 ± 0.048 | 3.7 ± 0.23 | | | |
| 60 | 0.93 ± 0.092 | 4.7 ± 0.28 | | | |
| 61 | 1.0 ± 0.094 | 2.9 ± 0.24 | | | |
| 62 | 3.1 ± 0.18 | 7.6 ± 0.55 | | | |
| 63 | 1.4 ± 0.20 | 4.3 ± 0.39 | | | |
| 64 | 5.4 ± 0.76 | 9.5 ± 1.5 | | | |
| 65 | 6.1 ± 0.76 | | | | |
| 66 | 3.7 ± 0.19 | 32 ± 3.8 | | | |
| 67 | 5.9 ± 0.37 | >22 | | | |
| 68 | >24 | >22 | | | |
| 69 | >24 | >22 | | | |
| 70 | 2.6 ± 0.57 | 0.22 ± 0.06 | 2.6 ± 0.32 | | |
| 71 | 0.18 ± 0.034 | 0.29 ± 0.026 | 0.34 ± 0.023 | 0.45 ± 0.028 | |
| 72 | 0.60 ± 0.039 | | | | |
| 73 | 1.0 ± 0.076 | | | | |
| 74 | 4.2 ± 0.29 | 6.0 ± 0.39 | | | |
| 75 | 1.8 ± 0.11 | 0.68 ± 0.059 | | | |
| 76 | 0.46 ± 0.031 | 0.62 ± 0.033 | 0.89 ± 0.039 | | |
| 77 | 1.6 ± 0.11 | | | | |
| 78 | 0.40 ± 0.14 | 0.97 ± 0.14 | 0.25 ± 0.079 | 0.36 ± 0.07 | 0.23 ± 0.028 |
| 79 | 0.57 ± 0.052 | 0.70 ± 0.060 | | | |
| 80 | 0.92 ± 0.10 | 1.9 ± 0.13 | | | |
| 81 | 1.2 ± 0.28 | 3.2 ± 0.79 | | | |
| 82 | 8.4 ± 0.58 | 30 ± 1.9 | | | |
| 83 | 20 ± 1.1 | | | | |
| 84 | | | | | |
| 85 | 0.81 ± 0.052 | 8.2 ± 0.19 | 0.52 ± 0.048 | | |
| 86 | 1.3 ± 0.40 | 1.2 ± 0.23 | | | |
| 87 | 3.4 ± 0.86 | 1.3 ± 0.066 | | | |
| 88 | 16 ± 0.71 | Around 24 | | | |
| 89 | >24 | | | | |
| 90 | 0.34 ± 0.043 | 0.24 ± 0.043 | | | |
| 91 | 31 ± 5.8 | | | | |
| 92 | 10 ± 1.6 | | | | |
| 93 | 7.2 ± 0.77 | 7.4 ± 0.23 | 13 ± 1.3 | | |
| 94 | 2.7 ± 0.26 | 4.9 ± 0.36 | 26 ± 2.7 | | |
| 95 | 3.1 ± 0.068 | 15 ± 2.8 | | | |
| 96 | >25 | >25 | | | |
| 97 | 17 ± 1.6 | | | | |
| 98 | | | | | |
| 99 | | | | | |
| 100 | | | | | |

FP Selectivity Assays. Experiments were performed in 96-well Microfluor 2 black plates on a Synergy 2 plate reader (Biotek). The polarization was measured at room temperature with an excitation wavelength at 485 nm and an emission wavelength at 535 nm. The FP experiments were performed in an assay buffer of 25 mM Hepes (pH 7.4), 100 mM NaCl, 0.01% Triton X-100, and 100 μg/ml γ-globulin. The final reaction volume was set to 100 μL. For the β-catenin/Tcf assay, 10 nM human β-catenin (residues 138-781) was incubated with 2.5 nM C-terminally fluorescein-labeled human Tcf4 (residues 7-51) for 30 min at 4° C., and then different concentrations of the compound in assay buffer were added. The negative control (equivalent to 0% inhibition) refers to 2.5 nM Tcf4 fluorescence tracer and 10 nM β-catenin in assay buffer without the tested compound. The positive control (equivalent to 100% inhibition) refers to only 2.5 nM Tcf4 fluorescence tracer in assay buffer. For the β-catenin/cadherin assay, 150 nM human β-catenin (residues 138-781) was incubated with 5 nM C-terminally fluorescent-labeled human E-cadherin (residues 819-873) in assay buffer for 30 min at 4° C. The negative control refers to 5 nM E-cadherin fluorescence tracer and 150 nM β-catenin in assay buffer with no inhibitor presenting. The positive control refers to 5 nM E-cadherin fluorescence tracer in assay buffer. For the β-catenin/APC-R3 assay, 2000 nM human β-catenin (residues 138-781) was incubated with 5 nM of C-terminally fluorescent-labeled human APC-R3 (residues 1477-1519) in assay buffer for 30 min at 4° C. The negative control refers to 5 nM APC-R3 fluorescence tracer and 2,000 nM β-catenin in assay buffer without the tested compound. The positive control refers to 5 nM APC-R3 fluorescence tracer in assay buffer. Each assay plate was covered black and gently mixed on an orbital shaker at 4° C. for 2.5 h to reach equilibrium before the polarization values were read. The background of the tested inhibitors was corrected by subtracting the raw intensity values of the sample background well (all components except probe) from the raw intensity values of the corresponding test wells (all components). The $IC_{50}$ values were determined by Graph-Pad Prism 5.0. The $K_i$ values were derived from the $IC_{50}$ values. The equation used is $K_i=[I]_{50}/([L]_{50}/K_d+[P]_0/K_d-1)$ (Where $[I]_{50}$ denotes the concentration of the free inhibitor at 50% inhibition, $[L]_{50}$ is the concentration of the free labeled ligand at 50% inhibition, $[P]_0$ is the concentration of the free protein at 0% inhibition, and $K_d$ is the dissociation constant of the protein-ligand complex). All of the experiments were performed in triplicate and carried out in the presence of 1% DMSO for small-molecule inhibitors. Each compound was assayed at least by two independent experiments. The results were expressed as mean±standard deviation. The Tcf/cahderin selectivity ratio was calculated on the basis of the respective $K_i$ value of the β-catenin/E-cadherin interaction over that of the β-catenin/Tcf4 interaction. The Tcf/APC selectivity ratio was calculated on the basis of the respective $K_i$ value of the β-catenin/APC-R3 interaction over that of the β-catenin/Tcf4 interaction.

C-terminally fluorescein-labeled human Tcf4 (residues 7-51), C-terminally fluorescein-labeled human E-cadherin (residues 819-873), and C-terminally fluorescein-labeled human APC-R3 (residues 1477-1519) were synthesized and HPLC purified with purity >95%. The structures were validated by LC/MS (liquid chromatography/mass spectrometry). The sequences of these peptides are shown in Table 2.

The inhibitor selectivities of 27 for β-catenin/Tcf over β-catenin/E-cadherin and β-catenin/APC interactions have also been evaluated using FP selectivity assays, as shown in Table 3. This compound exhibited 28- and 80-fold selectivities for β-catenin/Tcf over β-catenin/cadherin and β-catenin/APC PPIs, respectively.

TABLE 3

FP selectivity assays to determine inhibitor selectivity of small-molecule β-catenin/Tcf inhibitors. Data are expressed as mean ± standard deviation (n = 3).

| | Ki ± SD (μM) | | | Selectivity | |
| --- | --- | --- | --- | --- | --- |
| No. | β-catenin/Tcf4 | β-catenin/E-cadherin | β-catenin/APC-R3 | Tcf/E-cadherin | Tcf/APC |
| 27 | 0.93 ± 0.51 | 26 ± 8.0 | 74 ± 11 | 28 | 80 |

Cell-Based Studies

MTS Cell Viability Assay. Colorectal cancer cells (SW480 and HCT116), TNBC cells (MDA-MB-231, MDA-MB-468, and BT-20), and lung cancer A549 cells were seeded in 96-well plates at $5 \times 10^3$ cells/well, maintained overnight at 37° C., and incubated with the tested compounds at various concentrations. Cell viability was monitored after 72 h using a freshly prepared mixture of 1 part phenazine methosulfate (PMS, Sigma) solution (0.92 mg/mL) and 19 parts 3-(4,5-dimethylthiazol-2-yl)-5-(3-carboxymethoxyphenyl)-2-(4-sulfophenyl)-2H-tetrazolium (MTS, Promega) solution (2 mg/mL). Cells were incubated in 10 μL of this solution at 37° C. for 3 h, and $A_{490}$ was measured. The effect of each compound is expressed as the concentration required to reduce $A_{490}$ by 50% ($IC_{50}$) relative to DMSO-treated cells. Experiments were performed in triplicate. The results are shown below.

TABLE 2

Peptide Sequences.

| Peptides | Sequences |
| --- | --- |
| Fluorescein-labeled Tcf4 45-mer | H-$^7$GGGDDLGANDELISFKDEGEQEEKSSENSSAERDLADVKSSLVNE$^{51}$K(FITC)-NH$_2$ (SEQ ID NO.: 1) |
| Fluorescein-labeled E-cadherin 55-mer | H-$^{819}$DTDPTAPPYDSLLVEDYEGSGSEAASLSSLNSSESDKDQDYDYLNEWGNRFKKLA$^{873}$K(FITC)-NH$_2$ (SEQ ID NO.: 2) |
| Fluorescein-labeled APC-R3 43-mer | H-$^{1477}$QRVQVLPDADTLLHFAFESTPDGFSCSSSLSALSLDEPFIQKD$^{1519}$K(FITC)-NH$_2$ (SEQ ID NO.: 3) |

TABLE 4

The MTS assay to monitor the inhibitory activities of 34, 35, 43, 44, 48, and 70 on viability of cancer cells. Each set of data was expressed as mean ± standard deviation (n = 3).

| Compound | Wnt hyperactive SW480 Cells | Wnt normal A549 |
|---|---|---|
| 34 | 69 ± 11 | 120 ± 44 |
| 35 | 3.1 ± 1.8; 3.2 ± 1.6 | 13 ± 5.9 |
| 43 | >400 | |
| 44 | 12 ± 1.4 | 42 ± 5.8 |
| 48 | 9.3 ± 4.9 | |
| 70 | 160 ± 17 | 310 ± 27 |

TABLE 5

The MTS assay to monitor the inhibitory activities of 45, 54-58, 60-62, 78, 90, and 92-94 on viability of cancer cells. Each set of data was expressed as mean ± standard deviation (n = 3).

| | Wnt hyperactive cancer cells | |
|---|---|---|
| Compound | SW480 | HCT116 |
| 45 | 14 ± 2.2 | 12 ± 1.9 |
| 54 | 11 ± 1.5 | 11 ± 1.7 |
| 55 | 13 ± 1.7 | 20 ± 2.7 |
| 56 | 14 ± 1.7 | 23 ± 2.5 |
| 57 | 19 ± 1.6 | 24 ± 2.8 |
| 58 | 19 ± 1.8 | 12 ± 1.8 |
| 60 | 14 ± 1.9 | 18 ± 2.8 |
| 61 | 35 ± 4.3 | 40 ± 5.3 |
| 62 | 21 ± 2.1 | 28 ± 3.8 |
| 78 | >400 | >400 |
| 90 | 115 ± 22 | 133 ± 4.1 |
| 92 | 81 ± 17 | |
| 93 | 36 ± 3.9 | 44 ± 5.4 |
| 94 | 32 ± 3.6 | 46 ± 5.3 |

Cell Transfection and Luciferase Assay. FuGENE 6 (E2962, Promega) in the 96-well plate format was used for the transfection of HEK293 cells according to the manufacturer's instructions. HEK293 cells were co-transfected with 45 ng of the TOPFlash or FOPFlash reporter gene, and 135 ng of pcDNA3.1-β-catenin. Cells were cultured in DMEM and 10% fatal bovine serum (FBS) at 37° C. for 24 h, and different concentrations of inhibitors were then added. After 24 h, the luciferase reporter activity was measured using the Dual-Glo system (E2940, Promega). Normalized luciferase activity in response to the treatment with the inhibitors was compared with that obtained from the cells treated with DMSO. Experiments were performed in triplicate. The results are shown below.

TABLE 6

Wnt-responsive TOPFlash luciferase reporter assay to examine effect on Wnt/β-catenin transactivation. Each set of data was expressed as mean ± standard deviation (n = 3).

| Com- | TOPFlash IC$_{50}$ ± SD (μM) | |
|---|---|---|
| pounds | β-catenin-activated HEK239 | SW480 |
| 35 | 11 ± 2.3 | 4.3 ± 1.2 |
| 44 | 42 ± 5.8 | 12 ± 1.3 |

TABLE 7

Wnt-responsive TOPFlash luciferase reporter assay to examine effect on Wnt/β-catenin transactivation. Each set of data was expressed as mean ± standard deviation (n = 3).

| Compounds | TOPFlash IC$_{50}$ ± SD (μM) β-catenin-activated HEK239 |
|---|---|
| 92 | 50 ± 5.7 |
| 94 | 9.9 ± 1.5 |

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound having Formula I:

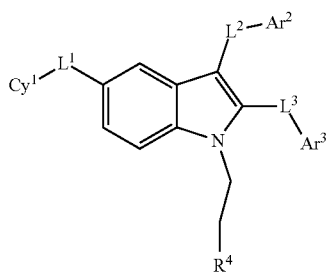

I wherein

Cy$^1$ is H or substituted or unsubstituted, mono or bicyclic aryl, heteroaryl, cycloalkyl, or cycloheteroalkyl;

L$^1$ is (CH$_2$)$_{2-4}$, CH$_2$NHC(O), C(O)NHCH$_2$, NHC(O)CH$_2$, CH$_2$C(O)NH, NHC(O), C(O)NH, CH$_2$C(O)NH, NHC(O)CH$_2$, C(O)NHCH$_2$, CH$_2$NHC(O), C(O)NHO, ONHC(O), C(O)NHOCH$_2$, CH$_2$ONHC(O), C(O)NHCH$_2$CH$_2$O, OCH$_2$CH$_2$NHC(O), C(O)NHCH$_2$CH(OH)CH(OH), CH$_2$C(O)O, OC(O)CH$_2$, C(O)OCH$_2$, CH$_2$OC(O), C(O)O, OC(O), CH$_2$C(O), C(O)CH$_2$, CH$_2$CH$_2$C(O), C(O)CH$_2$CH$_2$, NH$_2$, or O;

Ar$^2$ is substituted or unsubstituted, mono or bicyclic aryl, heteroaryl, or cycloheteroalkyl;

L$^2$ is (CH$_2$)$_{2-4}$;

Ar$^3$ is substituted or unsubstituted, mono or bicyclic heteroaryl;

L$^3$ is a bond, C≡C, or (CH$_2$)$_{1-4}$; and

R$^4$ is C(O)OC$_{1-6}$ alkyl, tetrazole, or CN;

wherein when substituted, the substituent is one or more of halo, C$_{1-6}$ alkyl, C$_{1-6}$ haloalky, C$_{1-6}$ alkoxyl, C$_{1-6}$ haloalkoxyl, or amino, or a pharmaceutically acceptable salt thereof.

2. The compound of claim 1, wherein L$^1$ is C(O)OCH$_2$ or C(O)O and Cy$^1$ is H.

3. The compound of claim 1, wherein L$^1$ is CH$_2$CH$_2$C(O) or CH$_2$NHC(O).

4. The compound of claim 1, wherein L$^1$ is NHC(O), C(O)NH, C(O)NHCH$_2$, CH$_2$NHC(O), C(O)NHO, ONHC(O), C(O)NHOCH$_2$, or CH$_2$ONHC(O).

5. The compound of claim 1, wherein Cy$^1$ is phenyl substituted with one or more halo, C$_{1-6}$ alkyl, C$_{1-6}$ haloalky, C$_{1-6}$ alkoxyl, or amino.

6. The compound of claim 1, wherein Cy$^1$ is pyridinyl, pyrimidinyl, pyrazinyl, pyrrolyl, isoxazolyl, isothiazolyl, oxazolyl, thiazolyl, pyranyl, or furanyl, any of which is optionally substituted with one or more halo, C$_{1-6}$ alkyl, C$_{1-6}$ haloalky, C$_{1-6}$ alkoxyl, or amino.

7. The compound of claim 1, wherein Cy$^1$ is cyclopenyl, cyclohexyl, tetrahydropyranyl, or tetrahydrofuranyl, any of which is optionally substituted with one or more halo, $C_{1-6}$ alkyl, $C_{1-6}$ haloalky, $C_{1-6}$ alkoxyl, or amino.

8. The compound of claim 1, wherein $L^2$ is $C_2H4$.

9. The compound of claim 1, wherein $Ar^2$ is phenyl substituted with one or more halo, $C_{1-6}$ alkyl, $C_{1-6}$ haloalky, $C_{1-6}$ alkoxyl, $C_{1-6}$ haloalkoxyl, amino, phenyl, or morpholino.

10. The compound of claim 1, wherein $Ar^2$ is phenyl substituted with chloro, fluoro, or methyl.

11. The compound of claim 1, wherein $Ar^2$ is pyridinyl, pyrimidinyl, pyrazinyl, pyrrolyl, isoxazolyl, isothiazolyl, oxazolyl, thiazolyl, pyranyl, or furanyl, any of which is optionally substituted with one or more halo, $C_{1-6}$ alkyl, $C_{1-6}$ haloalky, $C_{1-6}$ alkoxyl, $C_{1-6}$ haloalkoxyl, or amino.

12. The compound of claim 1, wherein $Ar^2$ is naphthyl.

13. The compound of claim 1, wherein $L^3$ is $C_2H_4$ or C≡C.

14. The compound of claim 1, wherein $Ar^3$ is pyridinyl, pyrimidinyl, pyrazinyl, pyrrolyl, isoxazolyl, isothiazolyl, oxazolyl, thiazolyl, pyranyl, pyrazolyl, furanyl, thiophenyl, benzothiophenyl, benzothiozolyl, any of which is optionally substituted with one or more halo, $C_{1-6}$ alkyl, $C_{1-6}$ haloalky, $C_{1-6}$ alkoxyl, $C_{1-6}$ haloalkoxyl, or amino.

15. The compound of claim 1, wherein $Ar^3$ has the following formula

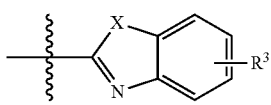

wherein X is O, S, NH, or $CH_2$; and $R^3$ is H, halogen, amino, $C_{1-6}$ alkyl, $C_{1-6}$ alkoxyl, $C_{1-6}$ haloalkyl, or $C_{1-6}$ haloalkoxyl.

16. The compound of claim 1, wherein $Ar^3$ is naphthyl.

17. The compound of claim 1, wherein $R^4$ is a tetrazole, or C(O)OMe.

18. The compound of claim 1, wherein the compound has Formula II

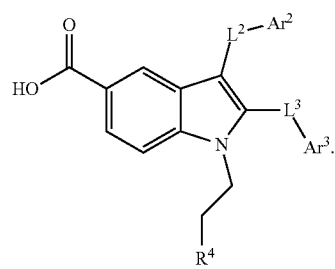

19. The compound of claim 1, wherein the compound has Formula III

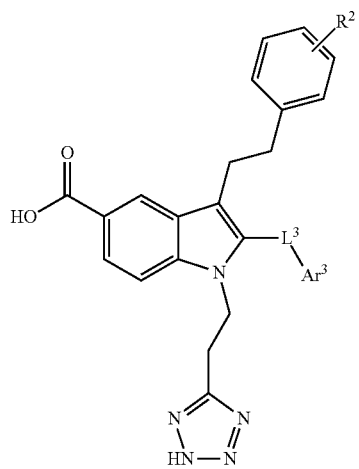

wherein $R^2$ is H, halogen, amino, $C_{1-6}$ alkyl, $C_{1-6}$ alkoxyl, $C_{1-6}$ haloalkyl, or $C_{1-6}$ haloalkoxyl.

20. The compound of claim 1, wherein the compound has Formula IV

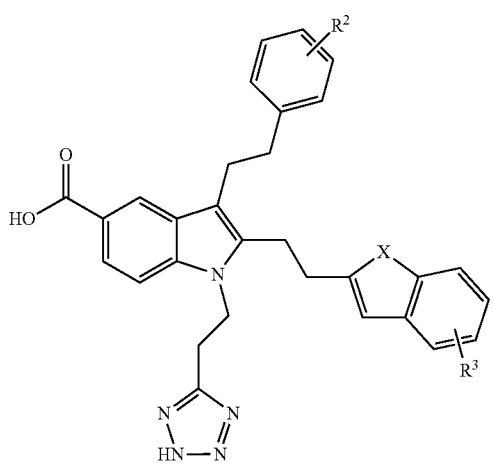

wherein $R^2$ and $R^3$ are independently selected from is H, halogen, amino, $C_{1-6}$ alkyl, $C_{1-6}$ alkoxyl, $C_{1-6}$ haloalkyl, or $C_{1-6}$ haloalkoxyl and X is O, S, NH, and $CH_2$.

21. The compound of claim 1, wherein the compound has Formula V

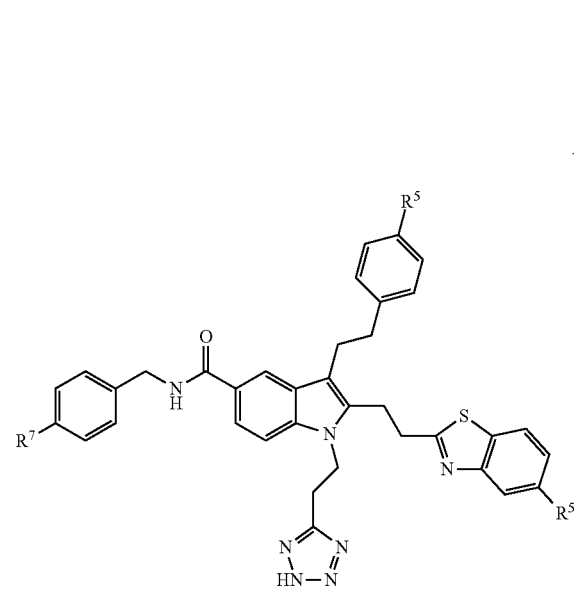

V wherein $R^5$, $R^6$, and $R^7$ are independently selected from H, halo, amino, $C_{1-6}$ alkyl, $C_{1-6}$ alkoxyl, $C_{1-6}$ haloalkyl, $C_{1-6}$ haloalkoxyl, and $C_{1-6}$ heteroalkyl.

22. The compound of claim 1, wherein the compound has Formula VI

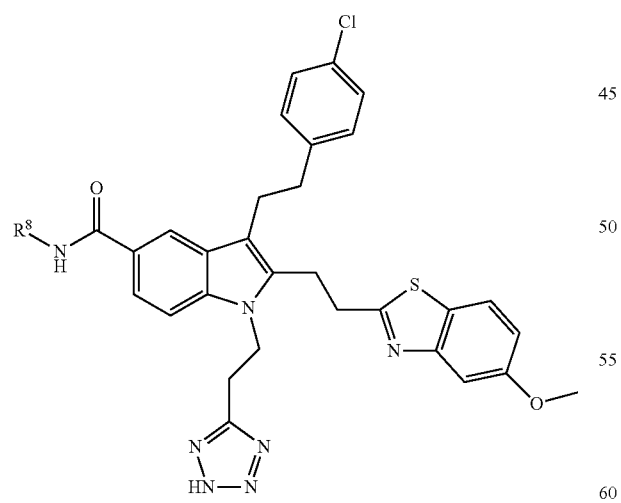

VI wherein $R^8$ is substituted or unsubstituted, mono or bicyclic aryl, heteroaryl, cycloalkyl, cycloheteroalkyl, or dihydroxysubstituted alkyl.

23. The compound of claim 1, wherein the compound has Formula VII-A or VII-B

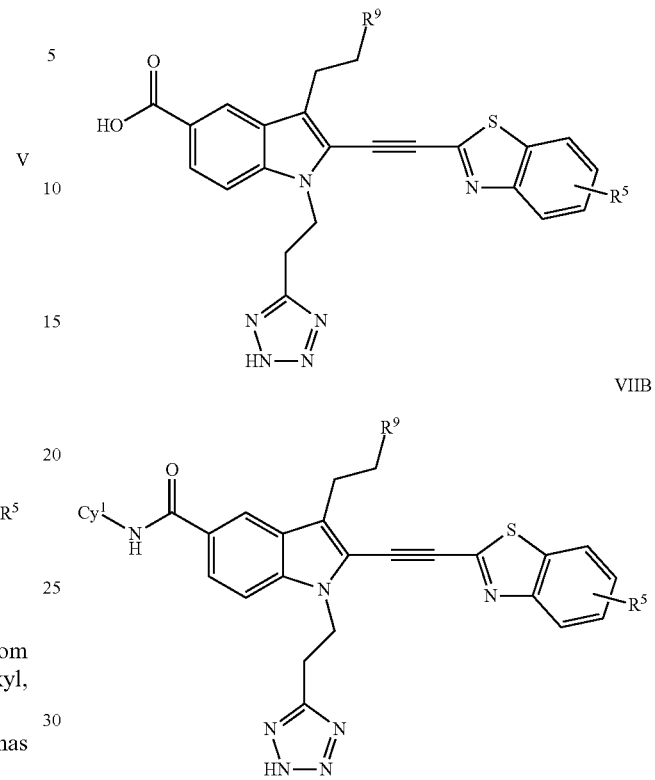

VIIA

VIIB wherein $R^5$ is selected from H, halo, amino, $C_{1-6}$ alkyl, $C_{1-6}$ alkoxyl, $C_{1-6}$ haloalkyl, $C_{1-6}$ haloalkoxyl, or $C_{1-6}$ heteroalkyl, and $R^9$ is substituted or unsubstituted, mono or bicyclic aryl, heteroaryl, or cycloheteroalkyl.

24. The compound of claim 1, wherein the compound has Formula VIII

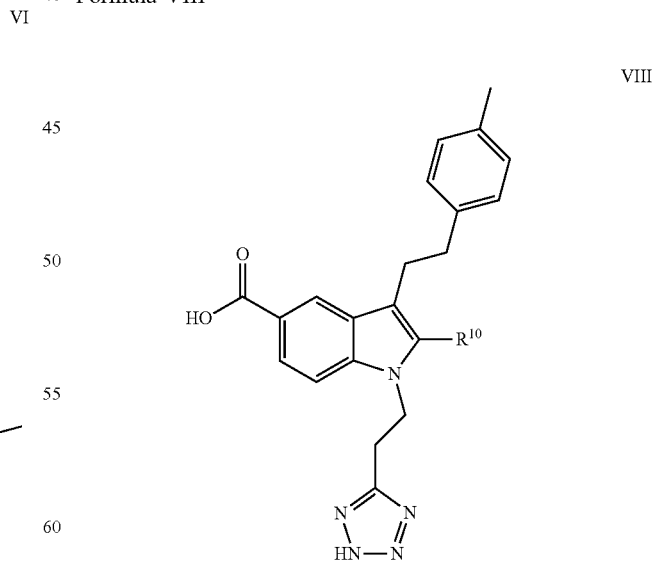

VIII wherein $R^{10}$ is substituted or unsubstituted, mono or bicyclic heteroaryl.

25. The compound of claim 1, wherein the compound has Formula IX

IX

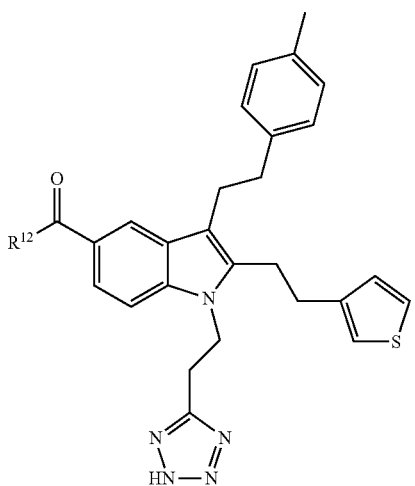

wherein R¹² is NH₂, NHC₁₋₆ alkyl, NHOH, NHOC₁₋₆ alkyl, NHO-cycloalkyl, or NHO-cycloheteroalkyl.

26. The compound of claim 1, wherein the compound has Formula X

X

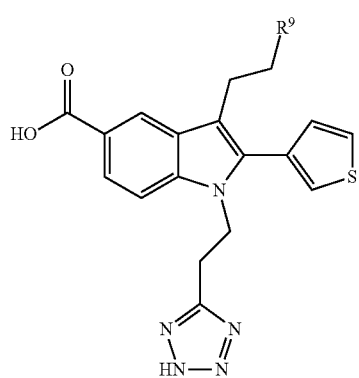

wherein R⁹ is substituted or unsubstituted, mono or bicyclic aryl, heteroaryl, or cycloheteroalkyl.

27. The compound of claim 1, wherein the compound has Formula XI

XI

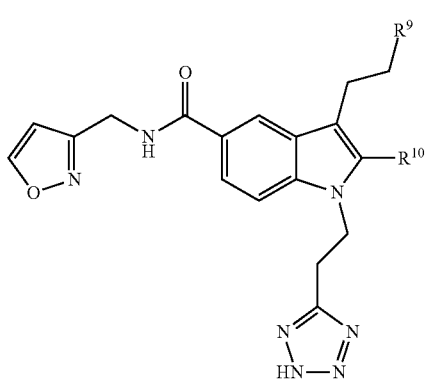

wherein R⁹ is substituted or unsubstituted, mono or bicyclic aryl, heteroaryl, or cycloheteroalkyl and R¹⁰ is substituted or unsubstituted, mono or bicyclic heteroaryl.

* * * * *